US006638973B2

(12) United States Patent
Holton

(10) Patent No.: US 6,638,973 B2
(45) Date of Patent: Oct. 28, 2003

(54) TAXANE FORMULATIONS

(75) Inventor: Robert A. Holton, Tallahassee, FL (US)

(73) Assignee: FSU Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 09/776,426

(22) Filed: Feb. 2, 2001

(65) Prior Publication Data

US 2002/0052403 A1 May 2, 2002

Related U.S. Application Data

(60) Provisional application No. 60/179,684, filed on Feb. 2, 2000, provisional application No. 60/179,793, filed on Feb. 2, 2000, provisional application No. 60/179,782, filed on Feb. 2, 2000, provisional application No. 60/179,669, filed on Feb. 2, 2000, provisional application No. 60/179,671, filed on Feb. 2, 2000, provisional application No. 60/179,670, filed on Feb. 2, 2000, provisional application No. 60/179,794, filed on Feb. 2, 2000, and provisional application No. 60/179,672, filed on Feb. 2, 2000.

(51) Int. Cl.[7] .................................................. A61K 31/34

(52) U.S. Cl. .................................................. 514/468

(58) Field of Search .................................................. 514/468

(56) References Cited

U.S. PATENT DOCUMENTS

| | | | | | |
|---|---|---|---|---|---|
| 4,960,790 | A | | 10/1990 | Stella et al. | |
| 5,407,683 | A | | 4/1995 | Shively | |
| 5,438,072 | A | * | 8/1995 | Bobee et al. | 514/449 |
| 5,478,860 | A | | 12/1995 | Wheeler et al. | |
| 5,527,537 | A | | 6/1996 | Dietl | |
| 5,616,330 | A | * | 4/1997 | Kaufman et al. | 424/400 |
| 5,877,205 | A | | 3/1999 | Andersson | |
| 5,922,754 | A | | 7/1999 | Burchett et al. | |
| 5,925,669 | A | | 7/1999 | Katz et al. | |
| 5,929,030 | A | | 7/1999 | Hamied et al. | |

* cited by examiner

*Primary Examiner*—Dwayne C. Jones
(74) *Attorney, Agent, or Firm*—Senniger, Powers, Leavitt & Roedel

(57) ABSTRACT

The present invention is directed to various formulations of taxanes having improved solubility as compared to paclitaxel, particularly formulations of such taxane derivatives for oral or parenteral administration to a patient.

33 Claims, No Drawings

TAXANE FORMULATIONS

REFERENCE TO RELATED APPLICATIONS

This application claims priority based on the following U.S. provisional applications: Ser. No. 60/179,684, filed on Feb. 2, 2000; Ser. No. 60/179,793, filed on Feb. 2, 2000; Ser. No. 60/179,782, filed on Feb. 2, 2000; Ser. No. 60/179,669, filed on Feb. 2, 2000; Ser. No. 60/179,671, filed on Feb. 2, 2000; Ser. No. 60/179,670, filed on Feb. 2, 2000; and Ser. No. 60/179,794, filed on Feb. 2, 2000, all incorporated herein by reference.

BACKGROUND OF THE INVENTION

The present invention is directed to various formulations of taxane derivatives having improved solubility as compared to paclitaxel, particularly formulations of such taxane derivatives for parenteral administration to a patient.

Paclitaxel has shown remarkable antineoplastic effect in a wide range of human cancers. Initially approved in 1992 for the treatment of refractory ovarian cancer, paclitaxel is now the first-line therapy for metastatic breast cancer and advanced ovarian cancer. Paclitaxel's effectiveness has also been demonstrated against non-small cell lung cancer, head and neck cancers, melanoma, colon cancer and Kaposi's sarcoma. In addition to its cytotoxic effects, paclitaxel has also been shown to be a potent inhibitor of angiogenesis. Despite its broad clinical utility, there has been difficulty formulating paclitaxel because of its insolubility in water. The aqueous solubility of paclitaxel is only 0.25 g per ml. Paclitaxel is also insoluble in most pharmaceutically-acceptable solvents, and lacks a suitable chemical functionality for formation of a more soluble salt. Consequently, special formulations are required for parenteral administration of paclitaxel. Paclitaxel is very poorly absorbed when administered orally (less than 1%). No oral formulation of paclitaxel has obtained regulatory approval for administration to patients.

Paclitaxel is currently formulated as Taxol®, which is a concentrated nonaqueous solution containing 6 mg paclitaxel per ml in a vehicle composed of 527 mg of polyoxyethylated castor oil (Cremophor® EL) and 49.7% (v/v) dehydrated ethyl alcohol, USP, per milliliter (available from Bristol-Myers Squibb Co., Princeton, N.J.). Cremophor® EL improves the physical stability of the solution, and ethyl alcohol solubilizes paclitaxel. The solution is stored under refrigeration and diluted just before use in 5% dextrose or 0.9% saline. Intravenous infusions of paclitaxel are generally prepared for patient administration within the concentration range of 0.3 to 1.2 mg/ml. In addition to paclitaxel, the diluted solution for administration consists of up to 10% ethanol, up to 10% Cremophor® EL and up to 80% aqueous solution. However, dilution to certain concentrations may produce a supersaturated solution that could precipitate. An inline 0.22 micron filter is used during Taxol® administration to guard against the potentially life-threatening infusion of particulates.

Several toxic side effects have resulted from the administration of paclitaxel in a Cremophor®/ethanol-based formulation including anaphylactic reactions, hypotension, angioedema, urticaria, peripheral neuropathy, arthralgia, mucositis, nausea, vomiting, alopecia, alcohol poisoning, respiratory distress such as dyspnea, cardiovascular irregularities, flu-like symptoms such as myalgia, gastrointestinal distress, hematologic complications such as neutropenia, genitourinary effects, and skin rashes. Some of these undesirable adverse effects were encountered in clinical trials, and in at least one case, the reaction was fatal. To reduce the incidence and severity of these reactions, patients are premedicated with corticosteroids, diphenhydramine, $H_2$-antagonists, antihistamines, or granulocyte colony-stimulating factor (G-CSF), and the duration of the infusion has been prolonged. Although such premedication has reduced the incidence of serious hypersensitivity reactions to less than 5%, milder reactions are still reported in approximately 30% of patients.

There is an additional drawback to the Cremophor®-based formulation. Cremophor® EL can leach phthalate plasticizers from polyvinyl chloride infusion bags and intravenous administration set tubing. This has led to the use of glass bottles or polyolefin containers for storing Taxol® solution and polyethylene-lined administration tubing or tubing made with tris (2-ethylhexyl) trimellitate plasticizer for Taxol® administration.

The physiological problems associated with paclitaxel administration have limited the dosage of paclitaxel that a patient can receive and prolonged the time of administration. Paclitaxel is typically given in a dose ranging from about 110 $mg/m^2$ to 300 $mg/m^2$ over a 3–24 hour period every 21 days or more, often with premedication. At dosages above 300 $mg/m^2$, peripheral neuropathy has been observed. Infusion times do not generally exceed 24 hours because the paclitaxel is physically stable for only 27 hours.

In instances where a patient receives a multi-day continuous infusion, the patient must have a new bag of Taxol® solution each day. In addition to the inconvenience for patients and staff and increased therapy cost, the bag exchange increases the risk of intravenous catheter microbial colonization. It would be advantageous to have a taxane product that remains stable for the entire period of the multi-day administration.

There is a strong need for reformulating taxane compositions using a safer and better-tolerated vehicle than Cremophor®. Alternative formulations of paclitaxel that avoid the use of Cremophor® have been proposed. One approach is incorporation of the drug into a liposomal formulation. However, it has been reported that there is difficulty in achieving a quantitative incorporation of the drug into the liposomal compartment, and that low loading capability and nonspecific uptake by the reticuloendothelial system have limited the clinical usefulness of such liposomes. This formulation is also not storage stable and must be freeze dried and reconstituted before use.

Another approach is to formulate paclitaxel as a lipid emulsion. Most of the efforts to create a paclitaxel formulation as a stable lipid emulsion have been unsuccessful. It has been widely reported in the literature that paclitaxel is insoluble in lipid emulsions containing soybean oil, such as Intralipid®, or lipid emulsions that are a mixture of soybean and safflower oils, such as Liposyn®. See, for example, L. C. Collins-Gold et al., "Parenteral Emulsions for Drug Delivery," Advanced Drug Delivery Reviews, 5, 189–208 (1990); B. D. Tarr, "A New Parenteral Emulsion for the Administration of Taxol," Pharmaceutical Research, 4(2), 163 (1987); Dolatrai M. Vyas, Paclitaxel (Taxol) Formulation And Prodrugs, The Chemistry and Pharmacology of Taxol and its Derivatives, Elsevier Science B. V., 107 (1995); J. M. Meerum Terwogt et al., "Alternative Formulations of Paclitaxel" Cancer Treatment Reviews, 23, 89 (1997). Paclitaxel's solubility in soybean oil is only 0.3 mg/ml. Vyas, supra. Physical methods for solubilizing paclitaxel in either soybean oil or safflower oil, such as heating or heating with sonication do not solubilize appreciable amounts of paclitaxel. Thus, the lipid emulsion formulations have significant drawbacks in that additives are still needed to solubilize paclitaxel and to prevent it from precipitating out of solution.

Tarr et al., supra, developed a parenteral triacetin emulsion formulation of paclitaxel. The emulsion contained 50% triacetin, 2.0% ethyl oleate, 1.5% Pluronic® F68, 1.5% purified soybean oil and 10 mg paclitaxel. Glycerol was added up to 10% to prevent creaming. This emulsion was reported to be adequately stable for parenteral administration. However, triacetin (glyceryl triacetate) itself proved to be toxic to mice when administered intravenously in concentrations required to deliver therapeutic doses of paclitaxel. Furthermore, no antitumor activity was observed with this formulation.

Andersson, U.S. Pat. No. 5,877,205, discloses a pharmaceutical composition for parenteral administration containing a taxane analog, dimethylacetamide, polyethylene glycol and an aqueous lipid emulsion. The aqueous lipid emulsion is preferably a soybean oil emulsion. Andersson solubilizes paclitaxel by dissolving it in an organic solvent of dimethylacetamide as the primary vehicle and adding a secondary polyethylene glycol solvent to stabilize the drug in solution for subsequent final dilution in an aqueous solvent, such as an aqueous lipid emulsion (e.g., emulsified soybean oil (Intralipid®), Liposyn®, Soyacal®, and Travemulsion®).

Kaufman et al., U.S. Pat. No. 5,616,330 report a composition of a taxine in a stable oil-in-water emulsion for intravenous administration. The taxine is dissolved in an alcohol and then mixed with an oil such as safflower or sunflower oil to form a solution. The alcohol is then removed from the solution by evaporation. The solution is added to an aqueous surfactant dispersion and stirred at high speed to form an emulsion. The emulsion is then refined through a homogenizer.

Although Taxol® and Taxotere® are useful chemotherapeutic formulations, there are limitations on their effectiveness, including limited efficacy against certain types of cancers and toxicity to subjects when administered at various doses. Accordingly, a need remains for additional formulations of chemotherapeutic agents with improved efficacy and less toxicity.

SUMMARY OF THE INVENTION

Among the various aspects of the present invention, therefore, is the provision of taxane-containing pharmaceutical compositions which compare favorably to Taxol® and Taxotere® formulations with respect to efficacy as antitumor agents and with respect to toxicity and stability.

Accordingly, it is an aspect of the invention to provide pharmaceutical compositions for oral or parenteral administration which comprise a taxane and at least one nonaqueous, pharmaceutically acceptable solvent. In one embodiment of the invention, the taxane has a solubility in ethanol of at least 100 mg/ml. In another aspect of the present invention, the taxane has a solubility in ethanol of at least 100 mg/ml and is capable of being crystallized from a solution. In yet another aspect, the pharmaceutical compositions comprise a taxane which has a solubility in ethanol of at least 60 mg/ml and an $ID_{50}$ value determined relative to the HCT116 cell line that is at least 4 times less than that of paclitaxel.

A further aspect of the present invention is the provision of pharmaceutical compositions for oral or parenteral administration which comprise a taxane of the invention and a pharmaceutically acceptable carrier.

Other objects and features of this invention will be in part apparent and in part pointed out hereinafter.

DETAILED DESCRIPTION OF THE PREFERRED EMBODIMENTS

The present invention provides compositions and methods for the solubilization of taxane antitumor compounds in pharmaceutically acceptable carriers. The taxanes of the invention are more soluble in the carriers and exhibit greater cytotoxic activity as compared to paclitaxel. Therefore, taxane compositions can be formulated to include significantly less ethanol and Cremophor® EL solution as compared to Taxol® solution, or can be formulated to be free of ethanol and/or Cremophor® solution. The taxanes remain physically and chemically stable in the compositions for an extended period of time, allowing for multi-day continuous infusion without replacement of the composition and for administration without the use of an inline filter. The taxane compositions can be administered systemically or locally without undue toxicity caused by the carrier or by precipitation or recrystallization of the taxane. The risk of anaphylactic reactions or other adverse side effects is minimized with the compositions of the invention.

The compositions of the invention allow for a broad range of administration protocols including oral administration. Oral administration has been found to decrease toxic side effects as compared with conventional intraveneous therapy. Rather than producing a sudden high taxane concentration in blood levels as is usually the case with an intravenous infusion, absorption of the taxane through the gut wall provides a more gradual appearance of taxane in the blood levels and enables a stable, steady-state maintenance of desired levels for a long period of time. The compositions can also be administered parenterally in less than 1, 2 or 3 hours so that patients can be treated on an out-patient basis while still providing an anti-neoplastic effective dosage without exceeding dose-limiting toxicities. The compositions are also effective in minimizing or eliminating premedication to reduce patient discomfort and the expense and duration of treatment. In instances where parenteral administration cannot be shortened in duration, the compositions contain lower taxane concentrations as compared to conventional paclitaxel compositions and result in minimal or no adverse side effects.

In one embodiment of the present invention, the taxanes of the present invention correspond to structure (1):

(1)

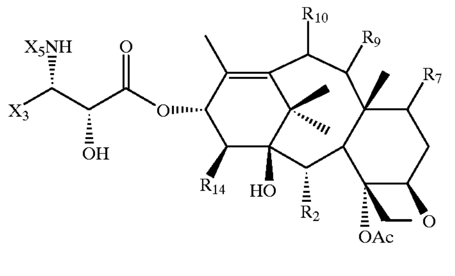

wherein one of $R_7$ and $R_{10}$ is hydroxy and the other is acyloxy;

$X_3$ is substituted or unsubstituted alkyl, alkenyl, alkynyl, phenyl or heterocyclo;

$X_5$ is —$COX_{10}$, —$COOX_{10}$, or —$CONHX_{10}$;

$X_{10}$ is hydrocarbyl, substituted hydrocarbyl, or heterocyclo;

$R_2$ is acyloxy;

$R_9$ is keto, hydroxy, or acyloxy;

$R_{14}$ is hydrido or hydroxy; and

Ac is acetyl.

$R_7$, $R_9$, and $R_{10}$ independently have the alpha or beta stereochemical configuration.

In one embodiment, $R_2$ is an ester ($R_{2a}C(O)O$—), a carbamate ($R_{2a}R_{2b}NC(O)O$—), a carbonate ($R_{2a}OC(O)O$—), or a thiocarbamate ($R_{2a}SC(O)O$—) wherein $R_{2a}$ and $R_{2b}$ are independently hydrogen, hydrocarbyl, substituted hydrocarbyl or heterocyclo. In a preferred embodiment, $R_2$ is an ester ($R_{2a}C(O)O$—), wherein $R_{2a}$ is aryl or heteroaromatic. In another preferred embodiment, $R_2$ is an ester ($R_{2a}C(O)O$—), wherein $R_{2a}$ is substituted or unsubstituted phenyl, furyl, thienyl, or pyridyl. In one particularly preferred embodiment, $R_2$ is benzoyloxy.

While $R_9$ is keto in one embodiment of the present invention, in other embodiments $R_9$ may have the alpha or beta stereochemical configuration, preferably the beta stereochemical configuration, and may be, for example, α- or β-hydroxy or α- or β-acyloxy. For example, when $R_9$ is acyloxy, it may be an ester ($R_{9a}C(O)O$—), a carbamate ($R_{9a}R_{9b}NC(O)O$—), a carbonate ($R_{9a}OC(O)O$—), or a thiocarbamate ($R_{9a}SC(O)O$—) wherein $R_{9a}$ and $R_{9b}$ are independently hydrogen, hydrocarbyl, substituted hydrocarbyl or heterocyclo. If $R_9$ is an ester ($R_{9a}C(O)O$—), $R_{9a}$ is substituted or unsubstituted alkyl, substituted or unsubstituted alkenyl, substituted or unsubstituted aryl or substituted or unsubstituted heteroaromatic. Still more preferably, $R_9$ is an ester ($R_{9a}C(O)O$—), wherein $R_{9a}$ is substituted or unsubstituted phenyl, substituted or unsubstituted furyl, substituted or unsubstituted thienyl, or substituted or unsubstituted pyridyl. In one embodiment $R_9$ is ($R_{9a}C(O)O$—) wherein $R_{9a}$ is methyl, ethyl, propyl (straight, branched or cyclic), butyl (straight, branched or cyclic), pentyl, (straight, branched or cyclic), or hexyl (straight, branched or cyclic). In another embodiment $R_9$ is ($R_{9a}C(O)O$—) wherein $R_{9a}$ is substituted methyl, substituted ethyl, substituted propyl (straight, branched or cyclic), substituted butyl (straight, branched or cyclic), substituted pentyl, (straight, branched or cyclic), or substituted hexyl (straight, branched or cyclic) wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

Exemplary $X_3$ substituents include substituted or unsubstituted $C_2$ to $C_8$ alkyl, substituted or unsubstituted $C_2$ to $C_8$ alkenyl, substituted or unsubstituted $C_2$ to $C_8$ alkynyl, substituted or unsubstituted heteroaromatics containing 5 or 6 ring atoms, and substituted or unsubstituted phenyl. Exemplary preferred $X_3$ substituents include substituted or unsubstituted ethyl, propyl, butyl, cyclopropyl, cyclobutyl, cyclohexyl, isobutenyl, furyl, thienyl, and pyridyl.

Exemplary $X_5$ substituents include —$COX_{10}$, —$COOX_{10}$ or —$CONHX_{10}$ wherein $X_{10}$ is substituted or unsubstituted alkyl, alkenyl, phenyl or heteroaromatic. Exemplary preferred $X_5$ substituents include —$COX_{10}$, —$COOX_{10}$ or —$CONHX_{10}$ wherein $X_{10}$ is (i) substituted or unsubstituted $C_1$ to $C_8$ alkyl such as substituted or unsubstituted methyl, ethyl, propyl (straight, branched or cyclic), butyl (straight, branched or cyclic), pentyl (straight, branched or cyclic), or hexyl (straight, branched or cyclic); (ii) substituted or unsubstituted $C_2$ to $C_8$ alkenyl such as substituted or unsubstituted ethenyl, propenyl (straight, branched or cyclic), butenyl (straight, branched or cyclic), pentenyl (straight, branched or cyclic) or hexenyl (straight, branched or cyclic); (iii) substituted or unsubstituted $C_2$ to $C_8$ alkynyl such as substituted or unsubstituted ethynyl, propynyl (straight or branched), butynyl (straight or branched), pentynyl (straight or branched), or hexynyl (straight or branched); (iv) substituted or unsubstituted phenyl, or (v) substituted or unsubstituted heteroaromatic such as furyl, thienyl, or pyridyl, wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

C10 Carbonates

In one embodiment, $R_{10}$ is $R_{10a}OCOO$— wherein $R_{10a}$ is (i) substituted or unsubstituted $C_1$ to $C_8$ alkyl (straight, branched or cyclic), such as methyl, ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heterocyclo such as furyl, thienyl, or pyridyl. The substituents may be hydrocarbyl or any of the heteroatom containing substituents identified elsewhere herein for substituted hydrocarbyl. In a preferred embodiment, $R_{10a}$ is methyl, ethyl, straight, branched or cyclic propyl, straight, branched or cyclic butyl, straight, branched or cyclic hexyl, straight or branched propenyl, isobutenyl, furyl or thienyl. In another embodiment, $R_{10a}$ is substituted ethyl, substituted propyl (straight, branched or cyclic), substituted propenyl (straight or branched), substituted isobutenyl, substituted furyl or substituted thienyl wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one of the preferred embodiments, the taxanes of the present invention correspond to structure (2):

(2)

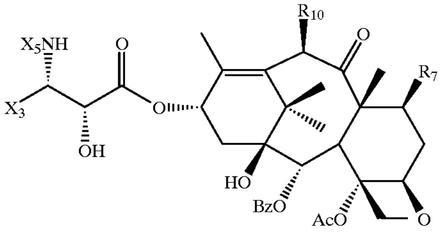

wherein $R_7$ is hydroxy;

$R_{10}$ is carbonate;

$X_3$ is substituted or unsubstituted alkyl, alkenyl, alkynyl, or heterocyclo, wherein alkyl comprises at least two carbon atoms;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_{10}$ may be $R_{10a}OCOO$— wherein $R_{10a}$ is substituted or unsubstituted methyl, ethyl, propyl, butyl, pentyl or hexyl, more preferably substituted or unsubstituted methyl, ethyl or propyl, still more preferably substituted or unsubstituted methyl, ethyl, and still more preferably unsubstituted methyl or ethyl. While $R_{7a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{10a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{10}$a and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{10a}$ is unsubstituted methyl, ethyl or propyl, more preferably methyl or ethyl.

Among the preferred embodiments are taxanes corresponding to structure 1 or 2 wherein $R_{10}$ is $R_{10a}OCOO$— wherein $R_{10a}$ is methyl. In this embodiment, $X_3$ is preferably cycloalkyl, isobutenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl, still more preferably t-butoxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10a}$ is $R_{10}OCOO$— wherein $R_{10a}$ is ethyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10}$ is $R_{10a}OCOO$— wherein $R_{10a}$ is propyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C10 Esters

In one embodiment, $R_{10}$ is $R_{10a}$COO— wherein $R_{10a}$ is (i) substituted or unsubstituted $C_2$ to $C_8$ alkyl (straight, branched or cyclic), such as ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heteroaromatic such as furyl, thienyl, or pyridyl. The substituents may be hydrocarbyl or any of the heteroatom containing substituents identified elsewhere herein for substituted hydrocarbyl. In a preferred embodiment, $R_{10a}$ is ethyl, straight, branched or cyclic propyl, straight, branched or cyclic butyl, straight, branched or cyclic pentyl, straight, branched or cyclic hexyl, straight or branched propenyl, isobutenyl, furyl or thienyl. In another embodiment, $R_{10a}$ is substituted ethyl, substituted propyl (straight, branched or cyclic), substituted propenyl (straight or branched), substituted isobutenyl, substituted furyl or substituted thienyl wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one of the preferred embodiments, the taxanes of the present invention correspond to structure (2):

(2)

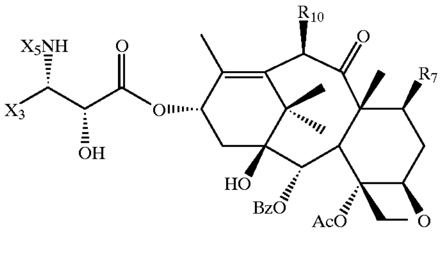

wherein $R_7$ is hydroxy;

$R_{10}$ is $R_{10a}$COO—;

$X_3$ is substituted or unsubstituted alkyl, alkenyl, alkynyl, or heterocyclo, wherein alkyl comprises at least two carbon atoms;

$X_5$ is —$COX_{10}$, —$COOX_{10}$, or —$CONHX_{10}$; and $X_{10}$ is hydrocarbyl, substituted hydrocarbyl, or heterocyclo; and $R_{10a}$, is hydrocarbyl, substituted hydrocarbyl, or heterocyclo wherein said hydrocarbyl or substituted hydrocarbyl contains carbon atoms in the alpha and beta positions relative to the carbon of which $R_{10a}$ is a substituent;

Bz is benzoyl; and

Ac is acetyl.

For example, in this preferred embodiment in which the taxane corresponds to the above structure (2), $R_{10a}$ may be substituted or unsubstituted ethyl, propyl or butyl, more preferably substituted or unsubstituted ethyl or propyl, still more preferably substituted or unsubstituted ethyl, and still more preferably unsubstituted ethyl. While $R_{10a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{10a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{10a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{7a}$ is unsubstituted ethyl or propyl, more preferably ethyl.

Among the preferred embodiments, therefore, are taxanes corresponding to structure 1 or 2 wherein $R_{10}$ is $R_{10a}$COO— wherein $R_{10a}$ is ethyl. In this embodiment, $X_3$ is preferably cycloalkyl, isobutenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10}$ is $R_{10a}COO$— wherein $R_{10a}$ is propyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C10 Carbamates

In one embodiment, $R_{10}$ is $R_{10a}R_{10b}NCOO$— wherein $R_{10a}$ and $R_{10b}$ are independently hydrogen, hydrocarbyl, substituted hydrocarbyl, or heterocyclo. Exemplary preferred $R_{10}$ substituents include $R_{10a}R_{10b}NCOO$— wherein (a) $R_{10a}$ and $R_{10a}$ are each hydrogen, (b) one of $R_{10a}$ and $R_{10b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl, or (c) $R_{10a}$ and $R_{10b}$ are independently (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_{10}$ substituents include $R_{10a}R_{10b}NCOO$— wherein one of $R_{10a}$ and $R_{10b}$ is hydrogen and the other is methyl, ethyl, or straight, branched or cyclic propyl.

In one of the preferred embodiments, the taxanes of the present invention correspond to structure (2):

(2)

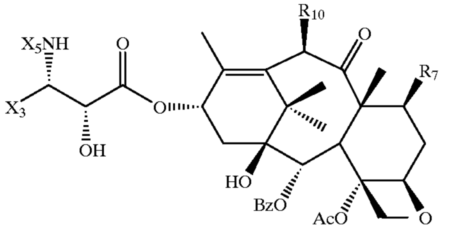

wherein $R_7$ is hydroxy;

$R_{10}$ is carbamoyloxy;

$X_3$ is substituted or unsubstituted alkyl, alkenyl, alkynyl, or heterocyclo, wherein alkyl comprises at least two carbon atoms;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_{10}$ may be $R_{10a}R_{10b}NCOO$— wherein one of $R_{10a}$ and $R_{10b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) phenyl or substituted phenyl such as nitro, alkoxy or halosubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_{10}$ substituents include $R_{10a}R_{10b}NCOO$— wherein one of $R_{10a}$ and $R_{10b}$ is hydrogen and the other is substituted or unsubstituted, preferably unsubstituted methyl, ethyl, or straight, branched or cyclic propyl. In another embodiment, preferred $R_{10}$ substituents include $R_{10a}R_{10b}NCOO$— wherein one of $R_{10a}$ and $R_{10b}$ is hydrogen and the other is substituted or unsubstituted phenyl or heterocyclo. While $R_{10a}$ and $R_{10b}$ are selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{10a}$, $R_{10b}$, and $X_3$ are selected from among these, in one embodiment $X_5$ is selected from —$COX_{10}$ wherein $X_{10}$ is phenyl, alkyl or heterocyclo, more preferably phenyl. Alternatively, while $R_{10a}$, $R_{10b}$, and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{10}$ is $R_{10a}R_{10b}NCOO$—, one of $R_{10a}$ and $R_{10b}$ is hydrogen and the other is substituted or unsubstituted substituted or unsubstituted $C_1$ to $C_8$ alkyl, phenyl or heterocyclo.

Among the preferred embodiments, therefore, are taxanes corresponding to structure 1 or 2 wherein $R_{10}$ is $R_{10a}R_{10b}NCOO$— wherein $R_{10a}$ is methyl and $R_{10b}$ is hydrido. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_{10}$ is $R_{10a}R_{10b}NCOO$— wherein $R_{10a}$ is ethyl and $R_{10b}$ is hydrido. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C10 Heterosubstituted Acetates

In one embodiment, $R_{10}$ is $R_{10a}C(O)O$— wherein $R_{10a}$ is heterosubstituted methyl, said heterosubstituted methyl moiety lacking a carbon atom which is in the beta position relative to the carbon atom of which $R_{10a}$ is a substituent. The heterosubstituted methyl is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety. Exemplary $R_{10}$ substituents include $R_{10a}COO$— wherein $R_{10a}$ is chloromethyl, hydroxymethyl, methoxymethyl, ethoxymethyl, acetoxymethyl, acyloxymethyl, or methylthiomethyl.

In one of the preferred embodiments, the taxane corresponds to structure 1, $X_5$ is —$COX_{10}$ wherein $X_{10}$ is phenyl or —$COOX_{10}$ wherein $X_{10}$ is t-butoxycarbonyl, and $R_{10}$ is $R_{10a}C(O)O$— wherein $R_{10a}$ is alkoxymethyl, preferably methoxymethyl or ethoxymethyl. In another embodiment of the present invention the taxane corresponds to structure 1, $X_5$ is —$COX_{10}$ wherein $X_{10}$ is phenyl or —$COOX_{10}$ wherein $X_{10}$ is t-butoxycarbonyl, and $R_{10}$ is $R_{10a}C(O)O$— wherein $R_{10a}$ is acyloxymethyl, preferably acetoxymethyl.

In another embodiment of the present invention, the taxane corresponds to structure 1, $X_5$ is —$COX_{10}$ wherein $X_{10}$ is phenyl or —$COOX_{10}$ wherein $X_{10}$ is t-butoxycarbonyl, $R_{10}$ is $R_{10a}C(O)O$— wherein $R_{10a}$ is alkoxymethyl such as methoxymethyl or ethoxymethyl, or aryloxymethyl such as phenoxymethyl, and $X_3$ is heterocyclo. In another embodiment of the present invention the taxane corresponds to structure 1, $X_5$ is —$COX_{10}$ wherein $X_{10}$ is phenyl or —$COOX_{10}$ wherein $X_{10}$ is t-butoxycarbonyl, and $R_{10}$ is $R_{10a}C(O)O$— wherein $R_{10a}$ is acyloxymethyl, preferably acetoxymethyl, and $X_3$ is heterocyclo.

In another embodiment, the taxanes correspond to structure (2):

(2)

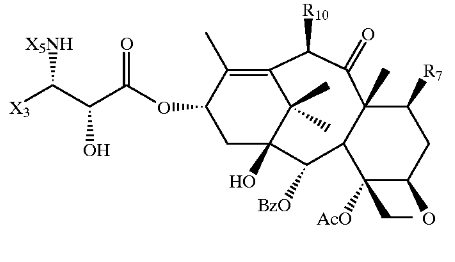

wherein $R_7$ is hydroxy;

$R_{10}$ is heterosubstituted acetate;

$X_3$ is substituted or unsubstituted alkyl, alkenyl, alkynyl, or heterocyclo, wherein alkyl comprises at least two carbon atoms;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_{10}$ is $R_{10a}COO$— wherein $R_{10a}$ is heterosubstituted methyl, more preferably heterosubstituted methyl wherein the heterosubsituents are selected from the group consisting of nitrogen, oxygen, silicon, phosphorous, boron, sulfur, or halogen atoms, still more preferably heterosubstituted methyl wherein the heterosubstituent is alkoxy or acyloxy. While $R_{10a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{10a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{10a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{10}$ is alkoxyacetyl aryloxyacetyl, or acyloxyacetyl.

C7 Carbonates

In one embodiment, $R_7$ is $R_{7a}OCOO$— wherein $R_{7a}$ is (i) substituted or unsubstituted $C_1$ to $C_8$ alkyl (straight, branched or cyclic), such as methyl, ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heterocyclo such as furyl, thienyl, or pyridyl. The substituents may be hydrocarbyl or any of the heteroatom containing substituents identified elsewhere herein for substituted hydrocarbyl. In a preferred embodiment, $R_{7a}$ is methyl, ethyl, straight, branched or cyclic propyl, straight, branched or cyclic butyl, straight, branched or cyclic hexyl, straight or branched propenyl, isobutenyl, furyl or thienyl. In another embodiment, $R_{7a}$ is substituted ethyl, substituted propyl (straight, branched or cyclic), substituted propenyl (straight or branched), substituted isobutenyl, substituted furyl or substituted thienyl wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one of the preferred embodiments, the taxanes of the present invention correspond to structure (2):

(2)

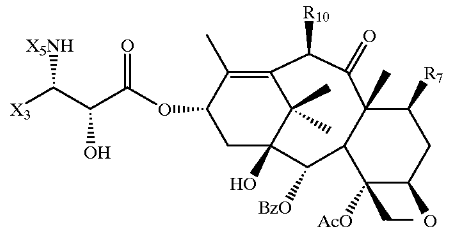

wherein $R_7$ is carbonate;

$R_{10}$ is hydroxy;

$X_3$ is substituted or unsubstituted alkyl, alkenyl, alkynyl, or heterocyclo, wherein alkyl comprises at least two carbon atoms;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_7$ may be $R_{7a}OCOO$— wherein $R_{7a}$ is substituted or unsubstituted methyl, ethyl, propyl, butyl, pentyl or hexyl, more preferably substituted or unsubstituted methyl, ethyl or propyl, still more preferably substituted or unsubstituted methyl, ethyl, and still more preferably unsubstituted methyl or ethyl. While $R_{7a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{7a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{7a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{7a}$ is unsubstituted methyl, ethyl or propyl, more preferably methyl or ethyl.

Among the preferred embodiments, therefore, are taxanes corresponding to structure 1 or 2 wherein $R_7$ is $R_{7a}OCOO$— wherein $R_{7a}$ is methyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_7$ is $R_{7a}OCOO$— wherein $R_{7a}$ is ethyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_7$ is $R_{7a}$OCOO— wherein $R_{7a}$ is propyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C7 Ester

In one embodiment, $R_7$ is $R_{7a}$COO— wherein $R_7$a is (i) substituted or unsubstituted $C_2$ to $C_8$ alkyl (straight, branched or cyclic), such as ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heteroaromatic such as furyl, thienyl, or pyridyl. The substituents may be hydrocarbyl or any of the heteroatom containing substituents identified elsewhere herein for substituted hydrocarbyl. In a preferred embodiment, $R_{7a}$ is ethyl, straight, branched or cyclic propyl, straight, branched or cyclic butyl, straight, branched or cyclic pentyl, straight, branched or cyclic hexyl, straight or branched propenyl, isobutenyl, furyl or thienyl. In another embodiment, $R_{7a}$ is substituted ethyl, substituted propyl (straight, branched or cyclic), substituted propenyl (straight or branched), substituted isobutenyl, substituted furyl or substituted thienyl wherein the substituent(s) is/are selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

In one of the preferred embodiments, the taxanes of the present invention correspond to the following structural formula (2):

(2)

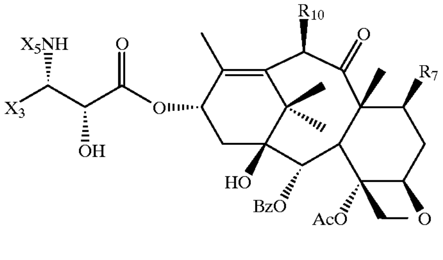

wherein $R_7$ is $R_{7a}$COO—;

$R_{10}$ is hydroxy;

$X_3$ is substituted or unsubstituted alkyl, alkenyl, alkynyl, or heterocyclo;

$X_5$ is —$COX_{10}$, —$COOX_{10}$, or —$CONHX_{10}$;

$X_{10}$ is hydrocarbyl, substituted hydrocarbyl, or heterocyclo;

$R_{7a}$ is hydrocarbyl, substituted hydrocarbyl, or heterocyclo wherein said hydrocarbyl or substituted hydrocarbyl contains carbon atoms in the alpha and beta positions relative to the carbon of which $R_a$ is a substituent;

Bz is benzoyl; and

Ac is acetyl.

For example, in this preferred embodiment in which the taxane corresponds to structure (2), $R_{7a}$ may be substituted or unsubstituted ethyl, propyl or butyl, more preferably substituted or unsubstituted ethyl or propyl, still more preferably substituted or unsubstituted ethyl, and still more preferably unsubstituted ethyl. While $R_{7a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{7a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{7a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_{7a}$ is unsubstituted ethyl or propyl, more preferably ethyl.

Among the preferred embodiments, therefore, are taxanes corresponding to structure 1 or 2 wherein $R_7$ is $R_{7a}$COO— wherein $R_{7a}$ is ethyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_7$ is $R_{7a}$COO— wherein $R_{7a}$ is propyl. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C7 Carbamates

In one embodiment, $R_7$ is $R_{7a}R_{7b}$NCOO— wherein $R_{7a}$ and $R_{7b}$ are independently hydrogen, hydrocarbyl, substituted hydrocarbyl, or heterocyclo. Exemplary preferred $R_7$ substituents include $R_{7a}R_{7b}$NCOO— wherein (a) $R_{7a}$ and $R_{7b}$ are each hydrogen, (b) one of $R_{7a}$ and $R_{7b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl, or (c) $R_{7a}$ and $R_7$b are independently (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_7$ substituents include $R_{7a}R_{7b}$NCOO— wherein one of $R_{7a}$ and $R_{7b}$ is hydrogen and the other is methyl, ethyl, or straight, branched or cyclic propyl.

In one of the preferred embodiments, the taxanes of the present invention correspond to structure (2):

(2)

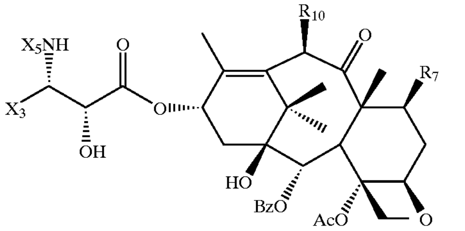

wherein $R_7$ is carbamoyloxy;

$R_{10}$ is hydroxy;

$X_3$ is substituted or unsubstituted alkyl, alkenyl, alkynyl, or heterocyclo;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_7$ may be $R_{7a}R_{7b}$NCOO— wherein one of $R_{7a}$ and $R_{7b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) phenyl or substituted phenyl such as nitro, alkoxy or halosubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_7$ substituents include $R_{7a}R_{7b}$NCOO— wherein one of $R_{7a}$ and $R_{7b}$ is hydrogen and the other is substituted or unsubstituted, preferably unsubstituted methyl, ethyl, or straight, branched or cyclic propyl. In another embodiment, preferred $R_7$ substituents include $R_{7a}R_{7b}$NCOO— wherein one of $R_{7a}$ and $R_{7b}$ is hydrogen and the other is substituted or unsubstituted phenyl or heterocyclo. While $R_{7a}$ and $R_{7b}$ are selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{7a}$, $R_{7b}$, and $X_3$ are selected from among these, in one embodiment $X_5$ is selected from —$COX_{10}$ wherein $X_{10}$ is phenyl, alkyl or heterocyclo, more preferably phenyl. Alternatively, while $R_{7a}$, $R_{7b}$, and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_7$ is $R_{7a}R_{7b}$NCOO—, one of $R_{7a}$ and $R_{7b}$ is hydrogen and the other is substituted or unsubstituted $C_1$ to $C_8$ alkyl, phenyl or heterocyclo.

Among the preferred embodiments, therefore, are taxanes corresponding to structure 1 or 2 wherein $R_7$ is $R_{7a}R_{7b}$NCOO— wherein $R_{7a}$ is methyl and $R_{7b}$ is hydrido. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

Also among the preferred embodiments are taxanes corresponding to structure 1 or 2 wherein $R_7$ is $R_{7a}R_{7b}NCOO$— wherein $R_{7a}$ is ethyl and $R_{7b}$ is hydrido. In this embodiment, $X_3$ is preferably cycloalkyl, isobutenyl, phenyl, substituted phenyl such as p-nitrophenyl, or heterocyclo, more preferably heterocyclo, still more preferably furyl, thienyl or pyridyl; and $X_5$ is preferably benzoyl, alkoxycarbonyl, or heterocyclocarbonyl, more preferably benzoyl, t-butoxycarbonyl or t-amyloxycarbonyl. In one alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is keto and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is hydroxy and $R_{14}$ is hydrido. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydroxy. In another alternative of this embodiment, $X_3$ is heterocyclo; $X_5$ is benzoyl, alkoxycarbonyl, or heterocyclocarbonyl, more preferably benzoyl, t-butoxycarbonyl or t-amyloxycarbonyl, still more preferably t-butoxycarbonyl; $R_2$ is benzoyl, $R_9$ is acyloxy and $R_{14}$ is hydrido. In each of the alternatives of this embodiment when the taxane has structure 1, $R_7$ and $R_{10}$ may each have the beta stereochemical configuration, $R_7$ and $R_{10}$ may each have the alpha stereochemical configuration, $R_7$ may have the alpha stereochemical configuration while $R_{10}$ has the beta stereochemical configuration or $R_7$ may have the beta stereochemical configuration while $R_{10}$ has the alpha stereochemical configuration.

C7 Heterosubstituted Acetates

In one embodiment, $R_7$ is $R_{7a}C(O)O$— wherein $R_{7a}$ is heterosubstituted methyl, said heterosubstituted methyl moiety lacking a carbon atom which is in the beta position relative to the carbon atom of which $R_{7a}$ is a substituent. The heterosubstituted methyl is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety. Exemplary $R_7$ substituents include $R_{7a}COO$— wherein $R_{7a}$ is chloromethyl, hydroxymethyl, methoxymethyl, ethoxymethyl, or methylthiomethyl.

In one of the preferred embodiments, the taxane corresponds to structure 1, $X_5$ is —$COX_{10}$ wherein $X_{10}$ is phenyl or —$COOX_{10}$ wherein $X_{10}$ is t-butoxycarbonyl, and $R_7$ is $R_{7a}C(O)O$— wherein $R_{7a}$ is alkoxymethyl, preferably methoxymethyl or ethoxymethyl. In another embodiment of the present invention the taxane corresponds to structure 1, $X_5$ is —$COX_{10}$ wherein $X_{10}$ is phenyl or —$COOX_{10}$ wherein $X_{10}$ is t-butoxycarbonyl, and $R_7$ is $R_{7a}C(O)O$— wherein $R_{7a}$ is acyloxymethyl, preferably acetoxymethyl.

In another embodiment of the present invention, the taxane corresponds to structure 1, $X_5$ is —$COX_{10}$ wherein $X_{10}$ is phenyl or —$COOX_{10}$ wherein $X_{10}$ is t-butoxycarbonyl, $R_7$ is $R_{7a}C(O)O$— wherein $R_{7a}$ is alkoxymethyl such as methoxymethyl or ethoxymethyl, or aryloxymethyl such as phenoxymethyl, and $X_3$ is heterocyclo. In another embodiment of the present invention the taxane corresponds to structure 1, $X_5$ is —$COX_{10}$ wherein $X_{10}$ is phenyl or —$COOX_{10}$ wherein $X_{10}$ is t-butoxycarbonyl, and $R_7$ is $R_{7a}C(O)O$— wherein $R_{7a}$ is acyloxymethyl, preferably acetoxymethyl, and $X_3$ is heterocyclo.

In one preferred embodiment, the taxanes of the present invention correspond to structure (2):

(2)

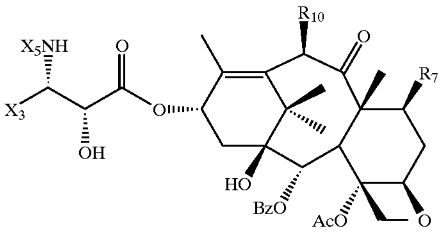

wherein $R_7$ is heterosubstituted acetate;

$R_{10}$ is hydroxy;

$X_3$ is substituted or unsubstituted alkyl, alkenyl, alkynyl, or heterocyclo;

$X_5$ is —$COX_{10}$, —$COOX_{10}$, or —$CONHX_{10}$; and $X_{10}$ is hydrocarbyl, substituted hydrocarbyl, or heterocyclo.

For example, in this preferred embodiment in which the taxane corresponds to structure (2), $R_7$ may be $R_{7a}COO$— wherein $R_{7a}$ is heterosubstituted methyl, more preferably heterosubstituted methyl wherein the heterosubsituents are selected from the group consisting of nitrogen, oxygen, silicon, phosphorous, boron, sulfur, or halogen atoms, still more preferably heterosubstituted methyl wherein the heterosubstituent is alkoxy or acyloxy. While $R_{7a}$ is selected from among these, in one embodiment $X_3$ is selected from substituted or unsubstituted alkyl, alkenyl, phenyl or heterocyclo, more preferably substituted or unsubstituted alkenyl, phenyl or heterocyclo, still more preferably substituted or unsubstituted phenyl or heterocyclo, and still more preferably heterocyclo such as furyl, thienyl or pyridyl. While $R_{7a}$ and $X_3$ are selected from among these, in one embodiment $X_5$ is selected from —$COX_{10}$ wherein $X_{10}$ is phenyl, alkyl or heterocyclo, more preferably phenyl. Alternatively, while $R_{7a}$ and $X_3$ are selected from among these, in one embodiment $X_5$ is selected from —$COX_{10}$ wherein $X_{10}$ is phenyl, alkyl or heterocyclo, more preferably phenyl, or $X_5$ is —$COOX_{10}$ wherein $X_{10}$ is alkyl, preferably t-butyl. Among the more preferred embodiments, therefore, are taxanes corresponding to structure (2) in which (i) $X_5$ is —$COOX_{10}$ wherein $X_{10}$ is tert-butyl or $X_5$ is —$COX_{10}$ wherein $X_{10}$ is phenyl, (ii) $X_3$ is substituted or unsubstituted cycloalkyl, alkenyl, phenyl or heterocyclo, more preferably substituted or unsubstituted isobutenyl, phenyl, furyl, thienyl, or pyridyl, still more preferably unsubstituted isobutenyl, furyl, thienyl or pyridyl, and (iii) $R_7$ is alkoxyacetyl or acyloxyacetyl.

Taxanes having the general formula 1 may be obtained by treatment of a β-lactam with an alkoxide having the taxane tetracyclic nucleus and a C-13 metallic oxide substituent to form compounds having a β-amido ester substituent at C(13), as described more fully in Holton U.S. Pat. No. 5,466,834, followed by removal of the hydroxy protecting groups.

Taxanes having C(10) carbonates may be prepared from 10-deacetylbaccatin III by selective formation of a carbonate of the C-10 hydroxyl group and then protection of the C-7 hydroxyl group (as described more fully in Holton et al., PCT Patent Application WO 99/09021, followed by treatment with a metallic amide. Acylating agents which may be used for the selective acylation of the C(10) hydroxyl group of a taxane include dimethyldicarbonate, diethyldicarbonate, di-t-butyldicarbonate, dibenzyldicarbonate and the like. While the acylation of the C(10) hydroxy group of the taxane will proceed at an adequate rate for many acylating agents, it has been discovered that the reaction rate may be increased by including a Lewis acid in the reaction mixture. Preferred Lewis acids include zinc chloride, stannic chloride, cerium trichloride, cuprous chloride, lanthanum trichloride, dysprosium trichloride, and ytterbium trichloride. Zinc chloride or cerium trichloride is particularly preferred when the acylating agent is a dicarbonate.

Taxanes having C(10) esters may be prepared from 10-deacetylbaccatin III (or a derivative thereof) by selective protection of the C(7) hydroxyl group and then esterification of the C(10) hydroxyl group followed by treatment with a metallic amide. The C(7) hydroxyl group of 10-deacetylbaccatin III, for example, may be selectively protected with a silyl group as described, for example, by Denis, et. al. (*J. Am. Chem. Soc.,* 1988, 110, 5917). In general, the silylating agents may be used either alone or in combination with a catalytic amount of a base such as an alkali metal base.

Taxanes having C(10) carbamates may be prepared from 10-deacetylbaccatin III by protecting the C-7 and C-10 hydroxyl groups of a taxane (as described more fully in Holton et al., PCT Patent Application WO 99/09021), coupling the protected alkoxide with the β-lactam, selectively removing the C(7) and C(10) hydroxy protecting groups, and treating this product with an isocyanate in the presence of a Lewis acid.

Taxanes having C(7) carbonates may be prepared from 10-deacetylbaccatin III (or a derivative thereof) by selective protection of the C-10 hydroxyl group and then acylation of the C-7 hydroxyl group followed by treatment with a metallic amide. The C(10) hydroxyl group of 10-deacetylbaccatin III is then selectively protected with a silyl group using, for example, a silylamide or bissilyamide as a silylating agent. Selective acylation of the C(7) hydroxyl group of a C(10) protected taxane to form a C(7) carbonate can be achieved using any of a variety of common acylating agents such as a haloformates.

Taxanes having C(7) carbamates may be obtained by treatment of a β-lactam with an alkoxide having the taxane tetracyclic nucleus and a C-13 metallic oxide substituent to form compounds having a β-amido ester substituent at C(1 3), as described more fully in Holton U.S. Pat. No. 5,466,834, followed by reaction with an isocyanate or a carbamoyl chloride, and removal of the hydroxy protecting groups.

Taxanes having C(7) esters may be prepared from 10-deacetylbaccatin III (or a derivative thereof) by selective protection of the C-10 hydroxyl group and then esterification of the C-7 hydroxyl group followed by treatment with a metallic amide. The C(10) hydroxyl group of 10-deacetylbaccatin III may be selectively protected with a silyl group using, for example, a silylamide or bissilyamide as a silylating agent. Selective esterification of the C(7) hydroxyl group of a C(10) protected taxane can be achieved using any of a variety of common acylating agents including, but not limited to, substituted and unsubstituted carboxylic acid derivatives, e.g., carboxylic acid halides, anhydrides, dicarbonates, isocyanates and haloformates.

Derivatives of 10-deacetylbaccatin III having alternative substituents at C(2), C(9) and C(14) and processes for their preparation are known in the art. Taxane derivatives having acyloxy substituents other than benzoyloxy at C(2) may be prepared, for example, as described in Holton et al., U.S. Pat. No. 5,728,725 or Kingston et al., U.S. Pat. No. 6,002, 023. Taxanes having acyloxy or hydroxy substituents at C(9) in place of keto may be prepared, for example as described in Holton et al., U.S. Pat. No. 6,011,056 or Gunawardana et al., U.S. Pat. No. 5,352,806. Taxanes having a beta hydroxy substituent at C(14) may be prepared from naturally occurring 14-hydroxy-10-deacetylbaccatin III.

Processes for the preparation and resolution of the β-lactam starting material are generally well known. For example, the β-lactam may be prepared as described in Holton, U.S. Pat. No. 5,430,160 and the resulting enatiomeric mixtures of β-lactams may be resolved by a stereoselective hydrolysis using a lipase or enzyme as described, for example, in Patel, U.S. Pat. No. 5,879,929 Patel U.S. Pat. No. 5,567,614 or a liver homogenate as described, for example, in PCT Patent Application No. 00/41204.

Compounds of formula 1 of the instant invention are useful for inhibiting tumor growth in mammals including humans and are preferably administered in the form of a pharmaceutical composition comprising an effective antitumor amount of a compound of the instant invention in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the antitumor compounds. The carrier is "pharmaceutically or pharmacologically acceptable" if it does not produce an adverse, allergic or other untoward reaction when administered to a mammal or human, as appropriate.

The pharmaceutical compositions containing the antitumor compounds of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular antitumor compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp. 1492–1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The compositions of the invention for oral administration comprise an effective antitumor amount of a compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The antitumor compounds of the present invention are also preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective antitumor amount of the antitumor compound in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2–30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N, N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or triglycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly $(ethoxylated)_{30-60}$ sorbitol $poly(oleate)_{2-4}$, poly $(oxyethylene)_{15-20}$ monooleate, $poly(oxyethylene)_{15-20}$ mono 12-hydroxystearate, and $poly(oxyethylene)_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$–$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2–30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3–30 carbon atoms (e.g., acetone, methyl ethyl ketone, methyl isobutyl ketone); aliphatic, cycloaliphatic or aromatic hydrocarbons having 4–30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1–30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients,* (American Pharmaceutical Association, Washington, D.C., and The Pharmaceutical Society of Great Britain, London, England, 1968), *Modern Pharmaceutics,* (G. Banker et al., eds., 3d ed.)(Marcel Dekker, Inc., New York, N.Y., 1995), *The Pharmacological Basis of Therapeutics,* (Goodman & Gilman, McGraw Hill Publishing), *Pharmaceutical Dosage Forms,* (H. Lieberman et al., eds., )(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No.10, pp. 917–927 (1963).

Preferred solvents include those known to stabilize the antitumor compounds, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglycerides include Intralipid® emulsified soybean oil (Kabi-Pharmacia Inc., Stockholm, Sweden), Nutralipid ® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn(® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the antitumor compound to form solutions, emulsions, and the like.

Additional minor components can be included in the compositions of the invention for a variety of purposes well known in the pharmaceutical industry. These components will for the most part impart properties which enhance retention of the antitumor compound at the site of administration, protect the stability of the composition, control the pH, facilitate processing of the antitumor compound into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the taxane, surface active, wetting or emulsifying agents (e.g., lecithin, polysorbate-80, Tween® 80, pluronic 60, polyoxyethylene stearate ), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

In a preferred embodiment, a pharmaceutical composition of the invention comprises at least one nonaqueous, pharmaceutically acceptable solvent and an antitumor compound having a solubility in ethanol of at least about 100, 200, 300, 400, 500, 600, 700 or 800 mg/ml. While not being bound to a particular theory, it is believed that the ethanol solubility of the antitumor compound may be directly related to its efficacy. The antitumor compound can also be capable of being crystallized from a solution. In other words, a crystalline antitumor compound, such as compound 1393, can be dissolved in a solvent to form a solution and then recrystallized upon evaporation of the solvent without the formation of any amorphous antitumor compound. It is also preferred that the antitumor compound have an ID50 value (i.e, the drug concentration producing 50% inhibition of colony formation) of at least 4, 5, 6, 7, 8, 9, or 10 times less that of paclitaxel when measured according to the protocol set forth in the working examples.

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the invention can be readily determined by those with ordinary skill in treating cancer. It is understood that the dosage of the antitumor compounds will be dependent upon the age, sex, health, and weight of the recipient, kind of concurrent treatment, if any, frequency of treatment, and the nature of the effect desired. For any mode of administration, the actual amount of antitumor compound delivered, as well as the dosing schedule necessary to achieve the advantageous effects described herein, will also depend, in part, on such factors as the bioavailability of the antitumor compound, the disorder being treated, the desired therapeutic dose, and other factors that will be apparent to those of skill in the art. The dose administered to an animal, particularly a human, in the context of the present invention should be sufficient to effect the desired therapeutic response in the animal over a reasonable period of time. Preferably, an effective amount of the antitumor compound, whether administered orally or by another route, is any amount which would result in a desired therapeutic response when administered by that route. Preferably, the compositions for oral administration are prepared in such a way that a single dose in one or more oral preparations contains at least 20 mg of the antitumor compound per $m^2$ of patient body surface area, or at least 50, 100, 150, 200, 300, 400, or 500 mg of the antitumor compound per $m^2$ of patient body surface area, wherein the average body surface area for a human is 1.8 $m^2$. Preferably, a single dose of a composition for oral administration contains from about 20 to about 600 mg of the antitumor compound per $m^2$ of patient body surface area, more preferably from about 25 to about 400 $mg/m^2$ even more preferably, from about 40 to about 300 $mg/m^2$, and even more preferably from about 50 to about 200 $mg/m^2$. Preferably, the compositions for parenteral administration are prepared in such a way that a single dose contains at least 20 mg of the antitumor compound per $m^2$ of patient body surface area, or at least 40, 50, 100, 150, 200, 300, 400, or 500 mg of the antitumor compound per $m^2$ of patient body surface area. Preferably, a single dose in one or more parenteral preparations contains from about 20 to about 500 mg of the antitumor compound per $m^2$ of patient body surface area, more preferably from about 40 to about 400 $mg/m^2$ and even more preferably, from about 60 to about 350 $mg/m^2$. However, the dosage may vary depending on the dosing schedule which can be adjusted as necessary to achieve the desired therapeutic effect. It should be noted that the ranges of effective doses provided herein are not intended to limit the invention and represent preferred dose ranges. The most preferred dosage will be tailored to the individual subject, as is understood and determinable by one of ordinary skill in the art without undue experimentation.

The concentration of the antitumor compound in a liquid pharmaceutical composition is preferably between about 0.01 mg and about 10 mg per ml of the composition, more preferably between about 0.1 mg and about 7 mg per ml, even more preferably between about 0.5 mg and about 5 mg per ml, and most preferably between about 1.5 mg and about 4 mg per ml. Relatively low concentrations are generally preferred because the antitumor compound is most soluble in the solution at low concentrations. The concentration of the antitumor compound in a solid pharmaceutical composition for oral administration is preferably between about 5 weight % and about 50 weight %, based on the total weight of the composition, more preferably between about 8 weight % and about 40 weight %, and most preferably between about 10 weight % and about 30 weight %.

In one embodiment, solutions for oral administration are prepared by dissolving an antitumor compound in any pharmaceutically acceptable solvent capable of dissolving the compound (e.g., ethanol or methylene chloride) to form a solution. An appropriate volume of a carrier which is a solution, such as Cremophor® EL solution, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving an antitumor compound in any pharmaceutically acceptable solvent capable of dissolving the compound (e.g.,ethanol or methylene chloride) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving an antitumor compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsion, is added to the solution while stirring to form a pharmaceutically acceptable emulsion for parenteral administration to a patient. If desired, such emulsions can be formulated to contain a minimal amount of, or to be free of, ethanol or Cremophor® solution, which are known in the art to cause adverse physiological effects when administered at certain concentrations in parenteral formulations.

Solutions for parenteral administration can be prepared by dissolving an antitumor compound in any pharmaceutically acceptable solvent capable of dissolving the compound (e.g., ethanol or methylene chloride) to form a solution. An appropriate volume of a carrier which is a solution, such as Cremophor® solution, is added to the solution while stirring to form a pharmaceutically acceptable solution for parenteral administration to a patient. If desired, such solutions can be formulated to contain a minimal amount of, or to be free of, ethanol or Cremophor® solution, which are known in the art to cause adverse physiological effects when administered at certain concentrations in parenteral formulations.

If desired, the emulsions or solutions described above for oral or parenteral administration can be packaged in IV bags, vials or other conventional containers in concentrated form and diluted with any pharmaceutically acceptable liquid, such as saline, to form an acceptable taxane concentration prior to use as is known in the art.

Definitions The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

The "heterosubstituted methyl" moieties described herein are methyl groups in which the carbon atom is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety.

The "heterosubstituted acetate" moieties described herein are acetate groups in which the carbon of the methyl group is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkoxycarbonyloxy moieties described herein comprise lower hydrocarbon or substituted hydrocarbon or substituted hydrocarbon moieties.

Unless otherwise indicated, the carbamoyloxy moieties described herein are derivatives of carbamic acid in which one or both of the amine hydrogens is optionally replaced by a hydrocarbyl, substituted hydrocarbyl or heterocyclo moiety.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, benzyloxymethyl, (.beta.-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

As used herein, "Ac" means acetyl; "Bz" means benzoyl; "Et" means ethyl; "Me" means methyl; "Ph" means phenyl; "Pr" means propyl; "iPr" means isopropyl; "Bu" means butyl; "Am" means amyl; "Cpro" means cyclopropyl; "tBu"

and “t-Bu” means tert-butyl; “R” means lower alkyl unless otherwise defined; “Py” means pyridine or pyridyl; “TES” means triethylsilyl; “TMS” means trimethylsilyl; “LAH” means lithium aluminum hydride; “10-DAB” means 10-desacetylbaccatin III”; “amine protecting group” includes, but is not limited to, carbamates, for example, 2,2,2-trichloroethylcarbamate or tertbutylcarbamate; “protected hydroxy” means —OP wherein P is a hydroxy protecting group; “PhCO” means phenylcarbonyl; “tBuOCO” and “Boc” mean tert-butoxycarbonyl; “tAmOCO” means tert-amyloxycarbonyl; “2-FuCO” means 2-furylcarbonyl; “2-ThCO” means 2-thienylcarbonyl; “2-PyCO” means 2-pyridylcarbonyl; “3-PyCO” means 3-pyridylcarbonyl; “4-PyCO” means 4-pyridylcarbonyl; “$C_4H_7CO$” means butenylcarbonyl; “$tC_3H_5CO$” means trans-propenylcarbonyl; “EtOCO” means ethoxycarbonyl; “ibueCO” means isobutenylcarbonyl; “iBuCO” means isobutylcarbonyl; “iBuOCO” means isobutoxycarbonyl; “iPrOCO” means isopropyloxycarbonyl; “nPrOCO” means n-propyloxycarbonyl; “nPrCO” means n-propylcarbonyl; “ibue” means isobutenyl; “THF” means tetrahydrofuran; “DMAP” means 4-dimethylamino pyridine; “LHMDS” means Lithium HexamethylDiSilazanide.

The term “storage stable composition” as used herein is a composition which, after storage at room temperature for one year and dilution prior to use, is suitable for administration to a patient and is cytotoxically active.

The following examples illustrate the invention.

EXAMPLE 1

Preparation of Taxane having C-7 Ester and C-10 Hydroxy Substituents

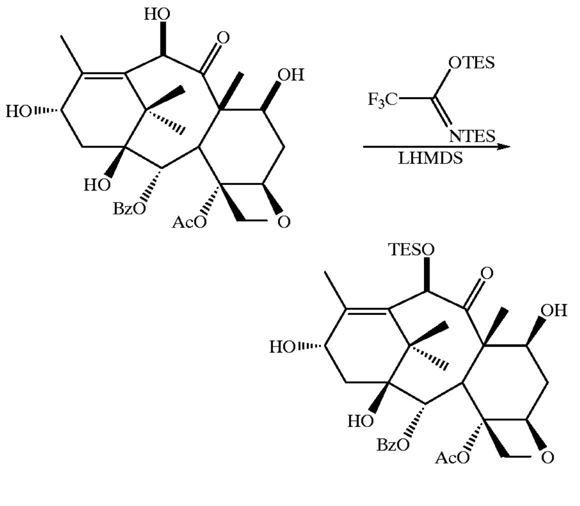

10-Triethylsilyl-10-deacetyl baccatin III.

To a solution of 1.0 g (1.84 mmol) of 10-deacetyl baccatin III in 50 mL of THF at −10° C. under a nitrogen atmosphere was added 0.857 mL (2.76 mmol, 1.5 mol equiv) of N,O-(bis)-TES-trifluoroacetamide over a period of 3 min. This was followed by the addition of 0.062 mL of a 0.89 M THF solution of lithium bis(trimethylsilyl)amide (0.055 mmol, 0.03 mol equiv). After 10 min 0.038 mL (0.92 mmol, 0.5 mol equiv) of methanol was added, and after an additional 5 min 4 mL (0.055 mmol, 0.03 mol equiv) of acetic acid was added. The solution was diluted with 300 mL of ethyl acetate and washed two times with 100 mL of saturated aqueous sodium bicarbonate solution. The combined aqueous layers were extracted with 100 mL of ethyl acetate and the combined organic layers were washed with brine, dried over sodium sulfate, and concentrated under reduced pressure. To the residue was added 100 mL of hexane and the solid (1.23 g, 101%) was collected by filtration. Recrystallization of the solid by dissolving in boiling ethyl acetate (20 mL, 17 mL/g) and cooling to room temperature gave 1.132 g (94%) of a white solid. m.p. 242° C.; $[\alpha]_D^{25}$ −60.4 (c 0.7, $CHCl_3$); $^1H$ NMR ($CDCl_3$, 400 MHz) δ (p.p.m): 8.10 (2H, d, Jm=7.5 Hz, Bzo), 7.60 (1H, t, Jm=7.5 Hz, Bzp), 7.47 (2H, t, Jo=7.5 Hz, Bzm), 5.64 (1H, d, J3=6.9 Hz, H2), 5.26 (1H, s, H10), 4.97 (1H, dd, J6β=2.2 Hz, J6α=9.9 Hz, H5), 4.85 (1H, dd, J14α=8.9 Hz, J14β=8.9 Hz, H13), 4.30 (1H, d, J20β=8.5 Hz, H20α), 4.23 (1H, ddd, J7OH=4.5 Hz, J6α=6.6 Hz, J6β=11.0 Hz, H7), 4.15 (1H, d, J20α=8.5 Hz, H20β), 4.00 (1H, d, J2=6.9 Hz, H3), 2.58 (1H, ddd, J7=6.6 Hz, J5=9.9 Hz, J6β=14.5 Hz, H6α), 2.28–2.25 (5H, m, 4 Ac, H14α, H14β), 2.02 (3H, s, 18 Me), 1.97 (1H, d, J7=4.5 Hz, H7OH), 1.78 (1H, ddd, J7=11.0 Hz, J5=2.2 Hz, J6α=14.5 Hz, H6β), 1.68 (3H, s, 19 Me), 1.56 (1H, S, OH1), 1.32 (1H, d, J13=8.8 Hz, OH13 ), 1.18 (3H, s, 17 Me), 1.06 (3H, s, 16 Me), 0.98 (9H, t, $JCH_2$(TES)=7.3 Hz, $CH_3$(TES)), 0.65 (6H, dq, $JCH_3$ (TES)=7.3 Hz, $CH_2$(TES)).

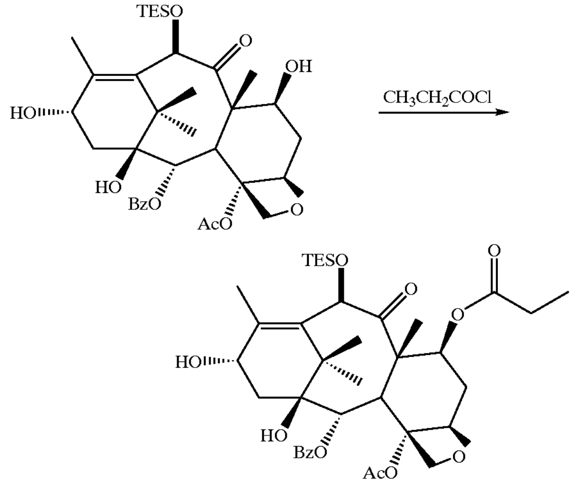

10-Triethylsilyl-10-deacetyl-7-propionyl baccatin III.

To a solution of 1.0 g (1.517 mmol) of 10-triethylsilyl-10-deacetyl baccatin III and 37.0 mg (0.303 mmol) of DMAP in 20 mL of dichloromethane at room temperature under a nitrogen atmosphere was added 0.920 mL (11.381 mmol) of pyridine and 0.329 mL (3.794 mmol, 2.5 mol equiv) of propionyl chloride in that order. The mixture was stirred at room temperature for 6 h, diluted with 350 mL of ethyl acetate and extracted with 50 mL of 10% aqueous copper sulfate solution. The organic layer was washed with 50 mL of saturated aqueous sodium bicarbonate solution, 50 mL of brine, dried over sodium sulfate and concentrated under reduced pressure. The crude product was dissolved in 75 mL of ethyl acetate, 100 mg of Norit A was added, the mixture was filtered through celite and concentrated under reduced pressure to give 1.13 g of material. Recrystallization from ethyl acetate/hexanes (dissolved in 6.5 mL of refluxing ethyl acetate, then 24 mL of hexanes added, allowed to cool to room temperature, and left to stand for 17 h) afforded 787 mg (72.5%) of a white crystalline solid. A second recrystallization (ca 340 mg material dissolved in 2 mL of refluxing ethyl acetate, then 10 mL of hexanes added, allowed to cool to room temperature, and allowed to stand for 17 h) afforded 181 mg (16.7%) of a white crystalline solid. The combined yield after recrystallization was 89.2%. m.p. 129°

C.; $[\alpha]_D^{25}$ −47.9 (c 1.0, $CHCl_3$); NMR $^1H$ ($CDCl_3$, 300 MHz) δ (ppm): 8.10 (2H, d, Jm=7.4 Hz, Bzo), 7.60 (1H, t, Jm=7.4 Hz, Bzp), 7.48 (2H, dd, Jo=7.4 Hz, Jp=7.4 Hz, Bzm), 5.64 (1H, d, J3=7.4 Hz, H2), 5.47 (1H, dd, J6α=7.4 Hz, J6β=10.1 Hz, H7), 5.28 (1H, s, H10), 4.94 (1H, d, J6α=9.4 Hz, H5), 4.80–4.90 (1H, m, H13), 4.31 (1H, d, J20β=8.1 Hz, H20α), 4.16 (1H, d, J20α=8.1 Hz, H20β), 4.06 (1H, d, J2=7.4 Hz, H3), 2.55 (1H, ddd, J7=7.4 Hz, J5 =9.4 Hz, J6β=14.8 Hz, H6α), 2.28 (3H, s, 4 Ac), 2.23–2.32 (4H, m, 7CH2, H14α, H14β), 2.07 (3H, s, 18 Me), 2.02 (1H, d, J13=4.7 Hz, OH13), 1.76–1.87 (4H, m, H6β, 19 Me), 1.60 (1H, s, OH1), 1.17 (3H, s, 17 Me), 1.09 (3H, t, $J7CH_2$=7.4 Hz, $7CH_3$), 1.04 (3H, s, 16 Me), 0.96 (9H, t, $JCH_2$(TES)=8.0 Hz, $CH_3$(TES)), 0.52–0.62 (6H, m, $CH_2$(TES)).

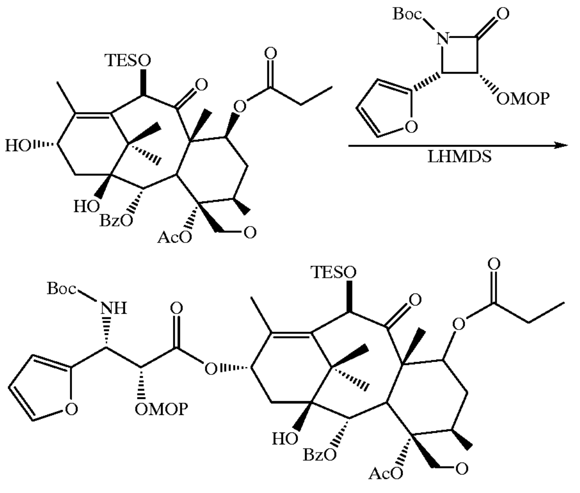

2'-O-MOP-3'-desphenyl-3'-(2-furyl)-10-triethylsilyl-7-propionyl taxotere.

To a solution of 493 mg (0.690 mmol) of 10-triethylsilyl-10-deacetyl-7-propionyl baccatin III in 4 mL of anhydrous THF under a nitrogen atmosphere at −45 ° C. was added 0.72 mL (0.72 mmol) of a 1M solution of LiHMDS in THF. After 0.5 h a solution of 263 mg (0.814 mmol) of the b-Lactam (predried as described above) in 2 mL of anhydrous THF was added. The mixture was warmed to 0° C., and after 2 h 0.5 mL of saturated aqueous sodium bicarbonate solution was added. The mixture was diluted with 50 ml of ethyl acetate and washed two times with 5 mL of brine. The organic phase was dried over sodium sulfate and concentrated under reduced pressure to give 742 mg (104%) of a slightly yellow solid. The solid was recrystallized by dissolving it in 12 mL of a 1:5 mixture of ethyl acetate and hexane at reflux and then cooling to room temperature to give 627 mg (88%) of a white crystalline solid. Evaporation of the mother liquor gave 96 mg of material which was recrystallized as above from 2 mL of a 1:5 mixture of ethyl acetate and hexane to give an additional 46 mg (6%) of white crystalline solid. The total yield from recrystallization was 94%. Evaporation of the mother liquor gave 46 mg of material which was purified by column chromatography on silica gel to give an additional 20 mg (3%) of product. m.p. 207–209° C.; $[a]_D^{25}$ −30.0 (c 5.0, methanol); $^1H$ NMR ($CDCl_3$, 400 MHz) d (ppm): 8.09–8.11 (m, 2H), 7.58–7.61 (m, 1H), 7.47–7.51 (m, 2H), 7.39 (d, J=0.8 Hz, 1H), 6.34 (dd, J=3.2, 1.6 Hz, 1H), 6.26 (d, J=3.2 Hz), 6.14 (dd, J=8.8, 8.8 Hz, 1H), 5.71 (d, J=6.8 Hz, 1H), 5.47 (dd, J=10.0, 7.2 Hz, 1H), 5.30–5.36 (m, 2H), 5.28 (s, 1H), 4.95 (d, J=7.6 Hz, 1H), 4.76 (s, 1H), 4.33 (d, J=8.0 Hz, 1H), 4,19 (d, J=8.4 Hz, 1H), 4.03 (d, J=6.8 Hz, 1H), 2.83 (s, 3H), 2.55 (ddd, J=17.2, 9.6, 7.6, 1H), 2.50 (s, 3H), 2.20–2.40 (m, 2H), 2.28 (q, J=7.6 Hz, 2H), 1.95 (s, 3H), 1.84 (ddd, J=14.8, 10.8, 2 Hz), 1.80 (s, 3H), 1.67 (s, 1H), 1.39 (s, 9H), 1.32 (s, 3H), 1.21 (s, 3H), 1.20 (s, 3H), 1.74 (s, 3H), 1.09 (t, J=7.6 Hz, 3H), 0.93–0.99 (m, 9H), 0.50–0.65 (m, 6H).

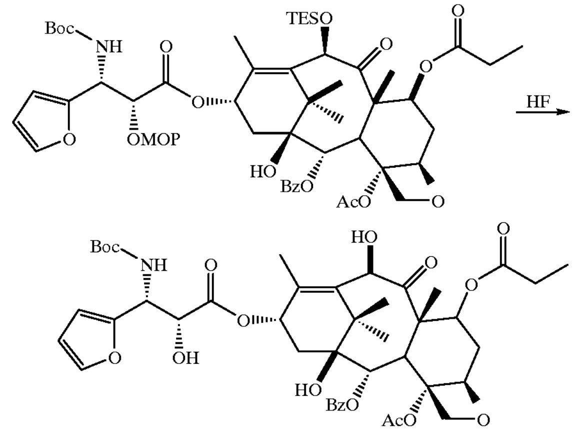

3'-Desphenyl-3'-(2-furyl)-7-propionyl taxotere. (1393)

To a solution of 206 mg (0.199 mmol) of 2'-O-MOP-3'-desphenyl-3'-(2-furyl)-10-triethylsilyl-7-propionyl taxotere in 1.7 mL of pyridine and 5.4 mL of acetonitrile at 0° C. was added 0.80 mL (2.0 mmol) of an aqueous solution containing 49% HF. The mixture was warmed to room temperature for 14 h and was then diluted with 20 mL of ethyl acetate and washed three times with 2 mL of saturated aqueous sodium bicarbonate and then with 8 mL of brine. The organic phase was dried over sodium sulfate and concentrated under reduced pressure to give 170 mg (100%) of a white solid. The crude product was crystallized with 2 mL of solvent ($CH_2Cl_2$:hexane=1:1.7) to give 155 mg (90.5%) of white crystals. Concentration of the mother liquor under reduced pressure gave 15 mg of material which was recrystallized using 0.2 mL of a 1:1.7 mixture of methylene chloride and hexane to give an additional 11 mg (7.5%) of white crystals. The total yield from recrystallization was 98%. m.p. 150–152° C.; $[a]_D^{25}$ −27.0 (c 5.0, methanol); Anal. Calcd for $C_{44}H_{55}NO_{16}$●$0.5H_2O$: C, 61.18; H, 6.48. Found: C, 61.40; H, 6.65. $^1H$ NMR ($CDCl_3$, 500 MHz) d (ppm): 8.11 (d, J=7.5 Hz, 2H), 7.61 (dd, J=7.5, 7.5 Hz, 1H), 7.50 (dd, J=8.0, 7.5 Hz 2H), 7.41 (d, J=1.0 Hz, 1H), 6.38 (dd, J=3.0, 2.0 Hz, 1H), 6.33 (d, J=3.5 Hz), 6.22 (dd, J=9.5, 9.5 Hz, 1H), 5.69 (d, J=7.0 Hz, 1H), 5.49 (dd, J=11.0, 7.5 Hz, 1 H), 5.35 (d, J=9.5 Hz, 1 H), 5.33 (d, J=1.5 Hz, 1H), 5.25 (d, J=9.5 Hz, 1H), 4.94 (d, J=8.5 Hz, 1H), 4.71 (dd, J=5.5, 2.0 Hz, 1H), 4.33 (d, J=8.5 Hz, 1H), 4,21 (d, J=8.5 Hz, 1H), 4.01 (d, J=6.5 Hz, 1H), 3.97 (d, J=1.5 Hz, 1 H), 3.30 (d, J=5.5 Hz, 1 H), 2.54 (ddd, J=16.5, 9.5, 7.0, 1H), 2.41 (s, 3H), 2.37 (dd, J=15.0, 9.0 Hz, 1H), 2.30 (dd, J=17.5, 9.5 Hz, 1H), 2.25 (q, J=7.5 Hz, 2H), 1.96 (s, 3H), 1.93 (ddd, J=14.5, 11.0, 2.5 Hz), 1.85 (s, 3H), 1.64 (s, 1H), 1.36 (s, 9H), 1.23 (s, 3H), 1.10 (t, J=7.5 Hz, 3H).

EXAMPLE 2

Additional Taxanes having C-7 Ester and C-10 Hydroxy Substituents

The procedures described in Example 1 were repeated, but other suitably protected β-lactams were substituted for the β-lactam of Example 1 to prepare the series of compounds having structural formula (3) and the combinations of substituents identified in the following table.

(3)

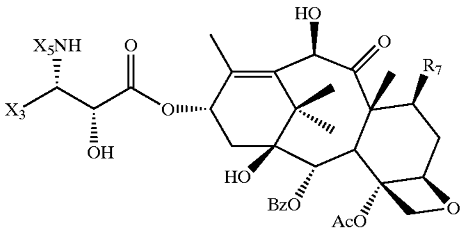

| Compound | $X_5$ | $X_3$ | $R_7$ |
|---|---|---|---|
| 1351 | tBuOCO— | ibue | EtCOO— |
| 1364 | tBuOCO— | 2-pyridyl | EtCOO— |
| 1372 | tBuOCO— | 3-pyridyl | EtCOO— |
| 1386 | tBuOCO— | 4-pyridyl | EtCOO— |
| 1393 | tBuOCO— | 2-furyl | EtCOO— |
| 1401 | tBuOCO— | 3-furyl | EtCOO— |
| 1481 | tBuOCO— | 2-thienyl | EtCOO— |
| 1424 | tBuOCO— | 3-thienyl | EtCOO— |
| 1434 | tBuOCO— | isopropyl | EtCOO— |
| 1447 | tBuOCO— | cyclobutyl | EtCOO— |
| 1458 | tBuOCO— | phenyl | EtCOO— |
| 3069 | 2-FuCO— | 2-thienyl | EtCOO— |
| 3082 | iPrOCO— | 2-thienyl | EtCOO— |
| 3171 | nPrCO— | 2-furyl | EtCOO— |
| 3196 | iBuOCO— | 2-furyl | EtCOO— |
| 3232 | iBuOCO— | 2-thienyl | EtCOO— |
| 3327 | nPrCO— | 2-thienyl | EtCOO— |
| 3388 | PhCO— | 3-thienyl | EtCOO— |
| 3444 | iPrOCO— | 2-furyl | EtCOO— |
| 3479 | 2-ThCO— | 2-thienyl | EtCOO— |
| 3555 | $C_4H_7CO$— | 2-thienyl | EtCOO— |
| 3560 | $tC_3H_5CO$— | 2-thienyl | EtCOO— |
| 3611 | EtOCO— | 2-furyl | EtCOO— |
| 3629 | 2-FuCO— | 2-furyl | EtCOO— |
| 3632 | 2-ThCO— | 2-furyl | EtCOO— |
| 3708 | $tC_3H_5CO$— | 2-furyl | EtCOO— |
| 3713 | $C_4H_7CO$— | 2-furyl | EtCOO— |
| 4017 | PhCO— | 2-furyl | EtCOO— |
| 4044 | EtOCO— | 2-thienyl | EtCOO— |
| 4106 | 3-PyCO— | 2-thienyl | EtCOO— |
| 4135 | iPrOCO— | 2-thienyl | PrCOO— |
| 4175 | PhCO— | 2-thienyl | PrCOO— |
| 4219 | 2-FuCO— | 2-thienyl | PrCOO— |
| 4256 | tBuOCO— | 2-thienyl | PrCOO— |
| 4283 | ibueCO— | 2-thienyl | PrCOO— |
| 4290 | ibuOCO— | 2-thienyl | PrCOO— |
| 4312 | ibueCO— | 2-thienyl | PrCOO— |
| 4388 | 2-ThCO— | 2-thienyl | PrCOO— |
| 4394 | tBuOCO— | 3-furyl | PrCOO— |
| 4406 | tBuOCO— | isobutenyl | PrCOO— |
| 4446 | tBuOCO— | 3-thienyl | PrCOO— |
| 4499 | tBuOCO— | 2-furyl | PrCOO— |
| 4544 | iBuOCO— | 3-thienyl | EtCOO— |
| 4600 | iBuOCO— | 3-thienyl | PrCOO— |
| 4616 | iBuOCO— | 2-furyl | PrCOO— |
| 4737 | $tC_3H_5CO$— | 2-furyl | PrCOO— |
| 4757 | $tC_3H_5CO$— | 2-thienyl | PrCOO— |
| 6171 | ibueOCO— | 2-furyl | EtCOO— |
| 6131 | ibueOCO— | 2-furyl | iBuCOO— |
| 5989 | ibueOCO— | 2-furyl | iPrCOO— |
| 6141 | ibueOCO— | 2-furyl | nBuCOO— |
| 6181 | ibueOCO— | 2-furyl | nPrCOO— |
| 6040 | ibuOCO— | 2-furyl | ibueCOO— |
| 6121 | iPrCO— | 2-furyl | iPrCOO— |
| 6424 | tAmOCO— | 2-furyl | EtCOO— |
| 6212 | tAmOCO— | 2-furyl | EtCOO— |
| 6282 | tAmOCO— | 2-furyl | iBuCOO— |
| 6252 | tAmOCO— | 2-furyl | iPrCOO— |
| 6343 | tAmOCO— | 2-furyl | nBuCOO— |
| 6272 | tAmOCO— | 2-furyl | nPrCOO— |
| 6202 | $tC_3H_5CO$— | 2-furyl | iPrCOO— |
| 4454 | 2-ThCO— | 2-thienyl | nPrCOO— |

-continued (3)

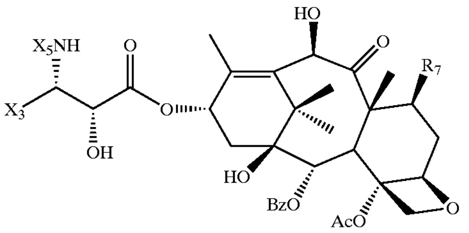

| Compound | $X_5$ | $X_3$ | $R_7$ |
|---|---|---|---|
| 4414 | PhCO— | 2-thienyl | nPrCOO— |
| 6333 | tBuOCO— | 2-thienyl | iPrCOO— |
| 6686 | tBuOCO— | 2-thienyl | $tC_3H_5COO$— |
| 6363 | tBuOCO— | 2-thiazo | EtCOO— |
| 4787 | iBuOCO— | 3-furyl | EtCOO— |
| 4828 | iBuOCO— | 3-furyl | nPrCOO— |
| 4898 | $tC_3H_5CO$— | 3-furyl | EtCOO— |
| 4939 | $tC_3H_5CO$— | 3-furyl | nPrCOO— |
| 5020 | $tC_3H_5CO$— | 3-thienyl | EtCOO— |
| 5030 | $tC_3H_5CO$— | 3-thienyl | nPrCOO— |
| 5191 | iBuOCO— | cpro | EtCOO— |
| 5202 | iBuOCO— | cpro | nPrCOO— |
| 5070 | tButOCO— | cpro | EtCOO— |
| 5080 | tBuOCO— | cpro | nPrCOO— |
| 5121 | iBuOCO— | ibue | EtCOO— |
| 5131 | iBuOCO— | ibue | nPrCOO— |

EXAMPLE 3

Additional Taxanes having C-7 Ester and C-10 Hydroxy Substituents

Following the processes described in Example 1 and elsewhere herein, the following specific taxanes having structural formula (4) may be prepared, wherein $R_7$ is as previously defined, including wherein $R_7$ is $R_aCOO$— and $R_a$ is (i) substituted or unsubstituted $C_2$ to $C_8$ alkyl (straight, branched or cyclic), such as ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heterocyclo such as furyl, thienyl, or pyridyl. The substituents may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(4)

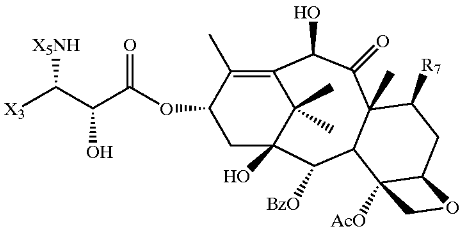

| $X_5$ | $X_3$ | $R_7$ |
|---|---|---|
| tBuOCO— | 2-furyl | $R_a$COO— |
| tBuOCO— | 3-furyl | $R_a$COO— |
| tBuOCO— | 2-thienyl | $R_a$COO— |
| tBuOCO— | 3-thienyl | $R_a$COO— |
| tBuOCO— | 2-pyridyl | $R_a$COO— |
| tBuOCO— | 3-pyridyl | $R_a$COO— |
| tBuOCO— | 4-pyridyl | $R_a$COO— |
| tBuOCO— | isobutenyl | $R_a$COO— |
| tBuOCO— | isopropyl | $R_a$COO— |
| tBuOCO— | cyclopropyl | $R_a$COO— |
| tBuOCO— | cyclobutyl | $R_a$COO— |
| tBuOCO— | cyclopentyl | $R_a$COO— |
| tBuOCO— | phenyl | $R_a$COO— |
| benzoyl | 2-furyl | $R_a$COO— |
| benzoyl | 3-furyl | $R_a$COO— |
| benzoyl | 2-thienyl | $R_a$COO— |
| benzoyl | 3-thienyl | $R_a$COO— |
| benzoyl | 2-pyridyl | $R_a$COO— |
| benzoyl | 3-pyridyl | $R_a$COO— |
| benzoyl | 4-pyridyl | $R_a$COO— |
| benzoyl | isobutenyl | $R_a$COO— |
| benzoyl | isopropyl | $R_a$COO— |
| benzoyl | cyclopropyl | $R_a$COO— |
| benzoyl | cyclobutyl | $R_a$COO— |
| benzoyl | cyclopentyl | $R_a$COO— |
| benzoyl | phenyl | $R_a$COO— |
| 2-FuCO— | 2-furyl | $R_a$COO— |
| 2-FuCO— | 3-furyl | $R_a$COO— |
| 2-FuCO— | 2-thienyl | $R_a$COO— |
| 2-FuCO— | 3-thienyl | $R_a$COO— |
| 2-FuCO— | 2-pyridyl | $R_a$COO— |
| 2-FuCO— | 3-pyridyl | $R_a$COO— |
| 2-FuCO— | 4-pyridyl | $R_a$COO— |
| 2-FuCO— | isobutenyl | $R_a$COO— |
| 2-FuCO— | isopropyl | $R_a$COO— |
| 2-FuCO— | cyclopropyl | $R_a$COO— |
| 2-FuCO— | cyclobutyl | $R_a$COO— |
| 2-FuCO— | cyclopentyl | $R_a$COO— |
| 2-FuCO— | phenyl | $R_a$COO— |
| 2-ThCO— | 2-furyl | $R_a$COO— |
| 2-ThCO— | 3-furyl | $R_a$COO— |
| 2-ThCO— | 2-thienyl | $R_a$COO— |
| 2-ThCO— | 3-thienyl | $R_a$COO— |
| 2-ThCO— | 2-pyridyl | $R_a$COO— |
| 2-ThCO— | 3-pyridyl | $R_a$COO— |
| 2-ThCO— | 4-pyridyl | $R_a$COO— |
| 2-ThCO— | isobutenyl | $R_a$COO— |
| 2-ThCO— | isopropyl | $R_a$COO— |
| 2-ThCO— | cyclopropyl | $R_a$COO— |
| 2-ThCO— | cyclobutyl | $R_a$COO— |
| 2-ThCO— | cyclopentyl | $R_a$COO— |
| 2-ThCO— | phenyl | $R_a$COO— |
| 2-PyCO— | 2-furyl | $R_a$COO— |
| 2-PyCO— | 3-furyl | $R_a$COO— |
| 2-PyCO— | 2-thienyl | $R_a$COO— |
| 2-PyCO— | 3-thienyl | $R_a$COO— |
| 2-PyCO— | 2-pyridyl | $R_a$COO— |
| 2-PyCO— | 3-pyridyl | $R_a$COO— |
| 2-PyCO— | 4-pyridyl | $R_a$COO— |
| 2-PyCO— | isobutenyl | $R_a$COO— |
| 2-PyCO— | isopropyl | $R_a$COO— |
| 2-PyCO— | cyclopropyl | $R_a$COO— |
| 2-PyCO— | cyclobutyl | $R_a$COO— |
| 2-PyCO— | cyclopentyl | $R_a$COO— |
| 2-PyCO— | phenyl | $R_a$COO— |
| 3PyCO— | 2-furyl | $R_a$COO— |
| 3-PyCO— | 3-furyl | $R_a$COO— |
| 3-PyCO— | 2-thienyl | $R_a$COO— |
| 3-PyCO— | 3-thienyl | $R_a$COO— |
| 3-PyCO— | 2-pyridyl | $R_a$COO— |
| 3-PyCO— | 3-pyridyl | $R_a$COO— |
| 3-PyCO— | 4-pyridyl | $R_a$COO— |
| 3-PyCO— | isobutenyl | $R_a$COO— |
| 3-PyCO— | isopropyl | $R_a$COO— |
| 3-PyCO— | cyclopropyl | $R_a$COO— |
| 3-PyCO— | cyclobutyl | $R_a$COO— |
| 3-PyCO— | cyclopentyl | $R_a$COO— |
| 3-PyCO— | phenyl | $R_a$COO— |
| 4-PyCO— | 2-furyl | $R_a$COO— |
| 4-PyCO— | 3-furyl | $R_a$COO— |
| 4-PyCO— | 2-thienyl | $R_a$COO— |
| 4-PyCO— | 3-thienyl | $R_a$COO— |
| 4-PyCO— | 2-pyridyl | $R_a$COO— |
| 4-PyCO— | 3-pyridyl | $R_a$COO— |
| 4-PyCO— | 4-pyridyl | $R_a$COO— |
| 4-PyCO— | isobutenyl | $R_a$COO— |
| 4-PyCO— | isopropyl | $R_a$COO— |
| 4-PyCO— | cyclopropyl | $R_a$COO— |
| 4-PyCO— | cyclobutyl | $R_a$COO— |
| 4-PyCO— | cyclopentyl | $R_a$COO— |
| 4-PyCO— | phenyl | $R_a$COO— |
| $C_4H_7$CO— | 2-furyl | $R_a$COO— |
| $C_4H_7$CO— | 3-furyl | $R_a$COO— |
| $C_4H_7$CO— | 2-thienyl | $R_a$COO— |
| $C_4H_7$CO— | 3-thienyl | $R_a$COO— |
| $C_4H_7$CO— | 2-pyridyl | $R_a$COO— |
| $C_4H_7$CO— | 3-pyridyl | $R_a$COO— |
| $C_4H_7$CO— | 4-pyridyl | $R_a$COO— |
| $C_4H_7$CO— | isobutenyl | $R_a$COO— |
| $C_4H_7$CO— | isopropyl | $R_a$COO— |
| $C_4H_7$CO— | cyclopropyl | $R_a$COO— |
| $C_4H_7$CO— | cyclobutyl | $R_a$COO— |
| $C_4H_7$CO— | cyclopentyl | $R_a$COO— |
| $C_4H_7$CO— | phenyl | $R_a$COO— |
| EtOCO— | 2-furyl | $R_a$COO— |
| EtOCO— | 3-furyl | $R_a$COO— |
| EtOCO— | 2-thienyl | $R_a$COO— |
| EtOCO— | 3-thienyl | $R_a$COO— |
| EtOCO— | 2-pyridyl | $R_a$COO— |
| EtOCO— | 3-pyridyl | $R_a$COO— |
| EtOCO— | 4-pyridyl | $R_a$COO— |
| EtOCO— | isobutenyl | $R_a$COO— |
| EtOCO— | isopropyl | $R_a$COO— |
| EtOCO— | cyclopropyl | $R_a$COO— |
| EtOCO— | cyclobutyl | $R_a$COO— |
| EtOCO— | cyclopentyl | $R_a$COO— |
| EtOCO— | phenyl | $R_a$COO— |
| ibueCO— | 2-furyl | $R_a$COO— |
| ibueCO— | 3-furyl | $R_a$COO— |
| ibueCO— | 2-thienyl | $R_a$COO— |
| ibueCO— | 3-thienyl | $R_a$COO— |
| ibueCO— | 2-pyridyl | $R_a$COO— |
| ibueCO— | 3-pyridyl | $R_a$COO— |
| ibueCO— | 4-pyridyl | $R_a$COO— |
| ibueCO— | isobutenyl | $R_a$COO— |
| ibueCO— | isopropyl | $R_a$COO— |
| ibueCO— | cyclopropyl | $R_a$COO— |
| ibueCO— | cycobutyl | $R_a$COO— |
| ibueCO— | cyclopentyl | $R_a$COO— |
| ibueCO— | phenyl | $R_a$COO— |
| iBuCO— | 2-furyl | $R_a$COO— |
| iBuCO— | 3-furyl | $R_a$COO— |
| iBuCO— | 2-thienyl | $R_a$COO— |
| iBuCO— | 3-thienyl | $R_a$COO— |
| iBuCO— | 2-pyridyl | $R_a$COO— |
| iBuCO— | 3-pyridyl | $R_a$COO— |
| iBuCO— | 4-pyridyl | $R_a$COO— |
| iBuCO— | isobutenyl | $R_a$COO— |
| iBuCO— | isopropyl | $R_a$COO— |
| iBuCO— | cyclopropyl | $R_a$COO— |
| iBuCO— | cyclobutyl | $R_a$COO— |
| iBuCO— | cyclopentyl | $R_a$COO— |
| iBuCO— | phenyl | $R_a$COO— |
| iBuOCO— | 2-furyl | $R_a$COO— |
| iBuOCO— | 3-furyl | $R_a$COO— |
| iBuOCO— | 2-thienyl | $R_a$COO— |
| iBuOCO— | 3-thienyl | $R_a$COO— |
| iBuOCO— | 2-pyridyl | $R_a$COO— |
| iBuOCO— | 3-pyridyl | $R_a$COO— |
| iBuOCO— | 4-pyridyl | $R_a$COO— |
| iBuOCO— | isobutenyl | $R_a$COO— |
| iBuOCO— | isopropyl | $R_a$COO— |
| iBuOCO— | cyclopropyl | $R_a$COO— |
| iBuOCO— | cyclobutyl | $R_a$COO— |
| iBuOCO— | cyclopentyl | $R_a$COO— |
| iBuOCO— | phenyl | $R_a$COO— |
| iPrOCO— | 2-furyl | $R_a$COO— |
| iPrOCO— | 3-furyl | $R_a$COO— |
| iPrOCO— | 2-thienyl | $R_a$COO— |
| iPrOCO— | 3-thienyl | $R_a$COO— |
| iPrOCO— | 2-pyridyl | $R_a$COO— |

| | | |
|---|---|---|
| iPrOCO— | 3-pyridyl | $R_aCOO$— |
| iPrOCO— | 4-pyridyl | $R_aCOO$— |
| iPrOCO— | isobutenyl | $R_aCOO$— |
| iPrOCO— | isopropyl | $R_aCOO$— |
| iPrOCO— | cyclopropyl | $R_aCOO$— |
| iPrOCO— | cyclobutyl | $R_aCOO$— |
| iPrOCO— | cyclopentyl | $R_aCOO$— |
| iPrOCO— | phenyl | $R_aCOO$— |
| nPrOCO— | 2-furyl | $R_aCOO$— |
| nPrOCO— | 3-furyl | $R_aCOO$— |
| nPrOCO— | 2-thienyl | $R_aCOO$— |
| nPrOCO— | 3-thienyl | $R_aCOO$— |
| nPrOCO— | 2-pyridyl | $R_aCOO$— |
| nPrOCO— | 3-pyridyl | $R_aCOO$— |
| nPrOCO— | 4-pyridyl | $R_aCOO$— |
| nPrOCO— | isobutenyl | $R_aCOO$— |
| nPrOCO— | isopropyl | $R_aCOO$— |
| nPrOCO— | cyclopropyl | $R_aCOO$— |
| nPrOCO— | cyclobutyl | $R_aCOO$— |
| nPrOCO— | cyclopentyl | $R_aCOO$— |
| nPrOCO— | phenyl | $R_aCOO$— |
| nPrCO— | 2-furyl | $R_aCOO$— |
| nPrCO— | 3-furyl | $R_aCOO$— |
| nPrCO— | 2-thienyl | $R_aCOO$— |
| nPrCO— | 3-thienyl | $R_aCOO$— |
| nPrCO— | 2-pyridyl | $R_aCOO$— |
| nPrCO— | 3-pyridyl | $R_aCOO$— |
| nPrCO— | 4-pyridyl | $R_aCOO$— |
| nPrCO— | isobutenyl | $R_aCOO$— |
| nPrCO— | isopropyl | $R_aCOO$— |
| nPrCO— | cyclopropyl | $R_aCOO$— |
| nPrCO— | cyclobutyl | $R_aCOO$— |
| nPrCO— | cyclopentyl | $R_aCOO$— |
| nPrCO— | phenyl | $R_aCOO$— |
| tBuOCO— | cyclopentyl | EtCOO— |
| benzoyl | 3-furyl | EtCOO— |
| benzoyl | 2-thienyl | EtCOO— |
| benzoyl | 2-pyridyl | EtCOO— |
| benzoyl | 3-pyridyl | EtCOO— |
| benzoyl | 4-pyridyl | EtCOO— |
| benzoyl | isobutenyl | EtCOO— |
| benzoyl | isopropyl | EtCOO— |
| benzoyl | cyclopropyl | EtCOO— |
| benzoyl | cyclobutyl | EtCOO— |
| benzoyl | cyclopentyl | EtCOO— |
| benzoyl | phenyl | EtCOO— |
| 2-FuCO— | 3-furyl | EtCOO— |
| 2-FuCO— | 3-thienyl | EtCOO— |
| 2-FuCO— | 2-pyridyl | EtCOO— |
| 2-FuCO— | 3-pyridyl | EtCOO— |
| 2-FuCO— | 4-pyridyl | EtCOO— |
| 2-FuCO— | isobutenyl | EtCOO— |
| 2-FuCO— | isopropyl | EtCOO— |
| 2-FuCO— | cyclopropyl | EtCOO— |
| 2-FuCO— | cyclobutyl | EtCOO— |
| 2-FuCO— | cyclopentyl | EtCOO— |
| 2-FuCO— | phenyl | EtCOO— |
| 2-ThCO— | 3-furyl | EtCOO— |
| 2-ThCO— | 3-thienyl | EtCOO— |
| 2-ThCO— | 2-pyridyl | EtCOO— |
| 2-ThCO— | 3-pyridyl | EtCOO— |
| 2-ThCO— | 4-pyridyl | EtCOO— |
| 2-ThCO— | isobutenyl | EtCOO— |
| 2-ThCO— | isopropyl | EtCOO— |
| 2-ThCO— | cyclopropyl | EtCOO— |
| 2-ThCO— | cyclobutyl | EtCOO— |
| 2-ThCO— | cyclopentyl | EtCOO— |
| 2-ThCO— | phenyl | EtCOO— |
| 2-PyCO— | 2-furyl | EtCOO— |
| 2-PyCO— | 3-furyl | EtCOO— |
| 2-PyCO— | 2-thienyl | EtCOO— |
| 2-PyCO— | 3-thienyl | EtCOO— |
| 2-PyCO— | 2-pyridyl | EtCOO— |
| 2-PyCO— | 3-pyridyl | EtCOO— |
| 2-PyCO— | 4-pyridyl | EtCOO— |
| 2-PyCO— | isobutenyl | EtCOO— |
| 2-PyCO— | isopropyl | EtCOO— |
| 2-PyCO— | cyclopropyl | EtCOO— |
| 2-PyCO— | cyclobutyl | EtCOO— |
| 2-PyCO— | cyclopentyl | EtCOO— |
| 2-PyCO— | phenyl | EtCOO— |
| 3PyCO— | 2-furyl | EtCOO— |

| | | |
|---|---|---|
| 3-PyCO— | 3-furyl | EtCOO— |
| 3-PyCO— | 3-thienyl | EtCOO— |
| 3-PyCO— | 2-pyridyl | EtCOO— |
| 3-PyCO— | 3-pyridyl | EtCOO— |
| 3-PyCO— | 4-pyridyl | EtCOO— |
| 3-PyCO— | isobutenyl | EtCOO— |
| 3-PyCO— | isopropyl | EtCOO— |
| 3-PyCO— | cyclopropyl | EtCOO— |
| 3-PyCO— | cyclobutyl | EtCOO— |
| 3-PyCO— | cyclopentyl | EtCOO— |
| 3-PyCO— | phenyl | EtCOO— |
| 4-PyCO— | 2-furyl | EtCOO— |
| 4-PyCO— | 3-furyl | EtCOO— |
| 4-PyCO— | 2-thienyl | EtCOO— |
| 4-PyCO— | 3-thienyl | EtCOO— |
| 4-PyCO— | 2-pyridyl | EtCOO— |
| 4-PyCO— | 3-pyridyl | EtCOO— |
| 4-PyCO— | 4-pyridyl | EtCOO— |
| 4-PyCO— | isobutenyl | EtCOO— |
| 4-PyCO— | isopropyl | EtCOO— |
| 4-PyCO— | cyclopropyl | EtCOO— |
| 4-PyCO— | cyclobutyl | EtCOO— |
| 4-PyCO— | cyclopentyl | EtCOO— |
| 4-PyCO— | phenyl | EtCOO— |
| $C_4H_7CO$— | 3-furyl | EtCOO— |
| $C_4H_7CO$— | 3-thienyl | EtCOO— |
| $C_4H_7CO$— | 2-pyridyl | EtCOO— |
| $C_4H_7CO$— | 3-pyridyl | EtCOO— |
| $C_4H_7CO$— | 4-pyridyl | EtCOO— |
| $C_4H_7CO$— | isobutenyl | EtCOO— |
| $C_4H_7CO$— | isopropyl | EtCOO— |
| $C_4H_7CO$— | cyclopropyl | EtCOO— |
| $C_4H_7CO$— | cyclobutyl | EtCOO— |
| $C_4H_7CO$— | cyclopentyl | EtCOO— |
| $C_4H_7CO$— | phenyl | EtCOO— |
| EtOCO— | 3-furyl | EtCOO— |
| EtOCO— | 3-thienyl | EtCOO— |
| EtOCO— | 2-pyridyl | EtCOO— |
| EtOCO— | 3-pyridyl | EtCOO— |
| EtOCO— | 4-pyridyl | EtCOO— |
| EtOCO— | isobutenyl | EtCOO— |
| EtOCO— | isopropyl | EtCOO— |
| EtOCO— | cyclopropyl | EtCOO— |
| EtOCO— | cyclobutyl | EtCOO— |
| EtOCO— | cyclopentyl | EtCOO— |
| EtOCO— | phenyl | EtCOO— |
| ibueCO— | 2-furyl | EtCOO— |
| ibueCO— | 3-furyl | EtCOO— |
| ibueCO— | 2-thienyl | EtCOO— |
| ibueCO— | 3-thienyl | EtCOO— |
| ibueCO— | 2-pyridyl | EtCOO— |
| ibueCO— | 3-pyridyl | EtCOO— |
| ibueCO— | 4-pyridyl | EtCOO— |
| ibueCO— | isobutenyl | EtCOO— |
| ibueCO— | isopropyl | EtCOO— |
| ibueCO— | cyclopropyl | EtCOO— |
| ibueCO— | cyclobutyl | EtCOO— |
| ibueCO— | cyclopentyl | EtCOO— |
| ibueCO— | phenyl | EtCOO— |
| iBuCO— | 2-furyl | EtCOO— |
| iBuCO— | 3-furyl | EtCOO— |
| iBuCO— | 2-thienyl | EtCOO— |
| iBuCO— | 3-thienyl | EtCOO— |
| iBuCO— | 2-pyridyl | EtCOO— |
| iBuCO— | 3-pyridyl | EtCOO— |
| iBuCO— | 4-pyridyl | EtCOO— |
| iBuCO— | isobutenyl | EtCOO— |
| iBuCO— | isopropyl | EtCOO— |
| iBuCO— | cyclopropyl | EtCOO— |
| iBuCO— | cyclobutyl | EtCOO— |
| iBuCO— | cyclopentyl | EtCOO— |
| iBuCO— | phenyl | EtCOO— |
| iBuOCO— | 2-pyridyl | EtCOO— |
| iBuOCO— | 3-pyridyl | EtCOO— |
| iBuOCO— | 4-pyridyl | EtCOO— |
| iBuOCO— | isobutenyl | EtCOO— |
| iBuOCO— | isopropyl | EtCOO— |
| iBuOCO— | cyclobutyl | EtCOO— |
| iBuOCO— | cyclopentyl | EtCOO— |
| iBuOCO— | phenyl | EtCOO— |
| iPrOCO— | 3-furyl | EtCOO— |
| iPrOCO— | 3-thienyl | EtCOO— |

| | | |
|---|---|---|
| iPrOCO— | 2-pyridyl | EtCOO— |
| iPrOCO— | 3-pyridyl | EtCOO— |
| iPrOCO— | 4-pyridyl | EtCOO— |
| iPrOCO— | isobutenyl | EtCOO— |
| iPrOCO— | isopropyl | EtCOO— |
| iPrOCO— | cyclopropyl | EtCOO— |
| iPrOCO— | cyclobutyl | EtCOO— |
| iPrOCO— | cyclopentyl | EtCOO— |
| iPrOCO— | phenyl | EtCOO— |
| nPrOCO— | 2-furyl | EtCOO— |
| nPrOCO— | 3-furyl | EtCOO— |
| nPrOCO— | 2-thienyl | EtCOO— |
| nPrOCO— | 3-thienyl | EtCOO— |
| nPrOCO— | 2-pyridyl | EtCOO— |
| nPrOCO— | 3-pyridyl | EtCOO— |
| nPrOCO— | 4-pyridyl | EtCOO— |
| nPrOCO— | isobutenyl | EtCOO— |
| nPrOCO— | isopropyl | EtCOO— |
| nPrOCO— | cyclopropyl | EtCOO— |
| nPrOCO— | cyclobutyl | EtCOO— |
| nPrOCO— | cyclopentyl | EtCOO— |
| nPrOCO— | phenyl | EtCOO— |
| nPrCO— | 3-furyl | EtCOO— |
| nPrCO— | 3-thienyl | EtCOO— |
| nPrCO— | 2-pyridyl | EtCOO— |
| nPrCO— | 3-pyridyl | EtCOO— |
| nPrCO— | 4-pyridyl | EtCOO— |
| nPrCO— | isobutenyl | EtCOO— |
| nPrCO— | isopropyl | EtCOO— |
| nPrCO— | cyclopropyl | EtCOO— |
| nPrCO— | cyclobutyl | EtCOO— |
| nPrCO— | cyclopentyl | EtCOO— |
| nPrCO— | phenyl | EtCOO— |

EXAMPLE 4

Additional Taxanes having C-7 Ester and C-10 Hydroxy Substituents

Following the processes described in Example 1 and elsewhere herein, the following specific taxanes having structural formula (5) may be prepared, wherein $R_{10}$ is hydroxy and $R_7$ in each of the series (that is, each of series "A" through "K") is as previously defined, including wherein $R_7$ is $R_{7a}$COO— and $R_{7a}$ is (i) substituted or unsubstituted, preferably unsubstituted, $C_2$ to $C_8$ alkyl (straight, branched or cyclic), such as ethyl, propyl, butyl, pentyl, or hexyl; (ii) substituted or unsubstituted, preferably unsubstituted, $C_2$ to $C_8$ alkenyl (straight, branched or cyclic), such as ethenyl, propenyl, butenyl, pentenyl or hexenyl; (iii) substituted or unsubstituted, preferably unsubstituted, $C_2$ to $C_8$ alkynyl (straight or branched) such as ethynyl, propynyl, butynyl, pentynyl, or hexynyl; (iv) substituted or unsubstituted, preferably unsubstituted, phenyl; or (v) substituted or unsubstituted, preferably unsubstituted, heteroaromatic such as furyl, thienyl, or pyridyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(5)

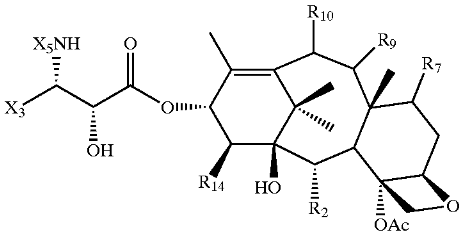

| Series | $X_5$ | $X_3$ | $R_7$ | $R_s$ | $R_9$ | $R_{14}$ |
|---|---|---|---|---|---|---|
| A1 | —$COOX_{10}$ | heterocyclo | $R_{7a}COO$— | $C_6H_5COO$— | O | H |
| A2 | —$COX_{10}$ | heterocyclo | $R_{7a}COO$— | $C_6H_5COO$— | O | H |
| A3 | —$CONHX_{10}$ | heterocyclo | $R_{7a}COO$— | $C_6H_5COO$— | O | H |
| A4 | —$COOX_{10}$ | optionally substituted $C_2$ to $C_8$ alkyl | $R_{7a}COO$— | $C_6H_5COO$— | O | H |
| A5 | —$COX_{10}$ | optionally substituted $C_2$ to $C_8$ alkyl | $R_{7a}COO$— | $C_6H_5COO$— | O | H |
| A6 | —$CONHX_{10}$ | optionally substituted $C_2$ to $C_8$ alkyl | $R_{7a}COO$— | $C_6H_5COO$— | O | H |
| A7 | —$COOX_{10}$ | optionally substituted $C_2$ to $C_8$ alkenyl | $R_{7a}COO$— | $C_6H_5COO$— | O | H |
| A8 | —$COX_{10}$ | optionally substituted $C_2$ to $C_8$ alkenyl | $R_{7a}COO$— | $C_6H_5COO$— | O | H |
| A9 | —$CONHX_{10}$ | optionally substituted $C_2$ to $C_8$ alkenyl | $R_{7a}COO$— | $C_6H_5COO$— | O | H |
| A10 | —$COX_{10}$ | optionally substituted $C_2$ to $C_8$ alkynyl | $R_{7a}COO$— | $C_6H_5COO$— | O | H |
| A11 | —$COX_{10}$ | optionally substituted $C_2$ to $C_8$ alkynyl | $R_{7a}COO$— | $C_6H_5COO$— | O | H |
| A12 | —$CONHX_{10}$ | optionally substituted $C_2$ to $C_8$ alkynyl | $R_{7a}COO$— | $C_6H_5COO$— | O | H |
| B1 | —$COOX_{10}$ | heterocyclo | $R_{7a}COO$— | $R_{2a}COO$— | O | H |
| B2 | —$COX_{10}$ | heterocyclo | $R_{7a}COO$— | $R_{2a}COO$— | O | H |
| B3 | —$CONHX_{10}$ | heterocyclo | $R_{7a}COO$— | $R_{2a}COO$— | O | H |
| B4 | —$COOX_{10}$ | optionally substituted $C_2$ to $C_8$ alkyl | $R_{7a}COO$— | $R_{2a}COO$— | O | H |
| B5 | —$COX_{10}$ | optionally substituted $C_2$ to $C_8$ alkyl | $R_{7a}COO$— | $R_{2a}COO$— | O | H |
| B6 | —$CONHX_{10}$ | optionally substituted $C_2$to $C_8$ alkyl | $R_{7a}COO$— | $R_{2a}COO$— | O | H |
| B7 | —$COOX_{10}$ | optionally substituted $C_2$ to $C_8$ alkenyl | $R_{7a}COO$— | $R_{2a}COO$— | O | H |
| B8 | —$COX_{10}$ | optionally substituted $C_2$ to $C_8$ alkenyl | $R_{7a}COO$— | $R_{2a}COO$— | O | H |
| B9 | —$CONHX_{10}$ | optionally substituted $C_2$ to $C_8$ alkenyl | $R_{7a}COO$— | $R_{2a}COO$— | O | H |
| B10 | —$COOX_{10}$ | optionally substituted $C_2$ to $C_8$ | $R_{7a}COO$— | $R_{2a}COO$— | O | H |

-continued (5)

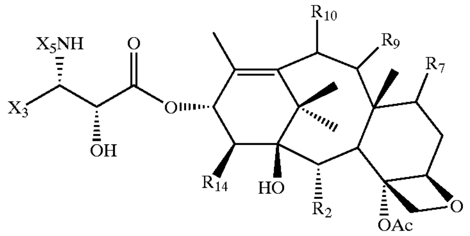

| Series | $X_5$ | $X_3$ | $R_7$ | $R_s$ | $R_9$ | $R_{14}$ |
|---|---|---|---|---|---|---|
| | | alkynyl | | | | |
| B11 | —$COX_{10}$ | optionally substituted $C_2$ to $C_8$ alkynyl | $R_{7a}COO$— | $R_{2a}COO$— | O | H |
| B12 | —$CONHX_{10}$ | optionally substituted $C_2$ to $C_8$ alkynyl | $R_{7a}COO$— | $R_{2a}COO$— | O | H |
| C1 | —$COOX_{10}$ | heterocyclo | $R_{7a}COO$— | $C_6H_5COO$— | $R_{9a}COO$— | H |
| C2 | —$COX_{10}$ | heterocyclo | $R_{7a}COO$— | $C_6H_5COO$— | $R_{9a}COO$— | H |
| C3 | —$CONHX_{10}$ | heterocyclo | $R_{7a}COO$— | $C_6H_5COO$— | $R_{9a}COO$— | H |
| C4 | —$COOX_{10}$ | optionally substituted $C_2$ to $C_8$ alkyl | $R_{7a}COO$— | $C_6H_5COO$— | $R_{9a}COO$— | H |
| C5 | —$COX_{10}$ | optionally substituted $C_2$ to $C_8$ alkyl | $R_{7a}COO$— | $C_6H_5COO$— | $R_{9a}COO$— | H |
| C6 | —$CONHX_{10}$ | optionally substituted $C_2$ to $C_8$ alkyl | $R_{7a}COO$— | $C_6H_5COO$— | $R_{9a}COO$— | H |
| C7 | —$COOX_{10}$ | optionally substituted $C_2$ to $C_8$ alkenyl | $R_{7a}COO$— | $C_6H_5COO$— | $R_{9a}COO$— | H |
| C8 | —$COX_{10}$ | optionally substituted $C_2$ to $C_8$ alkenyl | $R_{7a}COO$— | $C_6H_5COO$— | $R_{9a}COO$— | H |
| C9 | —$CONHX_{10}$ | optionally substituted $C_2$ to $C_8$ alkenyl | $R_{7a}COO$— | $C_6H_5COO$— | $R_{9a}COO$— | H |
| C10 | —$COOX_{10}$ | optionally substituted $C_2$ to $C_8$ alkynyl | $R_{7a}COO$— | $C_6H_5COO$— | $R_{9a}COO$— | H |
| C11 | —$COX_{10}$ | optionally substituted $C_2$ to $C_8$ alkynyl | $R_{7a}COO$— | $C_6H_5COO$— | $R_{9a}COO$— | H |
| C12 | —$CONHX_{10}$ | optionally substituted $C_2$ to $C_8$ alkynyl | $R_{7a}COO$— | $C_6H_5COO$— | $R_{9a}COO$— | H |
| D1 | —$COOX_{10}$ | heterocyclo | $R_{7a}COO$— | $C_6H_5COO$— | OH | H |
| D2 | —$COX_{10}$ | heterocyclo | $R_{7a}COO$— | $C_6H_5COO$— | OH | H |
| D3 | —$CONHX_{10}$ | heterocyclo | $R_{7a}COO$— | $C_6H_5COO$— | OH | H |
| D4 | —$COOX_{10}$ | optionally substituted $C_2$ to $C_8$ alkyl | $R_{7a}COO$— | $C_6H_5COO$— | OH | H |
| D5 | —$COX_{10}$ | optionally substituted $C_2$ to $C_8$ alkyl | $R_{7a}COO$— | $C_6H_5COO$— | OH | H |
| D6 | —$CONHX_{10}$ | optionally substituted $C_2$ to $C_8$ alkyl | $R_{7a}COO$— | $C_6H_5COO$— | OH | H |
| D7 | —$COOX_{10}$ | optionally substituted $C_2$ to $C_8$ alkenyl | $R_{7a}COO$— | $C_6H_5COO$— | OH | H |
| D8 | —$COX_{10}$ | optionally substituted | $R_{7a}COO$— | $C_6H_5COO$— | OH | H |

-continued (5)

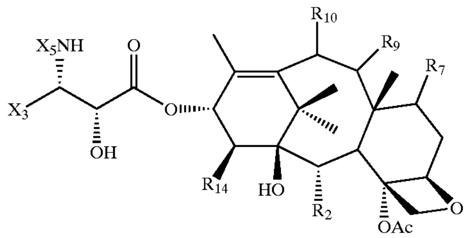

| Series | $X_5$ | $X_3$ | $R_7$ | $R_s$ | $R_9$ | $R_{14}$ |
|---|---|---|---|---|---|---|
| | | $C_2$ to $C_8$ alkenyl | | | | |
| D9 | $—CONHX_{10}$ | optionally substituted $C_2$ to $C_8$ alkenyl | $R_{7a}COO—$ | $C_6H_5COO—$ | OH | H |
| D10 | $—COOX_{10}$ | optionally substituted $C_2$ to $C_8$ alkynyl | $R_{7a}COO—$ | $C_6H_5COO—$ | OH | H |
| D11 | $—COX_{10}$ | optionally substituted $C_2$ to $C_8$ alkynyl | $R_{7a}COO—$ | $C_6H_5COO—$ | OH | H |
| D12 | $—CONHX_{10}$ | optionally substituted $C_2$ to $C_8$ alkynyl | $R_{7a}COO—$ | $C_6H_5COO—$ | OH | H |
| E1 | $—COOX_{10}$ | heterocyclo | $R_{7a}COO—$ | $C_6H_5COO—$ | O | OH |
| E2 | $—COX_{10}$ | heterocyclo | $R_{7a}COO—$ | $C_6H_5COO—$ | O | OH |
| E3 | $—CONHX_{10}$ | heterocyclo | $R_{7a}COO—$ | $C_6H_5COO—$ | O | OH |
| E4 | $—COOX_{10}$ | optionally substituted $C_2$ to $C_8$ alkyl | $R_{7a}COO—$ | $C_6H_5COO—$ | O | OH |
| E5 | $—COX_{10}$ | optionally substituted $C_2$ to $C_8$alkyl | $R_{7a}COO—$ | $C_6H_5COO—$ | O | OH |
| E6 | $—CONHX_{10}$ | optionally substituted $C_2$ to $C_8$ alkyl | $R_{7a}COO—$ | $C_6H_5COO—$ | O | OH |
| E7 | $—COOX_{10}$ | optionally substituted $C_2$ to $C_8$ alkenyl | $R_{7a}COO—$ | $C_6H_5COO—$ | O | OH |
| E8 | $—COX_{10}$ | optionally substituted $C_2$ to $C_8$ alkenyl | $R_{7a}COO—$ | $C_6H_5COO—$ | O | OH |
| E9 | $—CONHX_{10}$ | optionally substituted $C_2$ to $C_8$ alkenyl | $R_{7a}COO—$ | $C_6H_5COO—$ | O | OH |
| E10 | $—COOX_{10}$ | optionally substituted $C_2$ to $C_8$ alkynyl | $R_{7a}COO—$ | $C_6H_5COO—$ | O | OH |
| E11 | $—COX_{10}$ | optionally substituted $C_2$ to $C_8$ alkynyl | $R_{7a}COO—$ | $C_6H_5COO—$ | O | OH |
| E12 | $—CONHX_{10}$ | optionally substituted $C_2$ to $C_8$ alkynyl | $R_{7a}COO—$ | $C_6H_5COO—$ | O | OH |
| F1 | $—COOX_{10}$ | heterocyclo | $R_{7a}COO—$ | $R_{2a}COO—$ | $R_{9a}COO—$ | H |
| F2 | $—COX_{10}$ | heterocyclo | $R_{7a}COO—$ | $R_{2a}COO—$ | $R_{9a}COO—$ | H |
| F3 | $—CONHX_{10}$ | heterocyclo | $R_{7a}COO—$ | $R_{2a}COO—$ | $R_{9a}COO—$ | H |
| F4 | $—COOX_{10}$ | optionally substituted $C_2$ to $C_8$ alkyl | $R_{7a}COO—$ | $R_{2a}COO—$ | $R_{9a}COO—$ | H |
| F5 | $—COX_{10}$ | optionally substituted $C_2$ to $C_8$ alkyl | $R_{7a}COO—$ | $R_{2a}COO—$ | $R_{9a}COO—$ | H |

-continued (5)

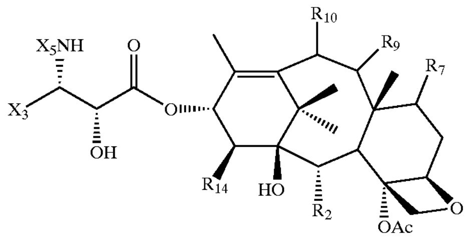

| Series | $X_5$ | $X_3$ | $R_7$ | $R_s$ | $R_9$ | $R_{14}$ |
|---|---|---|---|---|---|---|
| F6 | —$CONHX_{10}$ | optionally substituted $C_2$ to $C_8$ alkyl | $R_{7a}COO$— | $R_{2a}COO$— | $R_{9a}COO$— | H |
| F7 | —$COOX_{10}$ | optionally substituted $C_2$ to $C_8$ alkenyl | $R_{7a}COO$— | $R_{2a}COO$— | $R_{9a}COO$— | H |
| F8 | —$COX_{10}$ | optionally substituted $C_2$ to $C_8$ alkenyl | $R_{7a}COO$— | $R_{2a}COO$— | $R_{9a}COO$— | H |
| F9 | —$CONHX_{10}$ | optionally substituted $C_2$ to $C_8$ alkenyl | $R_{7a}COO$— | $R_{2a}COO$— | $R_{9a}COO$— | H |
| F10 | —$COOX_{10}$ | optionally substituted $C_2$ to $C_8$ alkynyl | $R_{7a}COO$— | $R_{2a}COO$— | $R_{9a}COO$— | H |
| F11 | —$COX_{10}$ | optionally substituted $C_2$ to $C_8$ alkynyl | $R_{7a}COO$— | $R_{2a}COO$— | $R_{9a}COO$— | H |
| F12 | —$CONHX_{10}$ | optionally substituted $C_2$ to $C_8$ alkynyl | $R_{7a}COO$— | $R_{2a}COO$— | $R_{9a}COO$— | H |
| G1 | —$COOX_{10}$ | heterocyclo | $R_{7a}COO$— | $R_{2a}COO$— | OH | H |
| G2 | —$COX_{10}$ | heterocyclo | $R_{7a}COO$— | $R_{2a}COO$— | OH | H |
| G3 | —$CONHX_{10}$ | heterocyclo | $R_{7a}COO$— | $R_{2a}COO$— | OH | H |
| G4 | —$COOX_{10}$ | optionally substituted $C_2$ to $C_8$ alkyl | $R_{7a}COO$— | $R_{2a}COO$— | OH | H |
| G5 | —$COX_{10}$ | optionally substituted $C_2$ to $C_8$ alkyl | $R_{7a}COO$— | $R_{2a}COO$— | OH | H |
| G6 | —$CONHX_{10}$ | optionally substituted $C_2$ to $C_8$ alkyl | $R_{7a}COO$— | $R_{2a}COO$— | OH | H |
| G7 | —$COOX_{10}$ | optionally substituted $C_2$ to $C_8$ alkenyl | $R_{7a}COO$— | $R_{2a}COO$— | OH | H |
| G8 | —$COX_{10}$ | optionally substituted $C_2$ to $C_8$ alkenyl | $R_{7a}COO$— | $R_{2a}COO$— | OH | H |
| G9 | —$CONHX_{10}$ | optionally substituted $C_2$ to $C_8$ alkenyl | $R_{7a}COO$— | $R_{2a}COO$— | OH | H |
| G10 | —$COOX_{10}$ | optionally substituted $C_2$ to $C_8$ alkynyl | $R_{7a}COO$— | $R_{2a}COO$— | OH | H |
| G11 | —$COX_{10}$ | optionally substituted $C_2$ to $C_8$ alkynyl | $R_{7a}COO$— | $R_{2a}COO$— | OH | H |
| G12 | —$CONHX_{10}$ | optionally substituted $C_2$ to $C_8$ alkynyl | $R_{7a}COO$— | $R_{2a}COO$— | OH | H |

-continued (5)

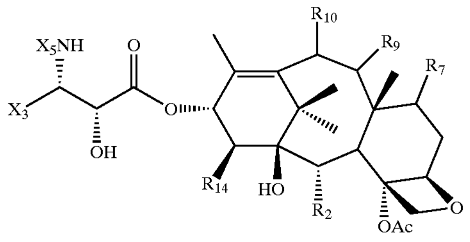

| Series | $X_5$ | $X_3$ | $R_7$ | $R_s$ | $R_9$ | $R_{14}$ |
|---|---|---|---|---|---|---|
| H1 | —$COOX_{10}$ | heterocyclo | $R_{7a}COO$— | $C_6H_5COO$— | OH | OH |
| H2 | —$COX_{10}$ | heterocyclo | $R_{7a}COO$— | $C_6H_5COO$— | OH | OH |
| H3 | —$CONHX_{10}$ | heterocyclo | $R_{7a}COO$— | $C_6H_5COO$— | OH | OH |
| H4 | —$COOX_{10}$ | optionally substituted $C_2$ to $C_8$ alkyl | $R_{7a}COO$— | $C_6H_5COO$— | OH | OH |
| H5 | —$COX_{10}$ | optionally substituted $C_2$ to $C_8$ alkyl | $R_{7a}COO$— | $C_6H_5COO$— | OH | OH |
| H6 | —$CONHX_{10}$ | optionally substituted $C_2$ to $C_8$ alkyl | $R_{7a}COO$— | $C_6H_5COO$— | OH | OH |
| H7 | —$COOX_{10}$ | optionally substituted $C_2$ to $C_8$ alkenyl | $R_{7a}COO$— | $C_6H_5COO$— | OH | OH |
| H8 | —$COX_{10}$ | optionally substituted $C_2$ to $C_8$ alkenyl | $R_{7a}COO$— | $C_6H_5COO$— | OH | OH |
| H9 | —$CONHX_{10}$ | optionally substituted $C_2$ to $C_8$ alkenyl | $R_{7a}COO$— | $C_6H_5COO$— | OH | OH |
| H10 | —$COOX_{10}$ | optionally substituted $C_2$ to $C_8$ alkynyl | $R_{7a}COO$— | $C_6H_5COO$— | OH | OH |
| H11 | —$COX_{10}$ | optionally substituted $C_2$ to $C_8$ alkynyl | $R_{7a}COO$— | $C_6H_5COO$— | OH | OH |
| H12 | —$CONHX_{10}$ | optionally substituted $C_2$ to $C_8$ alkynyl | $R_{7a}COO$— | $C_6H_5COO$— | OH | OH |
| I1 | —$COOX_{10}$ | heterocyclo | $R_{7a}COO$— | $R_{2a}COO$— | O | OH |
| I2 | —$COX_{10}$ | heterocyclo | $R_{7a}COO$— | $R_{2a}COO$— | O | OH |
| I3 | —$CONHX_{10}$ | heterocyclo | $R_{7a}COO$— | $R_{2a}COO$— | O | OH |
| I4 | —$COOX_{10}$ | optionally substituted $C_2$ to $C_8$ alkyl | $R_{7a}COO$— | $R_{2a}COO$— | O | OH |
| I5 | —$COX_{10}$ | optionally substitued $C_2$ to $C_8$ alkyl | $R_{7a}COO$— | $R_{2a}COO$— | O | OH |
| I6 | —$CONHX_{10}$ | optionally substituted $C_2$ to $C_8$ alkyl | $R_{7a}COO$— | $R_{2a}COO$— | O | OH |
| I7 | —$COOX_{10}$ | optionally substituted $C_2$ to $C_8$ alkenyl | $R_{7a}COO$— | $R_{2a}COO$— | O | OH |
| I8 | —$COX_{10}$ | optionally substituted $C_2$ to $C_8$ alkenyl | $R_{7a}COO$— | $R_{2a}COO$— | O | OH |
| I9 | —$CONHX_{10}$ | optionally substituted $C_2$ to $C_8$ alkenyl | $R_{7a}COO$— | $R_{2a}COO$— | O | OH |
| I10 | —$COOX_{10}$ | optionally substituted $C_2$ to $C_8$ | $R_{7a}COO$— | $R_{2a}COO$— | O | OH |

-continued (5)

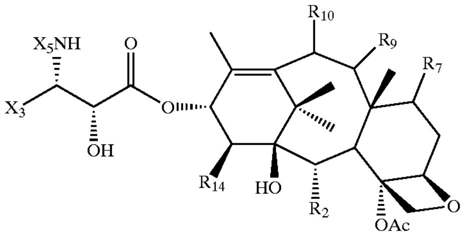

| Series | $X_5$ | $X_3$ | $R_7$ | $R_s$ | $R_9$ | $R_{14}$ |
|---|---|---|---|---|---|---|
| | | alkynyl | | | | |
| I11 | —$COX_{10}$ | optionally substituted $C_2$ to $C_8$ alkynyl | $R_{7a}COO$— | $R_{2a}COO$— | O | OH |
| I12 | —$CONHX_{10}$ | optionally substituted $C_2$ to $C_8$ alkynyl | $R_{7a}COO$— | $R_{2a}COO$— | O | OH |
| J1 | —$COOX_{10}$ | heterocyclo | $R_{7a}COO$— | $R_{2a}COO$— | OH | OH |
| J2 | —$COX_{10}$ | heterocyclo | $R_{7a}COO$— | $R_{2a}COO$— | OH | OH |
| J3 | —$CONHX_{10}$ | heterocyclo | $R_{7a}COO$— | $R_{2a}COO$— | OH | OH |
| J4 | —$COOX_{10}$ | optionally substituted $C_2$ to $C_8$ alkyl | $R_{7a}COO$— | $R_{2a}COO$— | OH | OH |
| J5 | —$COX_{10}$ | optionally substituted $C_2$ to $C_8$ alkyl | $R_{7a}COO$— | $R_{2a}COO$— | OH | OH |
| J6 | —$CONHX_{10}$ | optionally substituted $C_2$ to $C_8$ alkyl | $R_{7a}COO$— | $R_{2a}COO$— | OH | OH |
| J7 | —$COOX_{10}$ | optionally substituted $C_2$ to $C_8$ alkenyl | $R_{7a}COO$— | $R_{2a}COO$— | OH | OH |
| J8 | —$COX_{10}$ | optionally substituted $C_2$ to $C_8$ alkenyl | $R_{7a}COO$— | $R_{2a}COO$— | OH | OH |
| J9 | —$CONHX_{10}$ | optionally substituted $C_2$ to $C_8$ alkenyl | $R_{7a}COO$— | $R_{2a}COO$— | OH | OH |
| J10 | —$COOX_{10}$ | optionally substituted $C_2$ to $C_8$ alkynyl | $R_{7a}COO$— | $R_{2a}COO$— | OH | OH |
| J11 | —$COX_{10}$ | optionally substituted $C_2$ to $C_8$ alkynyl | $R_{7a}COO$— | $R_{2a}COO$— | OH | OH |
| J12 | —$CONHX_{10}$ | optionally substituted $C_2$ to $C_8$ alkynyl | $R_{7a}COO$— | $R_{2a}COO$— | OH | OH |
| K1 | —$COOX_{10}$ | heterocyclo | $R_{7a}COO$— | $R_{2a}COO$— | $R_{9a}COO$— | OH |
| K2 | —$COX_{10}$ | heterocyclo | $R_{7a}COO$— | $R_{2a}COO$— | $R_{9a}COO$— | OH |
| K3 | —$CONHX_{10}$ | heterocyclo | $R_{7a}COO$— | $R_{2a}COO$— | $R_{9a}COO$— | OH |
| K4 | —$COOX_{10}$ | optionally substituted $C_2$ to $C_8$ alkyl | $R_{7a}COO$— | $R_{2a}COO$— | $R_{9a}COO$— | OH |
| K5 | —$COX_{10}$ | optionally substituted $C_2$ to $C_8$ alkyl | $R_{7a}COO$— | $R_{2a}COO$— | $R_{9a}COO$— | OH |
| K6 | —$CONHX_{10}$ | optionally substituted $C_2$ to $C_8$ alkyl | $R_{7a}COO$— | $R_{2a}COO$— | $R_{9a}COO$— | OH |
| K7 | —$COOX_{10}$ | optionally substituted $C_2$ to $C_8$ alkenyl | $R_{7a}COO$— | $R_{2a}COO$— | $R_{9a}COO$— | OH |
| K8 | —$COX_{10}$ | optionally substituted | $R_{7a}COO$— | $R_{2a}COO$— | $R_{9a}COO$— | OH |

-continued (5)

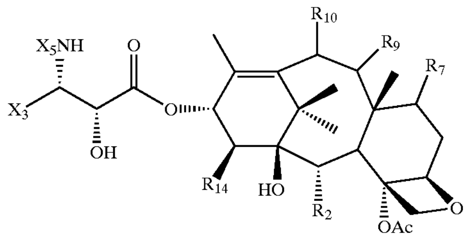

| Series | $X_5$ | $X_3$ | $R_7$ | $R_2$ | $R_9$ | $R_{14}$ |
|---|---|---|---|---|---|---|
| | | $C_2$ to $C_8$ alkenyl | | | | |
| K9 | —$CONHX_{10}$ | optionally substituted $C_2$ to $C_8$ alkenyl | $R_{7a}COO$— | $R_{2a}COO$— | $R_{9a}COO$— | OH |
| K10 | —$COOX_{10}$ | optionally substituted $C_2$ to $C_8$ alkynyl | $R_{7a}COO$— | $R_{2a}COO$— | $R_{9a}COO$— | OH |
| K11 | —$COX_{10}$ | optionally substituted $C_2$ to $C_8$ alkynyl | $R_{7a}COO$— | $R_{2a}COO$— | $R_{9a}COO$— | OH |
| K12 | —$CONHX_{10}$ | optionally substituted $C_2$ to $C_8$ alkynyl | $R_{7a}COO$— | $R_{2a}COO$— | $R_{9a}COO$— | OH |

EXAMPLE 5

In Vitro Cytotoxicity Measured by the Cell Colony Formation Assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 2 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 1351 | <1 |
| 1364 | <10 |
| 1372 | 26.1 |
| 1386 | <1 |
| 1393 | <1 |

-continued

| Compound | IN VITRO ID 50 (nm) HCT116 |
|---|---|
| 1401 | <1 |
| 1418 | <1 |
| 1424 | <1 |
| 1434 | <10 |
| 1447 | <10 |
| 1458 | <10 |
| 3069 | <1 |
| 3082 | <1 |
| 3171 | <1 |
| 3196 | <10 |
| 3232 | <1 |
| 3327 | <10 |
| 3388 | <10 |
| 3444 | <1 |
| 3479 | <1 |
| 3555 | <10 |
| 3560 | <1 |
| 3611 | <1 |
| 3629 | <1 |
| 3632 | <1 |
| 3708 | <1 |
| 3713 | <10 |
| 4017 | <10 |
| 4044 | <1 |
| 4106 | <10 |
| 4135 | <1 |
| 4175 | <10 |
| 4219 | 29.0 |
| 4256 | <1 |
| 4283 | <1 |
| 4290 | <10 |
| 4312 | <1 |
| 4388 | <1 |
| 4394 | <1 |
| 4406 | <1 |
| 4446 | <1 |

-continued

| Compound | IN VITRO ID 50 (nm) HCT116 |
|---|---|
| 4499 | <1 |
| 4544 | <10 |
| 4600 | <10 |
| 4616 | <1 |
| 4737 | <1 |
| 4757 | <1 |
| 6171 | <10 |
| 6131 | <1 |
| 5989 | <10 |
| 6141 | <1 |
| 6181 | <1 |
| 6040 | <10 |
| 6121 | <10 |
| 6424 | 21.7 |
| 6212 | <1 |
| 6282 | <10 |
| 6252 | <1 |
| 6343 | <10 |
| 6272 | <1 |
| 6202 | <1 |
| 4454 | <1 |
| 4414 | <1 |
| 6333 | <1 |
| 6686 | <1 |
| 6363 | <10 |
| 4787 | <10 |
| 4828 | <10 |
| 4898 | <1 |
| 4939 | <1 |
| 5020 | <1 |
| 5030 | <1 |
| 5191 | <10 |
| 5202 | <10 |
| 5070 | <10 |
| 5080 | <1 |
| 5121 | 21.1 |
| 5131 | <10 |

EXAMPLE 6

Preparation of Taxane having C-10 Ester and C-7 Hydroxy Substituents

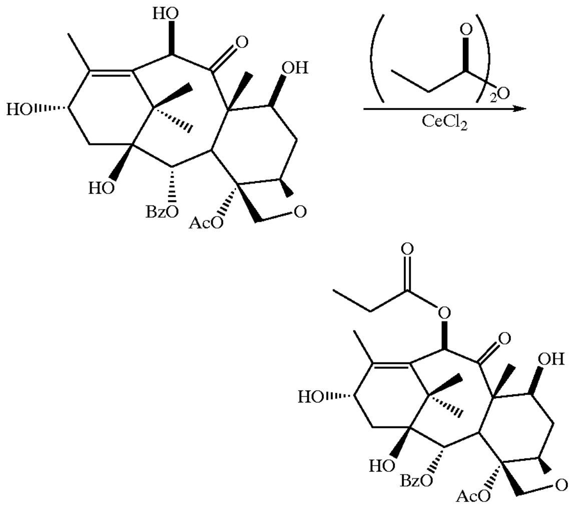

10-Propionyl-10-deacetyl baccatin III.

To a mixture of 0.2 g (0.367 mmol) of 10-deacetyl baccatin III and 0.272 g (1.10 mmol) of $CeCl_3$ in 10 mL of THF at 25° C. was added 2.35 mL (18.36 mmol) of propionic anhydride. After 30 min the reaction mixture was diluted with 200 mL of EtOAc, then washed three times with 50 mL of saturated aqueous $NaHCO_3$ solution and brine. The organic extract was dried over $Na_2SO_4$ and concentrated in vacuo. The crude solid was purified by flash column chromatography on silica gel using 70% EtOAc/hexane as eluent to give 0.199 g (90%) of 10-propionyl-10-deacetyl baccatin III as a solid.

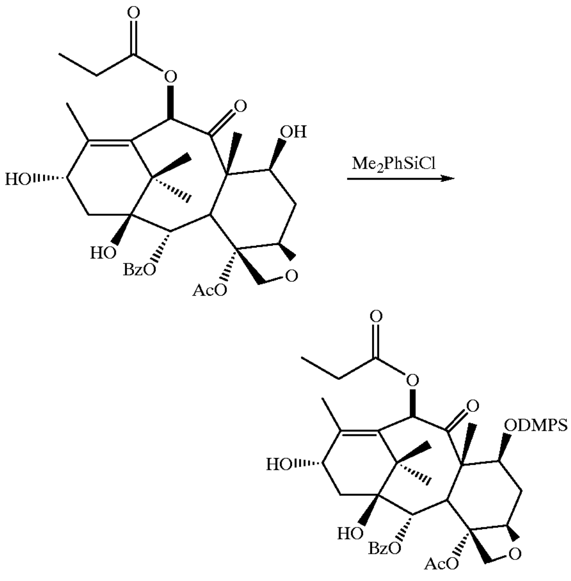

7-Dimethylphenylsilyl-10-propionyl-10-deacetyl baccatin III.

To a solution of 0.200 g (0.333 mmol) of 10-propionyl-10-deacetyl baccatin III in 12 mL of THF at −10° C. under a nitrogen atmosphere was added dropwise 0.668 mL (4.00 mmol) of chlorodimethyl-phenylsilane and 2.48 mL (30.64 mmol) of pyridine. After 90 min the mixture was diluted with 100 mL of a 1:1 mixture of ethyl acetate and hexane. The mixture was washed with 20 mL of saturated aqueous sodium bicarbonate solution and the organic layer separated. The aqueous layer was extracted with 30 mL of a 1:1 mixture of ethyl acetate and hexane, and the combined organic extracts were washed with brine, dried over $Na_2SO_4$, and concentrated in vacuo. The crude solid was purified by flash column chromatography on silica gel using 50% EtOAc/hexane as eluent to give 0.242 g (99%) of 7-dimethylphenylsilyl-10-propionyl-10-deacetyl baccatin III as a solid.

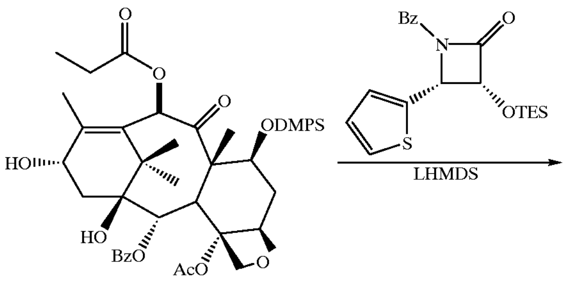

-continued

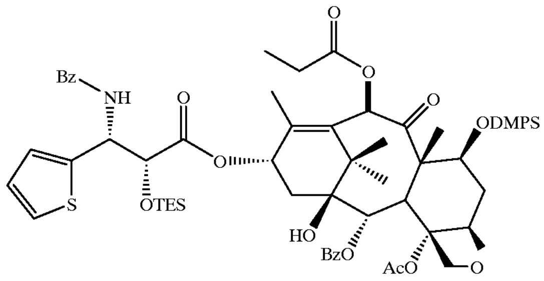

7-Dimethylphenylsilyl-2'-O-triethylsilyl-3'-desphenyl-3'-(2-thienyl)-10-propionyl-10-deacetyl taxol.

To a solution of 0.400 g (0.544 mmol) of 7-dimethylphenylsilyl-10-propionyl-10-deacetyl baccatin III in 5.5 mL of THF at −45° C. under a nitrogen atmosphere was added 0.681 mL (0.681 mmol) of a 1M solution of LHMDS in THF. After 1 h, a solution of 0.317 g (0.818 mmol) of cis-N-benzoyl-3-triethylsilyloxy-4-(2-thienyl) azetidin-2-one in 3 mL of THF was added slowly. The mixture was warmed to 0° C. and after 3 h 10 mL of saturated aqueous sodium bicarbonate solution was added and the mixture was extracted three times with 50 mL of ethyl acetate. The combined organic extracts were washed with brine, dried over $Na_2SO_4$, and concentrated in vacuo. The crude product was purified by flash column chromatography on silica gel using 40% EtOAc/hexane as eluent to give 0.531 g (87%) of 7-dimethylphenylsilyl-2'-O-triethylsilyl-3'-desphenyl-3'-(2-thienyl)-10-propionyl-10-deacetyl taxol as a solid.

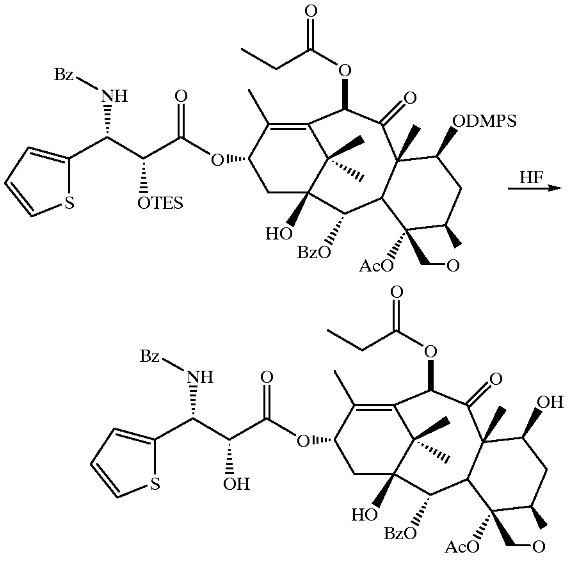

3'-Desphenyl-3'-(2-thienyl)-10-propionyl-10-deacetyl taxol.

To a solution of 0.521 g (0.464 mmol) of 7-dimethylphenylsilyl-2'-O-triethylsilyl-3'-desphenyl-3'-(2-thienyl)-10-propionyl-10-deacetyl taxol in 2 mL of CH3CN and 2 mL of pyridine at 0° C. was added 0.5 mL of a solution of 30% HF in $H_2O$. After 3 h 20 mL of a saturated aqueous sodium bicarbonate solution was added and the mixture was extracted three times with 50 mL of ethyl acetate. The combined organic extracts were washed with brine, dried over $Na_2SO_4$, and concentrated in vacuo. The crude product was purified by flash column chromatography on silica gel using 70% EtOAc/hexane as eluent to give 0.405 g (100%)

of 3'-desphenyl-3'-(2-thienyl)-10-propionyl-10-deacetyl taxol as a solid. m.p. 154–155° C.; $[a]_D^{25}$=−45.0 (c 0.1 in CHCl3); Anal. Calcd. for $C_{46}H_{51}NO_{14}S$: C, 63.22; H, 5.88; Found: C, 62.94; H, 5.97.

3'-Desphenyl-3'-(2-thienyl)-10-propionyl-10-deacetyl taxol
$^1$H NMR data ($CDCl_3$)

| Proton | ppm | pattern | J (Hz) |
|---|---|---|---|
| 2' | 4.78 | dd | H3'(2.1), 2'OH(4.1) |
| 2'OH | 3.51 | d | H2'(4.1) |
| 3' | 6.07 | dd | NH(8.6), H2'(2.1) |
| 5' | 7.04 | dd | (3.5), (5.0) |
| 1OH | 1.68 | s | |
| 2 | 5.69 | d | H3(7.0) |
| 3 | 3.85 | d | H2(7.0) |
| 4Ac | 2.42 | s | |
| 5 | 4.96 | app d | |
| 6a | 2.45–2.60 | app m | |
| 6b | 1.89 | ddd | H7(1 0.9), H5(2.5), H6a(14.5) |
| 7 | 4.42 | ddd | 7OH(4.2), H6a(6.8), H6b(10.8) |
| 7OH | 2.45–2.60 | app m | |
| 10 | 6.32 | s | |
| 13 | 6.27 | app t | H14a,b(9.0) |
| 14a | 2.40–2.43 | app m | |
| 14b | 2.34 | dd | H14a(15.5), H13(9.0) |
| Me 16 | 1.16 | s | |
| Me 17 | 1.25 | app m | |
| Me 18 | 1.84 | s | |
| Me 19 | 1.70 | s | |
| 20a | 4.31 | d | H20b(8.5) |
| 20b | 4.22 | d | H20a(8.5) |
| o-benzoate | 8.14–8.16 | m | |
| o-benzamide | 7.72–7.73 | m | |
| NH | 6.88 | d | H3'(8.6) |
| C<u>H</u>3CH2 | 1.24 | t | CH3C<u>H</u>2(7.0) |
| CH3C<u>H</u>2 | 2.45–2.60 | app m | |

EXAMPLE 7

Additional Taxanes having C-10 Ester and C-7 Hydroxy Substituents

The procedures described in Example 6 were repeated, but other suitably protected β-lactams were substituted for the β-lactam of Example 6 to prepare the series of compounds having structural formula (6) and the combinations of substituents identified in the following table.

(6)

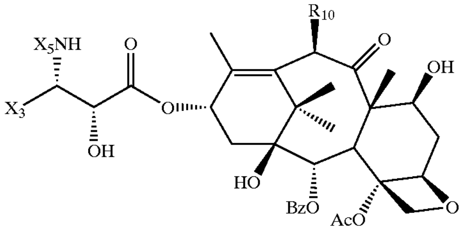

| Compound | $X_5$ | $X_3$ | $R_{10}$ |
|---|---|---|---|
| 0499 | tBuOCO— | isobutenyl | EtCOO— |

-continued (6)

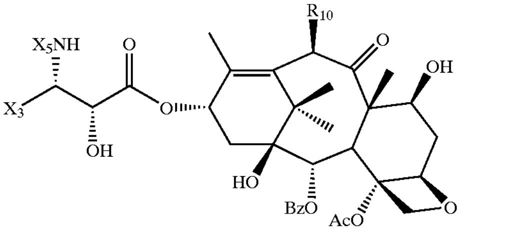

| Compound | $X_5$ | $X_3$ | $R_{10}$ |
|---|---|---|---|
| 0503 | tBuOCO— | 2-pyridyl | EtCOO— |
| 0517 | tBuOCO— | 3-pyridyl | EtCOO— |
| 0521 | tBuOCO— | 4-pyridyl | EtCOO— |
| 0536 | tBuOCO— | 2-furyl | EtCOO— |
| 0549 | tBuOCO— | 3-furyl | EtCOO— |
| 0550 | tBuOCO— | 2-thienyl | EtCOO— |
| 0562 | tBuOCO— | 3-thienyl | EtCOO— |
| 0578 | tBuOCO— | cyclopropyl | EtCOO— |
| 0583 | tBuOCO— | isopropyl | EtCOO— |
| 0596 | tBuOCO— | cyclobutyl | EtCOO— |
| 0602 | tBuOCO— | p-nitrophenyl | EtCOO— |
| 0611 | tBuOCO— | phenyl | EtCOO— |
| 0625 | PhCO— | isobutenyl | EtCOO— |
| 0634 | PhCO— | 2-pyridyl | EtCOO— |
| 0647 | PhCO— | 3-pyridyl | EtCOO— |
| 0659 | PhCO— | 4-pyridyl | EtCOO— |
| 0663 | PhCO— | 2-furyl | EtCOO— |
| 0670 | PhCO— | 3-furyl | EtCOO— |
| 0687 | PhCO— | 2-thienyl | EtCOO— |
| 0691 | PhCO— | 3-thienyl | EtCOO— |
| 0706 | PhCO— | cyclopropyl | EtCOO— |
| 0719 | PhCO— | isopropyl | EtCOO— |
| 0720 | PhCO— | cyclobutyl | EtCOO— |
| 0732 | PhCO— | p-nitrophenyl | EtCOO— |
| 0748 | PhCO— | phenyl | EtCOO— |
| 0838 | tBuOCO— | isobutenyl | cproCOO— |
| 0843 | tBuOCO— | 2-furyl | cproCOO— |
| 0854 | tBuOCO— | 2-thienyl | cproCOO— |
| 0860 | tBuOCO— | cyclopropyl | cproCOO— |
| 0879 | tBuOCO— | p-nitrophenyl | cproCOO— |
| 0882 | tBuOCO— | phenyl | cproCOO— |
| 0890 | PhCO— | isobutenyl | cproCOO— |
| 0908 | PhCO— | 2-furyl | cproCOO— |
| 0919 | PhCO— | 2-thienyl | cproCOO— |
| 0923 | PhCO— | cyclopropyl | cproCOO— |
| 0937 | PhCO— | phenyl | cproCOO— |
| 0947 | tBuOCO— | isobutenyl | PrCOO— |
| 0951 | tBuOCO— | 2-pyridyl | PrCOO— |
| 0966 | tBuOCO— | 3-pyridyl | PrCOO— |
| 0978 | tBuOCO— | 4-pyridyl | PrCOO— |
| 0983 | tBuOCO— | 2-furyl | PrCOO— |
| 0999 | tBuOCO— | 3-furyl | PrCOO— |
| 1003 | tBuOCO— | 2-thienyl | PrCOO— |
| 1011 | tBuOCO— | 3-thienyl | PrCOO— |
| 1020 | tBuOCO— | cyclopropyl | PrCOO— |
| 1031 | tBuOCO— | isopropyl | PrCOO— |
| 1044 | tBuOCO— | cyclobutyl | PrCOO— |
| 1060 | tBuOCO— | phenyl | PrCOO— |
| 1879 | tBuOCO— | isobutenyl | 2-ThCOO— |
| 1883 | tBuOCO— | 2-pyridyl | 2-ThCOO— |
| 1892 | tBuOCO— | 2-furyl | 2-ThCOO— |
| 1900 | tBuOCO— | 2-thienyl | 2-ThCOO— |
| 1911 | tBuOCO— | p-nitrophenyl | 2-ThCOO— |
| 1923 | tBuOCO— | 3-furyl | 2-ThCOO— |
| 1939 | tBuOCO— | 3-thienyl | 2-ThCOO— |
| 1948 | tBuOCO— | 3-pyridyl | 2-ThCOO— |
| 1954 | tBuOCO— | 4-pyridyl | 2-ThCOO— |
| 1964 | tBuOCO— | isopropyl | 2-ThCOO— |
| 1970 | tBuOCO— | cyclobutyl | 2-ThCOO— |
| 1988 | tBuOCO— | phenyl | 2-ThCOO— |
| 2101 | tBuOCO— | isobutenyl | 2-FuCOO— |
| 2111 | tBuOCO— | 2-pyridyl | 2-FuCOO— |
| 2124 | tBuOCO— | 3-pyridyl | 2-FuCOO— |
| 2132 | tBuOCO— | 4-pyridyl | 2-FuCOO— |

-continued (6)

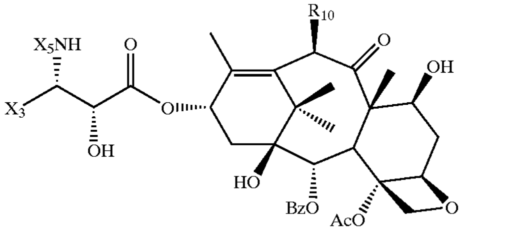

| Compound | $X_5$ | $X_3$ | $R_{10}$ |
|---|---|---|---|
| 2142 | tBuOCO— | 2-furyl | 2-FuCOO— |
| 2159 | tBuOCO— | 3-furyl | 2-FuCOO— |
| 2164 | tBuOCO— | 2-thienyl | 2-FuCOO— |
| 2173 | tBuOCO— | 3-thienyl | 2-FuCOO— |
| 2181 | tBuOCO— | isopropyl | 2-FuCOO— |
| 2199 | tBuOCO— | cyclobutyl | 2-FuCOO— |
| 2202 | tBuOCO— | p-nitrophenyl | 2-FuCOO— |
| 2212 | tBuOCO— | phenyl | 2-FuCOO— |
| 2226 | tBuOCO— | isobutenyl | iPrCOO— |
| 2238 | tBuOCO— | 2-pyridyl | iPrCOO— |
| 2242 | tBuOCO— | 3-pyridyl | iPrCOO— |
| 2255 | tBuOCO— | 4-pyridyl | iPrCOO— |
| 2269 | tBuOCO— | 2-furyl | iPrCOO— |
| 2273 | tBuOCO— | 3-furyl | iPrCOO— |
| 2287 | tBuOCO— | 2-thienyl | iPrCOO— |
| 2291 | tBuOCO— | 3-thienyl | iPrCOO— |
| 2306 | tBuOCO— | isopropyl | iPrCOO— |
| 2319 | tBuOCO— | cyclobutyl | iPrCOO— |
| 2320 | tBuOCO— | p-nitrophenyl | iprCOO— |
| 2332 | tBuOCO— | isobutenyl | $tC_3H_5COO$— |
| 2348 | tBuOCO— | 2-pyridyl | $tC_3H_5COO$— |
| 2353 | tBuOCO— | 3-pyridyl | $tC_3H_5COO$— |
| 2366 | tBuOCO— | 4-pyridyl | $tC_3H_5COO$— |
| 2379 | tBuOCO— | 2-furyl | $tC_3H_5COO$— |
| 2380 | tBuOCO— | 3-furyl | $tC_3H_5COO$— |
| 2392 | tBuOCO— | 2-thienyl | $tC_3H_5COO$— |
| 2408 | tBuOCO— | 3-thienyl | $tC_3H_5COO$— |
| 2413 | tBuOCO— | isopropyi | $tC_3H_5COO$— |
| 2424 | tBuOCO— | cyclobutyl | $tC_3H_5COO$— |
| 2439 | tBuOCO— | p-nitrophenyl | $tC_3H_5COO$— |
| 2442 | tBuOCO— | phenyl | $tC_3H_5COO$— |
| 2455 | tBuOCO— | isobutenyl | ibueCOO— |
| 2464 | tBuOCO— | 2-pyridyl | ibueCOO— |
| 2472 | tBuOCO— | 4-pyridyl | ibueCOO— |
| 2488 | tBuOCO— | 2-furyl | ibueCOO— |
| 2499 | tBuOCO— | 3-furyl | ibueCOO— |
| 2503 | tBuOCO— | 2-thienyl | ibueCOO— |
| 2511 | tBuOCO— | 3-thienyl | ibueCOO— |
| 2520 | tBuOCO— | phenyl | ibueCOO— |
| 2781 | tBuOCO— | 3-furyl | cproCOO— |
| 2794 | tBuOCO— | 3-thienyl | cproCOO— |
| 2802 | tBuOCO— | 2-pyridyl | cproCOO— |
| 2813 | tBuOCO— | 4-pyridyl | cproCOO— |
| 2826 | PhCO— | 3-furyl | cproCOO— |
| 2838 | PhCO— | 3-thienyl | cproCOO— |
| 2844 | PhCO— | 2-pyridyl | cproCOO— |
| 2855 | PhCO— | 4-pyridyl | cproCOO— |
| 2869 | PhCO— | p-nitrophenyl | cproCOO— |
| 3053 | 2-FuCO— | 2-thienyl | EtCOO— |
| 3071 | iPrOCO— | 2-thienyl | cproCOO— |
| 3096 | EtCOO— | 2-thienyl | PrCOO— |
| 3102 | iBuOCO— | 2-furyl | cproCOO— |
| 3110 | iBuOCO— | 2-furyl | PrCOO— |
| 3129 | iBuOCO— | 2-thienyl | cproCOO— |
| 3132 | nPrCO— | 2-thienyl | cproCOO— |
| 3148 | nPrCO— | 2-thienyl | PrCOO— |
| 3163 | iBuOCO— | 2-thienyl | EtCOO— |
| 3204 | PhCO— | 2-furyl | PrCOO— |
| 3219 | nPrCO— | 2-furyl | EtCOO— |
| 3222 | nPrCO— | 2-furyl | PrCOO— |
| 3258 | PhCO— | 2-thienyl | PrCOO— |
| 3265 | iBuOCO— | 2-thienyl | PrCOO— |
| 3297 | 2-FuCO— | 2-thienyl | cproCOO— |
| 3314 | nPrCO— | 2-thienyl | PrCOO— |

-continued (6)

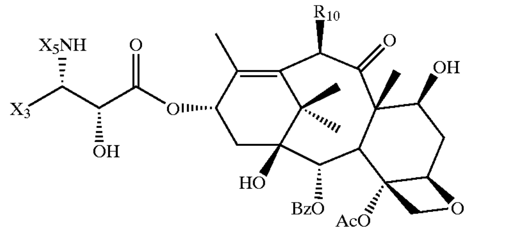

| Compound | $X_5$ | $X_3$ | $R_{10}$ |
|---|---|---|---|
| 3352 | 2-FuCO— | 2-thienyl | PrCOO— |
| 3361 | iPrOCO— | 2-thienyl | EtCOO— |
| 3370 | EtOCO— | 2-thienyl | EtCOO— |
| 3408 | 2-ThCO— | 2-thienyl | PrCOO— |
| 3417 | iPrOCO— | 2-furyl | PrCOO— |
| 3425 | 2-ThCO— | 2-thienyl | EtCOO— |
| 3453 | 2-ThCO— | 2-thienyl | cproCOO— |
| 3482 | PhCO— | cyclopropyl | PrCOO— |
| 3494 | $tC_3H_5CO$— | 2-thienyl | EtCOO— |
| 3513 | $tC_3H_5CO$— | 2-thienyl | cproCOO— |
| 3522 | iPrOCO— | 2-furyl | EtCOO— |
| 3535 | EtOCO— | 2-furyl | EtCOO— |
| 3543 | $C_4H_7CO$— | 2-thienyl | cproCOO— |
| 3588 | $C_4H_7CO$— | 2-thienyl | EtCOO— |
| 3595 | $tC_3H_5CO$— | 2-thienyl | PrCOO— |
| 3603 | $C_4H_7CO$— | 2-thienyl | PrCOO— |
| 3644 | 2-ThCO— | 2-furyl | EtCOO— |
| 3656 | 2-ThCO— | 2-furyl | PrCOO— |
| 3663 | 2-ThCO— | 2-furyl | cproCOO— |
| 3677 | EtOCO— | 2-furyl | cproCOO— |
| 3686 | 2-FuCO— | 2-furyl | PrCOO— |
| 3693 | EtOCO— | 2-furyl | PrCOO— |
| 3800 | $C_4H_7CO$— | 2-furyl | PrCOO— |
| 3818 | 2-FuCO— | 2-furyl | EtCOO— |
| 3853 | iPrOCO— | 2-furyl | cproCOO— |
| 3866 | 2-FuCO— | 2-furyl | cproCOO— |
| 3909 | iPrOCO— | 2-thienyl | PrCOO— |
| 3938 | $C_4H_7CO$— | 2-furyl | cproCOO— |
| 3945 | $C_4H_7CO$— | 2-furyl | EtCOO— |
| 3957 | iBuOCO— | 2-furyl | PrCOO— |
| 3971 | $tC_3H_5CO$— | 2-furyl | cproCOO— |
| 3982 | $tC_3H_5CO$— | 2-furyl | EtCOO— |
| 3994 | $tC_3H_5CO$— | 2-furyl | PrCOO— |
| 4051 | EtOCO— | 2-thienyl | cproCOO— |
| 4062 | nPrCO— | 2-furyl | cproCOO— |
| 4112 | 3-PyCO— | 2-thienyl | cproCOO— |
| 4121 | 3-PyCO— | 2-thienyl | EtCOO— |
| 4190 | 3-PyCO— | 2-thienyl | PrCOO— |
| 4207 | 4-PyCO— | 2-thienyl | EtCOO— |
| 4329 | ibueCO— | 2-thienyl | cproCOO— |
| 4335 | ibueCO— | 2-thienyl | EtCOO— |
| 4344 | ibueCO— | 2-thienyl | PrCOO— |
| 4665 | iBuOCO— | 3-furyl | cproCOO— |
| 4704 | iBuOCO— | 3-furyl | PrCOO— |
| 4711 | iBuOCO— | 3-thienyl | EtCOO— |
| 4720 | iBuOCO— | isobutenyl | cproCOO— |
| 4799 | iBuOCO— | cyclopropyl | EtCOO— |
| 4808 | iBuOCO— | cyclopropyl | nPrCOO— |
| 4834 | iBuOCO— | 3-thienyl | nPrCOO— |
| 4888 | $tC_3H_5CO$— | 3-furyl | EtCOO— |
| 4919 | $tC_3H_5CO$— | 3-furyl | nPrCOO— |
| 4944 | $tC_3H_5CO$— | 3-furyl | cproCOO— |
| 5011 | iBuOCO— | 3-thienyl | cproCOO— |
| 5040 | $tC_3H_5CO$— | 3-thienyl | cproCOO— |
| 5065 | iBuOCO— | isobutenyl | EtCOO— |
| 5144 | iBuOCO— | isobutenyl | nPrCOO— |
| 5232 | iBuOCO— | cyclopropyl | cproCOO— |
| 5495 | tBuOCO— | 3-furyl | EtCOO— |
| 6522 | tAmOCO— | 2-furyl | EtCOO— |

EXAMPLE 8

Additional Taxanes having C-10 Ester and C-7 Hydroxy Substituents

Following the processes described in Example 6 and elsewhere herein, the following specific taxanes having structural formula (7) may be prepared wherein $R_{10}$ is as previously defined, including wherein $R_{10}$ is $R_a$COO— and $R_a$ is (i) substituted or unsubstituted $C_2$ to $C_8$ alkyl such as ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl. The substituents may be those identified elsewhere herein for substituted hydrocarbyl. In one embodiment, $R_{10}$ may be $R_{10a}$COO— wherein $R_{10a}$ is ethyl, straight, branched or cyclic propyl, straight or branched propenyl, isobutenyl, furyl or thienyl.

(7)

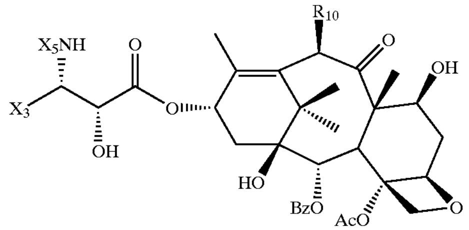

| $X_5$ | $X_3$ | $R_{10}$ |
|---|---|---|
| tBuOCO— | 2-furyl | $R_a$COO— |
| tBuOCO— | 3-furyl | $R_a$COO— |
| tBuOCO— | 2-thienyl | $R_a$COO— |
| tBuOCO— | 3-thienyl | $R_a$COO— |
| tBuOCO— | 2-pyridyl | $R_a$COO— |
| tBuOCO— | 3-pyridyl | $R_a$COO— |
| tBuOCO— | 4-pyridyl | $R_a$COO— |
| tBuOCO— | isobutenyl | $R_a$COO— |
| tBuOCO— | isopropyl | $R_a$COO— |
| tBuOCO— | cyclopropyl | $R_a$COO— |
| tBuOCO— | cyclobutyl | $R_a$COO— |
| tBuOCO— | cyclopentyl | $R_a$COO— |
| tBuOCO— | phenyl | $R_a$COO— |
| benzoyl | 2-furyl | $R_a$COO— |
| benzoyl | 3-furyl | $R_a$COO— |
| benzoyl | 2-thienyl | $R_a$COO— |
| benzoyl | 3-thienyl | $R_a$COO— |
| benzoyl | 2-pyridyl | $R_a$COO— |
| benzoyl | 3-pyridyl | $R_a$COO— |
| benzoyl | 4-pyridyl | $R_a$COO— |
| benzoyl | isobutenyl | $R_a$COO— |
| benzoyl | isopropyl | $R_a$COO— |
| benzoyl | cyclopropyl | $R_a$COO— |
| benzoyl | cyclobutyl | $R_a$COO— |
| benzoyl | cyclopentyl | $R_a$COO— |
| benzoyl | phenyl | $R_a$COO— |
| 2-FuCO— | 2-furyl | $R_a$COO— |
| 2-FuCO— | 3-furyl | $R_a$COO— |
| 2-FuCO— | 2-thienyl | $R_a$COO— |
| 2-FuCO— | 3-thienyl | $R_a$COO— |
| 2-FuCO— | 2-pyridyl | $R_a$COO— |
| 2-FuCO— | 3-pyridyl | $R_a$COO— |
| 2-FuCO— | 4-pyridyl | $R_a$COO— |
| 2-FuCO— | isobutenyl | $R_a$COO— |
| 2-FuCO— | isopropyl | $R_a$COO— |
| 2-FuCO— | cyclopropyl | $R_a$COO— |

-continued (7)

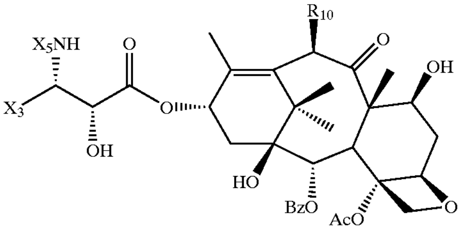

| $X_5$ | $X_3$ | $R_{10}$ |
|---|---|---|
| 2-FuCO— | cyclobutyl | $R_aCOO$— |
| 2-FuCO— | cyclopentyl | $R_aCOO$— |
| 2-FuCO— | phenyl | $R_aCOO$— |
| 2-ThCO— | 2-furyl | $R_aCOO$— |
| 2-ThCO— | 3-furyl | $R_aCOO$— |
| 2-ThCO— | 2-thienyl | $R_aCOO$— |
| 2-ThCO— | 3-thienyl | $R_aCOO$— |
| 2-ThCO— | 2-pyridyl | $R_aCOO$— |
| 2-ThCO— | 3-pyridyl | $R_aCOO$— |
| 2-ThCO— | 4-pyridyl | $R_aCOO$— |
| 2-ThCO— | isobutenyl | $R_aCOO$— |
| 2-ThCO— | isopropyl | $R_aCOO$— |
| 2-ThCO— | cyclopropyl | $R_aCOO$— |
| 2-ThCO— | cyclobutyl | $R_aCOO$— |
| 2-ThCO— | cyclopentyl | $R_aCOO$— |
| 2-ThCO— | phenyl | $R_aCOO$— |
| 2-PyCO— | 2-furyl | $R_aCOO$— |
| 2-PyCO— | 3-furyl | $R_aCOO$— |
| 2-PyCO— | 2-thienyl | $R_aCOO$— |
| 2-PyCO— | 3-thienyl | $R_aCOO$— |
| 2-PyCO— | 2-pyridyl | $R_aCOO$— |
| 2-PyCO— | 3-pyridyl | $R_aCOO$— |
| 2-PyCO— | 4-pyridyl | $R_aCOO$— |
| 2-PyCO— | isobutenyl | $R_aCOO$— |
| 2-PyCO— | isopropyl | $R_aCOO$— |
| 2-PyCO— | cyclopropyl | $R_aCOO$— |
| 2-PyCO— | cyclobutyl | $R_aCOO$— |
| 2-PyCO— | cyclopentyl | $R_aCOO$— |
| 2-PyCO— | phenyl | $R_aCOO$— |
| 3-PyCO— | 2-furyl | $R_aCOO$— |
| 3-PyCO— | 3-furyl | $R_aCOO$— |
| 3-PyCO— | 2-thienyl | $R_aCOO$— |
| 3-PyCO— | 3-thienyl | $R_aCOO$— |
| 3-PyCO— | 2-pyridyl | $R_aCOO$— |
| 3-PyCO— | 3-pyridyl | $R_aCOO$— |
| 3-PyCO— | 4-pyridyl | $R_aCOO$— |
| 3-PyCO— | isobutenyl | $R_aCOO$— |
| 3-PyCO— | isopropyl | $R_aCOO$— |
| 3-PyCO— | cyclopropyl | $R_aCOO$— |
| 3-PyCO— | cyclobutyl | $R_aCOO$— |
| 3-PyCO— | cyclopentyl | $R_aCOO$— |
| 3-PyCO— | phenyl | $R_aCOO$— |
| 4-PyCO— | 2-furyl | $R_aCOO$— |
| 4-PyCO— | 3-furyl | $R_aCOO$— |
| 4-PyCO— | 2-thienyl | $R_aCOO$— |
| 4-PyCO— | 3-thienyl | $R_aCOO$— |
| 4-PyCO— | 2-pyridyl | $R_aCOO$— |
| 4-PyCO— | 3-pyridyl | $R_aCOO$— |
| 4-PyCO— | 4-pyridyl | $R_aCOO$— |
| 4-PyCO— | isobutenyl | $R_aCOO$— |
| 4-PyCO— | isopropyl | $R_aCOO$— |
| 4-PyCO— | cyclopropyl | $R_aCOO$— |
| 4-PyCO— | cyclobutyl | $R_aCOO$— |
| 4-PyCO— | cyclopentyl | $R_aCOO$— |
| 4-PyCO— | phenyl | $R_aCOO$— |
| $C_4H_7CO$— | 2-furyl | $R_aCOO$— |
| $C_4H_7CO$— | 3-furyl | $R_aCOO$— |
| $C_4H_7CO$— | 2-thienyl | $R_aCOO$— |
| $C_4H_7CO$— | 3-thienyl | $R_aCOO$— |
| $C_4H_7CO$— | 2-pyridyl | $R_aCOO$— |
| $C_4H_7CO$— | 3-pyridyl | $R_aCOO$— |
| $C_4H_7CO$— | 4-pyridyl | $R_aCOO$— |
| $C_4H_7CO$— | isobutenyl | $R_aCOO$— |

-continued (7)

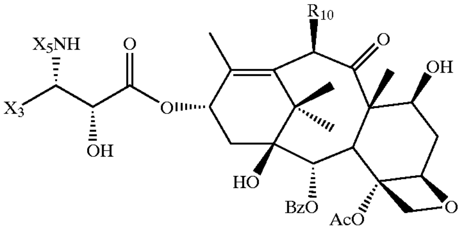

| $X_5$ | $X_3$ | $R_{10}$ |
|---|---|---|
| $C_4H_7CO$— | isopropyl | $R_aCOO$— |
| $C_4H_7CO$— | cyclopropyl | $R_aCOO$— |
| $C_4H_7CO$— | cyclobutyl | $R_aCOO$— |
| $C_4H_7CO$— | cyclopentyl | $R_aCOO$— |
| $C_4H_7CO$— | phenyl | $R_aCOO$— |
| EtOCO— | 2-furyl | $R_aCOO$— |
| EtOCO— | 3-furyl | $R_aCOO$— |
| EtOCO— | 2-thienyl | $R_aCOO$— |
| EtOCO— | 3-thienyl | $R_aCOO$— |
| EtOCO— | 2-pyridyl | $R_aCOO$— |
| EtOCO— | 3-pyridyl | $R_aCOO$— |
| EtOCO— | 4-pyridyl | $R_aCOO$— |
| EtOCO— | isobutenyl | $R_aCOO$— |
| EtOCO— | isopropyl | $R_aCOO$— |
| EtOCO— | cyclopropyl | $R_aCOO$— |
| EtOCO— | cyclobutyl | $R_aCOO$— |
| EtOCO— | cyclopentyl | $R_aCOO$— |
| EtOCO— | phenyl | $R_aCOO$— |
| ibueCO— | 2-furyl | $R_aCOO$— |
| ibueCO— | 3-furyl | $R_aCOO$— |
| ibueCO— | 2-thienyl | $R_aCOO$— |
| ibueCO— | 3-thienyl | $R_aCOO$— |
| ibueCO— | 2-pyridyl | $R_aCOO$— |
| ibueCO— | 3-pyridyl | $R_aCOO$— |
| ibueCO— | 4-pyridyl | $R_aCOO$— |
| ibueCO— | isobutenyl | $R_aCOO$— |
| ibueCO— | isopropyl | $R_aCOO$— |
| ibueCO— | cyclopropyl | $R_aCOO$— |
| ibueCO— | cyclobutyl | $R_aCOO$— |
| ibueCO— | cyclopentyl | $R_aCOO$— |
| ibueCO— | phenyl | $R_aCOO$— |
| iBuCO— | 2-furyl | $R_aCOO$— |
| iBuCO— | 3-furyl | $R_aCOO$— |
| iBuCO— | 2-thienyl | $R_aCOO$— |
| iBuCO— | 3-thienyl | $R_aCOO$— |
| iBuCO— | 2-pyridyl | $R_aCOO$— |
| iBuCO— | 3-pyridyl | $R_aCOO$— |
| iBuCO— | 4-pyridyl | $R_aCOO$— |
| iBuCO— | isobutenyl | $R_aCOO$— |
| iBuCO— | isopropyl | $R_aCOO$— |
| iBuCO— | cyclopropyl | $R_aCOO$— |
| iBuCO— | cyclobutyl | $R_aCOO$— |
| iBuCO— | cyclopentyl | $R_aCOO$— |
| iBuCO— | phenyl | $R_aCOO$— |
| iBuOCO— | 2-furyl | $R_aCOO$— |
| iBuOCO— | 3-furyl | $R_aCOO$— |
| iBuOCO— | 2-thienyl | $R_aCOO$— |
| iBuOCO— | 3-thienyl | $R_aCOO$— |
| iBuOCO— | 2-pyridyl | $R_aCOO$— |
| iBuOCO— | 3-pyridyl | $R_aCOO$— |
| iBuOCO— | 4-pyridyl | $R_aCOO$— |
| iBuOCO— | isobutenyl | $R_aCOO$— |
| iBuOCO— | isopropyl | $R_aCOO$— |
| iBuOCO— | cyclopropyl | $R_aCOO$— |
| iBuOCO— | cyclobutyl | $R_aCOO$— |
| iBuOCO— | cyclopentyl | $R_aCOO$— |
| iBuCO— | phenyl | $R_aCOO$— |
| iPrOCO— | 2-furyl | $R_aCOO$— |
| iPrOCO— | 3-furyl | $R_aCOO$— |
| iPrOCO— | 2-thienyl | $R_aCOO$— |
| iPrOCO— | 3-thienyl | $R_aCOO$— |
| iPrOCO— | 2-pyridyl | $R_aCOO$— |
| iPrOCO— | 3-pyridyl | $R_aCOO$— |

-continued (7)

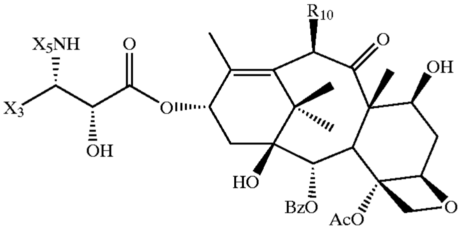

| $X_5$ | $X_3$ | $R_{10}$ |
|---|---|---|
| iPrOCO— | 4-pyridyl | $R_aCOO$— |
| iPrOCO— | isobutenyl | $R_aCOO$— |
| iPrOCO— | isopropyl | $R_aCOO$— |
| iPrOCO— | cyclopropyl | $R_aCOO$— |
| iPrOCO— | cyclobutyl | $R_aCOO$— |
| iPrOCO— | cyclopentyl | $R_aCOO$— |
| iPrOCO— | phenyl | $R_aCOO$— |
| nPrOCO— | 2-furyl | $R_aCOO$— |
| nPrOCO— | 3-furyl | $R_aCOO$— |
| nPrOCO— | 2-thienyl | $R_aCOO$— |
| nPrOCO— | 3-thienyl | $R_aCOO$— |
| nPrOCO— | 2-pyridyl | $R_aCOO$— |
| nPrOCO— | 3-pyridyl | $R_aCOO$— |
| nPrOCO— | 4-pyridyl | $R_aCOO$— |
| nPrOCO— | isobutenyl | $R_aCOO$— |
| nPrOCO— | isopropyl | $R_aCOO$— |
| nPrOCO— | cyclopropyl | $R_aCOO$— |
| nPrOCO— | cyclobutyl | $R_aCOO$— |
| nPrOCO— | cyclopentyl | $R_aCOO$— |
| nPrOCO— | phenyl | $R_aCOO$— |
| nPrCO— | 2-furyl | $R_aCOO$— |
| nPrCO— | 3-furyl | $R_aCOO$— |
| nPrCO— | 2-thienyl | $R_aCOO$— |
| nPrCO— | 3-thienyl | $R_aCOO$— |
| nPrCO— | 2-pyridyl | $R_aCOO$— |
| nPrCO— | 3-pyridyl | $R_aCOO$— |
| nPrCO— | 4-pyridyl | $R_aCOO$— |
| nPrCO— | isobutenyl | $R_aCOO$— |
| nPrCO— | isopropyl | $R_aCOO$— |
| nPrCO— | cyclopropyl | $R_aCOO$— |
| nPrCO— | cyclobutyl | $R_aCOO$— |
| nPrCO— | cyclopentyl | $R_aCOO$— |
| nPrOCO— | phenyl | $R_aCOO$— |
| tBuOCO— | cyclopentyl | EtCOO— |
| benzoyl | cyclopentyl | EtCOO— |
| 2-FuCO— | 3-furyl | EtCOO— |
| 2-FuCO— | 3-thienyl | EtCOO— |
| 2-FuCO— | 2-pyridyl | EtCOO— |
| 2-FuCO— | 3-pyridyl | EtCOO— |
| 2-FuCO— | 4-pyridyl | EtCOO— |
| 2-FuCO— | isobutenyl | EtCOO— |
| 2-FuCO— | isopropyl | EtCOO— |
| 2-FuCO— | cyclopropyl | EtCOO— |
| 2-FuCO— | cyclobutyl | EtCOO— |
| 2-FuCO— | cyclopentyl | EtCOO— |
| 2-FuCO— | phenyl | EtCOO— |
| 2-ThCO— | 3-furyl | EtCOO— |
| 2-ThCO— | 3-thienyl | EtCOO— |
| 2-ThCO— | 2-pyridyl | EtCOO— |
| 2-ThCO— | 3-pyridyl | EtCOO— |
| 2-ThCO— | 4-pyridyl | EtCOO— |
| 2-ThCO— | isobutenyl | EtCOO— |
| 2-ThCO— | isopropyl | EtCOO— |
| 2-ThCO— | cyclopropyl | EtCOO— |
| 2-ThCO— | cyclobutyl | EtCOO— |
| 2-ThCO— | cyclopentyl | EtCOO— |
| 2-ThCO— | phenyl | EtCOO— |
| 2-PyCO— | 2-furyl | EtCOO— |
| 2-PyCO— | 3-furyl | EtCOO— |
| 2-PyCO— | 2-thienyl | EtCOO— |
| 2-PyCO— | 3-thienyl | EtCOO— |
| 2-PyCO— | 2-pyridyl | EtCOO— |
| 2-PyCO— | 3-pyridyl | EtCOO— |

-continued (7)

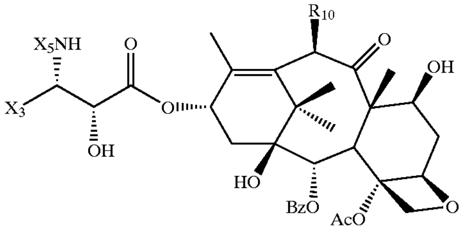

| $X_5$ | $X_3$ | $R_{10}$ |
|---|---|---|
| 2-PyCO— | 4-pyridyl | EtCOO— |
| 2-PyCO— | isobutenyl | EtCOO— |
| 2-PyCO— | isopropyl | EtCOO— |
| 2-PyCO— | cyclopropyl | EtCOO— |
| 2-PyCO— | cyclobutyl | EtCOO— |
| 2-PyCO— | cyclopentyl | EtCOO— |
| 2-PyCO— | phenyl | EtCOO— |
| 3-PyCO— | 2-furyl | EtCOO— |
| 3-PyCO— | 3-furyl | EtCOO— |
| 3-PyCO— | 3-thienyl | EtCOO— |
| 3-PyCO— | 2-pyridyl | EtCOO— |
| 3-PyCO— | 3-pyridyl | EtCOO— |
| 3-PyCO— | 4-pyridyl | EtCOO— |
| 3-PyCO— | isobutenyl | EtCOO— |
| 3-PyCO— | isopropyl | EtCOO— |
| 3-PyCO— | cyclopropyl | EtCOO— |
| 3-PyCO— | cyclobutyl | EtCOO— |
| 3-PyCO— | cyclopentyl | EtCOO— |
| 3-PyCO— | phenyl | EtCOO— |
| 4-PyCO— | 2-furyl | EtCOO— |
| 4-PyCO— | 3-furyl | EtCOO— |
| 4-PyCO— | 3-thienyl | EtCOO— |
| 4-PyCO— | 2-pyridyl | EtCOO— |
| 4-PyCO— | 3-pyridyl | EtCOO— |
| 4-PyCO— | 4-pyridyl | EtCOO— |
| 4-PyCO— | isobutenyl | EtCOO— |
| 4-PyCO— | isopropyl | EtCOO— |
| 4-PyCO— | cyclopropyl | EtCOO— |
| 4-PyCO— | cyclobutyl | EtCOO— |
| 4-PyCO— | cyclopentyl | EtCOO— |
| 4-PyCO— | phenyl | EtCOO— |
| $C_4H_7CO$— | 3-furyl | EtCOO— |
| $C_4H_7CO$— | 3-thienyl | EtCOO— |
| $C_4H_7CO$— | 2-pyridyl | EtCOO— |
| $C_4H_7CO$— | 3-pyridyl | EtCOO— |
| $C_4H_7CO$— | 4-pyridyl | EtCOO— |
| $C_4H_7CO$— | isobutenyl | EtCOO— |
| $C_4H_7CO$— | isopropyl | EtCOO— |
| $C_4H_7CO$— | cyclopropyl | EtCOO— |
| $C_4H_7CO$— | cyclobutyl | EtCOO— |
| $C_4H_7CO$— | cyclopentyl | EtCOO— |
| $C_4H_7CO$— | phenyl | EtCOO— |
| EtOCO— | 3-furyl | EtCOO— |
| EtOCO— | 3-thienyl | EtCOO— |
| EtOCO— | 2-pyridyl | EtCOO— |
| EtOCO— | 3-pyridyl | EtCOO— |
| EtOCO— | 4-pyridyl | EtCOO— |
| EtOCO— | isobutenyl | EtCOO— |
| EtOCO— | isopropyl | EtCOO— |
| EtOCO— | cyclopropyl | EtCOO— |
| EtOCO— | cyclobutyl | EtCOO— |
| EtOCO— | cyclopentyl | EtCOO— |
| EtOCO— | phenyl | EtCOO— |
| ibueCO— | 2-furyl | EtCOO— |
| ibueCO— | 3-furyl | EtCOO— |
| ibueCO— | 3-thienyl | EtCOO— |
| ibueCO— | 2-pyridyl | EtCOO— |
| ibueCO— | 3-pyridyl | EtCOO— |
| ibueCO— | 4-pyridyl | EtCOO— |
| ibueCO— | isobutenyl | EtCOO— |
| ibueCO— | isopropyl | EtCOO— |
| ibueCO— | cyclopropyl | EtCOO— |
| ibueCO— | cyclobutyl | EtCOO— |

-continued (7)

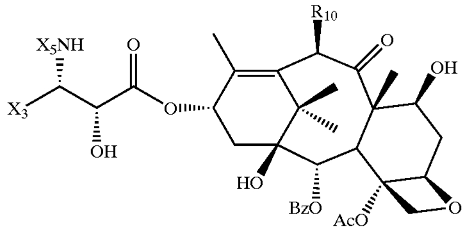

| $X_5$ | $X_3$ | $R_{10}$ |
|---|---|---|
| ibueCO— | cyclopentyl | EtCOO— |
| ibueCO— | phenyl | EtCOO— |
| iBuCO— | 2-furyl | EtCOO— |
| iBuCO— | 3-furyl | EtCOO— |
| iBuCO— | 2-thienyl | EtCOO— |
| iBuCO— | 3-thienyl | EtCOO— |
| iBuCO— | 2-pyridyl | EtCOO— |
| iBuCO— | 3-pyridyl | EtCOO— |
| iBuCO— | 4-pyridyl | EtCOO— |
| iBuCO— | isobutenyl | EtCOO— |
| iBuCO— | isopropyl | EtCOO— |
| iBuCO— | cyclopropyl | EtCOO— |
| iBuCO— | cyclobutyl | EtCOO— |
| iBuCO— | cyclopentyl | EtCOO— |
| iBuCO— | phenyl | EtCOO— |
| iBuOCO— | 2-furyl | EtCOO— |
| iBuOCO— | 2-pyridyl | EtCOO— |
| iBuOCO— | 3-pyridyl | EtCOO— |
| iBuOCO— | 4-pyridyl | EtCOO— |
| iBuOCO— | isopropyl | EtCOO— |
| iBuOCO— | cyclobutyl | EtCOO— |
| iBuOCO— | cyclopentyl | EtCOO— |
| iBuCO— | phenyl | EtCOO— |
| iPrOCO— | 3-furyl | EtCOO— |
| iPrOCO— | 3-thienyl | EtCOO— |
| iPrOCO— | 2-pyridyl | EtCOO— |
| iPrOCO— | 3-pyridyl | EtCOO— |
| iPrOCO— | 4-pyridyl | EtCOO— |
| iPrOCO— | isobutenyl | EtCOO— |
| iPrOCO— | isopropyl | EtCOO— |
| iPrOCO— | cyclopropyl | EtCOO— |
| iPrOCO— | cyclobutyl | EtCOO— |
| iPrOCO— | cyclopentyl | EtCOO— |
| iPrOCO— | phenyl | EtCOO— |
| nPrOCO— | 2-furyl | EtCOO— |
| nPrOCO— | 3-furyl | EtCOO— |
| nPrOCO— | 2-thienyl | EtCOO— |
| nPrOCO— | 3-thienyl | EtCOO— |
| nPrOCO— | 2-pyridyl | EtCOO— |
| nPrOCO— | 3-pyridyl | EtCOO— |
| nPrOCO— | 4-pyridyl | EtCOO— |
| nPrOCO— | isobutenyl | EtCOO— |
| nPrOCO— | isopropyl | EtCOO— |
| nPrOCO— | cyclopropyl | EtCOO— |
| nPrOCO— | cyclobutyl | EtCOO— |
| nPrOCO— | cyclopentyl | EtCOO— |
| nPrOCO— | phenyl | EtCOO— |
| nPrCO— | 3-furyl | EtCOO— |
| nPrCO— | 3-thienyl | EtCOO— |
| nPrCO— | 2-pyridyl | EtCOO— |
| nPrCO— | 3-pyridyl | EtCOO— |
| nPrCO— | 4-pyridyl | EtCOO |
| nPrCO— | isobutenyl | EtCOO— |
| nPrCO— | isopropyl | EtCOO— |
| nPrCO— | cyclopropyl | EtCOO— |
| nPrCO— | cyclobutyl | EtCOO— |
| nPrCO— | cyclopentyl | EtCOO— |
| nPrOCO— | phenyl | EtCOO— |

EXAMPLE 9

Additional Taxanes having C-10 Ester and C-7 Hydroxy Substituents

Following the processes described in Example 6 and elsewhere herein, the following specific taxanes having structural formula (8) may be prepared, wherein $R_7$ is hydroxy and $R_{10}$ in each of the series (that is, each of series "A" through "K") is as previously defined, including wherein $R_{10}$ is $R_{10a}$COO— and $R_{10a}$ is (i) substituted or unsubstituted, preferably unsubstituted, $C_2$ to $C_8$ alkyl (straight, branched or cyclic), such as ethyl, propyl, butyl, pentyl, or hexyl; (ii) substituted or unsubstituted, preferably unsubstituted, $C_2$ to $C_8$ alkenyl (straight, branched or cyclic), such as ethenyl, propenyl, butenyl, pentenyl or hexenyl; (iii) substituted or unsubstituted, preferably unsubstituted, $C_2$ to $C_8$ alkynyl (straight or branched) such as ethynyl, propynyl, butynyl, pentynyl, or hexynyl; (iv) substituted or unsubstituted, preferably unsubstituted, phenyl; or (v) substituted or unsubstituted, preferably unsubstituted, heteroaromatic such as furyl, thienyl, or pyridyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_9$a are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_a$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_9$, $R_{10}$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(8)

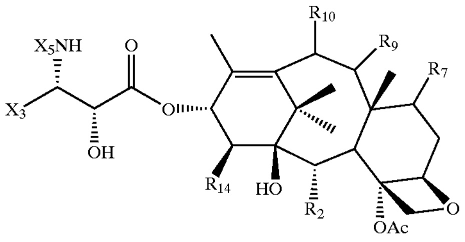

| Series | $X_5$ | $X_3$ | $R_{10}$ | $R_2$ | $R_9$ | $R_{14}$ |
|---|---|---|---|---|---|---|
| A1 | —$COOX_{10}$ | heterocyclo | $R_{10a}COO$— | $C_6H_5COO$— | O | H |
| A2 | —$COX_{10}$ | heterocyclo | $R_{10a}COO$— | $C_6H_5COO$— | O | H |
| A3 | —$CONHX_{10}$ | heterocyclo | $R_{10a}COO$— | $C_6H_5COO$— | O | H |
| A4 | —$COOX_{10}$ | optionally substituted $C_2$ to $C_8$ alkyl | $R_{10a}COO$— | $C_6H_5COO$— | O | H |
| A5 | —$COX_{10}$ | optionally substituted $C_2$ to $C_8$ alkyl | $R_{10a}COO$— | $C_6H_5COO$— | O | H |
| A6 | —$CONHX_{10}$ | optionally substituted $C_2$ to $C_8$ alkyl | $R_{10a}COO$— | $C_6H_5COO$— | O | H |
| A7 | —$COOX_{10}$ | optionally substituted $C_2$ to $C_8$ alkenyl | $R_{10a}COO$— | $C_6H_5COO$— | O | H |
| A8 | —$COX_{10}$ | optionally substituted $C_2$ to $C_8$ alkenyl | $R_{10a}COO$— | $C_6H_5COO$— | O | H |
| A9 | —$CONHX_{10}$ | optionally substituted $C_2$ to $C_8$ alkenyl | $R_{10a}COO$— | $C_6H_5COO$— | O | H |
| A10 | —$COOX_{10}$ | optionally substituted $C_2$ to $C_8$ alkenyl | $R_{10a}COO$— | $C_6H_5COO$— | O | H |
| A11 | —$COX_{10}$ | optionally substituted $C_2$ to $C_8$ alkenyl | $R_{10a}COO$— | $C_6H_5COO$— | O | H |
| A12 | —$CONHX_{10}$ | optionally substituted $C_2$ to $C_8$ alkenyl | $R_{10a}COO$— | $C_6H_5COO$— | O | H |
| B1 | —$COOX_{10}$ | heterocyclo | $R_{10a}COO$— | $R_{2a}COO$— | O | H |
| B2 | —$COX_{10}$ | heterocyclo | $R_{10a}COO$— | $R_{2a}COO$— | O | H |
| B3 | —$CONHX_{10}$ | heterocyclo | $R_{10a}COO$— | $R_{2a}COO$— | O | H |
| B4 | —$COOX_{10}$ | optionally substituted $C_2$ to $C_8$ alkyl | $R_{10a}COO$— | $R_{2a}COO$— | O | H |

-continued (8)

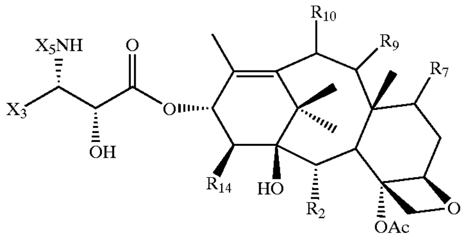

| Series | $X_5$ | $X_3$ | $R_{10}$ | $R_2$ | $R_9$ | $R_{14}$ |
|---|---|---|---|---|---|---|
| B5 | —$COX_{10}$ | optionally substituted $C_2$ to $C_8$ alkyl | $R_{10a}COO$— | $R_{2a}COO$— | O | H |
| B6 | —$CONHX_{10}$ | optionally substituted $C_2$ to $C_8$ alkyl | $R_{10a}COO$— | $R_{2a}COO$— | O | H |
| B7 | —$COOX_{10}$ | optionally substituted $C_2$ to $C_8$ alkenyl | $R_{10a}COO$— | $R_{2a}COO$— | O | H |
| B8 | —$COX_{10}$ | optionally substituted $C_2$ to $C_8$ alkenyl | $R_{10a}COO$— | $R_{2a}COO$— | O | H |
| B9 | —$CONHX_{10}$ | optionally substituted $C_2$ to $C_8$ alkenyl | $R_{10a}COO$— | $R_{2a}COO$— | O | H |
| B10 | —$COOX_{10}$ | optionally substituted $C_2$ to $C_8$ alkynyl | $R_{10a}COO$— | $R_{2a}COO$— | O | H |
| B11 | —$COX_{10}$ | optionally substituted $C_2$ to $C_8$ alkynyl | $R_{10a}COO$— | $R_{2a}COO$— | O | H |
| B12 | —$CONHX_{10}$ | optionally substituted $C_2$ to $C_8$ alkynyl | $R_{10a}COO$— | $R_{2a}COO$— | O | H |
| C1 | —$COOX_{10}$ | heterocyclo | $R_{10a}COO$— | $C_6H_5COO$— | $R_{9a}COO$— | H |
| C2 | —$COX_{10}$ | heterocyclo | $R_{10a}COO$— | $C_6H_5COO$— | $R_{9a}COO$— | H |
| C3 | —$CONHX_{10}$ | heterocyclo | $R_{10a}COO$— | $C_6H_5COO$— | $R_{9a}COO$— | H |
| C4 | —$COOX_{10}$ | optionally substituted $C_2$ to $C_8$ alkyl | $R_{10a}COO$— | $C_6H_5COO$— | $R_{9a}COO$— | H |
| C5 | —$COX_{10}$ | optionally substituted $C_2$ to $C_8$ alkyl | $R_{10a}COO$— | $C_6H_5COO$— | $R_{9a}COO$— | H |
| C6 | —$CONHX_{10}$ | optionally substituted $C_2$ to $C_8$ alkyl | $R_{10a}COO$— | $C_6H_5COO$— | $R_{9a}COO$— | H |
| C7 | —$COOX_{10}$ | optionally substituted $C_2$ to $C_8$ alkenyl | $R_{10a}COO$— | $C_6H_5COO$— | $R_{9a}COO$— | H |
| C8 | —$COX_{10}$ | optionally substituted $C_2$ to $C_8$ alkenyl | $R_{10a}COO$— | $C_6H_5COO$— | $R_{9a}COO$— | H |
| C9 | —$CONHX_{10}$ | optionally substituted $C_2$ to $C_8$ alkenyl | $R_{10a}COO$— | $C_6H_5COO$— | $R_{9a}COO$— | H |
| C10 | —$COOX_{10}$ | optionally substituted $C_2$ to $C_8$ alkynyl | $R_{10a}COO$— | $C_6H_5COO$— | $R_{9a}COO$— | H |
| C11 | —$COX_{10}$ | optionally substituted $C_2$ to $C_8$ alkynyl | $R_{10a}COO$— | $C_6H_5COO$— | $R_{9a}COO$— | H |
| C12 | —$CONHX_{10}$ | optionally substituted $C_2$ to $C_8$ alkynyl | $R_{10a}COO$— | $C_6H_5COO$— | $R_{9a}COO$— | H |
| D1 | —$COOX_{10}$ | heterocyclo | $R_{10a}COO$— | $C_6H_5COO$— | OH | H |
| D2 | —$COX_{10}$ | heterocyclo | $R_{10a}COO$— | $C_6H_5COO$— | OH | H |
| D3 | —$CONHX_{10}$ | heterocyclo | $R_{10a}COO$— | $C_6H_5COO$— | OH | H |
| D4 | —$COOX_{10}$ | optionally substituted $C_2$ to $C_8$ alkyl | $R_{10a}COO$— | $C_6H_5COO$— | OH | H |

-continued (8)

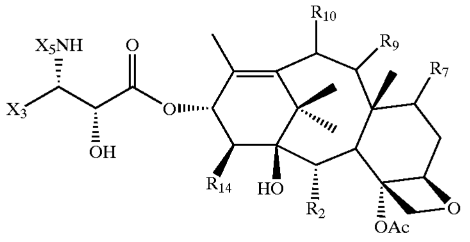

| Series | $X_5$ | $X_3$ | $R_{10}$ | $R_2$ | $R_9$ | $R_{14}$ |
|---|---|---|---|---|---|---|
| D5 | —$COX_{10}$ | optionally substituted $C_2$ to $C_8$ alkyl | $R_{10a}COO$— | $C_6H_5COO$— | OH | H |
| D6 | —$CONHX_{10}$ | optionally substituted $C_2$ to $C_8$ alkyl | $R_{10a}COO$— | $C_6H_5COO$— | OH | H |
| D7 | —$COOX_{10}$ | optionally substituted $C_2$ to $C_8$ alkenyl | $R_{10a}COO$— | $C_6H_5COO$— | OH | H |
| D8 | —$COX_{10}$ | optionally substituted $C_2$ to $C_8$ alkenyl | $R_{10a}COO$— | $C_6H_5COO$— | OH | H |
| D9 | —$CONHX_{10}$ | optionally substituted $C_2$ to $C_8$ alkenyl | $R_{10a}COO$— | $C_6H_5COO$— | OH | H |
| D10 | —$COOX_{10}$ | optionally substituted $C_2$ to $C_8$ alkynyl | $R_{10a}COO$— | $C_6H_5COO$— | OH | H |
| D11 | —$COX_{10}$ | optionally substituted $C_2$ to $C_8$ alkynyl | $R_{10a}COO$— | $C_6H_5COO$— | OH | H |
| D12 | —$CONHX_{10}$ | optionally substituted $C_2$ to $C_8$ alkynyl | $R_{10a}COO$— | $C_6H_5COO$— | OH | H |
| E1 | —$COOX_{10}$ | heterocyclo | $R_{10a}COO$— | $C_6H_5COO$— | O | OH |
| E2 | —$COX_{10}$ | heterocyclo | $R_{10a}COO$— | $C_6H_5COO$— | O | OH |
| E3 | —$CONHX_{10}$ | heterocyclo | $R_{10a}COO$— | $C_6H_5COO$— | O | OH |
| E4 | —$COOX_{10}$ | optionally substituted $C_2$ to $C_8$ alkyl | $R_{10a}COO$— | $C_6H_5COO$— | O | OH |
| E5 | —$COX_{10}$ | optionally substituted $C_2$ to $C_8$ alkyl | $R_{10a}COO$— | $C_6H_5COO$— | O | OH |
| E6 | —$CONHX_{10}$ | optionally substituted $C_2$ to $C_8$ alkyl | $R_{10a}COO$— | $C_6H_5COO$— | O | OH |
| E7 | —$COOX_{10}$ | optionally substituted $C_2$ to $C_8$ alkenyl | $R_{10a}COO$— | $C_6H_5COO$— | O | OH |
| E8 | —$COX_{10}$ | optionally substituted $C_2$ to $C_8$ alkenyl | $R_{10a}COO$— | $C_6H_5COO$— | O | OH |
| E9 | —$CONHX_{10}$ | optionally substituted $C_2$ to $C_8$ alkenyl | $R_{10a}COO$— | $C_6H_5COO$— | O | OH |
| E10 | —$COOX_{10}$ | optionally substituted $C_2$ to $C_8$ alkynyl | $R_{10a}COO$— | $C_6H_5COO$— | O | OH |
| E11 | —$COX_{10}$ | optionally substituted $C_2$ to $C_8$ alkynyl | $R_{10a}COO$— | $C_6H_5COO$— | O | OH |
| E12 | —$CONHX_{10}$ | optionally substituted $C_2$ to $C_8$ alkynyl | $R_{10a}COO$— | $C_6H_5COO$— | O | OH |
| F1 | —$COOX_{10}$ | heterocyclo | $R_{10a}COO$— | $R_{2a}COO$— | $R_{9a}COO$— | H |
| F2 | —$COX_{10}$ | heterocyclo | $R_{10a}COO$— | $R_{2a}COO$— | $R_{9a}COO$— | H |
| F3 | —$CONHX_{10}$ | heterocyclo | $R_{10a}COO$— | $R_{2a}COO$— | $R_{9a}COO$— | H |
| F4 | —$COOX_{10}$ | optionally substituted $C_2$ to $C_8$ alkyl | $R_{10a}COO$— | $R_{2a}COO$— | $R_{9a}COO$— | H |
| F5 | —$COX_{10}$ | optionally substituted $C_2$ to $C_8$ alkyl | $R_{10a}COO$— | $R_{2a}COO$— | $R_{9a}COO$— | H |

-continued (8)

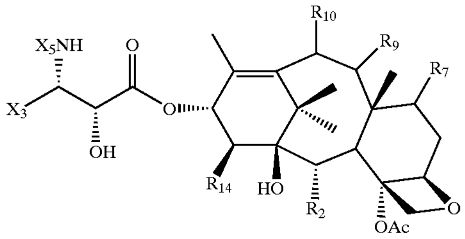

| Series | $X_5$ | $X_3$ | $R_{10}$ | $R_2$ | $R_9$ | $R_{14}$ |
|---|---|---|---|---|---|---|
| F6 | —$CONHX_{10}$ | optionally substituted $C_2$ to $C_8$ alkyl | $R_{10a}COO$— | $R_{2a}COO$— | $R_{9a}COO$— | H |
| F7 | —$COOX_{10}$ | optionally substituted $C_2$ to $C_8$ alkenyl | $R_{10a}COO$— | $R_{2a}COO$— | $R_{9a}COO$— | H |
| F8 | —$COX_{10}$ | optionally substituted $C_2$ to $C_8$ alkenyl | $R_{10a}COO$— | $R_{2a}COO$— | $R_{9a}COO$— | H |
| F9 | —$CONHX_{10}$ | optionally substituted $C_2$ to $C_8$ alkenyl | $R_{10a}COO$— | $R_{2a}COO$— | $R_{9a}COO$— | H |
| F10 | —$COOX_{10}$ | optionally substituted $C_2$ to $C_8$ alkynyl | $R_{10a}COO$— | $R_{2a}COO$— | $R_{9a}COO$— | H |
| F11 | —$COX_{10}$ | optionally substituted $C_2$ to $C_8$ alkynyl | $R_{10a}COO$— | $R_{2a}COO$— | $R_{9a}COO$— | H |
| F12 | —$CONHX_{10}$ | optionally substituted $C_2$ to $C_8$ alkynyl | $R_{10a}COO$— | $R_{2a}COO$— | $R_{9a}COO$— | H |
| G1 | —$COOX_{10}$ | heterocyclo | $R_{10a}COO$— | $R_{2a}COO$— | OH | H |
| G2 | —$COX_{10}$ | heterocyclo | $R_{10a}COO$— | $R_{2a}COO$— | OH | H |
| G3 | —$CONHX_{10}$ | heterocyclo | $R_{10a}COO$— | $R_{2a}COO$— | OH | H |
| G4 | —$COOX_{10}$ | optionally substituted $C_2$ to $C_8$ alkyl | $R_{10a}COO$— | $R_{2a}COO$— | OH | H |
| G5 | —$COX_{10}$ | optionally substituted $C_2$ to $C_8$ alkyl | $R_{10a}COO$— | $R_{2a}COO$— | OH | H |
| G6 | —$CONHX_{10}$ | optionally substituted $C_2$ to $C_8$ alkyl | $R_{10a}COO$— | $R_{2a}COO$— | OH | H |
| G7 | —$COOX_{10}$ | optionally substituted $C_2$ to $C_8$ alkenyl | $R_{10a}COO$— | $R_{2a}COO$— | OH | H |
| G8 | —$COX_{10}$ | optionally substituted $C_2$ to $C_8$ alkenyl | $R_{10a}COO$— | $R_{2a}COO$— | OH | H |
| G9 | —$CONHX_{10}$ | optionally substituted $C_2$ to $C_8$ alkenyl | $R_{10a}COO$— | $R_{2a}COO$— | OH | H |
| G10 | —$COOX_{10}$ | optionally substituted $C_2$ to $C_8$ alkynyl | $R_{10a}COO$— | $R_{2a}COO$— | OH | H |
| G11 | —$COX_{10}$ | optionally substituted $C_2$ to $C_8$ alkynyl | $R_{10a}COO$— | $R_{2a}COO$— | OH | H |
| G12 | —$CONHX_{10}$ | optionally substituted $C_2$ to $C_8$ alkynyl | $R_{10a}COO$— | $R_{2a}COO$— | OH | H |
| H1 | —$COOX_{10}$ | heterocyclo | $R_{10a}COO$— | $C_6H_5COO$— | OH | OH |
| H2 | —$COX_{10}$ | heterocyclo | $R_{10a}COO$— | $C_6H_5COO$— | OH | OH |
| H3 | —$CONHX_{10}$ | heterocyclo | $R_{10a}COO$— | $C_6H_5COO$— | OH | OH |
| H4 | —$COOX_{10}$ | optionally substituted $C_2$ to $C_8$ alkyl | $R_{10a}COO$— | $C_6H_5COO$— | OH | OH |
| H5 | —$COX_{10}$ | optionally substituted $C_2$ to $C_8$ alkyl | $R_{10a}COO$— | $C_6H_5COO$— | OH | OH |
| H6 | —$CONHX_{10}$ | optionally substituted $C_2$ to $C_8$ alkyl | $R_{10a}COO$— | $C_6H_5COO$— | OH | OH |

-continued (8)

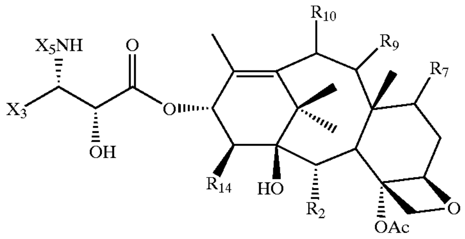

| Series | $X_5$ | $X_3$ | $R_{10}$ | $R_2$ | $R_9$ | $R_{14}$ |
|---|---|---|---|---|---|---|
| H7 | —$COOX_{10}$ | optionally substituted $C_2$ to $C_8$ alkenyl | $R_{10a}COO$— | $C_6H_5COO$— | OH | OH |
| H8 | —$COX_{10}$ | optionally substituted $C_2$ to $C_8$ alkenyl | $R_{10a}COO$— | $C_6H_5COO$— | OH | OH |
| H9 | —$CONHX_{10}$ | optionally substituted $C_2$ to $C_8$ alkenyl | $R_{10a}COO$— | $C_6H_5COO$— | OH | OH |
| H10 | —$COOX_{10}$ | optionally substituted $C_2$ to $C_8$ alkynyl | $R_{10a}COO$— | $C_6H_5COO$— | OH | OH |
| H11 | —$COX_{10}$ | optionally substituted $C_2$ to $C_8$ alkynyl | $R_{10a}COO$— | $C_6H_5COO$— | OH | OH |
| H12 | —$CONHX_{10}$ | optionally substituted $C_2$ to $C_8$ alkynyl | $R_{10a}COO$— | $C_6H_5COO$— | OH | OH |
| I1 | —$COOX_{10}$ | heterocyclo | $R_{10a}COO$— | $R_{2a}COO$— | O | OH |
| I2 | —$COX_{10}$ | heterocyclo | $R_{10a}COO$— | $R_{2a}COO$— | O | OH |
| I3 | —$CONHX_{10}$ | heterocyclo | $R_{10a}COO$— | $R_{2a}COO$— | O | OH |
| I4 | —$COOX_{10}$ | optionally substituted $C_2$ to $C_8$ alkyl | $R_{10a}COO$— | $R_{2a}COO$— | O | OH |
| I5 | —$COX_{10}$ | optionally substituted $C_2$ to $C_8$ alkyl | $R_{10a}COO$— | $R_{2a}COO$— | O | OH |
| I6 | —$CONHX_{10}$ | optionally substituted $C_2$ to $C_8$ alkyl | $R_{10a}COO$— | $R_{2a}COO$— | O | OH |
| I7 | —$COOX_{10}$ | optionally substituted $C_2$ to $C_8$ alkenyl | $R_{10a}COO$— | $R_{2a}COO$— | O | OH |
| I8 | —$COX_{10}$ | optionally substituted $C_2$ to $C_8$ alkenyl | $R_{10a}COO$— | $R_{2a}COO$— | O | OH |
| I9 | —$CONHX_{10}$ | optionally substituted $C_2$ to $C_8$ alkenyl | $R_{10a}COO$— | $R_{2a}COO$— | O | OH |
| I10 | —$COOX_{10}$ | optionally substituted $C_2$ to $C_8$ alkynyl | $R_{10a}COO$— | $R_{2a}COO$— | O | OH |
| I11 | —$COX_{10}$ | optionally substituted $C_2$ to $C_8$ alkynyl | $R_{10a}COO$— | $R_{2a}COO$— | O | OH |
| I12 | —$CONHX_{10}$ | optionally substituted $C_2$ to $C_8$ alkynyl | $R_{10a}COO$— | $R_{2a}COO$— | O | OH |
| J1 | —$COOX_{10}$ | heterocyclo | $R_{10a}COO$— | $R_{2a}COO$— | OH | OH |
| J2 | —$COX_{10}$ | heterocyclo | $R_{10a}COO$— | $R_{2a}COO$— | OH | OH |
| J3 | —$CONHX_{10}$ | heterocyclo | $R_{10a}COO$— | $R_{2a}COO$— | OH | OH |
| J4 | —$COOX_{10}$ | optionally substituted $C_2$ to $C_8$ alkyl | $R_{10a}COO$— | $R_{2a}COO$— | OH | OH |
| J5 | —$COX_{10}$ | optionally substituted $C_2$ to $C_8$ alkyl | $R_{10a}COO$— | $R_{2a}COO$— | OH | OH |
| J6 | —$CONHX_{10}$ | optionally substituted $C_2$ to $C_8$ alkyl | $R_{10a}COO$— | $R_{2a}COO$— | OH | OH |

-continued (8)

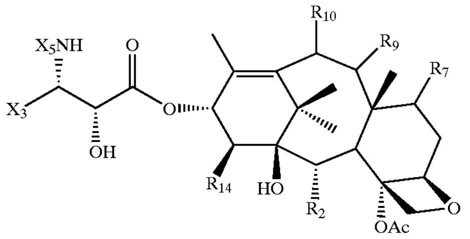

| Series | $X_5$ | $X_3$ | $R_{10}$ | $R_2$ | $R_9$ | $R_{14}$ |
|---|---|---|---|---|---|---|
| J7 | —$COOX_{10}$ | optionally substituted $C_2$ to $C_8$ alkenyl | $R_{10a}COO$— | $R_{2a}COO$— | OH | OH |
| J8 | —$COX_{10}$ | optionally substituted $C_2$ to $C_8$ alkenyl | $R_{10a}COO$— | $R_{2a}COO$— | OH | OH |
| J9 | —$CONHX_{10}$ | optionally substituted $C_2$ to $C_8$ alkenyl | $R_{10a}COO$— | $R_{2a}COO$— | OH | OH |
| J10 | —$COOX_{10}$ | optionally substituted $C_2$ to $C_8$ alkynyl | $R_{10a}COO$— | $R_{2a}COO$— | OH | OH |
| J11 | —$COX_{10}$ | optionally substituted $C_2$ to $C_8$ alkynyl | $R_{10a}COO$— | $R_{2a}COO$— | OH | OH |
| J12 | —$CONHX_{10}$ | optionally substituted $C_2$ to $C_8$ alkynyl | $R_{10a}COO$— | $R_{2a}COO$— | OH | OH |
| K1 | —$COOX_{10}$ | heterocyclo | $R_{10a}COO$— | $R_{2a}COO$— | $R_{9a}COO$— | OH |
| K2 | —$COX_{10}$ | heterocyclo | $R_{10a}COO$— | $R_{2a}COO$— | $R_{9a}COO$— | OH |
| K3 | —$CONHX_{10}$ | heterocyclo | $R_{10a}COO$— | $R_{2a}COO$— | $R_{9a}COO$— | OH |
| K4 | —$COOX_{10}$ | optionally substituted $C_2$ to $C_8$ alkyl | $R_{10a}COO$— | $R_{2a}COO$— | $R_{9a}COO$— | OH |
| K5 | —$COX_{10}$ | optionally substituted $C_2$ to $C_8$ alkyl | $R_{10a}COO$— | $R_{2a}COO$— | $R_{9a}COO$— | OH |
| K6 | —$CONHX_{10}$ | optionally substituted $C_2$ to $C_8$ alkyl | $R_{10a}COO$— | $R_{2a}COO$— | $R_{9a}COO$— | OH |
| K7 | —$COOX_{10}$ | optionally substituted $C_2$ to $C_8$ alkenyl | $R_{10a}COO$— | $R_{2a}COO$— | $R_{9a}COO$— | OH |
| K8 | —$COX_{10}$ | optionally substituted $C_2$ to $C_8$ alkenyl | $R_{10a}COO$— | $R_{2a}COO$— | $R_{9a}COO$— | OH |
| K9 | —$CONHX_{10}$ | optionally substituted $C_2$ to $C_8$ alkenyl | $R_{10a}COO$— | $R_{2a}COO$— | $R_{9a}COO$— | OH |
| K10 | —$COOX_{10}$ | optionally substituted $C_2$ to $C_8$ alkynyl | $R_{10a}COO$— | $R_{2a}COO$— | $R_{9a}COO$— | OH |
| K11 | —$COX_{10}$ | optionally substituted $C_2$ to $C_8$ alkynyl | $R_{10a}COO$— | $R_{2a}COO$— | $R_{9a}COO$— | OH |
| K12 | —$CONHX_{10}$ | optionally substituted $C_2$ to $C_8$ alkynyl | $R_{10a}COO$— | $R_{2a}COO$— | $R_{9a}COO$— | OH |

EXAMPLE 10

In Vitro Cytotoxicity Measured by the Cell Colony Formation Assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 7 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 0499 | <1 |
| 0503 | <1 |
| 0517 | <10 |
| 0521 | <1 |
| 0536 | <1 |
| 0549 | <10 |
| 0550 | <10 |
| 0562 | <1 |
| 0578 | <1 |
| 0583 | <10 |
| 0596 | <10 |
| 0602 | <1 |
| 0611 | <10 |
| 0625 | <1 |
| 0634 | <10 |
| 0647 | 12.0 |
| 0659 | <1 |
| 0663 | <1 |
| 0670 | <1 |
| 0687 | <1 |
| 0691 | <1 |
| 0706 | <1 |
| 0719 | <10 |
| 0720 | <10 |
| 0732 | <10 |
| 0748 | <10 |
| 0838 | <1 |
| 0843 | <1 |
| 0854 | <1 |
| 0860 | <1 |
| 0879 | <1 |
| 0882 | <1 |
| 0890 | <1 |
| 0908 | <1 |
| 0919 | <1 |
| 0923 | <1 |
| 0937 | <10 |
| 0947 | <1 |
| 0951 | <1 |
| 0966 | <10 |
| 0978 | <1 |
| 0983 | <1 |
| 0999 | <1 |
| 1003 | <1 |
| 1011 | <1 |
| 1020 | <1 |
| 1031 | <10 |
| 1044 | <1 |
| 1060 | <1 |
| 1879 | <10 |
| 1883 | <10 |
| 1892 | <1 |
| 1900 | <1 |
| 1911 | <10 |
| 1923 | <1 |
| 1939 | <1 |
| 1948 | <10 |
| 1954 | <1 |
| 1964 | <10 |
| 1970 | <10 |
| 1988 | <10 |
| 2101 | <1 |
| 2111 | <1 |
| 2124 | <10 |
| 2132 | <1 |
| 2142 | <1 |
| 2159 | <1 |
| 2164 | <1 |
| 2173 | <1 |
| 2181 | <10 |
| 2199 | <10 |

-continued

| Compound | IN VITRO ID 50 (nm) HCT116 |
|---|---|
| 2202 | <1 |
| 2212 | <10 |
| 2226 | <1 |
| 2238 | <1 |
| 2242 | <10 |
| 2255 | <1 |
| 2269 | <1 |
| 2273 | <1 |
| 2287 | <1 |
| 2291 | <1 |
| 2306 | <10 |
| 2319 | <10 |
| 2320 | <1 |
| 2332 | <1 |
| 2348 | <1 |
| 2353 | <10 |
| 2366 | <1 |
| 2379 | <1 |
| 2380 | <1 |
| 2392 | <1 |
| 2408 | <1 |
| 2413 | <10 |
| 2424 | <10 |
| 2439 | <10 |
| 2442 | <1 |
| 2455 | <10 |
| 2464 | <1 |
| 2472 | <1 |
| 2488 | <1 |
| 2499 | <1 |
| 2503 | <1 |
| 2511 | <1 |
| 2520 | <10 |
| 2781 | <1 |
| 2794 | <1 |
| 2802 | <1 |
| 2813 | <1 |
| 2826 | <1 |
| 2838 | <1 |
| 2844 | <10 |
| 2855 | <1 |
| 2869 | <10 |
| 3053 | <1 |
| 3071 | <1 |
| 3096 | <1 |
| 3102 | <1 |
| 3110 | <1 |
| 3129 | <10 |
| 3132 | <1 |
| 3148 | <1 |
| 3163 | <1 |
| 3204 | <1 |
| 3219 | <1 |
| 3222 | <1 |
| 3258 | <1 |
| 3265 | <10 |
| 3297 | <1 |
| 3314 | <1 |
| 3352 | <1 |
| 3361 | <1 |
| 3370 | <1 |
| 3408 | <1 |
| 3417 | <1 |
| 3425 | <1 |
| 3453 | <1 |
| 3482 | <1 |
| 3494 | <1 |
| 3513 | <1 |
| 3522 | <1 |
| 3535 | <1 |
| 3543 | <10 |
| 3588 | <10 |
| 3595 | <1 |
| 3603 | <10 |
| 3644 | <1 |
| 3656 | <1 |

-continued

| Compound | IN VITRO ID 50 (nm) HCT116 |
|---|---|
| 3663 | <1 |
| 3677 | <1 |
| 3686 | <1 |
| 3693 | <1 |
| 3800 | <1 |
| 3818 | <1 |
| 3853 | <1 |
| 3866 | <1 |
| 3909 | <1 |
| 3938 | <10 |
| 3945 | <1 |
| 3957 | <10 |
| 3971 | <1 |
| 3982 | <1 |
| 3994 | <1 |
| 4051 | <1 |
| 4062 | <1 |
| 4112 | <10 |
| 4121 | <10 |
| 4190 | <10 |
| 4207 | <10 |
| 4329 | <1 |
| 4335 | <1 |
| 4344 | <1 |
| 4665 | <10 |
| 4704 | <10 |
| 4711 | <10 |
| 4720 | <10 |
| 4799 | <1 |
| 4808 | <10 |
| 4834 | <10 |
| 4888 | <1 |
| 4919 | <1 |
| 4944 | <1 |
| 5011 | <10 |
| 5040 | <1 |
| 5065 | <10 |
| 5144 | <10 |
| 5232 | <10 |
| 5495 | <1 |
| 6522 | <1 |

EXAMPLE 11

Preparation of Taxane having C-7 Substituted Acetate and C-10 Hydroxy

N-Debenzoyl-N-tert-amyloxycarbonyl-3'-desphenyl-3'-(2-furyl)-10-deacetyl-7-methoxyacetyl taxol (6226)

To a solution of N-debenzoyl-N-tert-amyloxycarbonyl-3'-desphenyl-3'-(2-furyl)-2'-(2-methoxy-2-propyl)-7-benzyloxycarbonyl-10-deacetyl-10-trimethylsilyl taxol (2.50 g, 2.292 mmol) in 50 mL of ethyl acetate was added 10% Pd-C (500 mg) and the mixture stirred at ambient temperature under a $H_2$ atmosphere (latex balloons) for 45 minutes. TLC of the reaction (silica gel, 1:1 ethyl acetate:hexane) showed the presence of only the product. The mixture was then filtered through a celite bed (5 g) and the celite washed with 25 mL of ethyl acetate. The combined ethyl acetate fraction was concentrated under reduced pressure to give, the N-debenzoyl-N-tert-amyloxycarbonyl-3'-desphenyl-3'-(2-furyl)-2'-(2-methoxy-2-propyl)-10-deacetyl-10-trimethylsilyl taxol as a white solid 2.10 g (96%) which was directly used in the next step.

To a solution of N-debenzoyl-N-tert-amyloxycarbonyl-3'-desphenyl-3'-(2-furyl)-2'-(2-methoxy-2-propyl)-10-deacetyl-10-trimethylsilyl taxol (400 mg, 0.418 mmol) in 4 mL anhydrous pyridine at 0° C. was added DMAP (20 mg, 0.16 mmol) under a nitrogen atmosphere. To this mixture was added drop wise methoxyacetyl chloride (96 mL, 1.045 mmol). TLC (silica gel, 2:3 ethyl acetate:hexane) after 3 h showed no starting material. The reaction was cooled to 0° C. (ice-water bath) and quenched by adding 80 mL of water.

To the reaction at 0° C. (ice-water bath) was added 4 mL of acetonitrile and 2 mL of 48% aqueous hydrofluoric acid and the cooling bath was removed. The reaction was stirred at room temperature for 8.0 h and then diluted with 60 mL of ethyl acetate and washed with 2×10 mL of saturated aqueous $NaHCO_3$ followed by 15 mL of saturated aqueous NaCl. The organic layer was dried over $Na_2SO_4$ and concentrated under reduced pressure to give 365 mg of a yellow solid which was purified by flash-chromatography (silica gel, 1:1 ethyl acetate:hexane) to give 325 mg (88%) of N-debenzoyl-N-tert-amyloxycarbonyl-3'-desphenyl-3'-(2-furyl)-10-deacetyl-7-methoxyacetyl taxol: mp 166–167° C.; $^1H$ NMR ($CDCl_3$) 8.12 (m, 2H), 7.62(m, 1H), 7.46–7.51 (m, 2H), 7.40 (m, 1 H), 6.39(dd, J=3.1, 1.5 Hz, 1H), 6.25 (d, J=3.1 Hz, 1H), 6.21 (dd, J=8.8, 8.7 Hz, 1H), 5.67(1H), 5.58 (m, 1H), 5.26–5.38(m, 3H), 4.98(m, 1H), 4.76(m, 1H), 4.36 (d, J=9.3 Hz, 1H), 4.21 (d, J=9.3 Hz, 1H), 4.09(d, J=7.6 Hz, 1H), 3.99 (m, 3H), 3.42 (s, 3H), 3.30 (d, J=5.5 Hz, 1H), 2.55–2.60(m, 1H), 2.43 (s, 3H), 2.20–2.38(m,2H), 1.98 (s, 3H), 1.96–1.98 (m, 1H), 1.84 (bs, 3H), 1.62–1.68(m, 2H), 1.36(s, 3H), 1.34(s, 3H), 1.23(s, 3H), 1.10(s, 3H), 0.81(t, J=8.2 Hz, 3H); Anal. Calcd. for $C_{45}H_{57}NO_{17}$: C, 61.15; H, 6.50. Found: C, 61.01; H, 6.57.

EXAMPLE 12

Taxanes having C-7 Substituted Acetate and C-10 Hydroxy Substituents

The procedures described in Example 11 were repeated, but other suitably protected β-lactams were substituted for the β-lactam of Example 1 to prepare the series of compounds having structural formula (9) and the combinations of substituents identified in the following table:

(9)

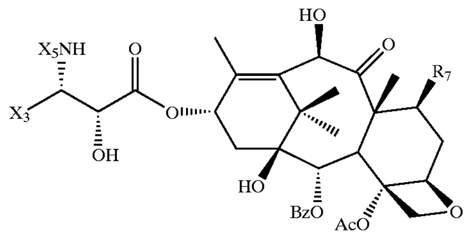

| Compound | $X_5$ | $X_3$ | $R_7$ |
|---|---|---|---|
| 5544 | ibueCO— | 2-furyl | AcOAcO— |
| 5474 | ibueCO— | 2-furyl | MeOAcO— |
| 5555 | ibueCO— | 2-furyl | PhOAcO— |
| 5999 | ibueCO— | 2-furyl | MeOAcO— |
| 6353 | tAmOCO— | 2-furyl | AcOAcO— |
| 6226 | tAmOCO— | 2-furyl | MeOAcO— |
| 5622 | tBuOCO— | 2-furyl | AcOAcO— |
| 5515 | tBuOCO— | 2-furyl | EtOAcO— |
| 5445 | tBuOCO— | 2-furyl | MeOAcO— |
| 5600 | tBuOCO— | 2-furyl | MeSAcO— |
| 5616 | tBuOCO— | 2-furyl | PhOAcO— |
| 5835 | $tC_3H_5CO$— | 2-furyl | MeOAcO— |
| 5811 | $tC_3H_5CO$— | 2-furyl | PhOAcO— |
| 5919 | $C_3H_5CO$— | 2-furyl | PhOAcO— |
| 6326 | tBuOCO— | 2-furyl | MeOAcO— |

EXAMPLE 13

Taxanes having C7 Substituted Acetate and C-10 Hydroxy Substituents

Following the processes described elsewhere herein, the following specific taxanes having structural formula (10)

may be prepared, wherein $R_7$ is as previously defined, including wherein $R_7$ is $R_{7a}$COO— and $R_{7a}$ is heterosubstituted methyl. In one embodiment, $R_{7a}$ is chloromethyl, hydroxymethyl, methoxymethyl, ethoxymethyl, phenoxymethyl, acetoxymethyl, or methylthiomethyl.

(10)

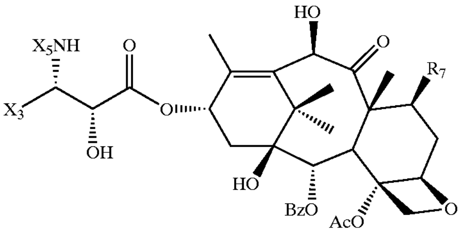

| $X_5$ | $X_3$ | $R_7$ |
|---|---|---|
| tBuOCO— | 2-furyl | $R_{7a}$COO— |
| tBuOCO— | 3-furyl | $R_{7a}$COO— |
| tBuOCO— | 2-thienyl | $R_{7a}$COO— |
| tBuOCO— | 3-thienyl | $R_{7a}$COO— |
| tBuOCO— | 2-pyridyl | $R_{7a}$COO— |
| tBuOCO— | 3-pyridyl | $R_{7a}$COO— |
| tBuOCO— | 4-pyridyl | $R_{7a}$COO— |
| tBuOCO— | isobutenyl | $R_{7a}$COO— |
| tBuOCO— | isopropyl | $R_{7a}$COO— |
| tBuOCO— | cyclopropyl | $R_{7a}$COO— |
| tBuOCO— | cyclobutyl | $R_{7a}$COO— |
| tBuOCO— | cyclopentyl | $R_{7a}$COO— |
| tBuOCO— | phenyl | $R_{7a}$COO— |
| benzoyl | 2-furyl | $R_{7a}$COO— |
| benzoyl | 3-furyl | $R_{7a}$COO— |
| benzoyl | 2-thienyl | $R_{7a}$COO— |
| benzoyl | 3-thienyl | $R_{7a}$COO— |
| benzoyl | 2-pyridyl | $R_{7a}$COO— |
| benzoyl | 3-pyridyl | $R_{7a}$COO— |
| benzoyl | 4-pyridyl | $R_{7a}$COO— |
| benzoyl | isobutenyl | $R_{7a}$COO— |
| benzoyl | isopropyl | $R_{7a}$COO— |
| benzoyl | cyclopropyl | $R_{7a}$COO— |
| benzoyl | cyclobutyl | $R_{7a}$COO— |
| benzoyl | cyclopentyl | $R_{7a}$COO— |
| benzoyl | phenyl | $R_{7a}$COO— |
| 2-FuCO— | 2-furyl | $R_{7a}$COO— |
| 2-FuCO— | 3-furyl | $R_{7a}$COO— |
| 2-FuCO— | 2-thienyl | $R_{7a}$COO— |
| 2-FuCO— | 3-thienyl | $R_{7a}$COO— |
| 2-FuCO— | 2-pyridyl | $R_{7a}$COO— |
| 2-FuCO— | 3-pyridyl | $R_{7a}$COO— |
| 2-FuCO— | 4-pyridyl | $R_{7a}$COO— |
| 2-FuCO— | isobutenyl | $R_{7a}$COO— |
| 2-FuCO— | isopropyl | $R_{7a}$COO— |
| 2-FuCO— | cyclopropyl | $R_{7a}$COO— |
| 2-FuCO— | cyclobutyl | $R_{7a}$COO— |
| 2-FuCO— | cyclopentyl | $R_{7a}$COO— |
| 2-FuCO— | phenyl | $R_{7a}$COO— |
| 2-ThCO— | 2-furyl | $R_{7a}$COO— |
| 2-ThCO— | 3-furyl | $R_{7a}$COO— |
| 2-ThCO— | 2-thienyl | $R_{7a}$COO— |
| 2-ThCO— | 3-thienyl | $R_{7a}$COO— |
| 2-ThCO— | 2-pyridyl | $R_{7a}$COO— |
| 2-ThCO— | 3-pyridyl | $R_{7a}$COO— |
| 2-ThCO— | 4-pyridyl | $R_{7a}$COO— |
| 2-ThCO— | isobutenyl | $R_{7a}$COO— |
| 2-ThCO— | isopropyl | $R_{7a}$COO— |
| 2-ThCO— | cyclopropyl | $R_{7a}$COO— |
| 2-ThCO— | cyclobutyl | $R_{7a}$COO— |
| 2-ThCO— | cyclopentyl | $R_{7a}$COO— |
| 2-ThCO— | phenyl | $R_{7a}$COO— |
| 2-PyCO— | 2-furyl | $R_{7a}$COO— |
| 2-PyCO— | 3-furyl | $R_{7a}$COO— |
| 2-PyCO— | 2-thienyl | $R_{7a}$COO— |
| 2-PyCO— | 3-thienyl | $R_{7a}$COO— |

-continued (10)

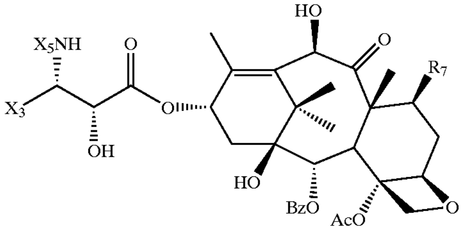

| $X_5$ | $X_3$ | $R_7$ |
|---|---|---|
| 2-PyCO— | 2-pyridyl | $R_{7a}$COO— |
| 2-PyCO— | 3-pyridyl | $R_{7a}$COO— |
| 2-PyCO— | 4-pyridyl | $R_{7a}$COO— |
| 2-PyCO— | isobutenyl | $R_{7a}$COO— |
| 2-PyCO— | isopropyl | $R_{7a}$COO— |
| 2-PyCO— | cyclopropyl | $R_{7a}$COO— |
| 2-PyCO— | cyclobutyl | $R_{7a}$COO— |
| 2-PyCO— | cyclopentyl | $R_{7a}$COO— |
| 2-PyCO— | phenyl | $R_{7a}$COO— |
| 3-PyCO— | 2-furyl | $R_{7a}$COO— |
| 3-PyCO— | 3-furyl | $R_{7a}$COO— |
| 3-PyCO— | 2-thienyl | $R_{7a}$COO— |
| 3-PyCO— | 3-thienyl | $R_{7a}$COO— |
| 3-PyCO— | 2-pyridyl | $R_{7a}$COO— |
| 3-PyCO— | 3-pyridyl | $R_{7a}$COO— |
| 3-PyCO— | 4-pyridyl | $R_{7a}$COO— |
| 3-PyCO— | isobutenyl | $R_{7a}$COO— |
| 3-PyCO— | isopropyl | $R_{7a}$COO— |
| 3-PyCO— | cyclopropyl | $R_{7a}$COO— |
| 3-PyCO— | cyclobutyl | $R_{7a}$COO— |
| 3-PyCO— | cyclopentyl | $R_{7a}$COO— |
| 3-PyCO— | phenyl | $R_{7a}$COO— |
| 4-PyCO— | 2-furyl | $R_{7a}$COO— |
| 4-PyCO— | 3-furyl | $R_{7a}$COO— |
| 4-PyCO— | 2-thienyl | $R_{7a}$COO— |
| 4-PyCO— | 3-thienyl | $R_{7a}$COO— |
| 4-PyCO— | 2-pyridyl | $R_{7a}$COO— |
| 4-PyCO— | 3-pyridyl | $R_{7a}$COO— |
| 4-PyCO— | 4-pyridyl | $R_{7a}$COO— |
| 4-PyCO— | isobutenyl | $R_{7a}$COO— |
| 4-PyCO— | isopropyl | $R_{7a}$COO— |
| 4-PyCO— | cyclopropyl | $R_{7a}$COO— |
| 4-PyCO— | cyclobutyl | $R_{7a}$COO— |
| 4-PyCO— | cyclopentyl | $R_{7a}$COO— |
| 4-PyCO— | phenyl | $R_{7a}$COO— |
| $C_4H_7$CO- | 2-furyl | $R_{7a}$COO— |
| $C_4H_7$CO- | 3-furyl | $R_{7a}$COO— |
| $C_4H_7$CO- | 2-thienyl | $R_{7a}$COO— |
| $C_4H_7$CO- | 3-thienyl | $R_{7a}$COO— |
| $C_4H_7$CO- | 2-pyridyl | $R_{7a}$COO— |
| $C_4H_7$CO- | 3-pyridyl | $R_{7a}$COO— |
| $C_4H_7$CO- | 4-pyridyl | $R_{7a}$COO— |
| $C_4H_7$CO- | isobutenyl | $R_{7a}$COO— |
| $C_4H_7$CO- | isopropyl | $R_{7a}$COO— |
| $C_4H_7$CO- | cyclopropyl | $R_{7a}$COO— |
| $C_4H_7$CO- | cyclobutyl | $R_{7a}$COO— |
| $C_4H_7$CO- | cyclopentyl | $R_{7a}$COO— |
| 4-PyCO— | phenyl | $R_{7a}$COO— |
| EtOCO— | 2-furyl | $R_{7a}$COO— |
| EtOCO— | 3-furyl | $R_{7a}$COO— |
| EtOCO— | 2-thienyl | $R_{7a}$COO— |
| EtOCO— | 3-thienyl | $R_{7a}$COO— |
| EtOCO— | 2-pyridyl | $R_{7a}$COO— |
| EtOCO— | 3-pyridyl | $R_{7a}$COO— |
| EtOCO— | 4-pyridyl | $R_{7a}$COO— |
| EtOCO— | isobutenyl | $R_{7a}$COO— |
| EtOCO— | isopropyl | $R_{7a}$COO— |
| EtOCO— | cyclopropyl | $R_{7a}$COO— |
| EtOCO— | cyclobutyl | $R_{7a}$COO— |
| EtOCO— | cyclopentyl | $R_{7a}$COO— |
| EtOCO— | phenyl | $R_{7a}$COO— |
| ibueCO— | 2-furyl | $R_{7a}$COO— |
| ibueCO— | 3-furyl | $R_{7a}$COO— |

-continued (10)

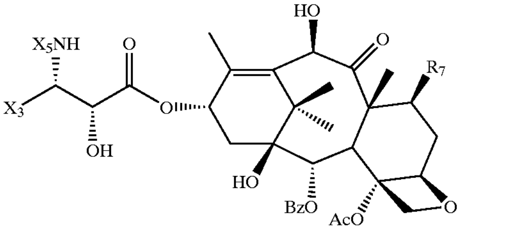

| $X_5$ | $X_3$ | $R_7$ |
|---|---|---|
| ibueCO— | 2-thienyl | $R_{7a}COO$— |
| ibueCO— | 3-thienyl | $R_{7a}COO$— |
| ibueCO— | 2-pyridyl | $R_{7a}COO$— |
| ibueCO— | 3-pyridyl | $R_{7a}COO$— |
| ibueCO— | 4-pyridyl | $R_{7a}COO$— |
| ibueCO— | isobutenyl | $R_{7a}COO$— |
| ibueCO— | isopropyl | $R_{7a}COO$— |
| ibueCO— | cyclopropyl | $R_{7a}COO$— |
| ibueCO— | cyclobutyl | $R_{7a}COO$— |
| ibueCO— | cyclopentyl | $R_{7a}COO$— |
| ibueCO— | phenyl | $R_{7a}COO$— |
| iBuCO— | 2-furyl | $R_{7a}COO$— |
| iBuCO— | 3-furyl | $R_{7a}COO$— |
| iBuCO— | 2-thienyl | $R_{7a}COO$— |
| iBuCO— | 3-thienyl | $R_{7a}COO$— |
| iBuCO— | 2-pyridyl | $R_{7a}COO$— |
| iBuCO— | 3-pyridyl | $R_{7a}COO$— |
| iBuCO— | 4-pyridyl | $R_{7a}COO$— |
| iBuCO— | isobutenyl | $R_{7a}COO$— |
| iBuCO— | isopropyl | $R_{7a}COO$— |
| iBuCO— | cyclopropyl | $R_{7a}COO$— |
| iBuCO— | cyclobutyl | $R_{7a}COO$— |
| iBuCO— | cyclopentyl | $R_{7a}COO$— |
| iBuCO— | phenyl | $R_{7a}COO$— |
| iBuOCO— | 2-furyl | $R_{7a}COO$— |
| iBuOCO— | 3-furyl | $R_{7a}COO$— |
| iBuOCO— | 2-thienyl | $R_{7a}COO$— |
| iBuOCO— | 3-thienyl | $R_{7a}COO$— |
| iBuOCO— | 2-pyridyl | $R_{7a}COO$— |
| iBuOCO— | 3-pyridyl | $R_{7a}COO$— |
| iBuOCO— | 4-pyridyl | $R_{7a}COO$— |
| iBuOCO— | isobutenyl | $R_{7a}COO$— |
| iBuOCO— | isopropyl | $R_{7a}COO$— |
| iBuOCO— | cyclopropyl | $R_{7a}COO$— |
| iBuOCO— | cyclobutyl | $R_{7a}COO$— |
| iBuOCO— | cyclopentyl | $R_{7a}COO$— |
| iBuOCO— | phenyl | $R_{7a}COO$— |
| iPrOCO— | 2-furyl | $R_{7a}COO$— |
| iPrOCO— | 3-furyl | $R_{7a}COO$— |
| iPrOCO— | 2-thienyl | $R_{7a}COO$— |
| iPrOCO— | 3-thienyl | $R_{7a}COO$— |
| iPrOCO— | 2-pyridyl | $R_{7a}COO$— |
| iPrOCO— | 3-pyridyl | $R_{7a}COO$— |
| iPrOCO— | 4-pyridyl | $R_{7a}COO$— |
| iPrOCO— | isobutenyl | $R_{7a}COO$— |
| iPrOCO— | isopropyl | $R_{7a}COO$— |
| iPrOCO— | cyclopropyl | $R_{7a}COO$— |
| iPrOCO— | cyclobutyl | $R_{7a}COO$— |
| iPrOCO— | cyclopentyl | $R_{7a}COO$— |
| iPrOCO— | phenyl | $R_{7a}COO$— |
| nPrOCO— | 2-furyl | $R_{7a}COO$— |
| nPrOCO— | 3-furyl | $R_{7a}COO$— |
| nPrOCO— | 2-thienyl | $R_{7a}COO$— |
| nPrOCO— | 3-thienyl | $R_{7a}COO$— |
| nPrOCO— | 2-pyridyl | $R_{7a}COO$— |
| nPrOCO— | 3-pyridyl | $R_{7a}COO$— |
| nPrOCO— | 4-pyridyl | $R_{7a}COO$— |
| nPrOCO— | isobutenyl | $R_{7a}COO$— |
| nPrOCO— | isopropyl | $R_{7a}COO$— |
| nPrOCO— | cyclopropyl | $R_{7a}COO$— |
| nPrOCO— | cyciobutyl | $R_{7a}COO$— |
| nPrOCO— | cyclopentyl | $R_{7a}COO$— |
| nPrOCO— | phenyl | $R_{7a}COO$— |

-continued (10)

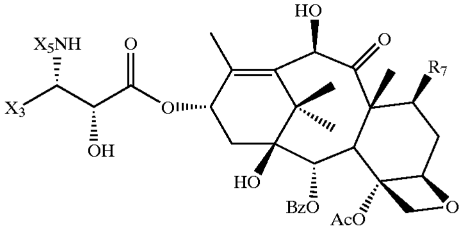

| $X_5$ | $X_3$ | $R_7$ |
|---|---|---|
| nPrCO— | 2-furyl | $R_{7a}COO$— |
| nPrCO— | 3-furyl | $R_{7a}COO$— |
| nPrCO— | 2-thienyl | $R_{7a}COO$— |
| nPrCO— | 3-thienyl | $R_{7a}COO$— |
| nPrCO— | 2-pyridyl | $R_{7a}COO$— |
| nPrCO— | 3-pyridyl | $R_{7a}COO$— |
| nPrCO— | 4-pyridyl | $R_{7a}COO$— |
| nPrCO— | isobutenyl | $R_{7a}COO$— |
| nPrCO— | isopropyl | $R_{7a}COO$— |
| nPrCO— | cyclopropyl | $R_{7a}COO$— |
| nPrCO— | cyclobutyl | $R_{7a}COO$— |
| nPrCO— | cyclopentyl | $R_{7a}COO$— |
| nPrCO— | phenyl | $R_{7a}COO$— |

EXAMPLE 14

Taxanes having C-7 Substituted Acetate and C-10 Hydroxy Substituents

Following the processes described in Example 11 and elsewhere herein, the following specific taxanes having structural formula (11) may be prepared, wherein $R_{10}$ is hydroxy and $R_7$ in each of the series (that is, each of series “A” through “K”) is as previously defined, including wherein $R_7$ is $R_{7a}COO$— wherein $R_{7a}$ is a heterosubstituted methyl moiety lacking a carbon atom which is in the beta position relative to the carbon atom of which $R_{7a}$ is a substituent. The heterosubstituted methyl is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety. Exemplary $R_7$ substituents include $R_{7a}COO$— wherein $R_{7a}$ is hydrogen, methyl, chloromethyl, hydroxymethyl, methoxymethyl, ethoxymethyl, phenoxymethyl, acetoxymethyl, acyloxymethyl, or methylthiomethyl.

In the “A” series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the “B” series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$, are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(11)

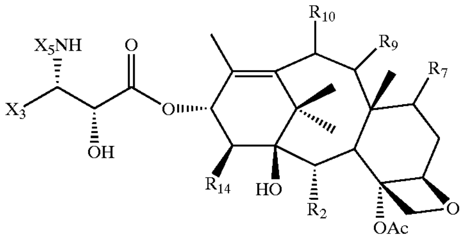

| Series | $X_5$ | $X_3$ | $R_7$ | $R_2$ | $R_9$ | $R_{14}$ |
|---|---|---|---|---|---|---|
| A1 | —$COOX_{10}$ | heterocyclo | $R_{7a}COO$— | $C_6H_5COO$— | O | H |
| A2 | —$COX_{10}$ | heterocyclo | $R_{7a}COO$— | $C_6H_5COO$— | O | H |
| A3 | —$CONHX_{10}$ | heterocyclo | $R_{7a}COO$— | $C_6H_5COO$— | O | H |
| A4 | —$COOX_{10}$ | optionally substituted $C_2$ to $C_8$ alkyl | $R_{7a}COO$— | $C_6H_5COO$— | O | H |
| A5 | —$COX_{10}$ | optionally substituted $C_2$ to $C_8$ alkyl | $R_{7a}COO$— | $C_6H_5COO$— | O | H |
| A6 | —$CONHX_{10}$ | optionally substituted $C_2$ to $C_8$ alkyl | $R_{7a}COO$— | $C_6H_5COO$— | O | H |
| A7 | —$COOX_{10}$ | optionally substituted $C_2$ to $C_8$ alkenyl | $R_{7a}COO$— | $C_6H_5COO$— | O | H |

-continued (11)

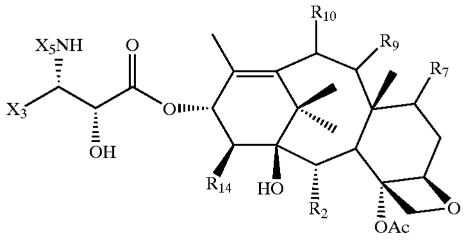

| Series | $X_5$ | $X_3$ | $R_7$ | $R_2$ | $R_9$ | $R_{14}$ |
|---|---|---|---|---|---|---|
| A8 | —$COX_{10}$ | optionally substituted $C_2$ to $C_8$ alkenyl | $R_{7a}COO$— | $C_6H_5COO$— | O | H |
| A9 | —$CONHX_{10}$ | optionally substituted $C_2$ to $C_8$ alkenyl | $R_{7a}COO$— | $C_6H_5COO$— | O | H |
| A10 | —$COOX_{10}$ | optionally substituted $C_2$ to $C_8$ alkynyl | $R_{7a}COO$— | $C_6H_5COO$— | O | H |
| A11 | —$COX_{10}$ | optionally substituted $C_2$ to $C_8$ alkynyl | $R_{7a}COO$— | $C_6H_5COO$— | O | H |
| A12 | —$CONHX_{10}$ | optionally substituted $C_2$ to $C_8$ alkynyl | $R_{7a}COO$— | $C_6H_5COO$— | O | H |
| B1 | —$COOX_{10}$ | heterocyclo | $R_{7a}COO$— | $R_{2a}COO$— | O | H |
| B2 | —$COX_{10}$ | heterocyclo | $R_{7a}COO$— | $R_{2a}COO$— | O | H |
| B3 | —$CONHX_{10}$ | heterocyclo | $R_{7a}COO$— | $R_{2a}COO$— | O | H |
| B4 | —$COOX_{10}$ | optionally substituted $C_2$ to $C_8$ alkyl | $R_{7a}COO$— | $R_{2a}COO$— | O | H |
| B5 | —$COX_{10}$ | optionally substituted $C_2$ to $C_8$ alkyl | $R_{7a}COO$— | $R_{2a}COO$— | O | H |
| B6 | —$CONHX_{10}$ | optionally substituted $C_2$ to $C_8$ alkyl | $R_{7a}COO$— | $R_{2a}COO$— | O | H |
| B7 | —$COOX_{10}$ | optionally substituted $C_2$ to $C_8$ alkenyl | $R_{7a}COO$— | $R_{2a}COO$— | O | H |
| B8 | —$COX_{10}$ | optionally substituted $C_2$ to $C_8$ alkenyl | $R_{7a}COO$— | $R_{2a}COO$— | O | H |
| B9 | —$CONHX_{10}$ | optionally substituted $C_2$ to $C_8$ alkenyl | $R_{7a}COO$— | $R_{2a}COO$— | O | H |
| B10 | —$COOX_{10}$ | optionally substituted $C_2$ to $C_8$ alkynyl | $R_{7a}COO$— | $R_{2a}COO$— | O | H |
| B11 | —$COX_{10}$ | optionally substituted $C_2$ to $C_8$ alkynyl | $R_{7a}COO$— | $R_{2a}COO$— | O | H |
| B12 | —$CONHX_{10}$ | optionally substituted $C_2$ to $C_8$ alkynyl | $R_{7a}COO$— | $R_{2a}COO$— | O | H |
| C1 | —$COOX_{10}$ | heterocyclo | $R_{7a}COO$— | $C_6H_5COO$— | $R_{9a}COO$— | H |
| C2 | —$COX_{10}$ | heterocyclo | $R_{7a}COO$— | $C_6H_5COO$— | $R_{9a}COO$— | H |
| C3 | —$CONHX_{10}$ | heterocyclo | $R_{7a}COO$— | $C_6H_5COO$— | $R_{9a}COO$— | H |
| C4 | —$COOX_{10}$ | optionally substituted $C_2$ to $C_8$ alkyl | $R_{7a}COO$— | $C_6H_5COO$— | $R_{9a}COO$— | H |
| C5 | —$COX_{10}$ | optionally substituted $C_2$ to $C_8$ alkyl | $R_{7a}COO$— | $C_6H_5COO$— | $R_{9a}COO$— | H |
| C6 | —$CONHX_{10}$ | optionally substituted $C_2$ to $C_8$ alkyl | $R_{7a}COO$— | $C_6H_5COO$— | $R_{9a}COO$— | H |
| C7 | —$COOX_{10}$ | optionally substituted $C_2$ to $C_8$ alkenyl | $R_{7a}COO$— | $C_6H_5COO$— | $R_{9a}COO$— | H |

-continued (11)

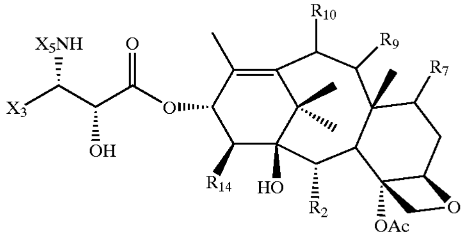

| Series | $X_5$ | $X_3$ | $R_7$ | $R_2$ | $R_9$ | $R_{14}$ |
|---|---|---|---|---|---|---|
| C8 | —$COX_{10}$ | optionally substituted $C_2$ to $C_8$ alkenyl | $R_{7a}COO$— | $C_6H_5COO$— | $R_{9a}COO$— | H |
| C9 | —$CONHX_{10}$ | optionally substituted $C_2$ to $C_8$ alkenyl | $R_{7a}COO$— | $C_6H_5COO$— | $R_{9a}COO$— | H |
| C10 | —$COOX_{10}$ | optionally substituted $C_2$ to $C_8$ alkynyl | $R_{7a}COO$— | $C_6H_5COO$— | $R_{9a}COO$— | H |
| C11 | —$COX_{10}$ | optionally substituted $C_2$ to $C_8$ alkynyl | $R_{7a}COO$— | $C_6H_5COO$— | $R_{9a}COO$— | H |
| C12 | —$CONHX_{10}$ | optionally substituted $C_2$ to $C_8$ alkynyl | $R_{7a}COO$— | $C_6H_5COO$— | $R_{9a}COO$— | H |
| D1 | —$COOX_{10}$ | heterocyclo | $R_{7a}COO$— | $C_6H_5COO$— | OH | H |
| D2 | —$COX_{10}$ | heterocyclo | $R_{7a}COO$— | $C_6H_5COO$— | OH | H |
| D3 | —$CONHX_{10}$ | heterocyclo | $R_{7a}COO$— | $C_6H_5COO$— | OH | H |
| D4 | —$COOX_{10}$ | optionally substituted $C_2$ to $C_8$ alkyl | $R_{7a}COO$— | $C_6H_5COO$— | OH | H |
| D5 | —$COX_{10}$ | optionally substituted $C_2$ to $C_8$ alkyl | $R_{7a}COO$— | $C_6H_5COO$— | OH | H |
| D6 | —$CONHX_{10}$ | optionally substituted $C_2$ to $C_8$ alkyl | $R_{7a}COO$— | $C_6H_5COO$— | OH | H |
| D7 | —$COOX_{10}$ | optionally substituted $C_2$ to $C_8$ alkenyl | $R_{7a}COO$— | $C_6H_5COO$— | OH | H |
| D8 | —$COX_{10}$ | optionally substituted $C_2$ to $C_8$ alkenyl | $R_{7a}COO$— | $C_6H_5COO$— | OH | H |
| D9 | —$CONHX_{10}$ | optionally substituted $C_2$ to $C_8$ alkenyl | $R_{7a}COO$— | $C_6H_5COO$— | OH | H |
| D10 | —$COOX_{10}$ | optionally substituted $C_2$ to $C_8$ alkynyl | $R_{7a}COO$— | $C_6H_5COO$— | OH | H |
| D11 | —$COX_{10}$ | optionally substituted $C_2$ to $C_8$ alkynyl | $R_{7a}COO$— | $C_6H_5COO$— | OH | H |
| D12 | —$CONHX_{10}$ | optionally substituted $C_2$ to $C_8$ alkynyl | $R_{7a}COO$— | $C_6H_5COO$— | OH | H |
| E1 | —$COOX_{10}$ | heterocyclo | $R_{7a}COO$— | $C_6H_5COO$— | O | OH |
| E2 | —$COX_{10}$ | heterocyclo | $R_{7a}COO$— | $C_6H_5COO$— | O | OH |
| E3 | —$CONHX_{10}$ | heterocyclo | $R_{7a}COO$— | $C_6H_5COO$— | O | OH |
| E4 | —$COOX_{10}$ | optionally substituted $C_2$ to $C_8$ alkyl | $R_{7a}COO$— | $C_6H_5COO$— | O | OH |
| E5 | —$COX_{10}$ | optionally substituted $C_2$ to $C_8$ alkyl | $R_{7a}COO$— | $C_6H_5COO$— | O | OH |
| E6 | —$CONHX_{10}$ | optionally substituted $C_2$ to $C_8$ alkyl | $R_{7a}COO$— | $C_6H_5COO$— | O | OH |
| E7 | —$COOX_{10}$ | optionally substituted $C_2$ to $C_8$ alkenyl | $R_{7a}COO$— | $C_6H_5COO$— | O | OH |

-continued (11)

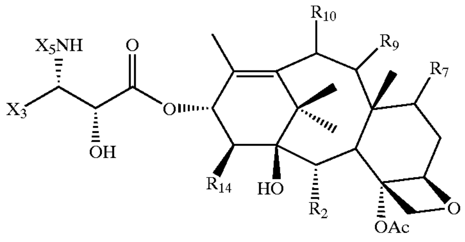

| Series | $X_5$ | $X_3$ | $R_7$ | $R_2$ | $R_9$ | $R_{14}$ |
|---|---|---|---|---|---|---|
| E8 | —$COX_{10}$ | optionally substituted $C_2$ to $C_8$ alkenyl | $R_{7a}COO$— | $C_6H_5COO$— | O | OH |
| E9 | —$CONHX_{10}$ | optionally substituted $C_2$ to $C_8$ alkenyl | $R_{7a}COO$— | $C_6H_5COO$— | O | OH |
| E10 | —$COOX_{10}$ | optionally substituted $C_2$ to $C_8$ alkynyl | $R_{7a}COO$— | $C_6H_5COO$— | O | OH |
| E11 | —$COX_{10}$ | optionally substituted $C_2$ to $C_8$ alkynyl | $R_{7a}COO$— | $C_6H_5COO$— | O | OH |
| E12 | —$CONHX_{10}$ | optionally substituted $C_2$ to $C_8$ alkynyl | $R_{7a}COO$— | $C_6H_5COO$— | O | OH |
| F1 | —$COOX_{10}$ | heterocyclo | $R_{7a}COO$— | $R_{2a}COO$— | $R_{9a}COO$— | H |
| F2 | —$COX_{10}$ | heterocyclo | $R_{7a}COO$— | $R_{2a}COO$— | $R_{9a}COO$— | H |
| F3 | —$CONHX_{10}$ | heterocyclo | $R_{7a}COO$— | $R_{2a}COO$— | $R_{9a}COO$— | H |
| F4 | —$COOX_{10}$ | optionally substituted $C_2$ to $C_8$ alkyl | $R_{7a}COO$— | $R_{2a}COO$— | $R_{9a}COO$— | H |
| F5 | —$COX_{10}$ | optionally substituted $C_2$ to $C_8$ alkyl | $R_{7a}COO$— | $R_{2a}COO$— | $R_{9a}COO$— | H |
| F6 | —$CONHX_{10}$ | optionally substituted $C_2$ to $C_8$ alkyl | $R_{7a}COO$— | $R_{2a}COO$— | $R_{9a}COO$— | H |
| F7 | —$COOX_{10}$ | optionally substituted $C_2$ to $C_8$ alkenyl | $R_{7a}COO$— | $R_{2a}COO$— | $R_{9a}COO$— | H |
| F8 | —$COX_{10}$ | optionally substituted $C_2$ to $C_8$ alkenyl | $R_{7a}COO$— | $R_{2a}COO$— | $R_{9a}COO$— | H |
| F9 | —$CONHX_{10}$ | optionally substituted $C_2$ to $C_8$ alkenyl | $R_{7a}COO$— | $R_{2a}COO$— | $R_{9a}COO$— | H |
| F10 | —$COOX_{10}$ | optionally substituted $C_2$ to $C_8$ alkynyl | $R_{7a}COO$— | $R_{2a}COO$— | $R_{9a}COO$— | H |
| F11 | —$COX_{10}$ | optionally substituted $C_2$ to $C_8$ alkynyl | $R_{7a}COO$— | $R_{2a}COO$— | $R_{9a}COO$— | H |
| F12 | —$CONHX_{10}$ | optionally substituted $C_2$ to $C_8$ alkynyl | $R_{7a}COO$— | $R_{2a}COO$— | $R_{9a}COO$— | H |
| G1 | —$COOX_{10}$ | heterocyclo | $R_{7a}COO$— | $R_{2a}COO$— | OH | H |
| G2 | —$COX_{10}$ | heterocyclo | $R_{7a}COO$— | $R_{2a}COO$— | OH | H |
| G3 | —$CONHX_{10}$ | heterocyclo | $R_{7a}COO$— | $R_{2a}COO$— | OH | H |
| G4 | —$COOX_{10}$ | optionally substituted $C_2$ to $C_8$ alkyl | $R_{7a}COO$— | $R_{2a}COO$— | OH | H |
| G5 | —$COX_{10}$ | optionally substituted $C_2$ to $C_8$ alkyl | $R_{7a}COO$— | $R_{2a}COO$— | OH | H |
| G6 | —$CONHX_{10}$ | optionally substituted $C_2$ to $C_8$ alkyl | $R_{7a}COO$— | $R_{2a}COO$— | OH | H |
| G7 | —$COOX_{10}$ | optionally substituted $C_2$ to $C_8$ alkenyl | $R_{7a}COO$— | $R_{2a}COO$— | OH | H |

-continued (11)

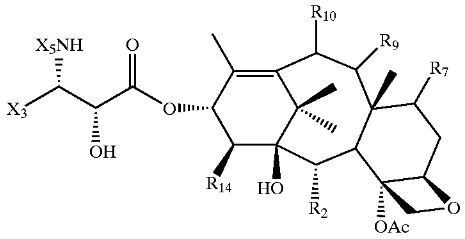

| Series | $X_5$ | $X_3$ | $R_7$ | $R_2$ | $R_9$ | $R_{14}$ |
|---|---|---|---|---|---|---|
| G8 | —$COX_{10}$ | optionally substituted $C_2$ to $C_8$ alkenyl | $R_{7a}COO$— | $R_{2a}COO$— | OH | H |
| G9 | —$CONHX_{10}$ | optionally substituted $C_2$ to $C_8$ alkenyl | $R_{7a}COO$— | $R_{2a}COO$— | OH | H |
| G10 | —$COOX_{10}$ | optionally substituted $C_2$ to $C_8$ alkynyl | $R_{7a}COO$— | $R_{2a}COO$— | OH | H |
| G11 | —$COX_{10}$ | optionally substituted $C_2$ to $C_8$ alkynyl | $R_{7a}COO$— | $R_{2a}COO$— | OH | H |
| G12 | —$CONHX_{10}$ | optionally substituted $C_2$ to $C_8$ alkynyl | $R_{7a}COO$— | $R_{2a}COO$— | OH | H |
| H1 | —$COOX_{10}$ | heterocyclo | $R_{7a}COO$— | $C_6H_5COO$— | OH | OH |
| H2 | —$COX_{10}$ | heterocyclo | $R_{7a}COO$— | $C_6H_5COO$— | OH | OH |
| H3 | —$CONHX_{10}$ | heterocyclo | $R_{7a}COO$— | $C_6H_5COO$— | OH | OH |
| H4 | —$COOX_{10}$ | optionally substituted $C_2$ to $C_8$ alkyl | $R_{7a}COO$— | $C_6H_5COO$— | OH | OH |
| H5 | —$COX_{10}$ | optionally substituted $C_2$ to $C_8$ alkyl | $R_{7a}COO$— | $C_6H_5COO$— | OH | OH |
| H6 | —$CONHX_{10}$ | optionally substituted $C_2$ to $C_8$ alkyl | $R_{7a}COO$— | $C_6H_5COO$— | OH | OH |
| H7 | —$COOX_{10}$ | optionally substituted $C_2$ to $C_8$ alkenyl | $R_{7a}COO$— | $C_6H_5COO$— | OH | OH |
| H8 | —$COX_{10}$ | optionally substituted $C_2$ to $C_8$ alkenyl | $R_{7a}COO$— | $C_6H_5COO$— | OH | OH |
| H9 | —$CONHX_{10}$ | optionally substituted $C_2$ to $C_8$ alkenyl | $R_{7a}COO$— | $C_6H_5COO$— | OH | OH |
| H10 | —$COOX_{10}$ | optionally substituted $C_2$ to $C_8$ alkynyl | $R_{7a}COO$— | $C_6H_5COO$— | OH | OH |
| H11 | —$COX_{10}$ | optionally substituted $C_2$ to $C_8$ alkynyl | $R_{7a}COO$— | $C_6H_5COO$— | OH | OH |
| H12 | —$CONHX_{10}$ | optionally substituted $C_2$ to $C_8$ alkynyl | $R_{7a}COO$— | $C_6H_5COO$— | OH | OH |
| I1 | —$COOX_{10}$ | heterocyclo | $R_{7a}COO$— | $R_{2a}COO$— | O | OH |
| I2 | —$COX_{10}$ | heterocyclo | $R_{7a}COO$— | $R_{2a}COO$— | O | OH |
| I3 | —$CONHX_{10}$ | heterocyclo | $R_{7a}COO$— | $R_{2a}COO$— | O | OH |
| I4 | —$COOX_{10}$ | optionally substituted $C_2$ to $C_8$ alkyl | $R_{7a}COO$— | $R_{2a}COO$— | O | OH |
| I5 | —$COX_{10}$ | optionally substituted $C_2$ to $C_8$ alkyl | $R_{7a}COO$— | $R_{2a}COO$— | O | OH |
| I6 | —$CONHX_{10}$ | optionally substituted $C_2$ to $C_8$ alkyl | $R_{7a}COO$— | $R_{2a}COO$— | O | OH |
| I7 | —$COOX_{10}$ | optionally substituted $C_2$ to $C_8$ alkenyl | $R_{7a}COO$— | $R_{2a}COO$— | O | OH |

-continued (11)

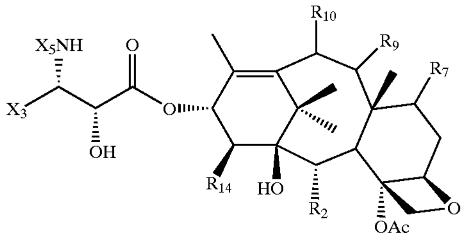

| Series | $X_5$ | $X_3$ | $R_7$ | $R_2$ | $R_9$ | $R_{14}$ |
|---|---|---|---|---|---|---|
| I8 | —$COX_{10}$ | optionally substituted $C_2$ to $C_8$ alkenyl | $R_{7a}COO$— | $R_{2a}COO$— | O | OH |
| I9 | —$CONHX_{10}$ | optionally substituted $C_2$ to $C_8$ alkenyl | $R_{7a}COO$— | $R_{2a}COO$— | O | OH |
| I10 | —$COOX_{10}$ | optionally substituted $C_2$ to $C_8$ alkynyl | $R_{7a}COO$— | $R_{2a}COO$— | O | OH |
| I11 | —$COX_{10}$ | optionally substituted $C_2$ to $C_8$ alkynyl | $R_{7a}COO$— | $R_{2a}COO$— | O | OH |
| I12 | —$CONHX_{10}$ | optionally substituted $C_2$ to $C_8$ alkynyl | $R_{7a}COO$— | $R_{2a}COO$— | O | OH |
| J1 | —$COOX_{10}$ | heterocyclo | $R_{7a}COO$— | $R_{2a}COO$— | OH | OH |
| J2 | —$COX_{10}$ | heterocyclo | $R_{7a}COO$— | $R_{2a}COO$— | OH | OH |
| J3 | —$CONHX_{10}$ | heterocyclo | $R_{7a}COO$— | $R_{2a}COO$— | OH | OH |
| J4 | —$COOX_{10}$ | optionally substituted $C_2$ to $C_8$ alkyl | $R_{7a}COO$— | $R_{2a}COO$— | OH | OH |
| J5 | —$COX_{10}$ | optionally substituted $C_2$ to $C_8$ alkyl | $R_{7a}COO$— | $R_{2a}COO$— | OH | OH |
| J6 | —$CONHX_{10}$ | optionally substituted $C_2$ to $C_8$ alkyl | $R_{7a}COO$— | $R_{2a}COO$— | OH | OH |
| J7 | —$COOX_{10}$ | optionally substituted $C_2$ to $C_8$ alkenyl | $R_{7a}COO$— | $R_{2a}COO$— | OH | OH |
| J8 | —$COX_{10}$ | optionally substituted $C_2$ to $C_8$ alkenyl | $R_{7a}COO$— | $R_{2a}COO$— | OH | OH |
| J9 | —$CONHX_{10}$ | optionally substituted $C_2$ to $C_8$ alkenyl | $R_{7a}COO$— | $R_{2a}COO$— | OH | OH |
| J10 | —$COOX_{10}$ | optionally substituted $C_2$ to $C_8$ alkynyl | $R_{7a}COO$— | $R_{2a}COO$— | OH | OH |
| J11 | —$COX_{10}$ | optionally substituted $C_2$ to $C_8$ alkynyl | $R_{7a}COO$— | $R_{2a}COO$— | OH | OH |
| J12 | —$CONHX_{10}$ | optionally substituted $C_2$ to $C_8$ alkynyl | $R_{7a}COO$— | $R_{2a}COO$— | OH | OH |
| K1 | —$COOX_{10}$ | heterocyclo | $R_{7a}COO$— | $R_{2a}COO$— | $R_{9a}COO$— | OH |
| K2 | —$COX_{10}$ | heterocyclo | $R_{7a}COO$— | $R_{2a}COO$— | $R_{9a}COO$— | OH |
| K3 | —$CONHX_{10}$ | heterocyclo | $R_{7a}COO$— | $R_{2a}COO$— | $R_{9a}COO$— | OH |
| K4 | —$COOX_{10}$ | optionally substituted $C_2$ to $C_8$ alkyl | $R_{7a}COO$— | $R_{2a}COO$— | $R_{9a}COO$— | OH |
| K5 | —$COX_{10}$ | optionally substituted $C_2$ to $C_8$ alkyl | $R_{7a}COO$— | $R_{2a}COO$— | $R_{9a}COO$— | OH |
| K6 | —$CONHX_{10}$ | optionally substituted $C_2$ to $C_8$ alkyl | $R_{7a}COO$— | $R_{2a}COO$— | $R_{9a}COO$— | OH |
| K7 | —$COOX_{10}$ | optionally substituted $C_2$ to $C_8$ alkenyl | $R_{7a}COO$— | $R_{2a}COO$— | $R_{9a}COO$— | OH |

-continued (11)

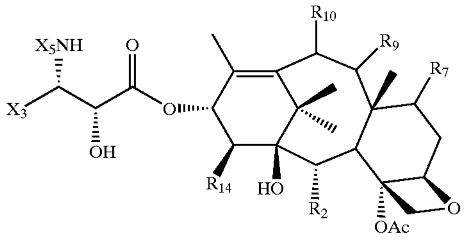

| Series | $X_5$ | $X_3$ | $R_7$ | $R_2$ | $R_9$ | $R_{14}$ |
|---|---|---|---|---|---|---|
| K8 | —$COX_{10}$ | optionally substituted $C_2$ to $C_8$ alkenyl | $R_{7a}COO$— | $R_{2a}COO$— | $R_{9a}COO$— | OH |
| K9 | —$CONHX_{10}$ | optionally substituted $C_2$ to $C_8$ alkenyl | $R_{7a}COO$— | $R_{2a}COO$— | $R_{9a}COO$— | OH |
| K10 | —$COOX_{10}$ | optionally substituted $C_2$ to $C_8$ alkynyl | $R_{7a}COO$— | $R_{2a}COO$— | $R_{9a}COO$— | OH |
| K11 | —$COX_{10}$ | optionally substituted $C_2$ to $C_8$ alkynyl | $R_{7a}COO$— | $R_{2a}COO$— | $R_{9a}COO$— | OH |
| K12 | —$CONHX_{10}$ | optionally substituted $C_2$ to $C_8$ alkynyl | $R_{7a}COO$— | $R_{2a}COO$— | $R_{9a}COO$— | OH |

EXAMPLE 15

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 2 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 5544 | <1 |
| 5474 | <1 |
| 5555 | <1 |
| 5999 | <1 |
| 6353 | <1 |
| 6226 | <1 |

-continued

| Compound | IN VITRO ID 50 (nm) HCT116 |
|---|---|
| 5622 | <1 |
| 5515 | <1 |
| 5445 | <1 |
| 5600 | <1 |
| 5616 | <1 |
| 5835 | <1 |
| 5811 | <1 |
| 5919 | <1 |
| 6326 | <1 |

EXAMPLE 16

Preparation of Taxane having C-10 Substituted Acetate and C-7 Hydroxy N-Debenzoyl-N-tert-amyloxycarbonyl-3'-desphenyl-3'-(2-furyl)-10-methoxyacetyl taxol (6515)

To a solution of N-debenzoyl-N-tert-amyloxycarbonyl-3'-desphenyl-3'-(2-furyl)-2'-(2-methoxy-2-propyl)-7-benzyloxycarbonyl-10-deacetyl-10-trimethylsilyl taxol (3.50 g) in 40 mL of 1:1 acetonitrile-pyridine at 0° C. (ice-water bath) was added dropwise over 10 minutes, 10 mL of 48% aqueous hydrofluoric acid. The cooling bath was then removed and the reaction stirred at ambient temperature for 8 h, diluted with 200 mL of ethyl acetate and washed with 25 mL of water, 2x20 mL of saturated aqueous $NaHCO_3$ and 25 mL of saturated aqueous NaCl. The organic layer was then dried over sodium sulfate and concentrated under reduced pressure to give N-debenzoyl-N-tert-amyloxycarbonyl-3'-desphenyl-3'-(2-furyl)-7-benzyloxycarbonyl-10-deacetyl taxol as a white solid which was dried under high vacuum (0.1 mmHg, 12 h) and used directly in the next step.

To a solution of N-debenzoyl-N-tert-amyloxycarbonyl-3'-desphenyl-3'-(2-furyl)-7-benzyloxycarbonyl-10-deacetyl taxol (2.17 g, 2.293 mmol) in anhydrous methylene chloride (6 mL) was added with stirring triethylamine (1.60 mL, 11.46 mmol) followed by the dropwise addition of 0.46 mL of triethylsilyl chloride. TLC of the mixture (silica gel, 2:3 ethyl acetate:hexane) after 2 h, showed the formation of only one product. Saturated aqueous $NaHCO_3$, 2 mL was added to the reaction which was then diluted with 70 mL of ethyl acetate, washed with 10 mL of saturated aqueous $NaHCO_3$ and 15 mL of saturated aqueous NaCl. The organic layer was dried over sodium sulfate and concentrated under reduced pressure to give pure N-debenzoyl-N-tert-amyloxycarbonyl-3'-desphenyl-3'-(2-furyl)-2'-triethylsilyl-7-benzyloxycarbonyl-10-deacetyl taxol as a white solid (2.21 g, 91%)

To a solution of N-debenzoyl-N-tert-amyloxycarbonyl-3'-desphenyl-3'-(2-furyl)-2'-triethylsilyl-7-benzyloxycarbonyl-10-deacetyl taxol (660 mg, 0.622 mmol) in 4 mL anhydrous pyridine at 0° C. was added DMAP (20 mg, 0.16 mmol) under a nitrogen atmosphere. To this mixture was added drop wise methoxyacetyl chloride (220 mL, 2.489 mmol). TLC (silica gel, 2:3 ethyl acetate:hexane) after 2 h showed no starting material. The reaction was cooled to 0° C. (ice-water bath) and quenched by adding 80 mL of water.

To the reaction at 0° C. (ice-water bath) was added 4 mL of acetonitrile and 2 mL of 48% aqueous hydrofluoric acid and the cooling bath was removed. The reaction was stirred at room temperature for 8.0 h, diluted with 60 mL of ethyl acetate and washed with 10 mL of saturated aqueous $NaHCO_3$ and 15 mL of saturated aqueous NaCl. The organic layer was dried over $Na_2SO_4$ and concentrated under reduce pressure to give 602 mg of a yellow solid which was purified by flash-chromatography (silica gel, 1:1 ethyl acetate:hexane) to give 538 mg (85%) of pure N-debenzoyl-N-tert-amyloxycarbonyl-3'-desphenyl-3'-(2-furyl)-7-benzyloxycarbonyl-10-deacetyl-10-methoxyacetyl taxol (TL-650): mp 145–146° C.; Anal. Calcd. for $C_{53}H_{63}NO_{19}$: C, 62.53; H, 6.24. Found: C, 62.26; H, 6.20.

To a solution of N-debenzoyl-N-tert-amyloxycarbonyl-3'-desphenyl-3'-(2-furyl)-7-benzyloxycarbonyl-10-deacetyl-10-methoxyacetyl taxol (TL-650, 350 mg, 0.343 mmol) in 15 mL ethyl acetate was added 10% Pd-C (100 mg). The mixture was stirred under a $H_2$ atmosphere (using latex balloons) for 1 h, when TLC (silica gel, 1:1 ethyl acetate:hexane) showed no starting material. The reaction was then filtered through celite (3 g) and the celite pad washed with 25 mL of ethyl acetate. The combined organic extract was concentrated under reduced pressure to give 315 mg of a white solid which was purified by flash-chromatography (silica gel, 55:45 ethyl acetate:hexane) to give 283 mg (93%) of pure N-debenzoyl-N-tert-amyloxycarbonyl-3'-desphenyl-3'-(2-furyl)- -10-deacetyl-10-methoxyacetyl taxol: mp 164–166° C.; $^1H$ NMR ($CDCl_3$) 8.13 (m, 2H), 7.62(m, 1H), 7.46–7.51(m, 2H), 7.41 (m, 1H), 6.41 (bs, 1H), 6.39(dd, J=3.1, 1.5 Hz, 1H), 6.25 (d, J=3.1 Hz, 1H), 6.22(dd, J=8.8, 8.7 Hz, 1H), 5.67(1H), 5.22–5.38(m, 2H), 4.98(m, 1H), 4.76(m, 1H), 4.42(m, 2H), 4.36 (d, J=9.3 Hz, 1H), 4.28(m, 1H), 4.21 (d, J=9.3 Hz, 1H), 3.82 (m, 1H), 3.42 (s, 3H), 3.41 (d, J=5.5 Hz, 1H), 2.55–2.60 (m, 1H), 2.41 (s, 3H), 2.20–2.38(m, 2H), 1.92 (s, 3H), 1.91–1.94 (m, 1H), 1.68 (bs, 3H), 1.62–1.68(m, 2H), 1.62(S, 3H), 1.36(s, 3H), 1.34(s, 3H), 1.23(s, 3H), 1.16(s, 3H), 0.80(t, J=8.2Hz, 3H); Anal. Calcd. for $C_{45}H_{57}NO_{17}.½H_2O$: C, 60.47; H, 6.49. Found: C, 60.64; H, 6.45.

EXAMPLE 17

Additional Taxanes having C-10 Acetate and C-7 Hydroxy Substituents

The procedures described in Example 16 were repeated, but other suitably protected β-lactams were substituted for the β-lactam of Example 16 to prepare the series of compounds having structural formula (12) and the combinations of substituents identified in the following table:

(12)

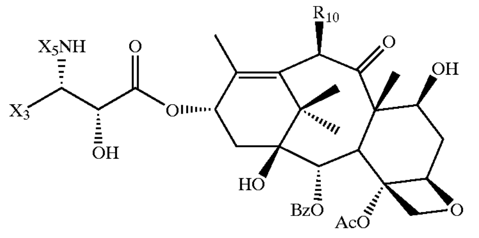

| Compound | $X_5$ | $X_3$ | $R_{10}$ |
|---|---|---|---|
| 6577 | tAmOCO | 2-furyl | AcOAcO— |
| 6515 | tAmOCO | 2-furyl | MeOAcO— |
| 6066 | $tC_3H_5CO$ | 2-furyl | MeOAcO— |
| 6111 | $tC_3H_5CO$ | 2-furyl | PhOAcO— |

EXAMPLE 18

Taxanes having C-10 Substituted Acetate and C-7 Hydroxy Substituents

Following the processes described in Example 16 and elsewhere herein, the following specific taxanes having structural formula (13 ) may be prepared, wherein $R_{10}$ is $R_{10a}COO$— and $R_{10a}$ is heterosubstituted methyl. In one embodiment, $R_{10a}$ is chloromethyl, hydroxymethyl, methoxymethyl, ethoxymethyl, phenoxymethyl, acetoxymethyl, acyloxymethyl, or methylthiomethyl.

(13)

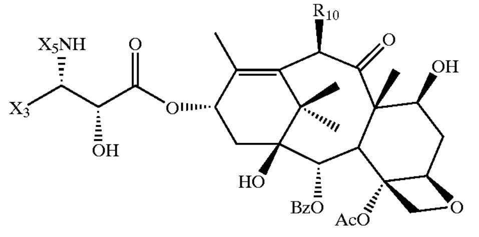

| $X_5$ | $X_3$ | $R_{10}$ |
|---|---|---|
| tBuOCO— | 2-furyl | $R_{10a}COO$— |
| tBuOCO— | 3-furyl | $R_{10a}COO$— |
| tBuOCO— | 2-thienyl | $R_{10a}COO$— |
| tBuOCO— | 3-thienyl | $R_{10a}COO$— |
| tBuOCO— | 2-pyridyl | $R_{10a}COO$— |
| tBuOCO— | 3-pyridyl | $R_{10a}COO$— |
| tBuOCO— | 4-pyridyl | $R_{10a}COO$— |
| tBuOCO— | isobutenyl | $R_{10a}COO$— |
| tBuOCO— | isopropyl | $R_{10a}COO$— |
| tBuOCO— | cyclopropyl | $R_{10a}COO$— |
| tBuOCO— | cyclobutyl | $R_{10a}COO$— |
| tBuOCO— | cyclopentyl | $R_{10a}COO$— |
| tBuOCO— | phenyl | $R_{10a}COO$— |
| benzoyl | 2-furyl | $R_{10a}COO$— |
| benzoyl | 3-furyl | $R_{10a}COO$— |
| benzoyl | 2-thienyl | $R_{10a}COO$— |
| benzoyl | 3-thienyl | $R_{10a}COO$— |
| benzoyl | 2-pyridyl | $R_{10a}COO$— |

-continued (13)

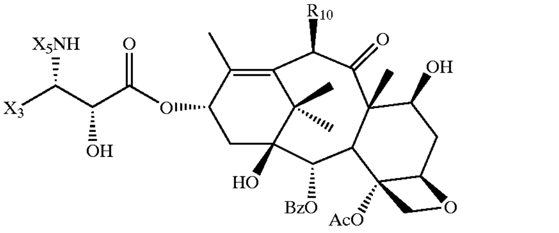

| $X_5$ | $X_3$ | $R_{10}$ |
|---|---|---|
| benzoyl | 3-pyridyl | $R_{10a}$COO— |
| benzoyl | 4-pyridyl | $R_{10a}$COO— |
| benzoyl | isobutenyl | $R_{10a}$COO— |
| benzoyl | isopropyl | $R_{10a}$COO— |
| benzoyl | cyclopropyl | $R_{10a}$COO— |
| benzoyl | cyclobutyl | $R_{10a}$COO— |
| benzoyl | cyclopentyl | $R_{10a}$COO— |
| benzoyl | phenyl | $R_{10a}$COO— |
| 2-FuCO— | 2-furyl | $R_{10a}$COO— |
| 2-FuCO— | 3-furyl | $R_{10a}$COO— |
| 2-FuCO— | 2-thienyl | $R_{10a}$COO— |
| 2-FuCO— | 3-thienyl | $R_{10a}$COO— |
| 2-FuCO— | 2-pyridyl | $R_{10a}$COO— |
| 2-FuCO— | 3-pyridyl | $R_{10a}$COO— |
| 2-FuCO— | 4-pyridyl | $R_{10a}$COO— |
| 2-FuCO— | isobutenyl | $R_{10a}$COO— |
| 2-FuCO— | isopropyl | $R_{10a}$COO— |
| 2-FuCO— | cyclopropyl | $R_{10a}$COO— |
| 2-FuCO— | cyclobutyl | $R_{10a}$COO— |
| 2-FuCO— | cyclopentyl | $R_{10a}$COO— |
| 2-FuCO— | phenyl | $R_{10a}$COO— |
| 2-ThCO— | 2-furyl | $R_{10a}$COO— |
| 2-ThCO— | 3-furyl | $R_{10a}$COO— |
| 2-ThCO— | 2-thienyl | $R_{10a}$COO— |
| 2-ThCO— | 3-thienyl | $R_{10a}$COO— |
| 2-ThCO— | 2-pyridyl | $R_{10a}$COO— |
| 2-ThCO— | 3-pyridyl | $R_{10a}$COO— |
| 2-ThCO— | 4-pyridyl | $R_{10a}$COO— |
| 2-ThCO— | isobutenyl | $R_{10a}$COO— |
| 2-ThCO— | isopropyl | F$R_{10a}$COO— |
| 2-ThCO— | cyclopropyl | $R_{10a}$COO— |
| 2-ThCO— | cyclobutyl | $R_{10a}$COO— |
| 2-ThCO— | cyclopentyl | $R_{10a}$COO— |
| 2-ThCO— | phenyl | $R_{10a}$COO— |
| 2-PyCO— | 2-furyl | $R_{10a}$COO— |
| 2-PyCO— | 3-furyl | $R_{10a}$COO— |
| 2-PyCO— | 2-thienyl | $R_{10a}$COO— |
| 2-PyCO— | 3-thienyl | $R_{10a}$COO— |
| 2-PyCO— | 2-pyridyl | $R_{10a}$COO— |
| 2-PyCO— | 3-pyridyl | $R_{10a}$COO— |
| 2-PyCO— | 4-pyridyl | $R_{10a}$COO— |
| 2-PyCO— | isobutenyl | $R_{10a}$COO— |
| 2-PyCO— | isopropyl | $R_{10a}$COO— |
| 2-PyCO— | cyclopropyl | $R_{10a}$COO— |
| 2-PyCO— | cyclobutyl | $R_{10a}$COO— |
| 2-PyCO— | cyclopentyl | $R_{10a}$COO— |
| 2-PyCO— | phenyl | $R_{10a}$COO— |
| 3-PyCO— | 2-furyl | $R_{10a}$COO— |
| 3-PyCO— | 3-furyl | $R_{10a}$COO— |
| 3-PyCO— | 2-thienyl | $R_{10a}$COO— |
| 3-PyCO— | 3-thienyl | $R_{10a}$COO— |
| 3-PyCO— | 2-pyridyl | $R_{10a}$COO— |
| 3-PyCO— | 3-pyridyl | $R_{10a}$COO— |
| 3-PyCO— | 4-pyridyl | $R_{10a}$COO— |
| 3-PyCO— | isobutenyl | $R_{10a}$COO— |
| 3-PyCO— | isopropyl | $R_{10a}$COO— |
| 3-PyCO— | cyclopropyl | $R_{10a}$COO— |
| 3-PyCO— | cyclobutyl | $R_{10a}$COO— |
| 3-PyCO— | cyclopentyl | $R_{10a}$COO— |
| 3-PyCO— | phenyl | $R_{10a}$COO— |
| 4-PyCO— | 2-furyl | $R_{10a}$COO— |
| 4-PyCO— | 3-furyl | $R_{10a}$COO— |
| 4-PyCO— | 2-thienyl | $R_{10a}$COO— |

-continued (13)

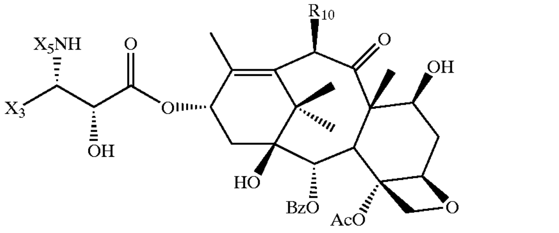

| $X_5$ | $X_3$ | $R_{10}$ |
|---|---|---|
| 4-PyCO— | 3-thienyl | $R_{10a}$COO— |
| 4-PyCO— | 2-pyridyl | $R_{10a}$COO— |
| 4-PyCO— | 3-pyridyl | $R_{10a}$COO— |
| 4-PyCO— | 4-pyridyl | $R_{10a}$COO— |
| 4-PyCO— | isobutenyl | $R_{10a}$COO— |
| 4-PyCO— | isopropyl | $R_{10a}$COO— |
| 4-PyCO— | cyclopropyl | $R_{10a}$COO— |
| 4-PyCO— | cyclobutyl | $R_{10a}$COO— |
| 4-PyCO— | cyclopentyl | $R_{10a}$COO— |
| 4-PyCO— | phenyl | $R_{10a}$COO— |
| $C_4H_7$CO— | 2-furyl | $R_{10a}$COO— |
| $C_4H_7$CO— | 3-furyl | $R_{10a}$COO— |
| $C_4H_7$CO— | 2-thienyl | $R_{10a}$COO— |
| $C_4H_7$CO— | 3-thienyl | $R_{10a}$COO— |
| $C_4H_7$CO— | 2-pyridyl | $R_{10a}$COO— |
| $C_4H_7$CO— | 3-pyridyl | $R_{10a}$COO— |
| $C_4H_7$CO— | 4-pyridyl | $R_{10a}$COO— |
| $C_4H_7$CO— | isobutenyl | $R_{10a}$COO— |
| $C_4H_7$CO— | isopropyl | $R_{10a}$COO— |
| $C_4H_7$CO— | cyclopropyl | $R_{10a}$COO— |
| $C_4H_7$CO— | cyclobutyl | $R_{10a}$COO— |
| $C_4H_7$CO— | cyclopentyl | $R_{10a}$COO— |
| $C_4H_7$CO— | phenyl | $R_{10a}$COO— |
| EtOCO— | 2-furyl | $R_{10a}$COO— |
| EtOCO— | 3-furyl | $R_{10a}$COO— |
| EtOCO— | 2-thienyl | $R_{10a}$COO— |
| EtOCO— | 3-thienyl | $R_{10a}$COO— |
| EtOCO— | 2-pyridyl | $R_{10a}$COO— |
| EtOCO— | 3-pyridyl | $R_{10a}$COO— |
| EtOCO— | 4-pyridyl | $R_{10a}$COO— |
| EtOCO— | isobutenyl | $R_{10a}$COO— |
| EtOCO— | isopropyl | $R_{10a}$COO— |
| EtOCO— | cyclopropyl | $R_{10a}$COO— |
| EtOCO— | cyclobutyl | $R_{10a}$COO— |
| EtOCO— | cyclopentyl | $R_{10a}$COO— |
| EtOCO— | phenyl | $R_{10a}$COO— |
| ibueCO— | 2-furyl | $R_{10a}$COO— |
| ibueCO— | 3-furyl | $R_{10a}$COO— |
| ibueCO— | 2-thienyl | $R_{10a}$COO— |
| ibueCO— | 3-thienyl | $R_{10a}$COO— |
| ibueCO— | 2-pyridyl | $R_{10a}$COO— |
| ibueCO— | 3-pyridyl | $R_{10a}$COO— |
| ibueCO— | 4-pyridyl | $R_{10a}$COO— |
| ibueCO— | isobutenyl | $R_{10a}$COO— |
| ibueCO— | isopropyl | $R_{10a}$COO— |
| ibueCO— | cyclopropyl | $R_{10a}$COO— |
| ibueCO— | cyclobutyl | $R_{10a}$COO— |
| ibueCO— | cyclopentyl | $R_{10a}$COO— |
| ibueCO— | phenyl | $R_{10a}$COO— |
| iBuCO— | 2-furyl | $R_{10a}$COO— |
| iBuCO— | 3-furyl | $R_{10a}$COO— |
| iBuCO— | 2-thienyl | $R_{10a}$COO— |
| iBuCO— | 3-thienyl | $R_{10a}$COO— |
| iBuCO— | 2-pyridyl | $R_{10a}$COO— |
| iBuCO— | 3-pyridyl | $R_{10a}$COO— |
| iBuCO— | 4-pyridyl | $R_{10a}$COO— |
| IBuCO— | isobutenyl | $R_{10a}$COO— |
| iBuCO— | isopropyl | $R_{10a}$COO— |
| iBuCO— | cyclopropyl | $R_{10a}$COO— |
| iBuCO— | cyclobutyl | $R_{10a}$COO— |
| iBuCO— | cyclopentyl | $R_{10a}$COO— |
| iBuCO— | phenyl | $R_{10a}$COO— |
| iBuOCO— | 2-furyl | $R_{10a}$COO— |

-continued (13)

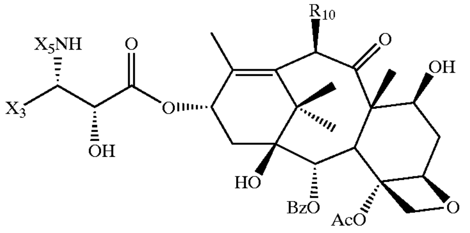

| $X_5$ | $X_3$ | $R_{10}$ |
|---|---|---|
| iBuOCO— | 3-furyl | $R_{10a}$COO— |
| iBuOCO— | 2-thienyl | $R_{10a}$COO— |
| iBuOCO— | 3-thienyl | $R_{10a}$COO— |
| iBuOCO— | 2-pyridyl | $R_{10a}$COO— |
| iBuOCO— | 3-pyridyl | $R_{10a}$COO— |
| iBuOCO— | 4-pyridyl | $R_{10a}$COO— |
| iBuOCO— | isobutenyl | $R_{10a}$COO— |
| iBuOCO— | isopropyl | $R_{10a}$COO— |
| iBuOCO— | cyclopropyl | $R_{10a}$COO— |
| iBuOCO— | cyclobutyl | $R_{10a}$COO— |
| iBuOCO— | cyclopentyl | $R_{10a}$COO— |
| iBuOCO— | phenyl | $R_{10a}$COO— |
| iPrOCO— | 2-furyl | $R_{10a}$COO— |
| iPrOCO— | 3-furyl | $R_{10a}$COO— |
| iPrOCO— | 2-thienyl | $R_{10a}$COO— |
| iPrOCO— | 3-thienyl | $R_{10a}$COO— |
| iPrOCO— | 2-pyridyl | $R_{10a}$COO— |
| iPrOCO— | 3-pyridyl | $R_{10a}$COO— |
| iPrOCO— | 4-pyridyl | $R_{10a}$COO— |
| iPrOCO— | isobutenyl | $R_{10a}$COO— |
| iPrOCO— | isopropyl | $R_{10a}$COO— |
| iPrOCO— | cyclopropyl | $R_{10a}$COO— |
| iPrOCO— | cyclobutyl | $R_{10a}$COO— |
| iPrOCO— | cyclopentyl | $R_{10a}$COO— |
| iPrOCO— | phenyl | $R_{10a}$COO— |
| nPrOCO— | 2-furyl | $R_{10a}$COO— |
| nPrOCO— | 3-furyl | $R_{10a}$COO— |
| nPrOCO— | 2-thienyl | $R_{10a}$COO— |
| nPrOCO— | 3-thienyl | $R_{10a}$COO— |
| nPrOCO— | 2-pyridyl | $R_{10a}$COO— |
| nPrOCO— | 3-pyridyl | $R_{10a}$COO— |
| nPrOCO— | 4-pyridyl | $R_{10a}$COO— |
| nPrOCO— | isobutenyl | $R_{10a}$COO— |
| nPrOCO— | isopropyl | $R_{10a}$COO— |
| nPrOCO— | cyolopropyl | $R_{10a}$COO— |
| nPrOCO— | cyclobutyl | $R_{10a}$COO— |
| nPrOCO— | cyclopentyl | $R_{10a}$COO— |
| nPrOCO— | phenyl | $R_{10a}$COO— |
| nPrCO— | 2-furyl | $R_{10a}$COO— |
| nPrCO— | 3-furyl | $R_{10a}$COO— |
| nPrCO— | 2-thienyl | $R_{10a}$COO— |
| nPrCO— | 3-thienyl | $R_{10a}$COO— |
| nPrCO— | 2-pyridyl | $R_{10a}$COO— |
| nPrCO— | 3-pyridyl | $R_{10a}$COO— |
| nPrCO— | 4-pyridyl | $R_{10a}$COO— |
| nPrCO— | isobutenyl | $R_{10a}$COO— |
| nPrCO— | isopropyl | $R_{10a}$COO— |
| nPrCO— | cyclopropyl | $R_{10a}$COO— |
| nPrCO— | cyclobutyl | $R_{10a}$COO— |
| nPrCO— | cyclopentyl | $R_{10a}$COO— |
| nPrCO— | phenyl | $R_{10a}$COO— |

EXAMPLE 19

Taxanes having C-10 Substituted Acetate and C-7 Hydroxy Substituents

Following the processes described in Example 16 and elsewhere herein, the following specific taxanes having structural formula (14) may be prepared, wherein $R_7$ is hydroxy and $R_{10}$ in each of the series (that is, each of series "A" through "K") is as previously defined, including wherein $R_{10}$ is $R_{10a}$COO— wherein $R_{10a}$ is a heterosubstituted methyl moiety lacking a carbon atom which is in the beta position relative to the carbon atom of which $R_{10a}$ is a substituent. The heterosubstituted methyl is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety. Exemplary $R_{10}$ substituents include $R_{10a}$COO— wherein $R_{10a}$ is chloromethyl, hydroxymethyl, methoxymethyl, ethoxymethyl, phenoxymethyl, acetoxymethyl, acyloxymethyl, or methylthiomethyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstituted furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(14)

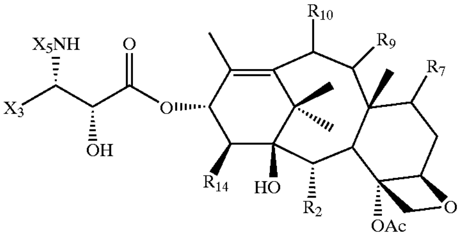

| Series | $X_5$ | $X_3$ | $R_{10}$ | $R_2$ | $R_9$ | $R_{14}$ |
|---|---|---|---|---|---|---|
| A1 | —$COOX_{10}$ | heterocyclo | $R_{10a}COO$— | $C_6H_5COO$— | O | H |
| A2 | —$COX_{10}$ | heterocyclo | $R_{10a}COO$— | $C_6H_5COO$— | O | H |
| A3 | —$CONHX_{10}$ | heterocyclo | $R_{10a}COO$— | $C_6H_5COO$— | O | H |
| A4 | —$COOX_{10}$ | optionally substituted $C_2$ to $C_8$ alkyl | $R_{10a}COO$— | $C_6H_5COO$— | O | H |
| A5 | —$COX_{10}$ | optionally substituted $C_2$ to $C_8$ alkyl | $R_{10a}COO$— | $C_6H_5COO$— | O | H |
| A6 | —$CONHX_{10}$ | optionally substituted $C_2$ to $C_8$ alkyl | $R_{10a}COO$— | $C_6H_5COO$— | O | H |
| A7 | —$COOX_{10}$ | optionally substituted $C_2$ to $C_8$ alkenyl | $R_{10a}COO$— | $C_6H_5COO$— | O | H |
| A8 | —$COX_{10}$ | optionally substituted $C_2$ to $C_8$ alkenyl | $R_{10a}COO$— | $C_6H_5COO$— | O | H |
| A9 | —$CONHX_{10}$ | optionally substituted $C_2$ to $C_8$ alkenyl | $R_{10a}COO$— | $C_6H_5COO$— | O | H |
| A10 | —$COOX_{10}$ | optionally substituted $C_2$ to $C_8$ alkynyl | $R_{10a}COO$— | $C_6H_5COO$— | O | H |
| A11 | —$COX_{10}$ | optionally substituted $C_2$ to $C_8$ alkynyl | $R_{10a}COO$— | $C_6H_5COO$— | O | H |
| A12 | —$CONHX_{10}$ | optionally substituted $C_2$ to $C_8$ alkynyl | $R_{10a}COO$— | $C_6H_5COO$— | O | H |
| B1 | —$COOX_{10}$ | heterocyclo | $R_{10a}COO$— | $R_{2a}COO$— | O | H |
| B2 | —$COX_{10}$ | heterocyclo | $R_{10a}COO$— | $R_{2a}COO$— | O | H |
| B3 | —$CONHX_{10}$ | heterocyclo | $R_{10a}COO$— | $R_{2a}COO$— | O | H |
| B4 | —$COOX_{10}$ | optionally substituted $C_2$ to $C_8$ alkyl | $R_{10a}COO$— | $R_{2a}COO$— | O | H |
| B5 | —$COX_{10}$ | optionally substituted $C_2$ to $C_8$ alkyl | $R_{10a}COO$— | $R_{2a}COO$— | O | H |

-continued (14)

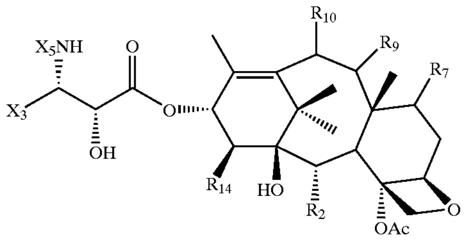

| Series | $X_5$ | $X_3$ | $R_{10}$ | $R_2$ | $R_9$ | $R_{14}$ |
|---|---|---|---|---|---|---|
| B6 | —$CONHX_{10}$ | optionally substituted $C_2$ to $C_8$ alkyl | $R_{10a}COO$— | $R_{2a}COO$— | O | H |
| B7 | —$COOX_{10}$ | optionally substituted $C_2$ to $C_8$ alkenyl | $R_{10a}COO$— | $R_{2a}COO$— | O | H |
| B8 | —$COX_{10}$ | optionally substituted $C_2$ to $C_8$ alkenyl | $R_{10a}COO$— | $R_{2a}COO$— | O | H |
| B9 | —$CONHX_{10}$ | optionally substituted $C_2$ to $C_8$ alkenyl | $R_{10a}COO$— | $R_{2a}COO$— | O | H |
| B10 | —$COOX_{10}$ | optionally substituted $C_2$ to $C_8$ alkynyl | $R_{10a}COO$— | $R_{2a}COO$— | O | H |
| B11 | —$COX_{10}$ | optionally substituted $C_2$ to $C_8$ alkynyl | $R_{10a}COO$— | $R_{2a}COO$— | O | H |
| B12 | —$CONHX_{10}$ | optionally substituted $C_2$ to $C_8$ alkynyl | $R_{10a}COO$— | $R_{2a}COO$— | O | H |
| C1 | —$COOX_{10}$ | heterocyclo | $R_{10a}COO$— | $C_6H_5COO$— | $R_{9a}COO$— | H |
| C2 | —$COX_{10}$ | heterocyclo | $R_{10a}COO$— | $C_6H_5COO$— | $R_{9a}COO$— | H |
| C3 | —$CONHX_{10}$ | heterocyclo | $R_{10a}COO$— | $C_6H_5COO$— | $R_{9a}COO$— | H |
| C4 | —$COOX_{10}$ | optionally substituted $C_2$ to $C_8$ alkyl | $R_{10a}COO$— | $C_6H_5COO$— | $R_{9a}COO$— | H |
| C5 | —$COX_{10}$ | optionally substituted $C_2$ to $C_8$ alkyl | $R_{10a}COO$— | $C_6H_5COO$— | $R_{9a}COO$— | H |
| C6 | —$CONHX_{10}$ | optionally substituted $C_2$ to $C_8$ alkyl | $R_{10a}COO$— | $C_6H_5COO$— | $R_{9a}COO$— | H |
| C7 | —$COOX_{10}$ | optionally substituted $C_2$ to $C_8$ alkenyl | $R_{10a}COO$— | $C_6H_5COO$— | $R_{9a}COO$— | H |
| C8 | —$COX_{10}$ | optionally substituted $C_2$ to $C_8$ alkenyl | $R_{10a}COO$— | $C_6H_5COO$— | $R_{9a}COO$— | H |
| C9 | —$CONHX_{10}$ | optionally substituted $C_2$ to $C_8$ alkenyl | $R_{10a}COO$— | $C_6H_5COO$— | $R_{9a}COO$— | H |
| C10 | —$COOX_{10}$ | optionally substituted $C_2$ to $C_8$ alkynyl | $R_{10a}COO$— | $C_6H_5COO$— | $R_{9a}COO$— | H |
| C11 | —$COX_{10}$ | optionally substituted $C_2$ to $C_8$ alkynyl | $R_{10a}COO$— | $C_6H_5COO$— | $R_{9a}COO$— | H |
| C12 | —$CONHX_{10}$ | optionally substituted $C_2$ to $C_8$ alkynyl | $R_{10a}COO$— | $C_6H_5COO$— | $R_{9a}COO$— | H |
| D1 | —$COOX_{10}$ | heterocyclo | $R_{10a}COO$— | $C_6H_5COO$— | OH | H |
| D2 | —$COX_{10}$ | heterocyclo | $R_{10a}COO$— | $C_6H_5COO$— | OH | H |
| D3 | —$CONHX_{10}$ | heterocyclo | $R_{10a}COO$— | $C_6H_5COO$— | OH | H |
| D4 | —$COOX_{10}$ | optionally substituted $C_2$ to $C_8$ alkyl | $R_{10a}COO$— | $C_6H_5COO$— | OH | H |
| D5 | —$COX_{10}$ | optionally substituted $C_2$ to $C_8$ alkyl | $R_{10a}COO$— | $C_6H_5COO$— | OH | H |
| D6 | —$CONHX_{10}$ | optionally substituted $C_2$ to $C_8$ alkyl | $R_{10a}COO$— | $C_6H_5COO$— | OH | H |

-continued (14)

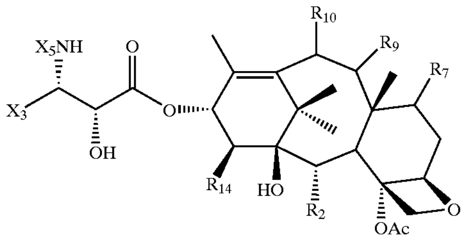

| Series | $X_5$ | $X_3$ | $R_{10}$ | $R_2$ | $R_9$ | $R_{14}$ |
|---|---|---|---|---|---|---|
| D7 | —$COOX_{10}$ | optionally substituted $C_2$ to $C_8$ alkenyl | $R_{10a}COO$— | $C_6H_5COO$— | OH | H |
| D8 | —$COX_{10}$ | optionally substituted $C_2$ to $C_8$ alkenyl | $R_{10a}COO$— | $C_6H_5COO$— | OH | H |
| D9 | —$CONHX_{10}$ | optionally substituted $C_2$ to $C_8$ alkenyl | $R_{10a}COO$— | $C_6H_5COO$— | OH | H |
| D10 | —$COOX_{10}$ | optionally substituted $C_2$ to $C_8$ alkynyl | $R_{10a}COO$— | $C_6H_5COO$— | OH | H |
| D11 | —$COX_{10}$ | optionally substituted $C_2$ to $C_8$ alkynyl | $R_{10a}COO$— | $C_6H_5COO$— | OH | H |
| D12 | —$CONHX_{10}$ | optionally substituted $C_2$ to $C_8$ alkynyl | $R_{10a}COO$— | $C_6H_5COO$— | OH | H |
| E1 | —$COOX_{10}$ | heterocyclo | $R_{10a}COO$ | $C_6H_5COO$— | O | OH |
| E2 | —$COX_{10}$ | heterocyclo | $R_{10a}COO$— | $C_6H_5COO$— | O | OH |
| E3 | —$CONHX_{10}$ | heterocyclo | $R_{10a}COO$— | $C_6H_5COO$— | O | OH |
| E4 | —$COOX_{10}$ | optionally substituted $C_2$ to $C_8$ alkyl | $R_{10a}COO$— | $C_6H_5COO$— | O | OH |
| E5 | —$COX_{10}$ | optionally substituted $C_2$ to $C_8$ alkyl | $R_{10a}COO$— | $C_6H_5COO$— | O | OH |
| E6 | —$CONHX_{10}$ | optionally substituted $C_2$ to $C_8$ alkyl | $R_{10a}COO$— | $C_6H_5COO$— | O | OH |
| E7 | —$COOX_{10}$ | optionally substituted $C_2$ to $C_8$ alkenyl | $R_{10a}COO$— | $C_6H_5COO$— | O | OH |
| E8 | —$COX_{10}$ | optionally substituted $C_2$ to $C_8$ alkenyl | $R_{10a}COO$— | $C_6H_5COO$— | O | OH |
| E9 | —$CONHX_{10}$ | optionally substituted $C_2$ to $C_8$ alkenyl | $R_{10a}COO$— | $C_6H_5COO$— | O | OH |
| E10 | —$COOX_{10}$ | optionally substituted $C_2$ to $C_8$ alkynyl | $R_{10a}COO$— | $C_6H_5COO$— | O | OH |
| E11 | —$COX_{10}$ | optionally substituted $C_2$ to $C_8$ alkynyl | $R_{10a}COO$— | $C_6H_5COO$— | O | OH |
| E12 | —$CONHX_{10}$ | optionally substituted $C_2$ to $C_8$ alkynyl | $R_{10a}COO$— | $C_6H_5COO$— | O | OH |
| F1 | —$COOX_{10}$ | heterocyclo | $R_{10a}COO$— | $R_{2a}COO$— | $R_{9a}COO$— | H |
| F2 | —$COX_{10}$ | heterocyclo | $R_{10a}COO$— | $R_{2a}COO$— | $R_{9a}COO$— | H |
| F3 | —$CONHX_{10}$ | heterocyclo | $R_{10a}COO$— | $R_{2a}COO$— | $R_{9a}COO$— | H |
| F4 | —$COOX_{10}$ | optionally substituted $C_2$ to $C_8$ alkyl | $R_{10a}COO$— | $R_{2a}COO$— | $R_{9a}COO$— | H |
| F5 | —$COX_{10}$ | optionally substituted $C_2$ to $C_8$ alkyl | $R_{10a}COO$— | $R_{2a}COO$— | $R_{9a}COO$— | H |
| F6 | —$CONHX_{10}$ | optionally substituted $C_2$ to $C_8$ alkyl | $R_{10a}COO$— | $R_{2a}COO$— | $R_{9a}COO$— | H |
| F7 | —$COOX_{10}$ | optionally substituted $C_2$ to $C_8$ alkenyl | $R_{10a}COO$— | $R_{2a}COO$— | $R_{9a}COO$— | H |

-continued (14)

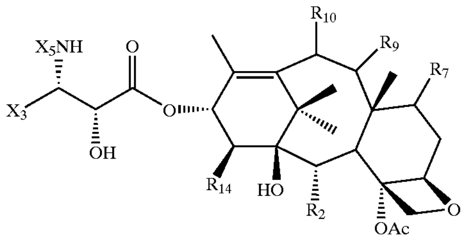

| Series | $X_5$ | $X_3$ | $R_{10}$ | $R_2$ | $R_9$ | $R_{14}$ |
|---|---|---|---|---|---|---|
| F8 | —$COX_{10}$ | optionally substituted $C_2$ to $C_8$ alkenyl | $R_{10a}COO$— | $R_{2a}COO$— | $R_{9a}COO$— | H |
| F9 | —$CONHX_{10}$ | optionally substituted $C_2$ to $C_8$ alkenyl | $R_{10a}COO$— | $R_{2a}COO$— | $R_{9a}COO$— | H |
| F10 | —$COOX_{10}$ | optionally substituted $C_2$ to $C_8$ alkynyl | $R_{10a}COO$— | $R_{2a}COO$— | $R_{9a}COO$— | H |
| F11 | —$COX_{10}$ | optionally substituted $C_2$ to $C_8$ alkynyl | $R_{10a}COO$— | $R_{2a}COO$— | $R_{9a}COO$— | H |
| F12 | —$CONHX_{10}$ | optionally substituted $C_2$ to $C_8$ alkynyl | $R_{10a}COO$— | $R_{2a}COO$— | $R_{9a}COO$— | H |
| G1 | —$COOX_{10}$ | heterocyclo | $R_{10a}COO$— | $R_{2a}COO$— | OH | H |
| G2 | —$COX_{10}$ | heterocyclo | $R_{10a}COO$— | $R_{2a}COO$— | OH | H |
| G3 | —$CONHX_{10}$ | heterocyclo | $R_{10a}COO$— | $R_{2a}COO$— | OH | H |
| G4 | —$COOX_{10}$ | optionally substituted $C_2$ to $C_8$ alkyl | $R_{10a}COO$— | $R_{2a}COO$— | OH | H |
| G5 | —$COX_{10}$ | optionally substituted $C_2$ to $C_8$ alkyl | $R_{10a}COO$— | $R_{2a}COO$— | OH | H |
| G6 | —$CONHX_{10}$ | optionally substituted $C_2$ to $C_8$ alkyl | $R_{10a}COO$— | $R_{2a}COO$— | OH | H |
| G7 | —$COOX_{10}$ | optionally substituted $C_2$ to $C_8$ alkenyl | $R_{10a}COO$— | $R_{2a}COO$— | OH | H |
| G8 | —$COX_{10}$ | optionally substituted $C_2$ to $C_8$ alkenyl | $R_{10a}COO$— | $R_{2a}COO$— | OH | H |
| G9 | —$CONHX_{10}$ | optionally substituted $C_2$ to $C_8$ alkenyl | $R_{10a}COO$— | $R_{2a}COO$— | OH | H |
| G10 | —$COOX_{10}$ | optionally substituted $C_2$ to $C_8$ alkynyl | $R_{10a}COO$— | $R_{2a}COO$— | OH | H |
| G11 | —$COX_{10}$ | optionally substituted $C_2$ to $C_8$ alkynyl | $R_{10a}COO$— | $R_{2a}COO$— | OH | H |
| G12 | —$CONHX_{10}$ | optionally substituted $C_2$ to $C_8$ alkynyl | $R_{10a}COO$— | $R_{2a}COO$— | OH | H |
| H1 | —$COOX_{10}$ | heterocyclo | $R_{10a}COO$— | $C_6H_5COO$— | OH | OH |
| H2 | —$COX_{10}$ | heterocyclo | $R_{10a}COO$— | $C_6H_5COO$— | OH | OH |
| H3 | —$CONHX_{10}$ | heterocyclo | $R_{10a}COO$— | $C_6H_5COO$— | OH | OH |
| H4 | —$COOX_{10}$ | optionally substituted $C_2$ to $C_8$ alkyl | $R_{10a}COO$— | $C_6H_5COO$— | OH | OH |
| H5 | —$COX_{10}$ | optionally substituted $C_2$ to $C_8$ alkyl | $R_{10a}COO$— | $C_6H_5COO$— | OH | OH |
| H6 | —$CONHX_{10}$ | optionally substituted $C_2$ to $C_8$ alkyl | $R_{10a}COO$— | $C_6H_5COO$— | OH | OH |
| H7 | —$COOX_{10}$ | optionally substituted $C_2$ to $C_8$ alkenyl | $R_{10a}COO$— | $C_6H_5COO$— | OH | OH |
| H8 | —$COX_{10}$ | optionally substituted $C_2$ to $C_8$ alkenyl | $R_{10a}COO$— | $C_6H_5COO$— | OH | OH |

-continued (14)

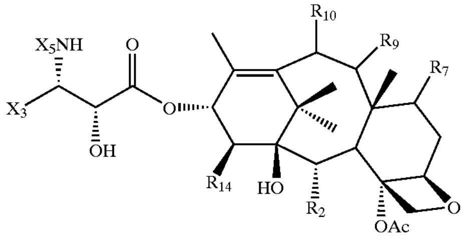

| Series | $X_5$ | $X_3$ | $R_{10}$ | $R_2$ | $R_9$ | $R_{14}$ |
|---|---|---|---|---|---|---|
| H9 | —$CONHX_{10}$ | optionally substituted $C_2$ to $C_8$ alkenyl | $R_{10a}COO$— | $C_6H_5COO$— | OH | OH |
| H10 | —$COOX_{10}$ | optionally substituted $C_2$ to $C_8$ alkynyl | $R_{10a}COO$— | $C_6H_5COO$— | OH | OH |
| H11 | —$COX_{10}$ | optionally substituted $C_2$ to $C_8$ alkynyl | $R_{10a}COO$— | $C_6H_5COO$— | OH | OH |
| H12 | —$CONHX_{10}$ | optionally substituted $C_2$ to $C_8$ alkynyl | $R_{10a}COO$— | $C_6H_5COO$— | OH | OH |
| I1 | —$COOX_{10}$ | heterocyclo | $R_{10a}COO$— | $R_{2a}COO$— | O | OH |
| I2 | —$COX_{10}$ | heterocyclo | $R_{10a}COO$— | $R_{2a}COO$— | O | OH |
| I3 | —$CONHX_{10}$ | heterocyclo | $R_{10a}COO$— | $R_{2a}COO$— | O | OH |
| I4 | —$COOX_{10}$ | optionally substituted $C_2$ to $C_8$ alkyl | $R_{10a}COO$— | $R_{2a}COO$— | O | OH |
| I5 | —$COX_{10}$ | optionally substituted $C_2$ to $C_8$ alkyl | $R_{10a}COO$— | $R_{2a}COO$— | O | OH |
| I6 | —$CONHX_{10}$ | optionally substituted $C_2$ to $C_8$ alkyl | $R_{10a}COO$— | $R_{2a}COO$— | O | OH |
| I7 | —$COOX_{10}$ | optionally substituted $C_2$ to $C_8$ alkenyl | $R_{10a}COO$— | $R_{2a}COO$— | O | OH |
| I8 | —$COX_{10}$ | optionally substituted $C_2$ to $C_8$ alkenyl | $R_{10a}COO$— | $R_{2a}COO$— | O | OH |
| I9 | —$CONHX_{10}$ | optionally substituted $C_2$ to $C_8$ alkenyl | $R_{10a}COO$— | $R_{2a}COO$— | O | OH |
| I10 | —$COOX_{10}$ | optionally substituted $C_2$ to $C_8$ alkynyl | $R_{10a}COO$— | $R_{2a}COO$— | O | OH |
| I11 | —$COX_{10}$ | optionally substituted $C_2$ to $C_8$ alkynyl | $R_{10a}COO$— | $R_{2a}COO$— | O | OH |
| I12 | —$CONHX_{10}$ | optionally substituted $C_2$ to $C_8$ alkynyl | $R_{10a}COO$— | $R_{2a}COO$— | O | OH |
| J1 | —$COOX_{10}$ | heterocyclo | $R_{10a}COO$— | $R_{2a}COO$— | OH | OH |
| J2 | —$COX_{10}$ | heterocyclo | $R_{10a}COO$— | $R_{2a}COO$— | OH | OH |
| J3 | —$CONHX_{10}$ | heterocyclo | $R_{10a}COO$— | $R_{2a}COO$— | OH | OH |
| J4 | —$COOX_{10}$ | optionally substituted $C_2$ to $C_8$ alkyl | $R_{10a}COO$— | $R_{2a}COO$— | OH | OH |
| J5 | —$COX_{10}$ | optionally substituted $C_2$ to $C_8$ alkyl | $R_{10a}COO$— | $R_{2a}COO$— | OH | OH |
| J6 | —$CONHX_{10}$ | optionally substituted $C_2$ to $C_8$ alkyl | $R_{10a}COO$— | $R_{2a}COO$— | OH | OH |
| J7 | —$COOX_{10}$ | optionally substituted $C_2$ to $C_8$ alkenyl | $R_{10a}COO$— | $R_{2a}COO$— | OH | OH |
| J8 | —$COX_{10}$ | optionally substituted $C_2$ to $C_8$ alkenyl | $R_{10a}COO$— | $R_{2a}COO$— | OH | OH |
| J9 | —$CONHX_{10}$ | optionally substituted $C_2$ to $C_8$ alkenyl | $R_{10a}COO$— | $R_{2a}COO$— | OH | OH |

-continued (14)

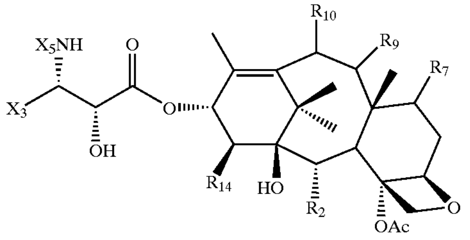

| Series | $X_5$ | $X_3$ | $R_{10}$ | $R_2$ | $R_9$ | $R_{14}$ |
|---|---|---|---|---|---|---|
| J10 | —$COOX_{10}$ | optionally substituted $C_2$ to $C_8$ alkynyl | $R_{10a}COO$— | $R_{2a}COO$— | OH | OH |
| J11 | —$COX_{10}$ | optionally substituted $C_2$ to $C_8$ alkynyl | $R_{10a}COO$— | $R_{2a}COO$— | OH | OH |
| J12 | —$CONHX_{10}$ | optionally substituted $C_2$ to $C_8$ alkynyl | $R_{10a}COO$— | $R_{2a}COO$— | OH | OH |
| K1 | —$COOX_{10}$ | heterocyclo | $R_{10a}COO$— | $R_{2a}COO$— | $R_{9a}COO$— | OH |
| K2 | —$COX_{10}$ | heterocyclo | $R_{10a}COO$— | $R_{2a}COO$— | $R_{9a}COO$— | OH |
| K3 | —$CONHX_{10}$ | heterocyclo | $R_{10a}COO$— | $R_{2a}COO$— | $R_{9a}COO$— | OH |
| K4 | —$COOX_{10}$ | optionally substituted $C_2$ to $C_8$ alkyl | $R_{10a}COO$— | $R_{2a}COO$— | $R_{9a}COO$— | OH |
| K5 | —$COX_{10}$ | optionally substituted $C_2$ to $C_8$ alkyl | $R_{10a}COO$— | $R_{2a}COO$— | $R_{9a}COO$— | OH |
| K6 | —$CONHX_{10}$ | optionally substituted $C_2$ to $C_8$ alkyl | $R_{10a}COO$— | $R_{2a}COO$— | R9aCOO— | OH |
| K7 | —$COOX_{10}$ | optionally substituted $C_2$ to $C_8$ alkenyl | $R_{10a}COO$— | $R_{2a}COO$— | $R_{9a}COO$— | OH |
| K8 | —$COX_{10}$ | optionally substituted $C_2$ to $C_8$ alkenyl | $R_{10a}COO$— | $R_{2a}COO$— | $R_{9a}COO$— | OH |
| K9 | —$CONHX_{10}$ | optionally substituted $C_2$ to $C_8$ alkenyl | $R_{10a}COO$— | $R_{2a}COO$— | $R_{9a}COO$— | OH |
| K10 | —$COOX_{10}$ | optionally substituted $C_2$ to $C_8$ alkynyl | $R_{10a}COO$— | $R_{2a}COO$— | $R_{9a}COO$— | OH |
| K11 | —$COX_{10}$ | optionally substituted $C_2$ to $C_8$ alkynyl | $R_{10a}COO$— | $R_{2a}COO$— | $R_{9a}COO$— | OH |
| K12 | —$CONHX_{10}$ | optionally substituted $C_2$ to $C_8$ alkynyl | $R_{10a}COO$— | $R_{2a}COO$— | $R_{9a}COO$— | OH |

EXAMPLE 20

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 2 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 6577 | <1 |
| 6515 | <1 |
| 6066 | <1 |
| 6111 | <1 |

EXAMPLE 21

Preparation of Taxane having C-7 Carbonate and C-10 Hydroxy

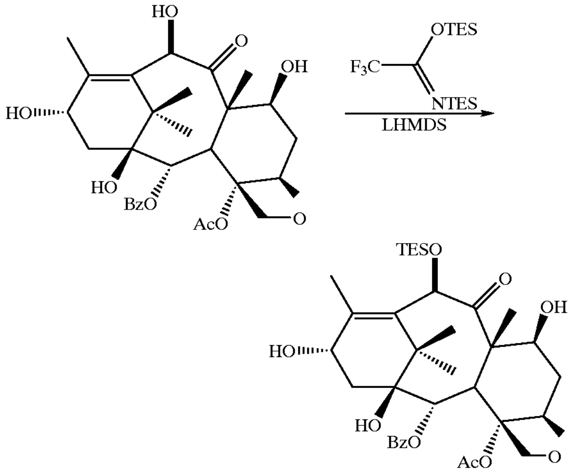

10-Triethylsilyl-10-deacetyl baccatin III.

To a solution of 1.0 g (1.84 mmol) of 10-deacetyl baccatin III in 50 mL of THF at −10° C. under a nitrogen atmosphere was added 0.857 mL (2.76 mmol, 1.5 mol equiv) of N,O—(bis)-TES-trifluoroacetamide over a period of 3 min. This was followed by the addition of 0.062 mL of a 0.89 M THF solution of lithium bis(trimethylsilyl)amide (0.055 mmol, 0.03 mol equiv). After 10 min 0.038 mL (0.92 mmol, 0.5 mol equiv) of methanol was added, and after an additional 5 min 4 mL (0.055 mmol, 0.03 mol equiv) of acetic acid was added. The solution was diluted with 300 mL of ethyl acetate and washed two times with 100 mL of saturated aqueous sodium bicarbonate solution. The combined aqueous layers were extracted with 100 mL of ethyl acetate and the combined organic layers were washed with brine, dried over sodium sulfate, and concentrated under reduced pressure. To the residue was added 100 mL of hexane and the solid (1.23 g, 101%) was collected by filtration. Recrystallization of the solid by dissolving in boiling ethyl acetate (20 mL, 17 mL/g) and cooling to room temperature gave 1.132 g (94%) of a white solid. m.p. 242° C.; $[\alpha]_D^{25}$ −60.4 (c 0.7, $CHCl_3$); $^1H$ NMR ($CDCl_3$, 400 MHz) δ (p.p.m): 8.10 (2H, d, Jm=7.5 Hz, Bzo), 7.60 (1H, t, Jm=7.5 Hz, Bzp), 7.47 (2H, t, Jo=7.5 Hz, Bzm), 5.64 (1H, d, J3=6.9 Hz, H2), 5.26 (1H, s, H10), 4.97 (1H, dd, J6β=2.2 Hz, J6α=9.9 Hz, H5),4.85(1H,dd,J14α=8.9 Hz,J14α=8.9 Hz, H13),4.30(1H,d,J20β=8.5 Hz, H20α), 4.23 (1H, ddd, J7OH=4.5Hz, J6α=6.6 Hz, J6β=11.0 Hz, H7),4.15 (1H, d, J20α=8.5 Hz, H20β), 4.00 (1H, d, J2=6.9 Hz, H3), 2.58 (1H, ddd, J7=6.6 Hz, J5=9.9 Hz, J6β=14.5 Hz, H6α), 2.28–2.25 (5H, m, 4Ac, H14α, H14β), 2.02 (3H, s, 18 Me), 1.97 (1H, d, J7=4.5 Hz, H7OH), 1.78 (1H, ddd, J7=11.0 Hz, J5=2.2 Hz, J6α=14.5 Hz, H6β), 1.68 (3H, s, 19 Me), 1.56 (1H, s, OH1), 1.32 (1H, d, J13 =8.8 Hz, OH13 ), 1.18 (3H, s, 17 Me), 1.06 (3H, s, 16 Me), 0.98 (9H, t, $JCH_2$(TES) =7.3 Hz, $CH_3$(TES)), 0.65 (6H, dq, $JCH_3$(TES)=7.3 Hz, $CH_2$(TES)).

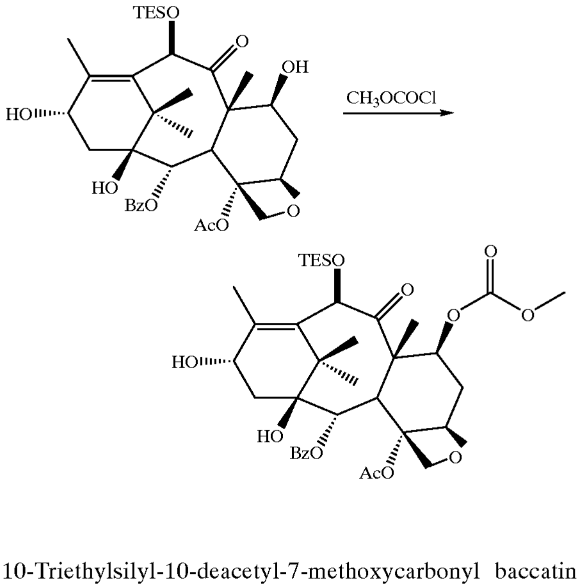

10-Triethylsilyl-10-deacetyl-7-methoxycarbonyl baccatin II.

To a solution of 9.3 g (14.1 mmol) of 10-triethylsilyl-10-deacetyl baccatin III and 10.35 g (84.6 mmol) of DMAP in 500 mL of dichloromethane at 0° C. under a nitrogen atmosphere was added 2.15 mL (22.7 mmol, 1.5 mol equiv) of methyl chloroformate. The mixture was stirred at 0° C. for 4 h, diluted with 300 mL of saturated aqueous ammonium chloride solution and extracted twice with 200 mL of ethyl acetate. The organic layer was washed with 500 mL of 10% aqueous copper sulfate solution, 500 mL of saturated aqueous sodium bicarbonate solution, 100 mL of brine, dried over sodium sulfate and concentrated under reduced pressure. The crude product was recrystallized from ethyl acetate to give 8.92 g (88%) of 10-triethylsilyl-1 0-deacetyl-7-methoxycarbonyl baccatin III. m.p. 260–262° C.; $[\alpha]_D^{25}$ −54.3 (c0.89, $CHCl_3$); $^1H$ NMR ($CDCl_3$, 500 MHz) δ (ppm): 8.10 (2H, d, Jm=8.5 Hz, Bzo), 7.60 (1H, t, Jm=8.5 Hz, Bzp), 7.47 (2H, t, Jo=8.5 Hz, Bzm), 5.64 (1H, d, J3=7.0 Hz, H2), 5.31 (1H, dd, J6α=7.0 Hz, J6β=10.0 Hz, H7), 5.28 (1H, s, H10), 4.96 (1H, d, J6α=8.5 Hz, H5), 4.86 (1H, t, J14α=14.0 Hz, J14β=7.0 Hz, H13), 4.31 (1H, d, J20β=8.0 Hz, H20α), 4.16 (1H, d, J20α=8.0 Hz, H20β), 4.06 (1H, d, J2=7.0 Hz, H3), 3.77 (3H, s, OMe) 2.65 (1H, ddd, J7=7.0 Hz, J5=8.5 Hz, J6β=10.0 Hz, H6α), 2.29–2.26 (5H, m, 4Ac, H14α, H14β), 2.08 (3H, s, 18 Me), 2.01 (1H, d, 13OH), 1.92 (3H, ddd, J7=10.0 Hz, J5=2.3 Hz, J6α=10.0 Hz, H6β), 1.80 (3H, s, 19 Me), 1.18 (3H, s, 17 Me), 1.05 (3H, s, 16 Me), 0.97 (9H, t, $JCH_2$(TES)=8.0 Hz, $CH_3$(TES)), 0.59 (6H, dq, $JCH_3$ (TES)=8.0 Hz, $CH_2$(TES)).

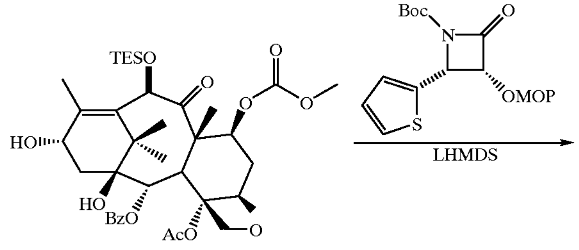

-continued

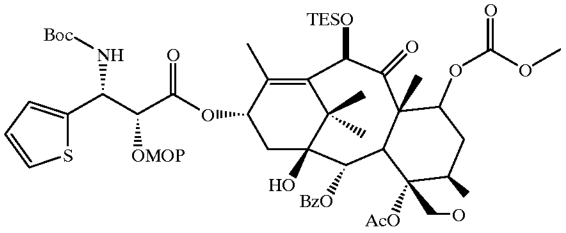

2'-O-MOP-3'-desphenyl-3'-(2-thienyl)-10-triethylsilyl-7-methoxycarbonyl taxotere.

To a solution of 495 mg (0.690 mmol) of 10-triethylsilyl-10-deacetyl-7-methoxycarbonyl baccatin III in 4 mL of anhydrous THF under a nitrogen atmosphere at −45° C. was added 0.72 mL (0.72 mmol) of a 1M solution of LiHMDS in THF. After 0.5 h a solution of 278 mg (0.814 mmol) of the b-Lactam in 2 mL of anhydrous THF was added. The mixture was warmed to 0° C., and after 2 h 0.5 mL of saturated aqueous sodium bicarbonate solution was added. The mixture was diluted with 50 ml of ethyl acetate and washed two times with 5 mL of brine. The organic phase was dried over sodium sulfate and concentrated under reduced pressure to give a slightly yellow solid. The solid was recrystallized by dissolving it in 12 mL of a 1:5 mixture of ethyl acetate and hexane at reflux and then cooling to room temperature to give 679 mg (93%) of a white crystalline solid which was used directly in the next reaction.

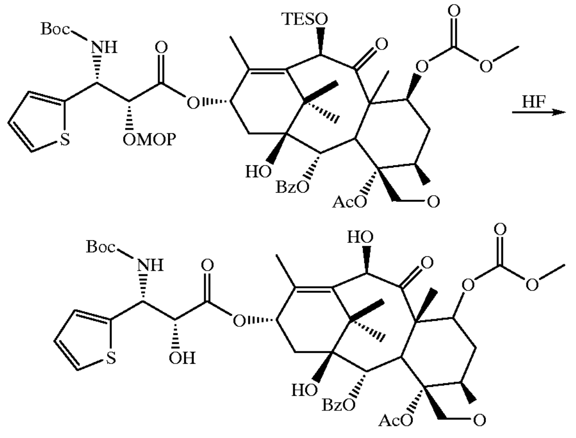

3'-Desphenyl-3'-(2-thienyl)-7-methoxycarbonyl taxotere.

To a solution of 211 mg (0.199 mmol) of 2'-O-MOP-3'-desphenyl-3'-(2-thienyl)-10-triethylsilyl-7-methoxycarbonyl taxotere in 1.7 mL of pyridine and 5.4 mL of acetonitrile at 0° C. was added 0.80 mL (2.0 mmol) of an aqueous solution containing 49% HF. The mixture was warmed to room temperature for 14 h and was then diluted with 20 mL of ethyl acetate and washed three times with 2 mL of saturated aqueous sodium bicarbonate and then with 8 mL of brine. The organic phase was dried over sodium sulfate and concentrated under reduced pressure to give 174 mg (100%) of a white solid. The crude product was crystallized with 2 mL of solvent ($CH_2Cl_2$:hexane=1:1.7) to give 168 mg (97%) of white crystals. m.p. 142.5–143° C.; $[\alpha]_D^{25}$−25.1 (c 0.53, $CHCl_3$); Anal. Calcd for $C_{43}H_{53}NO_{16}S$: C, 59.23; H, 6.13. Found: C, 58.99; H, 6.25. $^1H$ NMR (500 MHz, $CDCl_3$):

| Proton | d (ppm) | Pattern | J (Hz) |
|---|---|---|---|
| 2 | 5.69 | d | H3(6.5) |
| o-benzoate | 8.12 | d | m-benzoate(7.5) |
| m-benzoate | 7.51 | t | o-benzoate(7.5), p-benzoate(7.5) |
| p-benzoate | 7.62 | t | m-benzoate(7.5) |
| 3 | 4.01 | d | H2(6.5) |
| 4Ac | 2.39 | s | |
| 5 | 4.93 | d | H6a(8.0) |
| 6a | 2.53 | ddd | H7(7.5), H5(9.5), H6b(15.0) |
| 6b | 2.00 | ddd | H7(11.0), H5(2.5), H6a(15.0) |
| 7 | 5.29 | dd | H6a(7.5), H6b(11.0) |
| OMe | 3.76 | s | |
| 10 | 5.39 | s | |
| | 10-OH | 4.06 | brs |
| 13 | 6.23 | t | H14a(9.0), H14b(9.0) |
| 14a + 14b | 2.34 | m | |
| 16Me | 1.11 | s | |
| 17Me | 1.23 | s | |
| 18Me | 1.93 | s | |
| 19Me | 1.86 | s | |
| 20a | 4.33 | d | H20b(8.5) |
| 20b | 4.21 | d | H20a(8.5) |
| 2' | 4.64 | br | |
| 2'OH | 3.43 | br | |
| 3' | 5.51 | br | |
| 3" | 7.10 | d | H4"(3.5) |
| 4" | 7.01 | dd | H5"(5.0), H3"(3.5) |
| 5" | 7.28 | d | H4"(5.0) |
| NH | 5.34 | d | H3'(9.5) |
| (CH3)3C | 1.35 | s | |

EXAMPLE 22

Additional Taxanes having C-7 Carbonate and C-10 Hydroxy Substituents

The procedures described in Example 21 were repeated, but other suitably protected β-lactams were substituted for the β-lactam of Example 21 to prepare the series of compounds having structural formula (15) and the combinations of substituents identified in the following table.

(15)

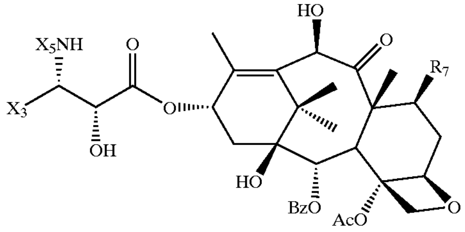

| Compound | $X_5$ | $X_3$ | $R_7$ |
|---|---|---|---|
| 4144 | iPrOCO— | 2-thienyl | MeOCOO— |
| 4151 | iPrOCO— | 2-thienyl | EtOCOO— |
| 4164 | ibueCO— | 2-thienyl | EtOCOO— |
| 4188 | PhCO— | 2-thienyl | EtOCOO— |
| 4222 | 2-FuCO— | 2-thienyl | MeOCOO— |
| 4234 | tBuOCO— | 2-thienyl | EtOCOO— |
| 4244 | ibueCO— | 2-thienyl | MeOCOO— |
| 4262 | tBuOCO— | 2-thienyl | MeOCOO— |
| 4304 | 2-FuCO— | 2-thienyl | EtOCOO— |
| 4355 | iBuOCO— | 2-thienyl | MeOCOO— |
| 4363 | iBuOCO— | 2-thienyl | EtOCOO— |
| 4411 | PhCO— | 2-thienyl | MeOCOO— |
| 4424 | 2-ThCO | 2-thienyl | MeOCOO— |
| 4434 | tBuOCO— | 3-furyl | MeOCOO— |

-continued (15)

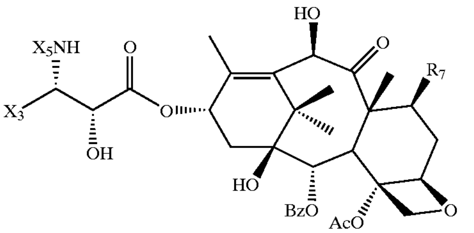

| Compound | $X_5$ | $X_3$ | $R_7$ |
|---|---|---|---|
| 4455 | 2-ThCO | 2-thienyl | EtOCOO— |
| 4474 | tBuOCO— | 3-thienyl | MeOCOO— |
| 4484 | tBuOCO— | isobutenyl | MeOCOO— |
| 4500 | tBuOCO— | 3-thienyl | EtOCOO— |
| 4515 | iBuOCO— | 3-thienyl | AcO— |
| 4524 | tBuOCO— | isobutenyl | EtOCOO— |
| 4533 | tBuOCO— | 2-furyl | MeOCOO— |
| 4555 | tBuOCO— | cyclopropyl | AcO— |
| 4584 | iBuOCO— | 3-furyl | MeOCOO— |
| 4566 | tBuOCO— | cyclopropyl | MeOCOO— |
| 4575 | tBuOCO— | 2-furyl | MeOCOO— |
| 4624 | iBuOCO— | 3-furyl | EtOCOO— |
| 4644 | iBuOCO— | isobutenyl | MeOCOO— |
| 4656 | iBuOCO— | 2-furyl | MeOCOO— |
| 4674 | iBuOCO— | 3-thienyl | MeOCOO— |
| 4688 | iBuOCO— | isobutenyl | EtOCOO— |
| 4696 | iBuOCO— | 2-furyl | EtOCOO— |
| 4744 | t$C_3H_5$CO— | 2-furyl | MeOCOO— |
| 4766 | t$C_3H_5$CO— | 2-thienyl | MeOCOO— |
| 5466 | ibueCO— | 2-furyl | BnOCOO— |
| 6151 | ibueCO— | 2-furyl | EtOCOO— |
| 6246 | tAmOCO— | 2-furyl | BnOCOO— |
| 5433 | tBuOCO— | 2-furyl | BnOCOO— |
| 4818 | t$C_3H_5$CO— | 2-furyl | EtOCOO— |
| 6566 | t$C_3H_5$CO— | 2-thienyl | BnOCOO— |
| 4855 | t$C_3H_5$CO— | 2-thienyl | EtOCOO— |
| 4464 | tBuOCO— | 3-furyl | EtOCOO— |
| 4904 | t$C_3H_5$CO— | 3-furyl | EtOCOO— |
| 4877 | t$C_3H_5$CO— | 3-furyl | MeOCOO— |
| 4979 | iBuOCO— | 3-thienyl | EtOCOO— |
| 4444 | tBuOCO— | 3-thienyl | MeOCOO— |
| 4999 | t$C_3H_5$CO— | 3-thienyl | EtOCOO— |
| 4969 | t$C_3H_5$CO— | 3-thienyl | MeOCOO— |
| 5225 | iBuOCO— | cpro | EtOCOO— |
| 5211 | iBuOCO— | cpro | MeOCOO— |
| 5165 | tBuOCO— | cpro | EtOCOO— |

EXAMPLE 23

Additional Taxanes having C-7 Carbonate and C-10 Hydroxy Substituents

Following the processes described in Example 21 and elsewhere herein, the following specific taxanes having structural formula (16) may be prepared, wherein $R_7$ is as previously defined, including wherein $R_7$ is $R_a$OCOO— and $R_a$ is (i) substituted or unsubstituted $C_1$ to $C_8$ alkyl (straight, branched or cyclic), such as methyl, ethyl, propyl, butyl, pentyl, or hexyl; (ii) substituted or unsubstituted $C_2$ to $C_8$ alkenyl (straight, branched or cyclic), such as ethenyl, propenyl, butenyl, pentenyl or hexenyl; (iii) substituted or unsubstituted $C_2$ to $C_8$ alkynyl (straight or branched) such as ethynyl, propynyl, butynyl, pentynyl, or hexynyl; (iv) substituted or unsubstituted phenyl; or (v) substituted or unsubstituted heterocyclo such as furyl, thienyl, or pyridyl. The substituents may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(16)

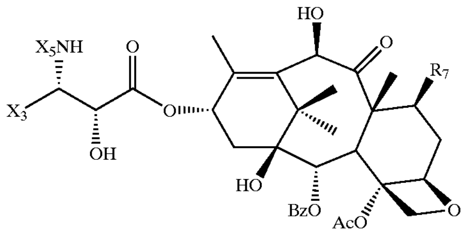

| $X_5$ | $X_3$ | $R_7$ |
|---|---|---|
| tBuOCO— | 2-furyl | $R_a$OCOO— |
| tBuOCO— | 3-furyl | $R_a$OCOO— |
| tBuOCO— | 2-thienyl | $R_a$OCOO— |
| tBuOCO— | 3-thienyl | $R_a$OCOO— |
| tBuOCO— | 2-pyridyl | $R_a$OCOO— |
| tBuOCO— | 3-pyridyl | $R_a$OCOO— |
| tBuOCO— | 4-pyridyl | $R_a$OCOO— |
| tBuOCO— | isobutenyl | $R_a$OCOO— |
| tBuOCO— | isopropyl | $R_a$OCOO— |
| tBuOCO— | cyclopropyl | $R_a$OCOO— |
| tBuOCO— | cyclobutyl | $R_a$OCOO— |
| tBuOCO— | cyclopentyl | $R_a$OCOO— |
| tBuOCO— | phenyl | $R_a$OCOO— |
| benzoyl | 2-furyl | $R_a$OCOO— |
| benzoyl | 3-furyl | $R_a$OCOO— |
| benzoyl | 2-thienyl | $R_a$OCOO— |
| benzoyl | 3-thienyl | $R_a$OCOO— |
| benzoyl | 2-pyridyl | $R_a$OCOO— |
| benzoyl | 3-pyridyl | $R_a$OCOO— |
| benzoyl | 4-pyridyl | $R_a$OCOO— |
| benzoyl | isobutenyl | $R_a$OCOO— |
| benzoyl | isopropyl | $R_a$OCOO— |
| benzoyl | cyclopropyl | $R_a$OCOO— |
| benzoyl | cyclobutyl | $R_a$OCOO— |
| benzoyl | cyclopentyl | $R_a$OCOO— |
| benzoyl | phenyl | $R_a$OCOO— |
| 2-FuCO— | 2-furyl | $R_a$OCOO— |
| 2-FuCO— | 3-furyl | $R_a$OCOO— |
| 2-FuCO— | 2-thienyl | $R_a$OCOO— |
| 2-FuCO— | 3-thienyl | $R_a$OCOO— |
| 2-FuCO— | 2-pyridyl | $R_a$OCOO— |
| 2-FuCO— | 3-pyridyl | $R_a$OCOO— |
| 2-FuCO— | 4-pyridyl | $R_a$OCOO— |
| 2-FuCO— | isobutenyl | $R_a$OCOO— |
| 2-FuCO— | isopropyl | $R_a$OCOO— |
| 2-FuCO— | cyclopropyl | $R_a$OCOO— |
| 2-FuCO— | cyclobutyl | $R_a$OCOO— |
| 2-FuCO— | cyclopentyl | $R_a$OCOO— |
| 2-FuCO— | phenyl | $R_a$OCOO— |
| 2-ThCO— | 2-furyl | $R_a$OCOO— |
| 2-ThCO— | 3-furyl | $R_a$OCOO— |
| 2-ThCO— | 2-thienyl | $R_a$OCOO— |
| 2-ThCO— | 3-thienyl | $R_a$OCOO— |
| 2-ThCO— | 2-pyridyl | $R_a$OCOO— |
| 2-ThCO— | 3-pyridyl | $R_a$OCOO— |
| 2-ThCO— | 4-pyridyl | $R_a$OCOO— |
| 2-ThCO— | isobutenyl | $R_a$OCOO— |
| 2-ThCO— | isopropyl | $R_a$OCOO— |
| 2-ThCO— | cyclopropyl | $R_a$OCOO— |
| 2-ThCO— | cyclobutyl | $R_a$OCOO— |
| 2-ThCO— | cyclopentyl | $R_a$OCOO— |
| 2-ThCO— | phenyl | $R_a$OCOO— |
| 2-PyCO— | 2-furyl | $R_a$OCOO— |
| 2-PyCO— | 3-furyl | $R_a$OCOO— |
| 2-PyCO— | 2-thienyl | $R_a$OCOO— |
| 2-PyCO— | 3-thienyl | $R_a$OCOO— |
| 2-PyCO— | 2-pyridyl | $R_a$OCOO— |
| 2-PyCO— | 3-pyridyl | $R_a$OCOO— |
| 2-PyCO— | 4-pyridyl | $R_a$OCOO— |
| 2-PyCO— | isobutenyl | $R_a$OCOO— |

-continued (16)

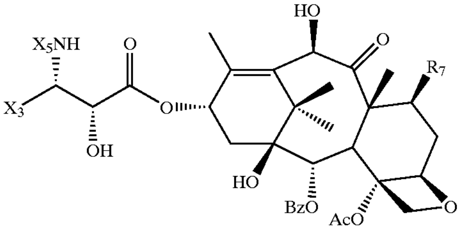

| $X_5$ | $X_3$ | $R_7$ |
|---|---|---|
| 2-PyCO— | isopropyl | $R_a$OCOO— |
| 2-PyCO— | cyclopropyl | $R_a$OCOO— |
| 2-PyCO— | cyclobutyl | $R_a$OCOO— |
| 2-PyCO— | cyclopentyl | $R_a$OCOO— |
| 2-PyCO— | phenyl | $R_a$OCOO— |
| 3-PyCO— | 2-furyl | $R_a$OCOO— |
| 3-PyCO— | 3-furyl | $R_a$OCOO— |
| 3-PyCO— | 2-thienyl | $R_a$OCOO— |
| 3-PyCO— | 3-thienyl | $R_a$OCOO— |
| 3-PyCO— | 2-pyridyl | $R_a$OCOO— |
| 3-PyCO— | 3-pyridyl | $R_a$OCOO— |
| 3-PyCO— | 4-pyridyl | $R_a$OCOO— |
| 3-PyCO— | isobutenyl | $R_a$OCOO— |
| 3-PyCO— | isopropyl | $R_a$OCOO— |
| 3-PyCO— | cyclopropyl | $R_a$OCOO— |
| 3-PyCO— | cyclobutyl | $R_a$OCOO— |
| 3-PyCO— | cyclopentyl | $R_a$OCOO— |
| 3-PyCO— | phenyl | $R_a$OCOO— |
| 4-PyCO— | 2-furyl | $R_a$OCOO— |
| 4-PyCO— | 3-furyl | $R_a$OCOO— |
| 4-PyCO— | 2-thienyl | $R_a$OCOO— |
| 4-PyCO— | 3-thienyl | $R_a$OCOO— |
| 4-PyCO— | 2-pyridyl | $R_a$OCOO— |
| 4-PyCO— | 3-pyridyl | $R_a$OCOO— |
| 4-PyCO— | 4-pyridyl | $R_a$OCOO— |
| 4-PyCO— | isobutenyl | $R_a$OCOO— |
| 4-PyCO— | isopropyl | $R_a$OCOO— |
| 4-PyCO— | cyclopropyl | $R_a$OCOO— |
| 4-PyCO— | cyclobutyl | $R_a$OCOO— |
| 4-PyCO— | cyclopentyl | $R_a$OCOO— |
| 4-PyCO— | phenyl | $R_a$OCOO— |
| $C_4H_7$CO— | 2-furyl | $R_a$OCOO— |
| $C_4H_7$CO— | 3-furyl | $R_a$OCOO— |
| $C_4H_7$CO— | 2-thienyl | $R_a$OCOO— |
| $C_4H_7$CO— | 3-thienyl | $R_a$OCOO— |
| $C_4H_7$CO— | 2-pyridyl | $R_a$OCOO— |
| $C_4H_7$CO— | 3-pyridyl | $R_a$OCOO— |
| $C_4H_7$CO— | 4-pyridyl | $R_a$OCOO— |
| $C_4H_7$CO— | isobutenyl | $R_a$OCOO— |
| $C_4H_7$CO— | isopropyl | $R_a$OCOO— |
| $C_4H_7$CO— | cyclopropyl | $R_a$OCOO— |
| $C_4H_7$CO— | cyclobutyl | $R_a$OCOO— |
| $C_4H_7$CO— | cyclopentyl | $R_a$OCOO— |
| $C_4H_7$CO— | phenyl | $R_a$OCOO— |
| EtOCO— | 2-furyl | $R_a$OCOO— |
| EtOCO— | 3-furyl | $R_a$OCOO— |
| EtOCO— | 2-thienyl | $R_a$OCOO— |
| EtOCO— | 3-thienyl | $R_a$OCOO— |
| EtOCO— | 2-pyridyl | $R_a$OCOO— |
| EtOCO— | 3-pyridyl | $R_a$OCOO— |
| EtOCO— | 4-pyridyl | $R_a$OCOO— |
| EtOCO— | isobutenyl | $R_a$OCOO— |
| EtOCO— | isopropyl | $R_a$OCOO— |
| EtOCO— | cyclopropyl | $R_a$OCOO— |
| EtOCO— | cyclobutyl | $R_a$OCOO— |
| EtOCO— | cyclopentyl | $R_a$OCOO— |
| EtOCO— | phenyl | $R_a$OCOO— |
| ibueCO— | 2-furyl | $R_a$OCOO— |
| ibueCO— | 3-furyl | $R_a$OCOO— |
| ibueCO— | 2-thienyl | $R_a$OCOO— |
| ibueCO— | 3-thienyl | $R_a$OCOO— |
| ibueCO— | 2-pyridyl | $R_a$OCOO— |
| ibueCO— | 3-pyridyl | $R_a$OCOO— |

-continued (16)

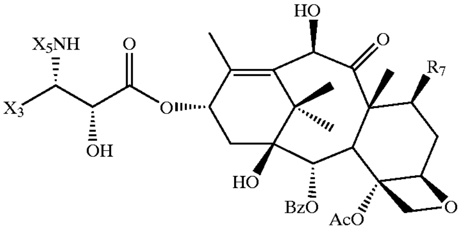

| $X_5$ | $X_3$ | $R_7$ |
|---|---|---|
| ibueCO— | 4-pyridyl | $R_a$OCOO— |
| ibueCO— | isobutenyl | $R_a$OCOO— |
| ibueCO— | isopropyl | $R_a$OCOO— |
| ibueCO— | cyclopropyl | $R_a$OCOO— |
| ibueCO— | cyclobutyl | $R_a$OCOO— |
| ibueCO— | cyclopentyl | $R_a$OCOO— |
| ibueCO— | phenyl | $R_a$OCOO— |
| iBuCO— | 2-furyl | $R_a$OCOO— |
| iBuCO— | 3-furyl | $R_a$OCOO— |
| iBuCO— | 2-thienyl | $R_a$OCOO— |
| iBuCO— | 3-thienyl | $R_a$OCOO— |
| iBuCO— | 2-pyridyl | $R_a$OCOO— |
| iBuCO— | 3-pyridyl | $R_a$OCOO— |
| iBuCO— | 4-pyridyl | $R_a$OCOO— |
| iBuCO— | isobutenyl | $R_a$OCOO— |
| iBuCO— | isopropyl | $R_a$OCOO— |
| IBuCO— | cyclopropyl | $R_a$OCOO— |
| iBuCO— | cyclobutyl | $R_a$OCOO— |
| iBuCO— | cyclopentyl | $R_a$OCOO— |
| iBuCO— | phenyl | $R_a$OCOO— |
| iBuOCO— | 2-furyl | $R_a$OCOO— |
| iBuOCO— | 3-furyl | $R_a$OCOO— |
| iBuOCO— | 2-thienyl | $R_a$OCOO— |
| iBuOCO— | 3-thienyl | $R_a$OCOO— |
| iBuOCO— | 2-pyridyl | $R_a$OCOO— |
| iBuOCO— | 3-pyridyl | $R_a$OCOO— |
| iBuOCO— | 4-pyridyl | $R_a$OCOO— |
| iBuOCO— | isobutenyl | $R_a$OCOO— |
| iBuOCO— | isopropyl | $R_a$OCOO— |
| iBuOCO— | cyclopropyl | $R_a$OCOO— |
| iBuOCO— | cyclobutyl | $R_a$OCOO— |
| iBuOCO— | cyclopentyl | $R_a$OCOO— |
| iBuOCO— | phenyl | $R_a$OCOO— |
| iPrOCO— | 2-furyl | $R_a$OCOO— |
| iPrOCO— | 3-furyl | $R_a$OCOO— |
| iPrOCO— | 2-thienyl | $R_a$OCOO— |
| iPrOCO— | 3-thienyl | $R_a$OCOO— |
| iPrOCO— | 2-pyridyl | $R_a$OCOO— |
| iPrOCO— | 3-pyridyl | $R_a$OCOO— |
| iPrOCO— | 4-pyridyl | $R_a$OCOO— |
| iPrOCO— | isobutenyl | $R_a$OCOO— |
| iPrOCO— | isopropyl | $R_a$OCOO— |
| iPrOCO— | cyclopropyl | $R_a$OCOO— |
| iPrOCO— | cyclobutyl | $R_a$OCOO— |
| iPrOCO— | cyclopentyl | $R_a$OCOO— |
| iPrOCO— | phenyl | $R_a$OCOO— |
| nPrOCO— | 2-furyl | $R_a$OCOO— |
| nPrOCO— | 3-furyl | $R_a$OCOO— |
| nPrOCO— | 2-thienyl | $R_a$OCOO— |
| nPrOCO— | 3-thienyl | $R_a$OCOO— |
| nPrOCO— | 2-pyridyl | $R_a$OCOO— |
| nPrOCO— | 3-pyridyl | $R_a$OCOO— |
| nPrOCO— | 4-pyridyl | $R_a$OCOO— |
| nPrOCO— | isobutenyl | $R_a$OCOO— |
| nPrOCO— | isopropyl | $R_a$OCOO— |
| nPrOCO— | cyclopropyl | $R_a$OCOO— |
| nPrOCO— | cyclobutyl | $R_a$OCOO— |
| nPrOCO— | cyclopentyl | $R_a$OCOO— |
| nPrOCO— | phenyl | $R_a$OCOO— |
| nPrCO— | 2-furyl | $R_a$OCOO— |
| nPrCO— | 3-furyl | $R_a$OCOO— |
| nPrCO— | 2-thienyl | $R_a$OCOO— |
| nPrCO— | 3-thienyl | $R_a$OCOO— |

-continued (16)

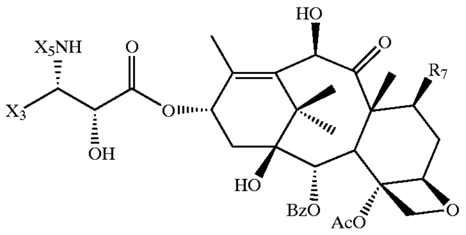

| $X_5$ | $X_3$ | $R_7$ |
|---|---|---|
| nPrCO— | 2-pyridyl | $R_aOCOO$— |
| nPrCO— | 3-pyridyl | $R_aOCOO$— |
| nPrCO— | 4-pyridyl | $R_aOCOO$— |
| nPrCO— | isobutenyl | $R_aOCOO$— |
| nPrCO— | isopropyl | $R_aOCOO$— |
| nPrCO— | cyclopropyl | $R_aOCOO$— |
| nPrCO— | cyclobutyl | $R_aOCOO$— |
| nPrCO— | cyclopentyl | $R_aOCOO$— |
| nPrCO— | phenyl | $R_aOCOO$— |
| tBuOCO— | 2-furyl | EtOCOO— |
| tBuOCO— | 2-pyridyl | EtOCOO— |
| tBuOCO— | 3-pyridyl | EtOCOO— |
| tBuOCO— | 4-pyridyl | EtOCOO— |
| tBuOCO— | isopropyl | EtOCOO— |
| tBuOCO— | cyclopropyl | EtOCOO— |
| tBuOCO— | cyclobutyl | EtOCOO— |
| tBuOCO— | cyclopentyl | EtOCOO— |
| tBuOCO— | phenyl | EtOCOO— |
| benzoyl | 2-furyl | EtOCOO— |
| benzoyl | 3-furyl | EtOCOO— |
| benzoyl | 3-thienyl | EtOCOO— |
| benzoyl | 2-pyridyl | EtOCOO— |
| benzoyl | 3-pyridyl | EtOCOO— |
| benzoyl | 4-pyridyl | EtOCOO— |
| benzoyl | isobutenyl | EtOCOO— |
| benzoyl | isopropyl | EtOCOO— |
| benzoyl | cyclopropyl | EtOCOO— |
| benzoyl | cyclobutyl | EtOCOO— |
| benzoyl | cyclopentyl | EtOCOO— |
| benzoyl | phenyl | EtOCOO— |
| 2-FuCO— | 2-furyl | EtOCOO— |
| 2-FuCO— | 3-furyl | EtOCOO— |
| 2-FuCO— | 3-thienyl | EtOCOO— |
| 2-FuCO— | 2-pyridyl | EtOCOO— |
| 2-FuCO— | 3-pyridyl | EtOCOO— |
| 2-FuCO— | 4-pyridyl | EtOCOO— |
| 2-FuCO— | isobutenyl | EtOCOO— |
| 2-FuCO— | isopropyl | EtOCOO— |
| 2-FuCO— | cyclopropyl | EtOCOO— |
| 2-FuCO— | cyclobutyl | EtOCOO— |
| 2-FuCO— | cyclopentyl | EtOCOO— |
| 2-FuCO— | phenyl | EtOCOO— |
| 2-ThCO— | 2-furyl | EtOCOO— |
| 2-ThCO— | 3-furyl | EtOCOO— |
| 2-ThCO— | 3-thienyl | EtOCOO— |
| 2-ThCO— | 2-pyridyl | EtOCOO— |
| 2-ThCO— | 3-pyridyl | EtOCOO— |
| 2-ThCO— | 4-pyridyl | EtOCOO— |
| 2-ThCO— | isobutenyl | EtOCOO— |
| 2-ThCO— | isopropyl | EtOCOO— |
| 2-ThCO— | cyclopropyl | EtOCOO— |
| 2-ThCO— | cyclobutyl | EtOCOO— |
| 2-ThCO— | cyclopentyl | EtOCOO— |
| 2-ThCO— | phenyl | EtOCOO— |
| 2-PyCO— | 2-furyl | EtOCOO— |
| 2-PyCO— | 3-furyl | EtOCOO— |
| 2-PyCO— | 2-thienyl | EtOCOO— |
| 2-PyCO— | 3-thienyl | EtOCOO— |
| 2-PyCO— | 2-pyridyl | EtOCOO— |
| 2-PyCO— | 3-pyridyl | EtOCOO— |
| 2-PyCO— | 4-pyridyl | EtOCOO— |
| 2-PyCO— | isobutenyl | EtOCOO— |
| 2-PyCO— | isopropyl | EtOCOO— |

-continued (16)

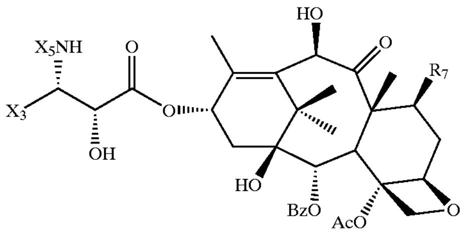

| $X_5$ | $X_3$ | $R_7$ |
|---|---|---|
| 2-PyCO— | cyclopropyl | EtOCOO— |
| 2-PyCO— | cyclobutyl | EtOCOO— |
| 2-PyCO— | cyclopentyl | EtOCOO— |
| 2-PyCO— | phenyl | EtOCOO— |
| 3-PyCO— | 2-furyl | EtOCOO— |
| 3-PyCO— | 3-furyl | EtOCOO— |
| 3-PyCO— | 2-thienyl | EtOCOO— |
| 3-PyCO— | 3-thienyl | EtOCOO— |
| 3-PyCO— | 2-pyridyl | EtOCOO— |
| 3-PyCO— | 3-pyridyl | EtOCOO— |
| 3-PyCO— | 4-pyridyl | EtOCOO— |
| 3-PyCO— | isobutenyl | EtOCOO— |
| 3-PyCO— | isopropyl | EtOCOO— |
| 3-PyCO— | cyclopropyl | EtOCOO— |
| 3-PyCO— | cyclobutyl | EtOCOO— |
| 3-PyCO— | cyclopentyl | EtOCOO— |
| 3-PyCO— | phenyl | EtOCOO— |
| 4-PyCO— | 2-furyl | EtOCOO— |
| 4-PyCO— | 3-furyl | EtOCOO— |
| 4-PyCO— | 2-thienyl | EtOCOO— |
| 4-PyCO— | 3-thienyl | EtOCOO— |
| 4-PyCO— | 2-pyridyl | EtOCOO— |
| 4-PyCO— | 3-pyridyl | EtOCOO— |
| 4-PyCO— | 4-pyridyl | EtOCOO— |
| 4-PyCO— | isobutenyl | EtOCOO— |
| 4-PyCO— | isopropyl | EtOCOO— |
| 4-PyCO— | cyclopropyl | EtOCOO— |
| 4-PyCO— | cyclobutyl | EtOCOO— |
| 4-PyCO— | cyclopentyl | EtOCOO— |
| 4-PyCO— | phenyl | EtOCOO— |
| $C_4H_7CO$— | 2-furyl | EtOCOO— |
| $C_4H_7CO$— | 3-furyl | EtOCOO— |
| $C_4H_7CO$— | 2-thienyl | EtOCOO— |
| $C_4H_7CO$— | 3-thienyl | EtOCOO— |
| $C_4H_7CO$— | 2-pyridyl | EtOCOO— |
| $C_4H_7CO$— | 3-pyridyl | EtOCOO— |
| $C_4H_7CO$— | 4-pyridyl | EtOCOO— |
| $C_4H_7CO$— | isobutenyl | EtOCOO— |
| $C_4H_7CO$— | isopropyl | EtOCOO— |
| $C_4H_7CO$— | cyclopropyl | EtOCOO— |
| $C_4H_7CO$— | cyclobutyl | EtOCOO— |
| $C_4H_7CO$— | cyclopentyl | EtOCOO— |
| $C_4H_7CO$— | phenyl | EtOCOO— |
| EtOCO— | 2-furyl | EtOCOO— |
| EtOCO— | 3-furyl | EtOCOO— |
| EtOCO— | 2-thienyl | EtOCOO— |
| EtOCO— | 3-thienyl | EtOCOO— |
| EtOCO— | 2-pyridyl | EtOCOO— |
| EtOCO— | 3-pyridyl | EtOCOO— |
| EtOCO— | 4-pyridyl | EtOCOO— |
| EtOCO— | isobutenyl | EtOCOO— |
| EtOCO— | isopropyl | EtOCOO— |
| EtOCO— | cyclopropyl | EtOCOO— |
| EtOCO— | cyclobutyl | EtOCOO— |
| EtOCO— | cyclopentyl | EtOCOO— |
| EtOCO— | phenyl | EtOCOO— |
| ibueCO— | 3-furyl | EtOCOO— |
| ibueCO— | 3-thienyl | EtOCOO— |
| ibueCO— | 2-pyridyl | EtOCOO— |
| ibueCO— | 3-pyridyl | EtOCOO— |
| ibueCO— | 4-pyridyl | EtOCOO— |
| ibueCO— | isobutenyl | EtOCOO— |
| ibueCO— | isopropyl | EtOCOO— |

-continued (16)

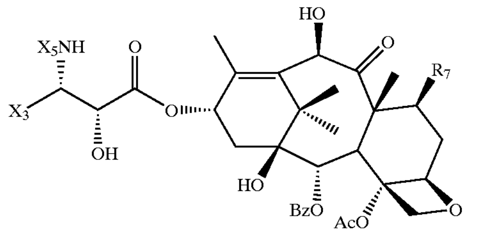

| X5 | X3 | R7 |
| --- | --- | --- |
| ibueCO— | cyclopropyl | EtOCOO— |
| ibueCO— | cyclobutyl | EtOCOO— |
| ibueCO— | cyclopentyl | EtOCOO— |
| ibueCO— | phenyl | EtOCOO— |
| iBuCO— | 2-furyl | EtOCOO— |
| iBuCO— | 3-furyl | EtOCOO— |
| iBuCO— | 2-thienyl | EtOCOO— |
| iBuCO— | 3-thienyl | EtOCOO— |
| iBuCO— | 2-pyridyl | EtOCOO— |
| iBuCO— | 3-pyridyl | EtOCOO— |
| iBuCO— | 4-pyridyl | EtOCOO— |
| iBuCO— | isobutenyl | EtOCOO— |
| iBuCO— | isopropyl | EtOCOO— |
| iBuCO— | cyclopropyl | EtOCOO— |
| iBuCO— | cyclobutyl | EtOCOO— |
| iBuCO— | cyclopentyl | EtOCOO— |
| iBuCO— | phenyl | EtOCOO— |
| iBuOCO— | 3-furyl | EtOCOO— |
| iBuOCO— | 2-pyridyl | EtOCOO— |
| iBuOCO— | 3-pyridyl | EtOCOO— |
| iBuOCO— | 4-pyridyl | EtOCOO— |
| iBuOCO— | isopropyl | EtOCOO— |
| iBuOCO— | cyclopropyl | EtOCOO— |
| iBuOCO— | cyclobutyl | EtOCOO— |
| iBuOCO— | cyclopentyl | EtOCOO— |
| iBuOCO— | phenyl | EtOCOO— |
| iPrOCO— | 2-furyl | EtOCOO— |
| iPrOCO— | 3-furyl | EtOCOO— |
| iPrOCO— | 3-thienyl | EtOCOO— |
| iPrOCO— | 2-pyridyl | EtOCOO— |
| iPrOCO— | 3-pyridyl | EtOCOO— |
| iPrOCO— | 4-pyridyl | EtOCOO— |
| iPrOCO— | isobutenyl | EtOCOO— |
| iPrOCO— | isopropyl | EtOCOO— |
| iPrOCO— | cyclopropyl | EtOCOO— |
| iPrOCO— | cyclobutyl | EtOCOO— |
| iPrOCO— | cyclopentyl | EtOCOO— |
| iPrOCO— | phenyl | EtOCOO— |
| nPrOCO— | 2-furyl | EtOCOO— |
| nPrOCO— | 3-furyl | EtOCOO— |
| nPrOCO— | 2-thienyl | EtOCOO— |
| nPrOCO— | 3-thienyl | EtOCOO— |
| nPrOCO— | 2-pyridyl | EtOCOO— |
| nPrOCO— | 3-pyridyl | EtOCOO— |
| nPrOCO— | 4-pyridyl | EtOCOO— |
| nPrOCO— | isobutenyl | EtOCOO— |
| nPrOCO— | isopropyl | EtOCOO— |
| nPrOCO— | cyclopropyl | EtOCOO— |
| nPrOCO— | cyclobutyl | EtOCOO— |
| nPrOCO— | cyclopentyl | EtOCOO— |
| nPrOCO— | phenyl | EtOCOO— |
| nPrCO— | 2-furyl | EtOCOO— |
| nPrCO— | 3-furyl | EtOCOO— |
| nPrCO— | 2-thienyl | EtOCOO— |
| nPrCO— | 3-thienyl | EtOCOO— |
| nPrCO— | 2-pyridyl | EtOCOO— |
| nPrCO— | 3-pyridyl | EtOCOO— |
| nPrCO— | 4-pyridyl | EtOCOO— |
| nPrCO— | isobutenyl | EtOCOO— |
| nPrCO— | isopropyl | EtOCOO— |
| nPrCO— | cyclopropyl | EtOCOO— |
| nPrCO— | cyclobutyl | EtOCOO— |
| nPrCO— | cyclopentyl | EtOCOO— |

-continued (16)

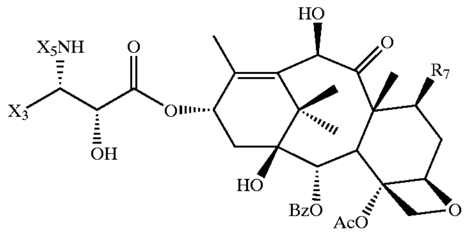

| X5 | X3 | R7 |
| --- | --- | --- |
| nPrCO— | phenyl | EtOCOO— |
| tBuOCO— | 2-pyridyl | MeOCOO— |
| tBuOCO— | 3-pyridyl | MeOCOO— |
| tBuOCO— | 4-pyridyl | MeOCOO— |
| tBuOCO— | isopropyl | MeOCOO— |
| tBuOCO— | cyclobutyl | MeOCOO— |
| tBuOCO— | cyclopentyl | MeOCOO— |
| tBuOCO— | phenyl | MeOCOO— |
| benzoyl | 2-furyl | MeOCOO— |
| benzoyl | 3-furyl | MeOCOO— |
| benzoyl | 3-thienyl | MeOCOO— |
| benzoyl | 2-pyridyl | MeOCOO— |
| benzoyl | 3-pyridyl | MeOCOO— |
| benzoyl | 4-pyridyl | MeOCOO— |
| benzoyl | isobutenyl | MeOCOO— |
| benzoyl | isopropyl | MeOCOO— |
| benzoyl | cyclopropyl | MeOCOO— |
| benzoyl | cyclobutyl | MeOCOO— |
| benzoyl | cyclopentyl | MeOCOO— |
| benzoyl | phenyl | MeOCOO— |
| 2-FuCO— | 2-furyl | MeOCOO— |
| 2-FuCO— | 3-furyl | MeOCOO— |
| 2-FuCO— | 3-thienyl | MeOCOO— |
| 2-FuCO— | 2-pyridyl | MeOCOO— |
| 2-FuCO— | 3-pyridyl | MeOCOO— |
| 2-FuCO— | 4-pyridyl | MeOCOO— |
| 2-FuCO— | isobutenyl | MeOCOO— |
| 2-FuCO— | isopropyl | MeOCOO— |
| 2-FuCO— | cyclopropyl | MeOCOO— |
| 2-FuCO— | cyciobutyl | MeOCOO— |
| 2-FuCO— | cyclopentyl | MeOCOO— |
| 2-FuCO— | phenyl | MeOCOO— |
| 2-ThCO— | 2-furyl | MeOCOO— |
| 2-ThCO— | 3-furyl | MeOCOO— |
| 2-ThCO— | 3-thienyl | MeOCOO— |
| 2-ThCO— | 2-pyridyl | MeOCOO— |
| 2-ThCO— | 3-pyridyl | MeOCOO— |
| 2-ThCO— | 4-pyridyl | MeOCOO— |
| 2-ThCO— | isobutenyl | MeOCOO— |
| 2-ThCO— | isopropyl | MeOCOO— |
| 2-ThCO— | cyclopropyl | MeOCOO— |
| 2-ThCO— | cyclobutyl | MeOCOO— |
| 2-ThCO— | cyclopentyl | MeOCOO— |
| 2-ThCO— | phenyl | MeOCOO— |
| 2-PyCO— | 2-furyl | MeOCOO— |
| 2-PyCO— | 3-furyl | MeOCOO— |
| 2-PyCO— | 2-thienyl | MeOCOO— |
| 2-PyCO— | 3-thienyl | MeOCOO— |
| 2-PyCO— | 2-pyridyl | MeOCOO— |
| 2-PyCO— | 3-pyridyl | MeOCOO— |
| 2-PyCO— | 4-pyridyl | MeOCOO— |
| 2-PyCO— | isobutenyl | MeOCOO— |
| 2-PyCO— | isopropyl | MeOCOO— |
| 2-PyCO— | cyclopropyl | MeOCOO— |
| 2-PyCO— | cyclobutyl | MeOCOO— |
| 2-PyCO— | cyclopentyl | MeOCOO— |
| 2-PyCO— | phenyl | MeOCOO— |
| 3-PyCO— | 2-furyl | MeOCOO— |
| 3-PyCO— | 3-furyl | MeOCOO— |
| 3-PyCO— | 2-thienyl | MeOCOO— |
| 3-PyCO— | 3-thienyl | MeOCOO— |
| 3-PyCO— | 2-pyridyl | MeOCOO— |
| 3-PyCO— | 3-pyridyl | MeOCOO— |

-continued (16)

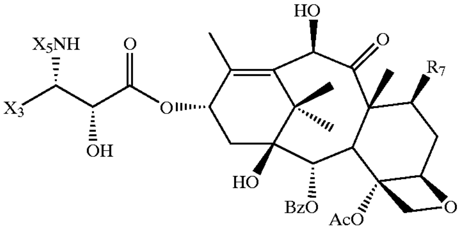

| $X_5$ | $X_3$ | $R_7$ |
|---|---|---|
| 3-PyCO— | 4-pyridyl | MeOCOO— |
| 3-PyCO— | isobutenyl | MeOCOO— |
| 3-PyCO— | isopropyl | MeOCOO— |
| 3-PyCO— | cyclopropyl | MeOCOO— |
| 3-PyCO— | cyclobutyl | MeOCOO— |
| 3-PyCO— | cyclopentyl | MeOCOO— |
| 3-PyCO— | phenyl | MeOCOO— |
| 4-PyCO— | 2-furyl | MeOCOO— |
| 4-PyCO— | 3-furyl | MeOCOO— |
| 4-PyCO— | 2-thienyl | MeOCOO— |
| 4-PyCO— | 3-thienyl | MeOCOO— |
| 4-PyCO— | 2-pyridyl | MeOCOO— |
| 4-PyCO— | 3-pyridyl | MeOCOO— |
| 4-PyCO— | 4-pyridyl | MeOCOO— |
| 4-PyCO— | isobutenyl | MeOCOO— |
| 4-PyCO— | isopropyl | MeOCOO— |
| 4-PyCO— | cyclopropyl | MeOCOO— |
| 4-PyCO— | cyclobutyl | MeOCOO— |
| 4-PyCO— | cyclopentyl | MeOCOO— |
| 4-PyCO— | phenyl | MeOCOO— |
| $C_4H_7CO$— | 2-furyl | MeOCOO— |
| $C_4H_7CO$— | 3-furyl | MeOCOO— |
| $C_4H_7CO$— | 2-thienyl | MeOCOO— |
| $C_4H_7CO$— | 3-thienyl | MeOCOO— |
| $C_4H_7CO$— | 2-pyridyl | MeOCOO— |
| $C_4H_7CO$— | 3-pyridyl | MeOCOO— |
| $C_4H_7CO$— | 4-pyridyl | MeOCOO— |
| $C_4H_7CO$— | isobutenyl | MeOCOO— |
| $C_4H_7CO$— | isopropyl | MeOCOO— |
| $C_4H_7CO$— | cyclopropyl | MeOCOO— |
| $C_4H_7CO$— | cyclobutyl | MeOCOO— |
| $C_4H_7CO$— | cyclopentyl | MeOCOO— |
| $C_4H_7CO$— | phenyl | MeOCOO— |
| EtOCO— | 2-furyl | MeOCOO— |
| EtOCO— | 3-furyl | MeOCOO— |
| EtOCO— | 2-thienyl | MeOCOO— |
| EtOCO— | 3-thienyl | MeOCOO— |
| EtOCO— | 2-pyridyl | MeOCOO— |
| EtOCO— | 3-pyridyl | MeOCOO— |
| EtOCO— | 4-pyridyl | MeOCOO— |
| EtOCO— | isobutenyl | MeOCOO— |
| EtOCO— | isopropyl | MeOCOO— |
| EtOCO— | cyclopropyl | MeOCOO— |
| EtOCO— | cyclobutyl | MeOCOO— |
| EtOCO— | cyclopentyl | MeOCOO— |
| EtOCO— | phenyl | MeOCOO— |
| ibueCO— | 2-furyl | MeOCOO— |
| ibueCO— | 3-furyl | MeOCOO— |
| ibueCO— | 3-thienyl | MeOCOO— |
| ibueCO— | 2-pyridyl | MeOCOO— |
| ibueCO— | 3-pyridyl | MeOCOO— |
| ibueCO— | 4-pyridyl | MeOCOO— |
| ibueCO— | isobutenyl | MeOCOO— |
| ibueCO— | isopropyl | MeOCOO— |
| ibueCO— | cyclopropyl | MeOCOO— |
| ibueCO— | cyclobutyl | MeOCOO— |
| ibueCO— | cyclopentyl | MeOCOO— |
| ibueCO— | phenyl | MeOCOO— |
| iBuCO— | 2-furyl | MeOCOO— |
| iBuCO— | 3-furyl | MeOCOO— |
| iBuCO— | 2-thienyl | MeOCOO— |
| iBuCO— | 3-thienyl | MeOCOO— |
| iBuCO— | 2-pyridyl | MeOCOO— |

-continued (16)

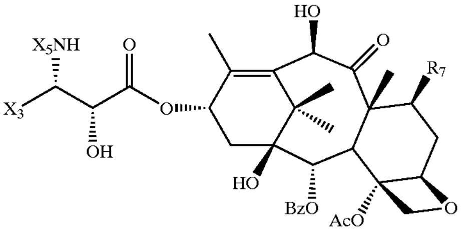

| $X_5$ | $X_3$ | $R_7$ |
|---|---|---|
| iBuCO— | 3-pyridyl | MeOCOO— |
| iBuCO— | 4-pyridyl | MeOCOO— |
| iBuCO— | isobutenyl | MeOCOO— |
| iBuCO— | isopropyl | MeOCOO— |
| iBuCO— | cyclopropyl | MeOCOO— |
| iBuCO— | cyclobutyl | MeOCOO— |
| iBuCO— | cyclopentyl | MeOCOO— |
| iBuCO— | phenyl | MeOCOO— |
| iBuOCO— | 2-pyridyl | MeOCOO— |
| iBuOCO— | 3-pyridyl | MeOCOO— |
| iBuOCO— | 4-pyridyl | MeOCOO— |
| iBuOCO— | isopropyl | MeOCOO— |
| iBuOCO— | cyclopropyl | MeOCOO— |
| iBuOCO— | cyclobutyl | MeOCOO— |
| iBuOCO— | cyclopentyl | MeOCOO— |
| iBuOCO— | phenyl | MeOCOO— |
| iPrOCO— | 2-furyl | MeOCOO— |
| iPrOCO— | 3-furyl | MeOCOO— |
| iPrOCO— | 3-thienyl | MeOCOO— |
| iPrOCO— | 2-pyridyl | MeOCOO— |
| iPrOCO— | 3-pyridyl | MeOCOO— |
| iPrOCO— | 4-pyridyl | MeOCOO— |
| iPrOCO— | isobutenyl | MeOCOO— |
| iPrOCO— | isopropyl | MeOCOO— |
| iPrOCO— | cyclopropyl | MeOCOO— |
| iPrOCO— | cyclobutyl | MeOCOO— |
| iPrOCO— | cyclopentyl | MeOCOO— |
| iPrOCO— | phenyl | MeOCOO— |
| nPrOCO— | 2-furyl | MeOCOO— |
| nPrOCO— | 3-furyl | MeOCOO— |
| nPrOCO— | 2-thienyl | MeOCOO— |
| nPrOCO— | 3-thienyl | MeOCOO— |
| nPrOCO— | 2-pyridyl | MeOCOO— |
| nPrOCO— | 3-pyridyl | MeOCOO— |
| nPrOCO— | 4-pyridyl | MeOCOO— |
| nPrOCO— | isobutenyl | MeOCOO— |
| nPrOCO— | isopropyl | MeOCOO— |
| nPrOCO— | cyclopropyl | MeOCOO— |
| nPrOCO— | cyclobutyl | MeOCOO— |
| nPrOCO— | cyclopentyl | MeOCOO— |
| nPrOCO— | phenyl | MeOCOO— |
| nPrCO— | 2-furyl | MeOCOO— |
| nPrCO— | 3-furyl | MeOCOO— |
| nPrCO— | 2-thienyl | MeOCOO— |
| nPrCO— | 3-thienyl | MeOCOO— |
| nPrCO— | 2-pyridyl | MeOCOO— |
| nPrCO— | 3-pyridyl | MeOCOO— |
| nPrCO— | 4-pyridyl | MeOCOO— |
| nPrCO— | isobutenyl | MeOCOO— |
| nPrCO— | isopropyl | MeOCOO— |
| nPrCO— | cyclopropyl | MeOCOO— |
| nPrCO— | cyclobutyl | MeOCOO— |
| nPrCO— | cyclopentyl | MeOCOO— |
| nPrCO— | phenyl | MeOCOO— |

EXAMPLE 24

Taxanes Having C-7 Carbonate and C-10 Hydroxy Substituents

Following the processes described in Example 21 and elsewhere herein, the following specific taxanes having structural formula (17) may be prepared, wherein $R_{10}$ is hydroxy and $R_7$ in each of the series (that is, each of series "A" through "K") is as previously defined, including wherein $R_7$ is $R_{7a}OCOO$— and $R_{7a}$ is (i) substituted or unsubstituted, preferably unsubstituted, $C_2$ to $C_8$ alkyl (straight, branched or cyclic), such as ethyl, propyl, butyl, pentyl, or hexyl; (ii) substituted or unsubstituted, preferably unsubstituted, $C_2$ to $C_8$ alkenyl (straight, branched or cyclic), such as ethenyl, propenyl, butenyl, pentenyl or hexenyl; (iii) substituted or unsubstituted, preferably unsubstituted, $C_2$ to $C_8$ alkynyl (straight or branched) such as ethynyl, propynyl, butynyl, pentynyl, or hexynyl; (iv) substituted or unsubstituted, preferably unsubstituted, phenyl; or (v) substituted or unsubstituted, preferably unsubstituted, heteroaromatic such as furyl, thienyl, or pyridyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_2$. are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(17)

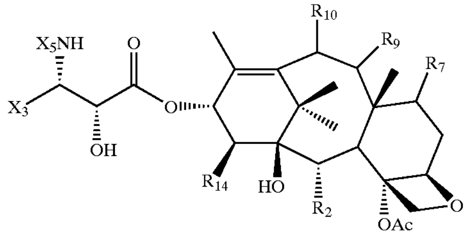

| Series | $X_5$ | $X_3$ | $R_7$ | $R_2$ | $R_9$ | $R_{14}$ |
|---|---|---|---|---|---|---|
| A1 | $—COOX_{10}$ | heterocyclo | $R_{7a}OCOO—$ | $C_6H_5COO—$ | O | H |
| A2 | $—COX_{10}$ | heterocyclo | $R_{7a}OCOO—$ | $C_6H_5COO—$ | O | H |
| A3 | $—CONHX_{10}$ | heterocyclo | $R_{7a}OCOO—$ | $C_6H_5COO—$ | O | H |
| A4 | $—COOX_{10}$ | optionally substituted $C_2$ to $C_8$ alkyl | $R_{7a}OCOO—$ | $C_6H_5COO—$ | O | H |
| A5 | $—COX_{10}$ | optionally substituted $C_2$ to $C_8$ alkyl | $R_{7a}OCOO—$ | $C_6H_5COO—$ | O | H |
| A6 | $—CONHX_{10}$ | optionally substituted $C_2$ to $C_8$ alkyl | $R_{7a}OCOO—$ | $C_6H_5COO—$ | O | H |
| A7 | $—COOX_{10}$ | optionally substituted $C_2$ to $C_8$ alkenyl | $R_{7a}OCOO—$ | $C_6H_5COO—$ | O | H |
| A8 | $—COX_{10}$ | optionally substituted $C_2$ to $C_8$ alkenyl | $R_{7a}OCOO—$ | $C_6H_5COO—$ | O | H |
| A9 | $—CONHX_{10}$ | optionally substituted $C_2$ to $C_8$ alkenyl | $R_{7a}OCOO—$ | $C_6H_5COO—$ | O | H |
| A10 | $—COOX_{10}$ | optionally substituted $C_2$ to $C_8$ alkynyl | $R_{7a}OCOO—$ | $C_6H_5COO—$ | O | H |
| A11 | $—COX_{10}$ | optionally substituted $C_2$ to $C_8$ alkynyl | $R_{7a}OCOO—$ | $C_6H_5COO—$ | O | H |
| A12 | $—CONHX_{10}$ | optionally substituted $C_2$ to $C_8$ alkynyl | $R_{7a}OCOO—$ | $C_6H_5COO—$ | O | H |
| B1 | $—COOX_{10}$ | heterocyclo | $R_{7a}OCOO—$ | $R_{2a}COO—$ | O | H |
| B2 | $—COX_{10}$ | heterocyclo | $R_{7a}OCOO—$ | $R_{2a}COO—$ | O | H |
| B3 | $—CONHX_{10}$ | heterocyclo | $R_{7a}OCOO—$ | $R_{2a}COO—$ | O | H |
| B4 | $—COOX_{10}$ | optionally substituted $C_2$ to $C_8$ alkyl | $R_{7a}OCOO—$ | $R_{2a}COO—$ | O | H |
| B5 | $—COX_{10}$ | optionally substituted $C_2$ to $C_8$alkyl | $R_{7a}OCOO—$ | $R_{2a}COO—$ | O | H |
| B6 | $—CONHX_{10}$ | optionally substituted $C_2$ to $C_8$ alkyl | $R_{7a}OCOO—$ | $R_{2a}COO—$ | O | H |
| B7 | $—COOX_{10}$ | optionally substituted $C_2$ to $C_8$ alkenyl | $R_{7a}OCOO—$ | $R_{2a}COO—$ | O | H |
| B8 | $—COX_{10}$ | optionally substituted $C_2$ to $C_8$ alkenyl | $R_{7a}OCOO—$ | $R_{2a}COO—$ | O | H |
| B9 | $—CONHX_{10}$ | optionally substituted $C_2$ to $C_8$ alkenyl | $R_{7a}OCOO—$ | $R_{2a}COO—$ | O | H |
| B10 | $—COOX_{10}$ | optionally substituted $C_2$ to $C_8$ alkynyl | $R_{7a}OCOO—$ | $R_{2a}COO—$ | O | H |
| B11 | $—COX_{10}$ | optionally substituted $C_2$ to $C_8$ alkynyl | $R_{7a}OCOO—$ | $R_{2a}COO—$ | O | H |
| B12 | $—CONHX_{10}$ | optionally substituted $C_2$ to $C_8$ alkynyl | $R_{7a}OCOO—$ | $R_{2a}COO—$ | O | H |
| C1 | $—COOX_{10}$ | heterocyclo | $R_{7a}OCOO—$ | $C_6H_5COO—$ | $R_{9a}COO—$ | H |
| C2 | $—COX_{10}$ | heterocyclo | $R_{7a}OCOO—$ | $C_6H_5COO—$ | $R_{9a}COO—$ | H |
| C3 | $—CONHX_{10}$ | heterocyclo | $R_{7a}OCOO—$ | $C_6H_5COO—$ | $R_{9a}COO—$ | H |

-continued (17)

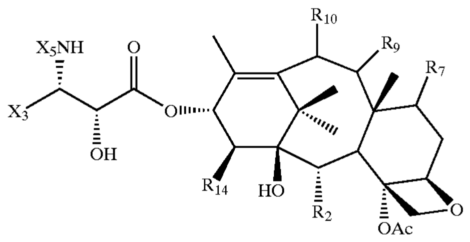

| Series | $X_5$ | $X_3$ | $R_7$ | $R_2$ | $R_9$ | $R_{14}$ |
|---|---|---|---|---|---|---|
| C4 | —$COOX_{10}$ | optionally substituted $C_2$ to $C_8$ alkyl | $R_{7a}OCOO$— | $C_6H_5COO$— | $R_{9a}COO$— | H |
| C5 | —$COX_{10}$ | optionally substituted $C_2$ to $C_8$ alkyl | $R_{7a}OCOO$— | $C_6H_5COO$— | $R_{9a}COO$— | H |
| C6 | —$CONHX_{10}$ | optionally substituted $C_2$ to $C_8$ alkyl | $R_{7a}OCOO$— | $C_6H_5COO$— | $R_{9a}COO$— | H |
| C7 | —$COOX_{10}$ | optionally substituted $C_2$ to $C_8$ alkenyl | $R_{7a}OCOO$— | $C_6H_5COO$— | $R_{9a}COO$— | H |
| C8 | —$COX_{10}$ | optionally substituted $C_2$ to $C_8$ alkenyl | $R_{7a}OCOO$— | $C_6H_5COO$— | $R_{9a}COO$— | H |
| C9 | —$CONHX_{10}$ | optionally substituted $C_2$ to $C_8$ alkenyl | $R_{7a}OCOO$— | $C_6H_5COO$— | $R_{9a}COO$— | H |
| C10 | —$COOX_{10}$ | optionally substituted $C_2$ to $C_5$ alkynyl | $R_{7a}OCOO$— | $C_6H_5COO$— | $R_{9a}COO$— | H |
| C11 | —$COX_{10}$ | optionally substituted $C_2$ to $C_8$ alkynyl | $R_{7a}OCOO$— | $C_6H_5COO$— | $R_{9a}COO$— | H |
| C12 | —$CONHX_{10}$ | optionally substituted $C_2$ to $C_8$ alkynyl | $R_{7a}OCOO$— | $C_6H_5COO$— | $R_{9a}COO$— | H |
| D1 | —$COOX_{10}$ | heterocyclo | $R_{7a}OCOO$— | $C_6H_5COO$— | OH | H |
| D2 | —$COX_{10}$ | heterocyclo | $R_{7a}OCOO$— | $C_6H_5COO$— | OH | H |
| D3 | —$CONHX_{10}$ | heterocyclo | $R_{7a}OCOO$— | $C_6H_5COO$— | OH | H |
| D4 | —$COOX_{10}$ | optionally substituted $C_2$ to $C_8$ alkyl | $R_{7a}OCOO$— | $C_6H_5COO$— | OH | H |
| D5 | —$COX_{10}$ | optionally substituted $C_2$ to $C_8$ alkyl | $R_{7a}OCOO$— | $C_6H_5COO$— | OH | H |
| D6 | —$CONHX_{10}$ | optionally substituted $C_2$ to $C_8$ alkyl | $R_{7a}OCOO$— | $C_6H_5COO$— | OH | H |
| D7 | —$COOX_{10}$ | optionally substituted $C_2$ to $C_8$ alkenyl | $R_{7a}OCOO$— | $C_6H_5COO$— | OH | H |
| D8 | —$COX_{10}$ | optionally substituted $C_2$ to $C_8$ alkenyl | $R_{7a}OCOO$— | $C_6H_5COO$— | OH | H |
| D9 | —$CONHX_{10}$ | optionally substituted $C_2$ to $C_8$ alkenyl | $R_{7a}OCOO$— | $C_6H_5COO$— | OH | H |
| D10 | —$COOX_{10}$ | optionally substituted $C_2$ to $C_8$ alkynyl | $R_{7a}OCOO$— | $C_6H_5COO$— | OH | H |
| D11 | —$COX_{10}$ | optionally substituted $C_2$ to $C_8$ alkynyl | $R_{7a}OCOO$— | $C_6H_5COO$— | OH | H |
| D12 | —$CONHX_{10}$ | optionally substituted $C_2$ to $C_8$ alkynyl | $R_{7a}OCOO$— | $C_6H_5COO$— | OH | H |
| E1 | —$COOX_{10}$ | heterocyclo | $R_{7a}OCOO$— | $C_6H_5COO$— | O | OH |
| E2 | —$COX_{10}$ | heterocyclo | $R_{7a}OCOO$— | $C_6H_5COO$— | O | OH |
| E3 | —$CONHX_{10}$ | heterocyclo | $R_{7a}OCOO$— | $C_6H_5COO$— | O | OH |
| E4 | —$COOX_{10}$ | optionally substituted $C_2$ to $C_8$ alkyl | $R_{7a}OCOO$— | $C_6H_5COO$— | O | OH |

-continued (17)

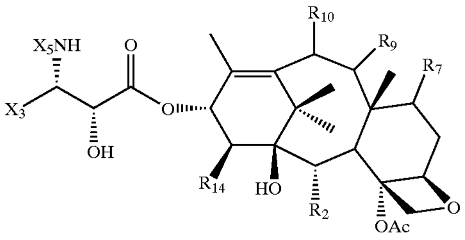

| Series | $X_5$ | $X_3$ | $R_7$ | $R_2$ | $R_9$ | $R_{14}$ |
|---|---|---|---|---|---|---|
| E5 | —$COX_{10}$ | optionally substituted $C_2$ to $C_8$ alkyl | $R_{7a}OCOO$— | $C_6H_5COO$— | O | OH |
| E6 | —$CONHX_{10}$ | optionally substituted $C_2$ to $C_8$ alkyl | $R_{7a}OCOO$— | $C_6H_5COO$— | O | OH |
| E7 | —$COOX_{10}$ | optionally substituted $C_2$ to $C_8$ alkenyl | $R_{7a}OCOO$— | $C_6H_5COO$— | O | OH |
| E8 | —$COX_{10}$ | optionally substituted $C_2$ to $C_8$ alkenyl | $R_{7a}OCOO$— | $C_6H_5COO$— | O | OH |
| E9 | —$CONHX_{10}$ | optionally substituted $C_2$ to $C_8$ alkenyl | $R_{7a}OCOO$— | $C_6H_5COO$— | O | OH |
| E10 | —$COOX_{10}$ | optionally substituted $C_2$ to $C_8$ alkynyl | $R_{7a}OCOO$— | $C_6H_5COO$— | O | OH |
| E11 | —$COX_{10}$ | optionally substituted $C_2$ to $C_8$ alkynyl | $R_{7a}OCOO$— | $C_6H_5COO$— | O | OH |
| E12 | —$CONHX_{10}$ | optionally substituted $C_2$ to $C_8$ alkynyl | $R_{7a}OCOO$— | $C_6H_5COO$— | O | OH |
| F1 | —$COOX_{10}$ | heterocyclo | $R_{7a}OCOO$— | $R_{2a}COO$— | $R_{9a}COO$— | H |
| F2 | —$COX_{10}$ | heterocyclo | $R_{7a}OCOO$— | $R_{2a}COO$— | $R_{9a}COO$— | H |
| F3 | —$CONHX_{10}$ | heterocyclo | $R_{7a}OCOO$— | $R_{2a}COO$— | $R_{9a}COO$— | H |
| F4 | —$COOX_{10}$ | optionally substituted $C_2$ to $C_8$ alkyl | $R_{7a}OCOO$— | $R_{2a}COO$— | $R_{9a}COO$— | H |
| F5 | —$COX_{10}$ | optionally substituted $C_2$ to $C_8$ alkyl | $R_{7a}OCOO$— | $R_{2a}COO$— | $R_{9a}COO$— | H |
| F6 | —$CONHX_{10}$ | optionally substituted $C_2$ to $C_8$ alkyl | $R_{7a}OCOO$— | $R_{2a}COO$— | $R_{9a}COO$— | H |
| F7 | —$COOX_{10}$ | optionally substituted $C_2$ to $C_8$ alkenyl | $R_{7a}OCOO$— | $R_{2a}COO$— | $R_{9a}COO$— | H |
| F8 | —$COX_{10}$ | optionally substituted $C_2$ to $C_8$ alkenyl | $R_{7a}OCOO$— | $R_{2a}COO$— | $R_{9a}COO$— | H |
| F9 | —$CONHX_{10}$ | optionally substituted $C_2$ to $C_8$ alkenyl | $R_{7a}OCOO$— | $R_{2a}COO$— | $R_{9a}COO$— | H |
| F10 | —$COOX_{10}$ | optionally substituted $C_2$ to $C_8$ alkynyl | $R_{7a}OCOO$— | $R_{2a}COO$— | $R_{9a}COO$— | H |
| F11 | —$COX_{10}$ | optionally substituted $C_2$ to $C_8$ alkynyl | $R_{7a}OCOO$— | $R_{2a}COO$— | $R_{9a}COO$— | H |
| F12 | —$CONHX_{10}$ | optionally substituted $C_2$ to $C_8$ alkynyl | $R_{7a}OCOO$— | $R_{2a}COO$— | $R_{9a}COO$— | H |
| G1 | —$COOX_{10}$ | heterocyclo | $R_{7a}OCOO$— | $R_{2a}COO$— | OH | H |
| G2 | —$COX_{10}$ | heterocyclo | $R_{7a}OCOO$— | $R_{2a}COO$— | OH | H |
| G3 | —$CONHX_{10}$ | heterocyclo | $R_{7a}OCOO$— | $R_{2a}COO$— | OH | H |
| G4 | —$COOX_{10}$ | optionally substituted $C_2$ to $C_8$ alkyl | $R_{7a}OCOO$— | $R_{2a}COO$— | OH | H |
| G5 | —$COX_{10}$ | optionally substituted $C_2$ to $C_8$ alkyl | $R_{7a}OCOO$— | $R_{2a}COO$— | OH | H |

-continued (17)

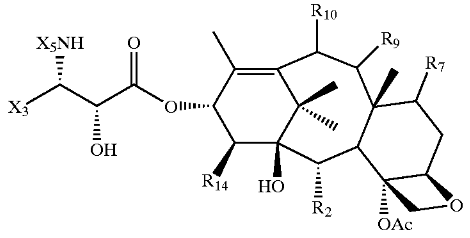

| Series | $X_5$ | $X_3$ | $R_7$ | $R_2$ | $R_9$ | $R_{14}$ |
|---|---|---|---|---|---|---|
| G6 | —CONHX$_{10}$ | optionally substituted $C_2$ to $C_8$ alkyl | $R_{7a}$OCOO— | $R_{2a}$COO— | OH | H |
| G7 | —COOX$_{10}$ | optionally substituted $C_2$ to $C_8$ alkenyl | $R_{7a}$OCOO— | $R_{2a}$COO— | OH | H |
| G8 | —COX$_{10}$ | optionally substituted $C_2$ to $C_8$ alkenyl | $R_{7a}$OCOO— | $R_{2a}$COO— | OH | H |
| G9 | —CONHX$_{10}$ | optionally substituted $C_2$ to $C_8$ alkenyl | $R_{7a}$OCOO— | $R_{2a}$COO— | OH | H |
| G10 | —COOX$_{10}$ | optionally substituted $C_2$ to $C_8$ alkynyl | $R_{7a}$OCOO— | $R_{2a}$COO— | OH | H |
| G11 | —COX$_{10}$ | optionally substituted $C_2$ to $C_8$ alkynyl | $R_{7a}$OCOO— | $R_{2a}$COO— | OH | H |
| G12 | —CONHX$_{10}$ | optionally substituted $C_2$ to $C_8$ alkynyl | $R_{7a}$OCOO— | $R_{2a}$COO— | OH | H |
| H1 | —COOX$_{10}$ | heterocyclo | $R_{7a}$OCOO— | $C_6H_5$COO— | OH | OH |
| H2 | —COX$_{10}$ | heterocyclo | $R_{7a}$OCOO— | $C_6H_5$COO— | OH | OH |
| H3 | —CONHX$_{10}$ | heterocyclo | $R_{7a}$OCOO— | $C_6H_5$COO— | OH | OH |
| H4 | —COOX$_{10}$ | optionally substituted $C_2$ to $C_8$ alkyl | $R_{7a}$OCOO— | $C_6H_5$COO— | OH | OH |
| H5 | —COX$_{10}$ | optionally substituted $C_2$ to $C_8$ alkyl | $R_{7a}$OCOO— | $C_6H_5$COO— | OH | OH |
| H6 | —CONHX$_{10}$ | optionally substituted $C_2$ to $C_8$ alkyl | $R_{7a}$OCOO— | $C_6H_5$COO— | OH | OH |
| H7 | —COOX$_{10}$ | optionally substituted $C_2$ to $C_8$ alkenyl | $R_{7a}$OCOO— | $C_6H_5$COO— | OH | OH |
| H8 | —COX$_{10}$ | optionally substituted $C_2$ to $C_8$ alkenyl | $R_{7a}$OCOO— | $C_6H_5$COO— | OH | OH |
| H9 | —CONHX$_{10}$ | optionally substituted $C_2$ to $C_8$ aklkenyl | $R_{7a}$OCOO— | $C_6H_5$COO— | OH | OH |
| H10 | —COOX$_{10}$ | optionally substituted $C_2$ to $C_8$ alkynyl | $R_{7a}$OCOO— | $C_6H_5$COO— | OH | OH |
| H11 | —COX$_{10}$ | optionally substituted $C_2$ to $C_8$ alkynyl | $R_{7a}$OCOO— | $C_6H_5$COO— | OH | OH |
| H12 | —CONHX$_{10}$ | optionally substituted $C_2$ to $C_8$ alkynyl | $R_{7a}$OCOO— | $C_6H_5$COO— | OH | OH |
| I1 | —COOX$_{10}$ | heterocyclo | $R_{7a}$OCOO— | $R_{2a}$COO— | O | OH |
| I2 | —COX$_{10}$ | heterocyclo | $R_{7a}$OCOO— | $R_{2a}$COO— | O | OH |
| I3 | —CONHX$_{10}$ | heterocyclo | $R_{7a}$OCOO— | $R_{2a}$COO— | O | OH |
| I4 | —COOX$_{10}$ | optionally substituted $C_2$ to $C_8$ alkyl | $R_{7a}$OCOO— | $R_{2a}$COO— | O | OH |
| I5 | —COX$_{10}$ | optionally substituted $C_2$ to $C_8$ alkyl | $R_{7a}$OCOO— | $R_{2a}$COO— | O | OH |
| I6 | —CONHX$_{10}$ | optionally substituted $C_2$ to $C_8$ alkyl | $R_{7a}$OCOO— | $R_{2a}$COO— | O | OH |

-continued (17)

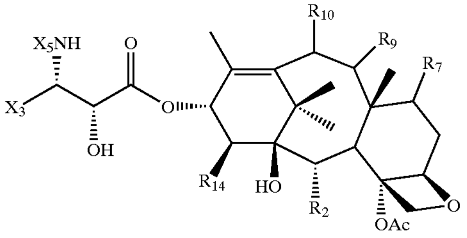

| Series | $X_5$ | $X_3$ | $R_7$ | $R_2$ | $R_9$ | $R_{14}$ |
|---|---|---|---|---|---|---|
| I7 | —$COOX_{10}$ | optionally substituted $C_2$ to $C_8$ alkenyl | $R_{7a}OCOO$— | $R_{2a}COO$— | O | OH |
| I8 | —$COX_{10}$ | optionally substituted $C_2$ to $C_8$ alkenyl | $R_{7a}OCOO$— | $R_{2a}COO$— | O | OH |
| I9 | —$CONHX_{10}$ | optionally substituted $C_2$ to $C_8$ alkenyl | $R_{7a}OCOO$— | $R_{2a}COO$— | O | OH |
| I10 | —$COOX_{10}$ | optionally substituted $C_2$ to $C_8$ alkynyl | $R_{7a}OCOO$— | $R_{2a}COO$— | O | OH |
| I11 | —$COX_{10}$ | optionally substituted $C_2$ to $C_8$ alkynyl | $R_{7a}OCOO$— | $R_{2a}COO$— | O | OH |
| I12 | —$CONHX_{10}$ | optionally substituted $C_2$ to $C_8$ alkynyl | $R_{7a}OCOO$— | $R_{2a}COO$— | O | OH |
| J1 | —$COOX_{10}$ | heterocyclo | $R_{7a}OCOO$— | $R_{2a}COO$— | OH | OH |
| J2 | —$COX_{10}$ | heterocyclo | $R_{7a}OCOO$— | $R_{2a}COO$— | OH | OH |
| J3 | —$CONHX_{10}$ | heterocyclo | $R_{7a}OCOO$— | $R_{2a}COO$— | OH | OH |
| J4 | —$COOX_1$ | optionally substituted $C_2$ to $C_8$ alkyl | $R_{7a}OCOO$— | $R_{2a}COO$— | OH | OH |
| J5 | —$COX_{10}$ | optionally substituted $C_2$ to $C_8$ alkyl | $R_{7a}OCOO$— | $R_{2a}COO$— | OH | OH |
| J6 | —$CONHX_{10}$ | optionally substituted $C_2$ to $C_8$ alkyl | $R_{7a}OCOO$— | $R_{2a}COO$— | OH | OH |
| J7 | —$COOX_{10}$ | optionally substituted $C_2$ to $C_8$ alkenyl | $R_{7a}OCOO$— | $R_{2a}COO$— | OH | OH |
| J8 | —$COX_{10}$ | optionally substituted $C_2$ to $C_8$ alkenyl | $R_{7a}OCOO$— | $R_{2a}COO$— | OH | OH |
| J9 | —$CONHX_{10}$ | optionally substituted $C_2$ to $C_8$ alkenyl | $R_{7a}OCOO$— | $R_{2a}COO$— | OH | OH |
| J10 | —$COOX_{10}$ | optionally substituted $C_2$ to $C_8$ alkynyl | $R_{7a}OCOO$— | $R_{2a}COO$— | OH | OH |
| J11 | —$COX_{10}$ | optionally substituted $C_2$ to $C_8$ alkynyl | $R_{7a}OCOO$— | $R_{2a}COO$— | OH | OH |
| J12 | —$CONHX_{10}$ | optionally substituted $C_2$ to $C_8$ alkynyl | $R_{7a}OCOO$— | $R_{2a}COO$— | OH | OH |
| K1 | —$COOX_{10}$ | heterocyclo | $R_{7a}OCOO$— | $R_{2a}COO$— | $R_{9a}COO$— | OH |
| K2 | —$COX_{10}$ | heterocyclo | $R_{7a}OCOO$— | $R_{2a}COO$— | $R_{9a}COO$— | OH |
| K3 | —$CONHX_{10}$ | heterocyclo | $R_{7a}OCOO$— | $R_{2a}COO$— | $R_{9a}COO$— | OH |
| K4 | —$COOX_{10}$ | optionally substituted $C_2$ to $C_8$ alkyl | $R_{7a}OCOO$— | $R_{2a}COO$— | $R_{9a}COO$— | OH |
| K5 | —$COX_{10}$ | optionally substituted $C_2$ to $C_8$ alkyl | $R_{7a}OCOO$— | $R_{2a}COO$— | $R_{9a}COO$— | OH |
| K6 | —$CONHX_{10}$ | optionally substituted $C_2$ to $C_8$ alkyl | $R_{7a}OCOO$— | $R_{2a}COO$— | $R_{9a}COO$— | OH |
| K7 | —$COOX_{10}$ | optionally substituted $C_2$ to $C_8$ alkenyl | $R_{7a}OCOO$— | $R_{2a}COO$— | $R_{9a}COO$— | OH |

-continued (17)

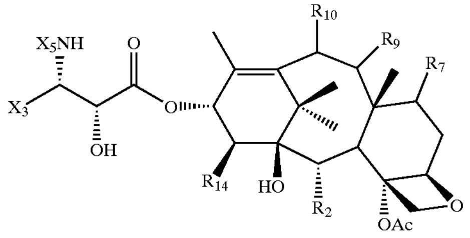

| Series | $X_5$ | $X_3$ | $R_7$ | $R_2$ | $R_9$ | $R_{14}$ |
|---|---|---|---|---|---|---|
| K8 | —$COX_{10}$ | optionally substituted $C_2$ to $C_8$ alkenyl | $R_{7a}OCOO$— | $R_{2a}COO$— | $R_{9a}COO$— | OH |
| K9 | —$CONHX_{10}$ | optionally substituted $C_2$ to $C_8$ alkenyl | $R_{7a}OCOO$— | $R_{2a}COO$— | $R_{9a}COO$— | OH |
| K10 | —$COOX_{10}$ | optionally substituted $C_2$ to $C_8$ alkynyl | $R_{7a}OCOO$— | $R_{2a}COO$— | $R_{9a}COO$— | OH |
| K11 | —$COX_{10}$ | optionally substituted $C_2$ to $C_8$ alkynyl | $R_{7a}OCOO$— | $R_{2a}COO$— | $R_{9a}COO$— | OH |
| K12 | —$CONHX_{10}$ | optionally substituted $C_2$ to $C_8$ alkynyl | $R_{7a}OCOO$— | $R_{2a}COO$— | $R_{9a}COO$— | OH |

EXAMPLE 25

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 22 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 4144 | <1 |
| 4151 | <1 |
| 4164 | <1 |
| 4188 | <10 |
| 4222 | <1 |
| 4234 | <1 |
| 4244 | <1 |
| 4262 | <1 |

-continued

| Compound | IN VITRO ID 50 (nm) HCT116 |
|---|---|
| 4304 | <10 |
| 4355 | <1 |
| 4363 | <10 |
| 4411 | <1 |
| 4424 | <1 |
| 4434 | <1 |
| 4455 | <1 |
| 4474 | <1 |
| 4484 | <1 |
| 4500 | <1 |
| 4515 | <10 |
| 4524 | <1 |
| 4533 | <1 |
| 4555 | <1 |
| 4584 | <10 |
| 4566 | <1 |
| 4575 | <1 |
| 4624 | <10 |
| 4644 | <10 |
| 4656 | <1 |
| 4674 | <1 |
| 4688 | <10 |
| 4696 | <1 |
| 4744 | <1 |
| 4766 | <1 |
| 5466 | <1 |
| 6151 | <1 |
| 6246 | <1 |
| 5433 | <1 |
| 4818 | <1 |
| 6566 | <10 |
| 4855 | <1 |
| 4464 | <1 |
| 4904 | <10 |
| 4877 | <1 |
| 4979 | <10 |
| 4444 | <1 |
| 4999 | <1 |
| 4969 | <1 |

-continued

| Compound | IN VITRO ID 50 (nm) HCT116 |
| --- | --- |
| 5225 | <10 |
| 5211 | <10 |
| 5165 | <1 |

EXAMPLE 26

Preparation of Taxanes having C-10 Carbonate and C-7 Hydroxy

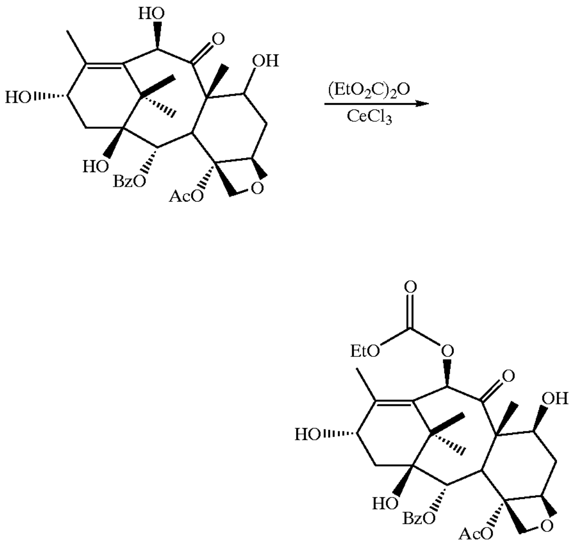

10-Ethoxycarbonyl-10-deacetyl baccatin III.

To a mixture of 0.941 g (1.73 mmol) of 10-deacetyl baccatin III and 0.043 g (0.17 mmol) of $CeCl_3$ in 40 mL of THF at 25° C. was added 0.64 mL (4.32 mmol) of diethyl pyrocarbonate. After 3 h the reaction mixture was diluted with 200 mL of EtOAc, then washed three times with 50 mL of saturated aqueous $NaHCO_3$ solution and brine. The organic extract was dried over $Na_2SO_4$ and concentrated in vacuo. The crude solid was purified by flash column chromatography on silica gel using 40% EtOAc/hexane as eluent to give 0.960 g (90%) of 10-ethoxycarbonyl-10-deacetyl baccatin III as a solid.

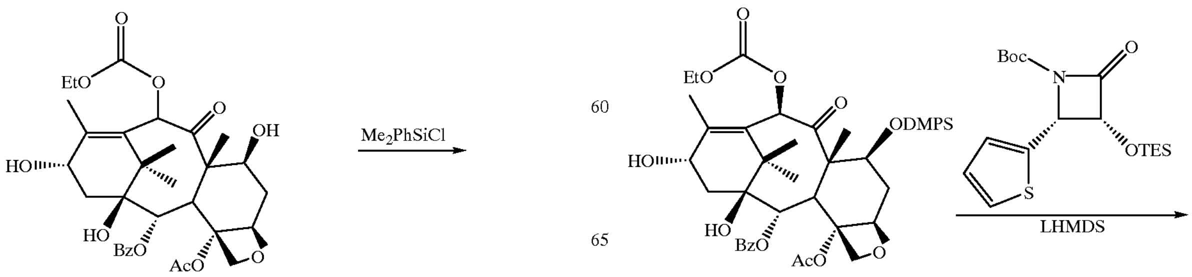

-continued

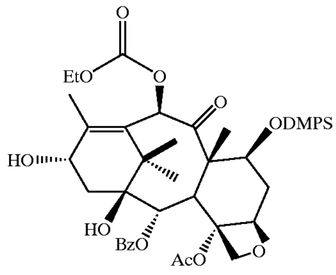

7-Dimethylphenylsilyl-10-ethoxycarbonyl-10-deacetyl baccatin III.

To a solution of 1.02 g (1.65 mmol)of 10-ethoxycarbonyl-10-deacetyl baccatin III in 30 mL of THF at −10° C. under a nitrogen atmosphere was added dropwise 0.668 mL (4.00 mmol) of chlorodimethylphenylsilane and 2.48 mL (30.64 mmol) of pyridine. After 90 min the mixture was diluted with 200 mL of a 1:1 mixture of ethyl acetate and hexane. The mixture was washed with 30 mL of saturated aqueous sodium bicarbonate solution and the organic layer separated. The aqueous layer was extracted with 50 mL of a 1:1 mixture of ethyl acetate and hexane, and the combined organic extracts were washed with brine, dried over $Na_2SO_4$, and concentrated in vacuo. The crude solid was purified by flash column chromatography on silica gel using 30% EtOAc/hexane as eluent to give 1.16 g (94%) of 7-dimethylphenylsilyl-10-ethoxycarbonyl-10-deacetyl baccatin III as a solid. $^1H$ NMR (400 MHz, $CDCl_3$): d 8.09 (dm, J=7.64 Hz, 2 H, benzoate, o), 7.59 (tt, J=7.54, 1.43 Hz, 1H, benzoate, p), 7.57 (m, 2 H, phenyl, o), 7.46 (t, J=7.54 Hz, 2H, benzoate, m), 7.37–7.33 (m, 3 H, phenyl, m,p), 6.21 (s, 1H, H10), 5.63 (d, J=7.05 Hz, 1H, H2),4.87–4.80 (m, 2 H, H5 and H13), 4.44 (dd, J=6.84, 10.37 Hz, 1H, H7), 4.27 (d, J=8.27 Hz, 1H, H20a), 4.16 (qm, J=7.00 Hz, 2H, $CH_3$—$CH_2$—), 4.13 (d, J=8.27 Hz, 1H, H20b), 3.83 (d, J=7.05 Hz, 1H, H3), 2.34 (ddd, J=6.84, 9.63, 14.66 Hz, 1H, H6a), 2.26 (d, J=7.65 Hz, 2 H, H14a,b), 2.25 (s, 3H, Ac4),2.03 (s, 3H, Me18),1.98 (d, J=5.29, 1H, C13OH), 1.77 (ddd, J=2.12, 10.37, 14.66 Hz, 1H, H6b), 1.73 (s, 1H, Me19), 1.59 (s, 1H, C1 OH), 1.32 (t, J=7.00 Hz, 3 H, $CH_3$—$CH_2$—), 1.19 (s, 3H, Me17), 1.07 (s, 3H, Me16), 0.45 (s, 3 H, $PhMe_2Si$-), 0.35 (s, 3 H, $PhMe_2Si$-).

-continued

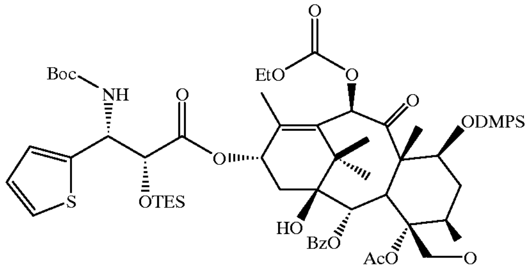

7-Dimethylphenylsilyl-2'-O-triethylsilyi-3'-desphenyl-3'-(2-thienyl)-10-ethoxycarbonyl-10-deacetyl taxotere.

To a solution of 0.409 g (0.544 mmol) of 7-dimethylphenylsilyl-10-ethoxycarbonyl-10-deacetyl baccatin III in 5.5 mL of THF at −45° C. under a nitrogen atmosphere was added 0.681 mL (0.681 mmol) of a 1M solution of LHMDS in THF. After 1 h, a solution of 0.317 g (0.818 mmol) of cis-N-benzoyl-3-triethylsilyloxy4-(2-thienyl) azetidin-2-one in 3 mL of THF was added slowly. The mixture was warmed to 0° C. and after 3 h 10 mL of saturated aqueous sodium bicarbonate solution was added and the mixture was extracted three times with 50 mL of ethyl acetate. The combined organic extracts were washed with brine, dried over $Na_2SO_4$, and concentrated in vacuo. The crude product was purified by flash column chromatography on silica gel using 40% EtOAc/hexane as eluent to give 0.574 g (93%) of 7-dimethylphenylsilyl-2'-O-triethylsilyl-3'-desphenyl-3'-(2-thienyl)-10-ethoxycarbonyl-10-deacetyl taxotere as a solid.

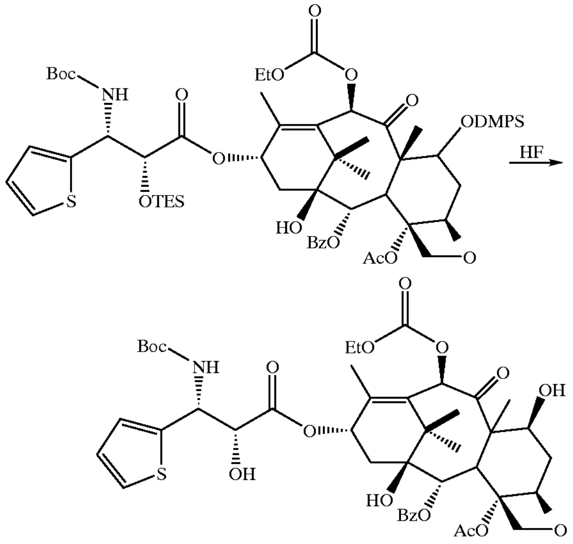

3'-Desphenyl-3'-(2-thienyl)-10-ethoxycarbonyl-10-deacetyl taxotere.

To a solution of 0.527 g (0.464 mmol) of 7-dimethylphenylsilyl-2'-O-triethylsilyl-3'-desphenyl-3'-(2-thienyl)-10-ethoxycarbonyl-10-deacetyl taxotere in 2 mL of $CH_3CN$ and 2 mL of pyridine at 0° C. was added 0.5 mL of a solution of 30% HF in $H_2O$. After 3 h 20 mL of a saturated aqueous sodium bicarbonate solution was added and the mixture was extracted three times with 50 mL of ethyl acetate. The combined organic extracts were washed with brine, dried over $Na_2SO_4$, and concentrated in vacuo. The crude product was purified by flash column chromatography on silica gel using 70% EtOAc/hexane as eluent to give 0.411 g (100%) of 3'-desphenyl-3'-(2-thienyl)-10-ethoxycarbonyl-10-deacetyl taxotere as a solid. m.p. 160–161° C.; $[a]_D^{25}$=−59.1 (c 1.0 in $CH_2Cl_2$); Anal. Calcd. for $C_{44}H_{55}NO_{16}S$: C, 59.65; H, 6.26; Found: C, 59.39; H, 6.34.

3'-Desphenyl-3'-(2-thienyl)-10-ethoxycarbonyl-10-deacetyl taxotere $^1H$ NMR data (500 MHz, $CDCl_3$)

| Proton | d (ppm) | Pattern | J (Hz) |
|---|---|---|---|
| 1OH | 1.68 | s | |
| 2 | 5.68 | d | H3(7.0) |
| 3 | 3.80 | d | H3(7.0) |
| 4Ac | 2.38 | s | |
| 5 | 4.95 | dd | H6b(2.0), H6b(9.8) |
| 6a | 2.56 | ddd | H7(6.6), H5(9.8), H6b(14.65) |
| 6b | 1.89 | ddd | H5(2.0), H7(10.9), H6a(14.65) |
| 7 | 4.40 | ddd | C7OH(4.2), H6a(6.6), H6b(10.9) |
| 7OH | 2.50 | d | H7(4.2) |
| 10 | 6.12 | s | |
| 13 | 6.25 | t | H14a(9.1), H14b(9.1) |
| 14a | 2.35 | dd | H13(9.1), H14b(14.2) |
| 14b | 2.34 | dd | H13(9.1), H14a(14.2) |
| 16Me | 1.17 | s | |
| 17Me | 1.26 | s | |
| 18Me | 1.90 | s | |
| 19Me | 1.70 | s | |
| 20a | 4.31 | d | H20b(8.6) |
| 20b | 4.19 | d | H20a(8.6) |
| 2' | 4.64 | dd | C2'OH(5.5), H3'(2.0) |
| 2'OH | 3.38 | d | H3'(5.5) |
| 3' | 5.51 | br d | NH(9.5) |
| NH | 5.28 | d | H3'(9.5) |
| 3'(2-thienyl), H3" | 7.29 | dd | 3'(2-thienyl), H5"(1.1), 3'(2-thienyl), H3"(5.1) |
| 3'(2-thienyl), H4" | 7.02 | dd | 3'(2-thienyl), H5"(3.6), 3'(2-thienyl), H3"(5.1) |
| 3'(2-thienyl), H5" | 7.09 | d | 3'(2-thienyl), H4"(3.6) |
| Boc | 1.34 | s | |
| benzoate, m | 7.51 | t | benzoate, o(7.8), benzoate, p(7.8) |
| benzoate, o | 8.12 | d | benzoate, m(7.8) |
| benzoate, p | 7.61 | t | benzoate, m(7.8) |
| $CH_3$—$CH_2$—OCO | 1.37 | t | $CH_3$—$CH_2$—OCO(7.1) |
| $CH_3$—$CH_2$—OCO | 4.28 | m | |

EXAMPLE 27

Additional Taxanes having C-10 Carbonate and C-7 Hydroxy Substituents

The procedures described in Example 26 were repeated, but other suitably protected β-lactams were substituted for the β-lactam of Example 26 to prepare the series of compounds having structural formula (18) and the combinations of substituents identified in the following table.

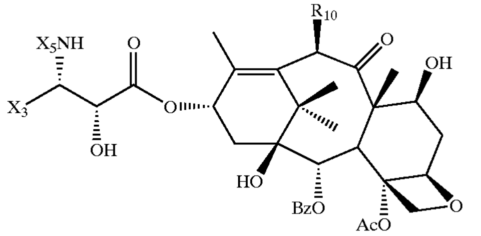

| Compound | $X_5$ | $X_3$ | $R_{10}$ |
|---|---|---|---|
| 1755 | tBuOCO— | 2-thienyl | EtOCOO— |
| 1767 | tBuOCO— | isopropyl | EtOCOO— |
| 1781 | tBuOCO— | isobutenyl | EtOCOO— |
| 1799 | tBuOCO— | 2-pyridyl | EtOCOO— |
| 1808 | tBuOCO— | 3-pyridyl | EtOCOO— |
| 1811 | tBuOCO— | 4-pyridyl | EtOCOO— |
| 1822 | tBuOCO— | 2-furyl | EtOCOO— |
| 1838 | tBuOCO— | 3-furyl | EtOCOO— |
| 1841 | tBuOCO— | 3-thienyl | EtOCOO— |
| 1855 | tBuOCO— | cyclobutyl | EtOCOO— |
| 1999 | tBuOCO— | isobutenyl | MeOCOO— |
| 2002 | tBuOCO— | 2-pyridyl | MeOCOO— |
| 2011 | tBuOCO— | 3-pyridyl | MeOCOO— |
| 2020 | tBuOCO— | 4-pyridyl | MeOCOO— |
| 2032 | tBuOCO— | 3-furyl | MeOCOO— |
| 2044 | tBuOCO— | 2-thienyl | MeOCOO— |
| 2050 | tBuOCO— | 3-thienyl | MeOCOO— |
| 2062 | tBuOCO— | isopropyl | MeOCOO— |
| 2077 | tBuOCO— | cyclobutyl | MeOCOO— |
| 2666 | tBuOCO— | 2-furyl | MeOCOO— |
| 2972 | PhCO— | 2-thienyl | EtOCOO— |
| 2988 | EtOCO— | 2-thienyl | EtOCOO— |
| 2999 | iPrOCO— | 2-htienyl | EtOCOO— |
| 3003 | iBuOCO— | 2-thienyl | EtOCOO— |
| 3011 | 2-FuCO— | 2-thienyl | EtOCOO— |
| 3020 | 2-ThCO— | 2-thienyl | EtOCOO— |
| 3033 | $C_4H_7CO$— | 2-thienyl | EtOCOO— |
| 3155 | nPrCO— | 2-thienyl | EtOCOO— |
| 3181 | iBuOCO— | 2-furyl | EtOCOO— |
| 3243 | $tC_3H_5CO$— | 2-thienyl | EtOCOO— |
| 3300 | 3-PyCO— | 2-thienyl | EtOCOO— |
| 3393 | 4-PyCO— | 2-thienyl | EtOCOO— |
| 3433 | 2-PyCO— | 2-thienyl | EtOCOO— |
| 3911 | 2-FuCO— | 2-furyl | EtOCOO— |
| 3929 | nPrCO— | 2-furyl | EtOCOO— |
| 3963 | iPrOCO— | 2-furyl | EtOCOO— |
| 4000 | $tC_3H_5CO$— | 2-furyl | EtOCOO— |
| 4020 | EtOCO— | 2-furyl | EtOCOO— |
| 4074 | $C_4H_7CO$— | 2-furyl | EtOCOO— |
| 4088 | 2-ThCO— | 2-furyl | EtOCOO— |
| 40980 | PhCO— | 2-furyl | EtOCOO— |
| 4374 | ibueCO— | 2-thienyl | EtOCOO— |
| 4636 | iBuOCO— | 3-furyl | EtOCOO— |
| 6466 | iPrCO— | 2-furyl | EtOCOO— |
| 4959 | $tC_3H_5CO$— | 3-furyl | EtOCOO— |
| 4924 | iBuOCO— | 3-thienyl | EtOCOO— |
| 4844 | iBuOCO— | cpro | EtOCOO— |
| 5171 | tBuOCO— | cpro | EtOCOO— |
| 5155 | iBuOCO— | isobutenyl | EtOCOO— |
| 1788 | tBuOCO— | isobutenyl | EtOCOO— |
| 1767 | tBuOCO— | isopropyl | EtOCOO— |
| 1771 | tBuOCO— | phenyl | EtOCOO— |
| 1866 | tBuOCO— | p-nitrobenyl | EtOCOO— |
| 2060 | tBuOCO— | isopropyl | MeOCOO— |
| 2092 | tBuOCO— | phenyl | MeOCOO— |
| 2088 | tBuOCO— | p-nitrophenyl | MeOCOO— |

EXAMPLE 28

Additional Taxanes having C-10 Carbonate and C-7 Hydroxy Substituents

Following the processes described in Example 26 and elsewhere herein, the following specific taxanes having structural formula (19) may be prepared, wherein $R_{10}$ is as previously defined including wherein $R_{10}$ is $R_aOCOO$— and $R_a$ is (i) substituted or unsubstituted $C_1$ to $C_8$ alkyl such as methyl, ethyl, or straight, branched or cyclic propyl, butyl, pentyl, or hexyl; (ii) substituted or unsubstituted $C_3$ to $C_8$ alkenyl such as propenyl or straight, branched or cyclic butenyl, pentenyl or hexenyl; (iii) substituted or unsubstituted $C_3$ to $C_8$ alkynyl such as propynyl or straight or branched butynyl, pentynyl, or hexynyl; (iv) substituted or unsubstituted phenyl, or (v) substituted or unsubstituted heteroaromatic such as pyridyl. The substituents may be those identified elsewhere herein for substituted hydrocarbyl. For example, $R_{10}$ may be $R_{10a}OCOO$— wherein $R_{10a}$ is methyl, ethyl, or straight, branched or cyclic propyl.

(19)

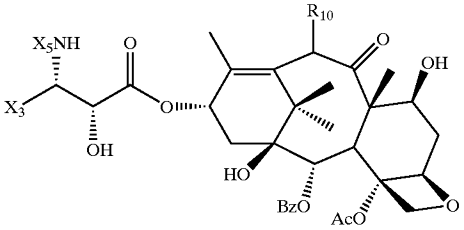

| $X_5$ | $X_3$ | $R_{10}$ |
|---|---|---|
| tBuOCO | 2-furyl | $R_{10a}OCOO$— |
| tBuOCO | 3-furyl | $R_{10a}OCOO$— |
| tBuOCO | 2-thienyl | $R_{10a}OCOO$— |
| tBuOCO | 3-thienyl | $R_{10a}OCOO$— |
| tBuOCO | 2-pyridyl | $R_{10a}OCOO$— |
| tBuOCO | 3-pyridyl | $R_{10a}OCOO$— |
| tBuOCO | 4-pyridyl | $R_{10a}OCOO$— |
| tBuOCO | isobutenyl | $R_{10a}OCOO$— |
| tBuOCO | isopropyl | $R_{10a}OCOO$— |
| tBuOCO | cyclopropyl | $R_{10a}OCOO$— |
| tBuOCO | cyclobutyl | $R_{10a}OCOO$— |
| tBuOCO | cyclopentyl | $R_{10a}OCOO$— |
| tBuOCO | phenyl | $R_{10a}OCOO$— |
| benzoyl | 2-furyl | $R_{10a}OCOO$— |
| benzoyl | 3-furyl | $R_{10a}OCOO$— |
| benzoyl | 2-thienyl | $R_{10a}OCOO$— |
| benzoyl | 3-thienyl | $R_{10a}OCOO$— |
| benzoyl | 2-pyridyl | $R_{10a}OCOO$— |
| benzoyl | 3-pyridyl | $R_{10a}OCOO$— |
| benzoyl | 4-pyridyl | $R_{10a}OCOO$— |
| benzoyl | isobutenyl | $R_{10a}OCOO$— |
| benzoyl | isopropyl | $R_{10a}OCOO$— |
| benzoyl | cyclopropyl | $R_{10a}OCOO$— |
| benzoyl | cyclobutyl | $R_{10a}OCOO$— |
| benzoyl | cyclopentyl | $R_{10a}OCOO$— |
| benzoyl | phenyl | $R_{10a}OCOO$— |
| 2-FuCO— | 2-furyl | $R_{10a}OCOO$— |
| 2-FuCO— | 3-furyl | $R_{10a}OCOO$— |
| 2-FuCO— | 2-thienyl | $R_{10a}OCOO$— |
| 2-FuCO— | 3-thienyl | $R_{10a}OCOO$— |
| 2-FuCO— | 2-pyridyl | $R_{10a}OCOO$— |
| 2-FuCO— | 3-pyridyl | $R_{10a}OCOO$— |
| 2-FuCO— | 4-pyridyl | $R_{10a}OCOO$— |
| 2-FuCO— | isobutenyl | $R_{10a}OCOO$— |
| 2-FuCO— | isopropyl | $R_{10a}OCOO$— |
| 2-FuCO— | cyclopropyl | $R_{10a}OCOO$— |
| 2-FuCO— | cyclobutyl | $R_{10a}OCOO$— |
| 2-FuCO— | cyclopentyl | $R_{10a}OCOO$— |
| 2-FuCO— | phenyl | $R_{10a}OCOO$— |
| 2-ThCO— | 2-furyl | $R_{10a}OCOO$— |
| 2-ThCO— | 3-furyl | $R_{10a}OCOO$— |
| 2-ThCO— | 2-thienyl | $R_{10a}OCOO$— |
| 2-ThCO— | 3-thienyl | $R_{10a}OCOO$— |
| 2-ThCO— | 2-pyridyl | $R_{10a}OCOO$— |
| 2-ThCO— | 3-pyridyl | $R_{10a}OCOO$— |
| 2-ThCO— | 4-pyridyl | $R_{10a}OCOO$— |

-continued (19)

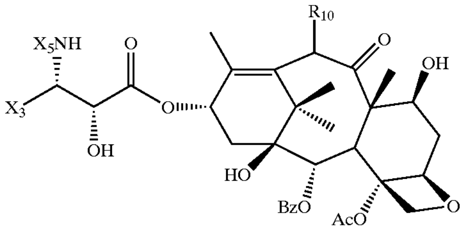

| $X_5$ | $X_3$ | $R_{10}$ |
|---|---|---|
| 2-ThCO— | isobutenyl | $R_{10a}$OCOO— |
| 2-ThCO— | isopropyl | $R_{10a}$OCOO— |
| 2-ThCO— | cyclopropyl | $R_{10a}$OCOO— |
| 2-ThCO— | cyclobutyl | $R_{10a}$OCOO— |
| 2-ThCO— | cyclopentyl | $R_{10a}$OCOO— |
| 2-ThCO— | phenyl | $R_{10a}$OCOO— |
| 2-PyCO— | 2-furyl | $R_{10a}$OCOO— |
| 2-PyCO— | 3-furyl | $R_{10a}$OCOO— |
| 2-PyCO— | 2-thienyl | $R_{10a}$OCOO— |
| 2-PyCO— | 3-thienyl | $R_{10a}$OCOO— |
| 2-PyCO— | 2-pyridyl | $R_{10a}$OCOO— |
| 2-PyCO— | 3-pyridyl | $R_{10a}$OCOO— |
| 2-PyCO— | 4-pyridyl | $R_{10a}$OCOO— |
| 2-PyCO— | isobutenyl | $R_{10a}$OCOO— |
| 2-PyCO— | isopropyl | $R_{10a}$OCOO— |
| 2-PyCO— | cyclopropyl | $R_{10a}$OCOO— |
| 2-PyCO— | cyclobutyl | $R_{10a}$OCOO— |
| 2-PyCO— | cyclopentyl | $R_{10a}$OCOO— |
| 2-PyCO— | phenyl | $R_{10a}$OCOO— |
| 3PyCO— | 2-furyl | $R_{10a}$OCOO— |
| 3-PyCO— | 3-furyl | $R_{10a}$OCOO— |
| 3-PyCO— | 2-thienyl | $R_{10a}$OCOO— |
| 3-PyCO— | 3-thienyl | $R_{10a}$OCOO— |
| 3-PyCO— | 2-pyridyl | $R_{10a}$OCOO— |
| 3-PyCO— | 3-pyridyl | $R_{10a}$OCOO— |
| 3-PyCO— | 4-pyridyl | $R_{10a}$OCOO— |
| 3-PyCO— | isobutenyl | $R_{10a}$OCOO— |
| 3-PyCO— | isopropyl | $R_{10a}$OCOO— |
| 3-PyCO— | cyclopropyl | $R_{10a}$OCOO— |
| 3-PyCO— | cyclobutyl | $R_{10a}$OCOO— |
| 3-PyCO— | cyclopentyl | $R_{10a}$OCOO— |
| 3-PyCO— | phenyl | $R_{10a}$OCOO— |
| 4-PyCO— | 2-furyl | $R_{10a}$OCOO— |
| 4-PyCO— | 3-furyl | $R_{10a}$OCOO— |
| 4-PyCO— | 2-thienyl | $R_{10a}$OCOO— |
| 4-PyCO— | 3-thienyl | $R_{10a}$OCOO— |
| 4-PyCO— | 2-pyridyl | $R_{10a}$OCOO— |
| 4-PyCO— | 3-pyridyl | $R_{10a}$OCOO— |
| 4-PyCO— | 4-pyridyl | $R_{10a}$OCOO— |
| 4-PyCO— | isobutenyl | $R_{10a}$OCOO— |
| 4-PyCO— | isopropyl | $R_{10a}$OCOO— |
| 4-PyCO— | cyclopropyl | $R_{10a}$OCOO— |
| 4-PyCO— | cyclobutyl | $R_{10a}$OCOO— |
| 4-PyCO— | cyclopentyl | $R_{10a}$OCOO— |
| 4-PyCO— | phenyl | $R_{10a}$OCOO— |
| $C_4H_7$CO— | 2-furyl | $R_{10a}$OCOO— |
| $C_4H_7$CO— | 3-furyl | $R_{10a}$OCOO— |
| $C_4H_7$CO— | 2-thienyl | $R_{10a}$OCOO— |
| $C_4H_7$CO— | 3-thienyl | $R_{10a}$OCOO— |
| $C_4H_7$CO— | 2-pyridyl | $R_{10a}$OCOO— |
| $C_4H_7$CO— | 3-pyridyl | $R_{10a}$OCOO— |
| $C_4H_7$CO— | 4-pyridyl | $R_{10a}$OCOO— |
| $C_4H_7$CO— | isobutenyl | $R_{10a}$OCOO— |
| $C_4H_7$CO— | isopropyl | $R_{10a}$OCOO— |
| $C_4H_7$CO— | cyclopropyl | $R_{10a}$OCOO— |
| $C_4H_7$CO— | cyclobutyl | $R_{10a}$OCOO— |
| $C_4H_7$CO— | cyclopentyl | $R_{10a}$OCOO— |
| $C_4H_7$CO— | phenyl | $R_{10a}$OCOO— |
| EtOCO— | 2-furyl | $R_{10a}$OCOO— |
| EtOCO— | 3-furyl | $R_{10a}$OCOO— |
| EtOCO— | 2-thienyl | $R_{10a}$OCOO— |
| EtOCO— | 3-thienyl | $R_{10a}$OCOO— |
| EtOCO— | 2-pyridyl | $R_{10a}$OCOO— |
| EtOCO— | 3-pyridyl | $R_{10a}$OCOO— |

-continued (19)

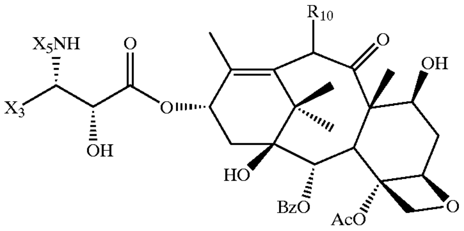

| $X_5$ | $X_3$ | $R_{10}$ |
|---|---|---|
| EtOCO— | 4-pyridyl | $R_{10a}$OCOO— |
| EtOCO— | isobutenyl | $R_{10a}$OCOO— |
| EtOCO— | isopropyl | $R_{10a}$OCOO— |
| EtOCO— | cyclopropyl | $R_{10a}$OCOO— |
| EtOCO— | cyclobutyl | $R_{10a}$OCOO— |
| EtOCO— | cyclopentyl | $R_{10a}$OCOO— |
| EtOCO— | phenyl | $R_{10a}$OCOO— |
| ibueCO— | 2-furyl | $R_{10a}$OCOO— |
| ibueCO— | 3-furyl | $R_{10a}$OCOO— |
| ibueCO— | 2-thienyl | $R_{10a}$OCOO— |
| ibueCO— | 3-thienyl | $R_{10a}$OCOO— |
| ibueCO— | 2-pyridyl | $R_{10a}$OCOO— |
| ibueCO— | 3-pyridyl | $R_{10a}$OCOO— |
| ibueCO— | 4-pyridyl | $R_{10a}$OCOO— |
| ibueCO— | isobutenyl | $R_{10a}$OCOO— |
| ibueCO— | isopropyl | $R_{10a}$OCOO— |
| ibueCO— | cyclopropyl | $R_{10a}$OCOO— |
| ibueCO— | cyclobutyl | $R_{10a}$OCOO— |
| ibueCO— | cyclopentyl | $R_{10a}$OCOO— |
| ibueCO— | phenyl | $R_{10a}$OCOO— |
| iBuCO— | 2-furyl | $R_{10a}$OCOO— |
| iBuCO— | 3-furyl | $R_{10a}$OCOO— |
| iBuCO— | 2-thienyl | $R_{10a}$OCOO— |
| iBuCO— | 3-thienyl | $R_{10a}$OCOO— |
| iBuCO— | 2-pyridyl | $R_{10a}$OCOO— |
| iBuCO— | 3-pyridyl | $R_{10a}$OCOO— |
| iBuCO— | 4-pyridyl | $R_{10a}$OCOO— |
| iBuCO— | isobutenyl | $R_{10a}$OCOO— |
| iBuCO— | isopropyl | $R_{10a}$OCOO— |
| iBuCO— | cyclopropyl | $R_{10a}$OCOO— |
| iBuCO— | cyclobutyl | $R_{10a}$OCOO— |
| iBuCO— | cyclopentyl | $R_{10a}$OCOO— |
| iBuCO— | phenyl | $R_{10a}$OCOO— |
| iBuOCO— | 2-furyl | $R_{10a}$OCOO— |
| iBuOCO— | 3-furyl | $R_{10a}$OCOO— |
| iBuOCO— | 2-thienyl | $R_{10a}$OCOO— |
| iBuOCO— | 3-thienyl | $R_{10a}$OCOO— |
| iBuOCO— | 2-pyridyl | $R_{10a}$OCOO— |
| iBuOCO— | 3-pyridyl | $R_{10a}$OCOO— |
| iBuOCO— | 4-pyridyl | $R_{10a}$OCOO— |
| iBuOCO— | isobutenyl | $R_{10a}$OCOO— |
| iBuOCO— | isopropyl | $R_{10a}$OCOO— |
| iBuOCO— | cyclopropyl | $R_{10a}$OCOO— |
| iBuOCO— | cyclobutyl | $R_{10a}$OCOO— |
| iBuOCO— | cyclopentyl | $R_{10a}$OCOO— |
| iBuOCO— | phenyl | $R_{10a}$OCOO— |
| iPrOCO— | 2-furyl | $R_{10a}$OCOO— |
| iPrOCO— | 3-furyl | $R_{10a}$OCOO— |
| iPrOCO— | 2-thienyl | $R_{10a}$OCOO— |
| iPrOCO— | 3-thienyl | $R_{10a}$OCOO— |
| iPrOCO— | 2-pyridyl | $R_{10a}$OCOO— |
| iPrOCO— | 3-pyridyl | $R_{10a}$OCOO— |
| iPrOCO— | 4-pyridyl | $R_{10a}$OCOO— |
| iPrOCO— | isobutenyl | $R_{10a}$OCOO— |
| iPrOCO— | isopropyl | $R_{10a}$OCOO— |
| iPrOCO— | cyclopropyl | $R_{10a}$OCOO— |
| iPrOCO— | cyclobutyl | $R_{10a}$OCOO— |
| iPrOCO— | cyclopentyl | $R_{10a}$OCOO— |
| iPrOCO— | phenyl | $R_{10a}$OCOO— |
| nPrOCO— | 2-furyl | $R_{10a}$OCOO— |
| nPrOCO— | 3-furyl | $R_{10a}$OCOO— |
| nPrOCO— | 2-thienyl | $R_{10a}$OCOO— |
| nPrOCO— | 3-thienyl | $R_{10a}$OCOO— |
| nPrOCO— | 2-pyridyl | $R_{10a}$OCOO— |

-continued (19)

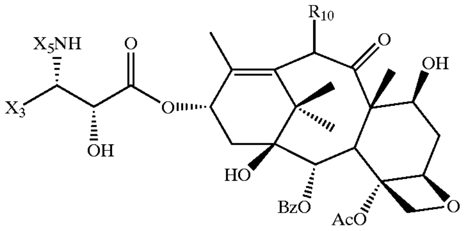

| $X_5$ | $X_3$ | $R_{10}$ |
|---|---|---|
| nPrOCO— | 3-pyridyl | $R_{10a}$OCOO— |
| nPrOCO— | 4-pyridyl | $R_{10a}$OCOO— |
| nPrOCO— | isobutenyl | $R_{10a}$OCOO— |
| nPrOCO— | isopropyl | $R_{10a}$OCOO— |
| nPrOCO— | cyclopropyl | $R_{10a}$OCOO— |
| nPrOCO— | cyclobutyl | $R_{10a}$OCOO— |
| nPrOCO— | cyclopentyl | $R_{10a}$OCOO— |
| nPrOCO— | phenyl | $R_{10a}$OCOO— |
| nPrCO— | 2-furyl | $R_{10a}$OCOO— |
| nPrCO— | 3-furyl | $R_{10a}$OCOO— |
| nPrCO— | 2-thienyl | $R_{10a}$OCOO— |
| nPrCO— | 3-thienyl | $R_{10a}$OCOO— |
| nPrCO— | 2-pyridyl | $R_{10a}$OCOO— |
| nPrCO— | 3-pyridyl | $R_{10a}$OCOO— |
| nPrCO— | 4-pyridyl | $R_{10a}$OCOO— |
| nPrCO— | isobutenyl | $R_{10a}$OCOO— |
| nPrCO— | isopropyl | $R_{10a}$OCOO— |
| nPrCO— | cyclopropyl | $R_{10a}$OCOO— |
| nPrCO— | cyclobutyl | $R_{10a}$OCOO— |
| nPrCO— | cyclopentyl | $R_{10}$OCOO— |
| nPrCO— | phenyl | $R_{10a}$OCOO— |
| tBuOCO | cyclopentyl | EtOCOO— |
| benzoyl | 3-furyl | EtOCOO— |
| benzoyl | 3-thienyl | EtOCOO— |
| benzoyl | 2-pyridyl | EtOCOO— |
| benzoyl | 3-pyridyl | EtOCOO— |
| benzoyl | 4-pyridyl | EtOCOO— |
| benzoyl | isobutenyl | EtOCOO— |
| benzoyl | isopropyl | EtOCOO— |
| benzoyl | cyclopropyl | EtOCOO— |
| benzoyl | cyclobutyl | EtOCOO— |
| benzoyl | cyclopentyl | EtOCOO— |
| benzoyl | phenyl | EtOCOO— |
| 2-FuCO— | 3-furyl | EtOCOO— |
| 2-FuCO— | 3-thienyl | EtOCOO— |
| 2-FuCO— | 2-pyridyl | EtOCOO— |
| 2-FuCO— | 3-pyridyl | EtOCOO— |
| 2-FuCO— | 4-pyridyl | EtOCOO— |
| 2-FuCO— | isobutenyl | EtOCOO— |
| 2-FuCO— | isopropyl | EtOCOO— |
| 2-FuCO— | cyclopropyl | EtOCOO— |
| 2-FuCO— | cyclobutyl | EtOCOO— |
| 2-FuCO— | cyclopentyl | EtOCOO— |
| 2-FuCO— | phenyl | EtOCOO— |
| 2-ThCO— | 3-furyl | EtOCOO— |
| 2-ThCO— | 3-thienyl | EtOCOO— |
| 2-ThCO— | 2-pyridyl | EtOCOO— |
| 2-ThCO— | 3-pyridyl | EtOCOO— |
| 2-ThCO— | 4-pyridyl | EtOCOO— |
| 2-ThCO— | isobutenyl | EtOCOO— |
| 2-ThCO— | isopropyl | EtOCOO— |
| 2-ThCO— | cyclopropyl | EtOCOO— |
| 2-ThCO— | cyclobutyl | EtOCOO— |
| 2-ThCO— | cyclopentyl | EtOCOO— |
| 2-ThCO— | phenyl | EtOCOO— |
| 2-PyCO— | 2-furyl | EtOCOO— |
| 2-PyCO— | 3-furyl | EtOCOO— |
| 2-PyCO— | 3-thienyl | EtOCOO— |
| 2-PyCO— | 2-pyridyl | EtOCOO— |
| 2-PyCO— | 3-pyridyl | EtOCOO— |
| 2-PyCO— | 4-pyridyl | EtOCOO— |
| 2-PyCO— | isobutenyl | EtOCOO— |
| 2-PyCO— | isopropyl | EtOCOO— |
| 2-PyCO— | cyclopropyl | EtOCOO— |

-continued (19)

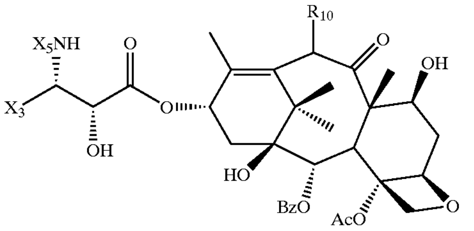

| $X_5$ | $X_3$ | $R_{10}$ |
|---|---|---|
| 2-PyCO— | cyclobutyl | EtOCOO— |
| 2-PyCO— | cyclopentyl | EtOCOO— |
| 2-PyCO— | phenyl | EtOCOO— |
| 3PyCO— | 2-furyl | EtOCOO— |
| 3-PyCO— | 3-furyl | EtOCOO— |
| 3-PyCO— | 3-thienyl | EtOCOO— |
| 3-PyCO— | 2-pyridyl | EtOCOO— |
| 3-PyCO— | 3-pyridyl | EtOCOO— |
| 3-PyCO— | 4-pyridyl | EtOCOO— |
| 3-PyCO— | isobutenyl | EtOCOO— |
| 3-PyCO— | isopropyl | EtOCOO— |
| 3-PyCO— | cyclopropyl | EtOCOO— |
| 3-PyCO— | cyclobutyl | EtOCOO— |
| 3-PyCO— | cyclopentyl | EtOCOO— |
| 3-PyCO— | phenyl | EtOCOO— |
| 4-PyCO— | 2-furyl | EtOCOO— |
| 4-PyCO— | 3-furyl | EtOCOO— |
| 4-PyCO— | 3-thienyl | EtOCOO— |
| 4-PyCO— | 2-pyridyl | EtOCOO— |
| 4-PyCO— | 3-pyridyl | EtOCOO— |
| 4-PyCO— | 4-pyridyl | EtOCOO— |
| 4-PyCO— | isobutenyl | EtOCOO— |
| 4-PyCO— | isopropyl | EtOCOO— |
| 4-PyCO— | cyclopropyl | EtOCOO— |
| 4-PyCO— | cyclobutyl | EtOCOO— |
| 4-PyCO— | cyclopentyl | EtOCOO— |
| 4-PyCO— | phenyl | EtOCOO— |
| $C_4H_7$CO— | 3-furyl | EtOCOO— |
| $C_4H_7$CO— | 3-thienyl | EtOCOO— |
| $C_4H_7$CO— | 2-pyridyl | EtOCOO— |
| $C_4H_7$CO— | 3-pyridyl | EtOCOO— |
| $C_4H_7$CO— | 4-pyridyl | EtOCOO— |
| $C_4H_7$CO— | isobutenyl | EtOCOO— |
| $C_4H_7$CO— | isopropyl | EtOCOO— |
| $C_4H_7$CO— | cyclopropyl | EtOCOO— |
| $C_4H_7$CO— | cyclobutyl | EtOCOO— |
| $C_4H_7$CO— | cyclopentyl | EtOCOO— |
| $C_4H_7$CO— | phenyl | EtOCOO— |
| EtOCO— | 3-furyl | EtOCOO— |
| EtOCO— | 3-thienyl | EtOCOO— |
| EtOCO— | 2-pyridyl | EtOCOO— |
| EtOCO— | 3-pyridyl | EtOCOO— |
| EtOCO— | 4-pyridyl | EtOCOO— |
| EtOCO— | isobutenyl | EtOCOO— |
| EtOCO— | isopropyl | EtOCOO— |
| EtOCO— | cyclopropyl | EtOCOO— |
| EtOCO— | cyclobutyl | EtOCOO— |
| EtOCO— | cyclopentyl | EtOCOO— |
| EtOCO— | phenyl | EtOCOO— |
| ibueCO— | 2-furyl | EtOCOO— |
| ibueCO— | 3-furyl | EtOCOO— |
| ibueCO— | 2-thienyl | EtOCOO— |
| ibueCO— | 3-thienyl | EtOCOO— |
| ibueCO— | 2-pyridyl | EtOCOO— |
| ibueCO— | 3-pyridyl | EtOCOO— |
| ibueCO— | 4-pyridyl | EtOCOO— |
| ibueCO— | isobutenyl | EtOCOO— |
| ibueCO— | isopropyl | EtOCOO— |
| ibueCO— | cyclopeopyl | EtOCOO— |
| ibueCO— | cyclobutyl | EtOCOO— |
| ibueCO— | cyclopentyl | EtOCOO— |
| ibueCO— | phenyl | EtOCOO— |
| iBuCO— | 2-furyl | EtOCOO— |
| iBuCO— | 3-furyl | EtOCOO— |

-continued (19)

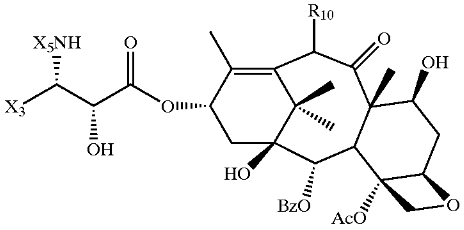

| $X_5$ | $X_3$ | $R_{10}$ |
|---|---|---|
| iBuCO— | 2-thienyl | EtOCOO— |
| iBuCO— | 3-thienyl | EtOCOO— |
| iBuCO— | 2-pyridyl | EtOCOO— |
| iBuCO— | 3-pyridyl | EtOCOO— |
| iBuCO— | 4-pyridyl | EtOCOO— |
| iBuCO— | isobutenyl | EtOCOO— |
| iBuCO— | isopropyl | EtOCOO— |
| iBuCO— | cyclopropyl | EtOCOO— |
| iBuCO— | cyclobutyl | EtOCOO— |
| iBuCO— | cyclopentyl | EtOCOO— |
| iBuCO— | phenyl | EtOCOO— |
| iBuOCO— | 2-pyridyl | EtOCOO— |
| iBuOCO— | 3-pyridyl | EtOCOO— |
| iBuOCO— | 4-pyridyl | EtOCOO— |
| iBuOCO— | isopropyl | EtOCOO— |
| iBuOCO— | cyclobutyl | EtOCOO— |
| iBuOCO— | cyclopentyl | EtOCOO— |
| iBuOCO— | phenyl | EtOCOO— |
| iPrOCO— | 3-furyl | EtOCOO— |
| iPrOCO— | 3-thienyl | EtOCOO— |
| iPrOCO— | 2-pyridyl | EtOCOO— |
| iPrOCO— | 3-pyridyl | EtOCOO— |
| iPrOCO— | 4-pyridyl | EtOCOO— |
| iPrOCO— | isobutenyl | EtOCOO— |
| iPrOCO— | isopropyl | EtOCOO— |
| iPrOCO— | cyclopropyl | EtOCOO— |
| iPrOCO— | cyclobutyl | EtOCOO— |
| iPrOCO— | cyclopentyl | EtOCOO— |
| iPrOCO— | phenyl | EtOCOO— |
| nPrOCO— | 2-furyl | EtOCOO— |
| nPrOCO— | 3-furyl | EtOCOO— |
| nPrOCO— | 2-thienyl | EtOCOO— |
| nPrOCO— | 3-thienyl | EtOCOO— |
| nPrOCO— | 2-pyridyl | EtOCOO— |
| nPrOCO— | 3-pyridyl | EtOCOO— |
| nPrOCO— | 4-pyridyl | EtOCOO— |
| nPrOCO— | isobutenyl | EtOCOO— |
| nPrOCO— | isopropyl | EtOCOO— |
| nPrOCO— | cyclopropyl | EtOCOO— |
| nPrOCO— | cyclobutyl | EtOCOO— |
| nPrOCO— | cyclopentyl | EtOCOO— |
| nPrOCO— | phenyl | EtOCOO— |
| nPrCO— | 3-furyl | EtOCOO— |
| nPrCO— | 3-thienyl | EtOCOO— |
| nPrCO— | 2-pyridyl | EtOCOO— |
| nPrCO— | 3-pyridyl | EtOCOO— |
| nPrCO— | 4-pyridyl | EtOCOO— |
| nPrCO— | isobutenyl | EtOCOO— |
| nPrCO— | isopropyl | EtOCOO— |
| nPrCO— | cyclopropyl | EtOCOO— |
| nPrCO— | cyclobutyl | EtOCOO— |
| nPrCO— | cyclopentyl | EtOCOO— |
| nPrCO— | phenyl | EtOCOO— |
| tBuOCO | cyclopropyl | MeOCOO— |
| tBuOCO | cyclopentyl | MeOCOO— |
| benzoyl | 2-furyl | MeOCOO— |
| benzoyl | 3-furyl | MeOCOO— |
| benzoyl | 2-thienyl | MeOCOO— |
| benzoyl | 3-thienyl | MeOCOO— |
| benzoyl | 2-pyridyl | MeOCOO— |
| benzoyl | 3-pyridyl | MeOCOO— |
| benzoyl | 4-pyridyl | MeOCOO— |
| benzoyl | isobutenyl | MeOCOO— |
| benzoyl | isopropyl | MeOCOO— |

-continued (19)

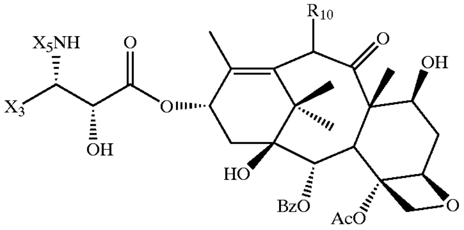

| $X_5$ | $X_3$ | $R_{10}$ |
|---|---|---|
| benzoyl | cyclopropyl | MeOCOO— |
| benzoyl | cyclobutyl | MeOCOO— |
| benzoyl | cyclopentyl | MeOCOO— |
| benzoyl | phenyl | MeOCOO— |
| 2-FuCO— | 2-furyl | MeOCOO— |
| 2-FuCO— | 3-furyl | MeOCOO— |
| 2-FuCO— | 2-thienyl | MeOCOO— |
| 2-FuCO— | 3-thienyl | MeOCOO— |
| 2-FuCO— | 2-pyridyl | MeOCOO— |
| 2-FuCO— | 3-pyridyl | MeOCOO— |
| 2-FuCO— | 4-pyridyl | MeOCOO— |
| 2-FuCO— | isobutenyl | MeOCOO— |
| 2-FuCO— | isopropyl | MeOCOO— |
| 2-FuCO— | cyclopropyl | MeOCOO— |
| 2-FuCO— | cyclobutyl | MeOCOO— |
| 2-FuCO— | cyclopentyl | MeOCOO— |
| 2-FuCO— | phenyl | MeOCOO— |
| 2-ThCO— | 2-furyl | MeOCOO— |
| 2-ThCO— | 3-furyl | MeOCOO— |
| 2-ThCO— | 2-thienyl | MeOCOO— |
| 2-ThCO— | 3-thienyl | MeOCOO— |
| 2-ThCO— | 2-pyridyl | MeOCOO— |
| 2-ThCO— | 3-pyridyl | MeOCOO— |
| 2-ThCO— | 4-pyridyl | MeOCOO— |
| 2-ThCO— | isobutenyl | MeOCOO— |
| 2-ThCO— | isopropyl | MeOCOO— |
| 2-ThCO— | cyclopropyl | MeOCOO— |
| 2-ThCO— | cyclobutyl | MeOCOO— |
| 2-ThCO— | cyclopentyl | MeOCOO— |
| 2-ThCO— | phenyl | MeOCOO— |
| 2-PyCO— | 2-furyl | MeOCOO— |
| 2-PyCO— | 3-furyl | MeOCOO— |
| 2-PyCO— | 2-thienyl | MeOCOO— |
| 2-PyCO— | 3-thienyl | MeOCOO— |
| 2-PyCO— | 2-pyridyl | MeOCOO— |
| 2-PyCO— | 3-pyridyl | MeOCOO— |
| 2-PyCO— | 4-pyridyl | MeOCOO— |
| 2-PyCO— | isobutenyl | MeOCOO— |
| 2-PyCO— | isopropyl | MeOCOO— |
| 2-PyCO— | cyclopropyl | MeOCOO— |
| 2-PyCO— | cyclobutyl | MeOCOO— |
| 2-PyCO— | cyclopentyl | MeOCOO— |
| 2-PyCO— | phenyl | MeOCOO— |
| 3PyCO— | 2-furyl | MeOCOO— |
| 3-PyCO— | 3-furyl | MeOCOO— |
| 3-PyCO— | 3-thienyl | MeOCOO— |
| 3-PyCO— | 2-pyridyl | MeOCOO— |
| 3-PyCO— | 3-pyridyl | MeOCOO— |
| 3-PyCO— | 4-pyridyl | MeOCOO— |
| 3-PyCO— | isobutenyl | MeOCOO— |
| 3-PyCO— | isopropyl | MeOCOO— |
| 3-PyCO— | cyclopropyl | MeOCOO— |
| 3-PyCO— | cyclobutyl | MeOCOO— |
| 3-PyCO— | cyclopentyl | MeOCOO— |
| 3-PyCO— | phenyl | MeOCOO— |
| 4-PyCO— | 2-furyl | MeOCOO— |
| 4-PyCO— | 3-furyl | MeOCOO— |
| 4-PyCO— | 2-thienyl | MeOCOO— |
| 4-PyCO— | 3-thienyl | MeOCOO— |
| 4-PyCO— | 2-pyridyl | MeOCOO— |
| 4-PyCO— | 3-pyridyl | MeOCOO— |
| 4-PyCO— | 4-pyridyl | MeOCOO— |
| 4-PyCO— | isobutenyl | MeOCOO— |
| 4-PyCO— | isopropyl | MeOCOO— |

-continued (19)

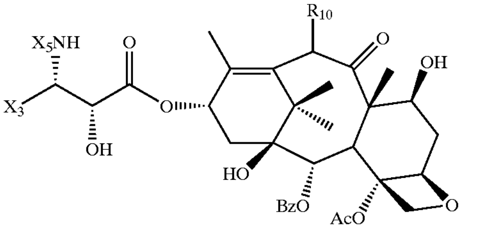

| $X_5$ | $X_3$ | $R_{10}$ |
|---|---|---|
| 4-PyCO— | cyclopropyl | MeOCOO— |
| 4-PyCO— | cyclobutyl | MeOCOO— |
| 4-PyCO— | cyclopentyl | MeOCOO— |
| 4-PyCO— | phenyl | MeOCOO— |
| $C_4H_7CO$— | 2-furyl | MeOCOO— |
| $C_4H_7CO$— | 3-furyl | MeOCOO— |
| $C_4H_7CO$— | 2-thienyl | MeOCOO— |
| $C_4H_7CO$— | 3-thienyl | MeOCOO— |
| $C_4H_7CO$— | 2-pyridyl | MeOCOO— |
| $C_4H_7CO$— | 3-pyridyl | MeOCOO— |
| $C_4H_7CO$— | 4-pyridyl | MeOCOO— |
| $C_4H_7CO$— | isobutenyl | MeOCOO— |
| $C_4H_7CO$— | isopropyl | MeOCOO— |
| $C_4H_7CO$— | cyclopropyl | MeOCOO— |
| $C_4H_7CO$— | cyclobutyl | MeOCOO— |
| $C_4H_7CO$— | cyclopentyl | MeOCOO— |
| $C_4H_7CO$— | phenyl | MeOCOO— |
| EtOCO— | 2-furyl | MeOCOO— |
| EtOCO— | 3-furyl | MeOCOO— |
| EtOCO— | 2-thienyl | MeOCOO— |
| EtOCO— | 3-thienyl | MeOCOO— |
| EtOCO— | 2-pyridyl | MeOCOO— |
| EtOCO— | 3-pyridyl | MeOCOO— |
| EtOCO— | 4-pyridyl | MeOCOO— |
| EtOCO— | isobutenyl | MeOCOO— |
| EtOCO— | isopropyl | MeOCOO— |
| EtOCO— | cyclopropyl | MeOCOO— |
| EtOCO— | cyclobutyl | MeOCOO— |
| EtOCO— | cyclopentyl | MeOCOO— |
| EtOCO— | phenyl | MeOCOO— |
| ibueCO— | 2-furyl | MeOCOO— |
| ibueCO— | 3-furyl | MeOCOO— |
| ibueCO— | 2-thienyl | MeOCOO— |
| ibueCO— | 3-thienyl | MeOCOO— |
| ibueCO— | 2-pyridyl | MeOCOO— |
| ibueCO— | 3-pyridyl | MeOCOO— |
| ibueCO— | 4-pyridyl | MeOCOO— |
| ibueCO— | isobutenyl | MeOCOO— |
| ibueCO— | isopropyl | MeOCOO— |
| ibueCO— | cyclopropyl | MeOCOO— |
| ibueCO— | cyclobutyl | MeOCOO— |
| ibueCO— | cyclopentyl | MeOCOO— |
| ibueCO— | phenyl | MeOCOO— |
| iBuCO— | 2-furyl | MeOCOO— |
| iBuCO— | 3-furyl | MeOCOO— |
| iBuCO— | 2-thienyl | MeOCOO— |
| iBuCO— | 3-thienyl | MeOCOO— |
| iBuCO— | 2-pyridyl | MeOCOO— |
| iBuCO— | 3-pyridyl | MeOCOO— |
| iBuCO— | 4-pyridyl | MeOCOO— |
| iBuCO— | isobutenyl | MeOCOO— |
| iBuCO— | isopropyl | MeOCOO— |
| iBuCO— | cyclopropyl | MeOCOO— |
| iBuCO— | cyclobutyl | MeOCOO— |
| iBuCO— | cyclopentyl | MeOCOO— |
| iBuCO— | phenyl | MeOCOO— |
| iBuOCO— | 2-furyl | MeOCOO— |
| iBuOCO— | 3-furyl | MeOCOO— |
| iBuOCO— | 2-thienyl | MeOCOO— |
| iBuOCO— | 3-thienyl | MeOCOO— |
| iBuOCO— | 2-pyridyl | MeOCOO— |
| iBuOCO— | 3-pyridyl | MeOCOO— |
| iBuOCO— | 4-pyridyl | MeOCOO— |
| iBuOCO— | isobutenyl | MeOCOO— |

-continued (19)

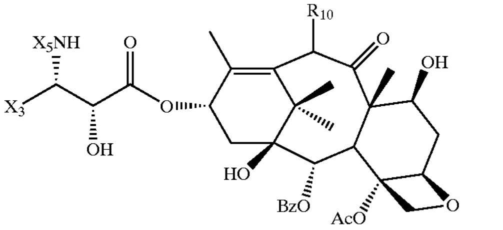

| $X_5$ | $X_3$ | $R_{10}$ |
|---|---|---|
| iBuOCO— | isopropyl | MeOCOO— |
| iBuOCO— | cyclopropyl | MeOCOO— |
| iBuOCO— | cyclobutyl | MeOCOO— |
| iBuOCO— | cyclopentyl | MeOCOO— |
| iBuOCO— | phenyl | MeOCOO— |
| iPrOCO— | 2-furyl | MeOCOO— |
| iPrOCO— | 3-furyl | MeOCOO— |
| iPrOCO— | 2-thienyl | MeOCOO— |
| iPrOCO— | 3-thienyl | MeOCOO— |
| iPrOCO— | 2-pyridyl | MeOCOO— |
| iPrOCO— | 3-pyridyl | MeOCOO— |
| iPrOCO— | 4-pyridyl | MeOCOO— |
| iPrOCO— | isobutenyl | MeOCOO— |
| iPrOCO— | isopropyl | MeOCOO— |
| iPrOCO— | cyclopropyl | MeOCOO— |
| iPrOCO— | cyclobutyl | MeOCOO— |
| iPrOCO— | cyclopentyl | MeOCOO— |
| iPrOCO— | phenyl | MeOCOO— |
| nPrOCO— | 2-furyl | MeOCOO— |
| nPrOCO— | 3-furyl | MeOCOO— |
| nPrOCO— | 2-thienyl | MeOCOO— |
| nPrOCO— | 3-thienyl | MeOCOO— |
| nPrOCO— | 2-pyridyl | MeOCOO— |
| nPrOCO— | 3-pyridyl | MeOCOO— |
| nPrOCO— | 4-pyridyl | MeOCOO— |
| nPrOCO— | isobutenyl | MeOCOO— |
| nPrOCO— | isopropyl | MeOCOO— |
| nPrOCO— | cyclopropyl | MeOCOO— |
| nPrOCO— | cyclobutyl | MeOCOO— |
| nPrOCO— | cyclopentyl | MeOCOO— |
| nPrOCO— | phenyl | MeOCOO— |
| nPrCO— | 2-furyl | MeOCOO— |
| nPrCO— | 3-furyl | MeOCOO— |
| nPrCO— | 2-thienyl | MeOCOO— |
| nPrCO— | 3-thienyl | MeOCOO— |
| nPrCO— | 2-pyridyl | MeOCOO— |
| nPrCO— | 3-pyridyl | MeOCOO— |
| nPrCO— | 4-pyridyl | MeOCOO— |
| nPrCO— | isobutenyl | MeOCOO— |
| nPrCO— | isopropyl | MeOCOO— |
| nPrCO— | cyclopropyl | MeOCOO— |
| nPrCO— | cyclobutyl | MeOCOO— |
| nPrCO— | cyclopentyl | MeOCOO— |
| nPrCO— | phenyl | MeOCOO— |

EXAMPLE 29

Additional Taxanes having C-10 Carbonate and C-7 Hydroxy Substituents

Following the processes described in Example 26 and elsewhere herein, the following specific taxanes having structural formula (20) may be prepared, wherein in each of the series (that is, each of series "A" through "K") $R_7$ is hydroxy and $R_{10}$ is as previously defined, including wherein $R_{10}$ is $R_{10a}$OCOO— and $R_{10a}$ is (i) substituted or unsubstituted, preferably unsubstituted, $C_2$ to $C_8$ alkyl (straight, branched or cyclic), such as ethyl, propyl, butyl, pentyl, or hexyl; (ii) substituted or unsubstituted, preferably unsubstituted, $C_2$ to $C_8$ alkenyl (straight, branched or cyclic), such as ethenyl, propenyl, butenyl, pentenyl or hexenyl; (iii) substituted or unsubstituted, preferably unsubstituted, $C_2$ to $C_8$ alkynyl (straight or branched) such as ethynyl, propynyl, butynyl, pentynyl, or hexynyl; (iv) substituted or unsubstituted, preferably unsubstituted, phenyl; or (v) substituted or unsubstituted, preferably unsubstituted, heteroaromatic such as furyl, thienyl, or pyridyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each of $X_3$, $X_5$, $R_2$, $R_9$ and $R_{10}$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(20)

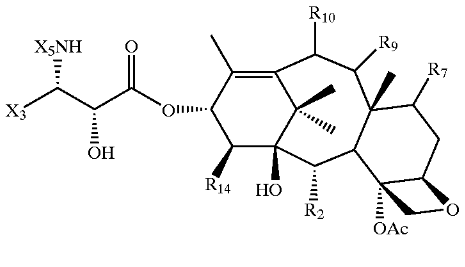

| Series | $X_5$ | $X_3$ | $R_{10}$ | $R_2$ | $R_9$ | $R_{14}$ |
|---|---|---|---|---|---|---|
| A1 | —$COOX_{10}$ | heterocyclo | $R_{10a}OCOO$— | $C_6H_5COO$— | O | H |
| A2 | —$COX_{10}$ | heterocyclo | $R_{10a}OCOO$— | $C_6H_5COO$— | O | H |
| A3 | —$CONHX_{10}$ | heterocyclo | $R_{10a}OCOO$— | $C_6H_5COO$— | O | H |

-continued (20)

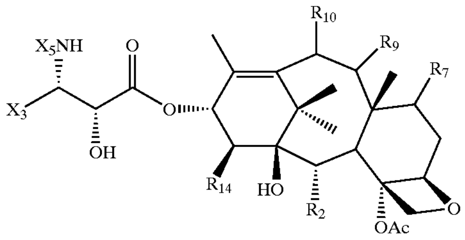

| Series | $X_5$ | $X_3$ | $R_{10}$ | $R_2$ | $R_9$ | $R_{14}$ |
|---|---|---|---|---|---|---|
| A4 | —$COOX_{10}$ | optionally substituted $C_2$ to $C_8$ alkyl | $R_{10a}OCOO$— | $C_6H_5COO$— | O | H |
| A5 | —$COX_{10}$ | optionally substituted $C_2$ to $C_8$ alkyl | $R_{10a}OCOO$— | $C_6H_5COO$— | O | H |
| A6 | —$CONHX_{10}$ | optionally substituted $C_2$ to $C_8$ alkyl | $R_{10a}OCOO$— | $C_6H_5COO$— | O | H |
| A7 | —$COOX_{10}$ | optionally substituted $C_2$ to $C_8$ alkenyl | $R_{10a}OCOO$— | $C_6H_5COO$— | O | H |
| A8 | —$COX_{10}$ | optionally substituted $C_2$ to $C_8$ alkenyl | $R_{10a}OCOO$— | $C_6H_5COO$— | O | H |
| A9 | —$CONHX_{10}$ | optionally substituted $C_2$ to $C_8$ alkenyl | $R_{10a}OCOO$— | $C_6H_5COO$— | O | H |
| A10 | —$COOX_{10}$ | optionally substituted $C_2$ to $C_8$ alkynyl | $R_{10a}OCOO$— | $C_6H_5COO$— | O | H |
| A11 | —$COX_{10}$ | optionally substituted $C_2$ to $C_8$ alkynyl | $R_{10a}OCOO$— | $C_6H_5COO$— | O | H |
| A12 | —$CONHX_{10}$ | optionally substituted $C_2$ to $C_8$ alkynyl | $R_{10a}OCOO$— | $C_6H_5COO$— | O | H |
| B1 | —$COOX_{10}$ | heterocyclo | $R_{10a}OCOO$— | $R_{2a}COO$— | O | H |
| B2 | —$COX_{10}$ | heterocyclo | $R_{10a}OCOO$— | $R_{2a}COO$— | O | H |
| B3 | —$CONHX_{10}$ | heterocyclo | $R_{10a}OCOO$— | $R_{2a}COO$— | O | H |
| B4 | —$COOX_{10}$ | optionally substituted $C_2$ to $C_8$ alkyl | $R_{10a}OCOO$— | $R_{2a}COO$— | O | H |
| B5 | —$COX_{10}$ | optionally substituted $C_2$ to $C_8$ alkyl | $R_{10a}OCOO$— | $R_{2a}COO$— | O | H |
| B6 | —$CONHX_{10}$ | optionally substituted $C_2$ to $C_8$ alkyl | $R_{10a}OCOO$— | $R_{2a}COO$— | O | H |
| B7 | —$COOX_{10}$ | optionally substituted $C_2$ to $C_8$ alkenyl | $R_{10a}OCOO$— | $R_{2a}COO$— | O | H |
| B8 | —$COX_{10}$ | optionally substituted $C_2$ to $C_8$ alkenyl | $R_{10a}OCOO$— | $R_{2a}COO$— | O | H |
| B9 | —$CONHX_{10}$ | optionally substituted $C_2$ to $C_8$ alkenyl | $R_{10a}OCOO$— | $R_{2a}COO$— | O | H |
| B10 | —$COOX_{10}$ | optionally substituted $C_2$ to $C_8$ alkynyl | $R_{10a}OCOO$— | $R_{2a}COO$— | O | H |
| B11 | —$COX_{10}$ | optionally substituted $C_2$ to $C_8$ alkynyl | $R_{10a}OCOO$— | $R_{2a}COO$— | O | H |
| B12 | —$CONHX_{10}$ | optionally substituted $C_2$ to $C_8$ alkynyl | $R_{10a}OCOO$— | $R_{2a}COO$— | O | H |
| C1 | —$COOX_{10}$ | heterocyclo | $R_{10a}OCOO$— | $C_6H_5COO$— | $R_{9a}COO$— | H |
| C2 | —$COX_{10}$ | heterocyclo | $R_{10a}OCOO$— | $C_6H_5COO$— | $R_{9a}COO$— | H |
| C3 | —$CONHX_{10}$ | heterocyclo | $R_{10a}OCOO$— | $C_6H_5COO$— | $R_{9a}COO$— | H |

-continued (20)

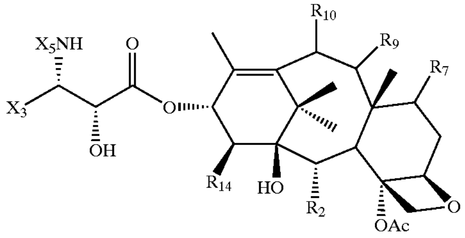

| Series | $X_5$ | $X_3$ | $R_{10}$ | $R_2$ | $R_9$ | $R_{14}$ |
|---|---|---|---|---|---|---|
| C4 | —$COOX_{10}$ | optionally substituted $C_2$ to $C_8$ alkyl | $R_{10a}OCOO$— | $C_6H_5COO$— | $R_{9a}COO$— | H |
| C5 | —$COX_{10}$ | optionally substituted $C_2$ to $C_8$ alkyl | $R_{10a}OCOO$— | $C_6H_5COO$— | $R_{9a}COO$— | H |
| C6 | —$CONHX_{10}$ | optionally substituted $C_2$ to $C_8$ alkyl | $R_{10a}OCOO$— | $C_6H_5COO$— | $R_{9a}COO$— | H |
| C7 | —$COOX_{10}$ | optionally substituted $C_2$ to $C_8$ alkenyl | $R_{10a}OCOO$— | $C_6H_5COO$— | $R_{9a}COO$— | H |
| C8 | —$COX_{10}$ | optionally substituted $C_2$ to $C_8$ alkenyl | $R_{10a}OCOO$— | $C_6H_5COO$— | $R_{9a}COO$— | H |
| C9 | —$CONHX_{10}$ | optionally substituted $C_2$ to $C_8$ alkenyl | $R_{10a}OCOO$— | $C_6H_5COO$— | $R_{9a}COO$— | H |
| C10 | —$COOX_{10}$ | optionally substituted $C_2$ to $C_8$ alkynyl | $R_{10a}OCOO$— | $C_6H_5COO$— | $R_{9a}COO$— | H |
| C11 | —$COX_{10}$ | optionally substituted $C_2$ to $C_8$ alkynyl | $R_{10a}OCOO$— | $C_6H_5COO$— | $R_{9a}COO$— | H |
| C12 | —$CONHX_{10}$ | optionally substituted $C_2$ to $C_8$ alkynyl | $R_{10a}OCOO$— | $C_6H_5COO$— | $R_{9a}COO$— | H |
| D1 | —$COOX_{10}$ | heterocyclo | $R_{10a}OCOO$— | $C_6H_5COO$— | OH | H |
| D2 | —$COX_{10}$ | heterocyclo | $R_{10a}OCOO$— | $C_6H_5COO$— | OH | H |
| D3 | —$CONHX_{10}$ | heterocyclo | $R_{10a}OCOO$— | $C_6H_5COO$— | OH | H |
| D4 | —$COOX_{10}$ | optionally substituted $C_2$ to $C_8$ alkyl | $R_{10a}OCOO$— | $C_6H_5COO$— | OH | H |
| D5 | —$COX_{10}$ | optionally substituted $C_2$ to $C_8$ alkyl | $R_{10a}OCOO$— | $C_6H_5COO$— | OH | H |
| D6 | —$CONHX_{10}$ | optionally substituted $C_2$ to $C_8$ alkyl | $R_{10a}OCOO$— | $C_6H_5COO$— | OH | H |
| D7 | —$COOX_{10}$ | optionally substituted $C_2$ to $C_8$ alkenyl | $R_{10a}OCOO$— | $C_6H_5COO$— | OH | H |
| D8 | —$COX_{10}$ | optionally substituted $C_2$ to $C_8$ alkenyl | $R_{10a}OCOO$— | $C_6H_5COO$— | OH | H |
| D9 | —$CONHX_{10}$ | optionally substituted $C_2$ to $C_8$ alkenyl | $R_{10a}OCOO$— | $C_6H_5COO$— | OH | H |
| D10 | —$COOX_{10}$ | optionally substituted $C_2$ to $C_8$ alkynyl | $R_{10a}OCOO$— | $C_6H_5COO$— | OH | H |
| D11 | —$COX_{10}$ | optionally substituted $C_2$ to $C_8$ alkynyl | $R_{10a}OCOO$— | $C_6H_5COO$— | OH | H |
| D12 | —$CONHX_{10}$ | optionally substituted $C_2$ to $C_8$ alkynyl | $R_{10a}OCOO$— | $C_6H_5COO$— | OH | H |
| E1 | —$COOX_{10}$ | heterocyclo | $R_{10a}OCOO$— | $C_6H_5COO$— | O | OH |
| E2 | —$COX_{10}$ | heterocyclo | $R_{10a}OCOO$— | $C_6H_5COO$— | O | OH |
| E3 | —$CONHX_{10}$ | heterocyclo | $R_{10a}OCOO$— | $C_6H_5COO$— | O | OH |

-continued (20)

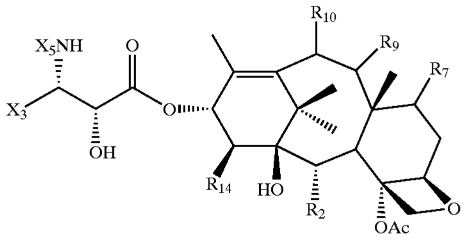

| Series | $X_5$ | $X_3$ | $R_{10}$ | $R_2$ | $R_9$ | $R_{14}$ |
|---|---|---|---|---|---|---|
| E4 | —$COOX_{10}$ | optionally substituted $C_2$ to $C_8$ alkyl | $R_{10a}OCOO$— | $C_6H_5COO$— | O | OH |
| E5 | —$COX_{10}$ | optionally substituted $C_2$ to $C_8$ alkyl | $R_{10a}OCOO$— | $C_6H_5COO$— | O | OH |
| E6 | —$CONHX_{10}$ | optionally substituted $C_2$ to $C_8$ alkyl | $R_{10a}OCOO$— | $C_6H_5COO$— | O | OH |
| E7 | —$COOX_{10}$ | optionally substituted $C_2$ to $C_8$ alkenyl | $R_{10a}OCOO$— | $C_6H_5COO$— | O | OH |
| E8 | —$COX_{10}$ | optionally substituted $C_2$ to $C_8$ alkenyl | $R_{10a}OCOO$— | $C_6H_5COO$— | O | OH |
| E9 | —$CONHX_{10}$ | optionally substituted $C_2$ to $C_8$ alkenyl | $R_{10a}OCOO$— | $C_6H_5COO$— | O | OH |
| E10 | —$COOX_{10}$ | optionally substituted $C_2$ to $C_8$ alkynyl | $R_{10a}OCOO$— | $C_6H_5COO$— | O | OH |
| E11 | —$COX_{10}$ | optionally substituted $C_2$ to $C_8$ alkynyl | $R_{10a}OCOO$— | $C_6H_5COO$— | O | OH |
| E12 | —$CONHX_{10}$ | optionally substituted $C_2$ to $C_8$ alkynyl | $R_{10a}OCOO$— | $C_6H_5COO$— | O | OH |
| F1 | —$COOX_{10}$ | heterocyclo | $R_{10a}OCOO$— | $R_{2a}COO$— | $R_{9a}COO$— | H |
| F2 | —$COX_{10}$ | heterocyclo | $R_{10a}OCOO$— | $R_{2a}COO$— | $R_{9a}COO$— | H |
| F3 | —$CONHX_{10}$ | heterocyclo | $R_{10a}OCOO$— | $R_{2a}COO$— | $R_{9a}COO$— | H |
| F4 | —$COOX_{10}$ | optionally substituted $C_2$ to $C_8$ alkyl | $R_{10a}OCOO$— | $R_{2a}COO$— | $R_{9a}COO$— | H |
| F5 | —$COX_{10}$ | optionally substituted $C_2$ to $C_8$ alkyl | $R_{10a}OCOO$— | $R_{2a}COO$— | $R_{9a}COO$— | H |
| F6 | —$CONHX_{10}$ | optionally substituted $C_2$ to $C_8$ alkyl | $R_{10a}OCOO$— | $R_{2a}COO$— | $R_{9a}COO$— | H |
| F7 | —$COOX_{10}$ | optionally substituted $C_2$ to $C_8$ alkenyl | $R_{10a}OCOO$— | $R_{2a}COO$— | $R_{9a}COO$— | H |
| F8 | —$COX_{10}$ | optionally substituted $C_2$ to $C_8$ alkenyl | $R_{10a}OCOO$— | $R_{2a}COO$— | $R_{9a}COO$— | H |
| F9 | —$CONHX_{10}$ | optionally substituted $C_2$ to $C_8$ alkenyl | $R_{10a}OCOO$— | $R_{2a}COO$— | $R_{9a}COO$— | H |
| F10 | —$COOX_{10}$ | optionally substituted $C_2$ to $C_8$ alkynyl | $R_{10a}OCOO$— | $R_{2a}COO$— | $R_{9a}COO$— | H |
| F11 | —$COX_{10}$ | optionally substituted $C_2$ to $C_8$ alkynyl | $R_{10a}COO$— | $R_{2a}COO$— | $R_{9a}COO$— | H |
| F12 | —$CONHX_{10}$ | optionally substituted $C_2$ to $C_8$ alkynyl | $R_{10a}COO$— | $R_{2a}COO$— | $R_{9a}COO$— | H |
| G1 | —$COOX_{10}$ | heterocyclo | $R_{10a}OCOO$— | $R_{2a}COO$— | OH | H |
| G2 | —$COX_{10}$ | heterocyclo | $R_{10a}OCOO$— | $R_{2a}COO$— | OH | H |
| G3 | —$CONHX_{10}$ | heterocyclo | $R_{10a}OCOO$— | $R_{2a}COO$— | OH | H |

-continued (20)

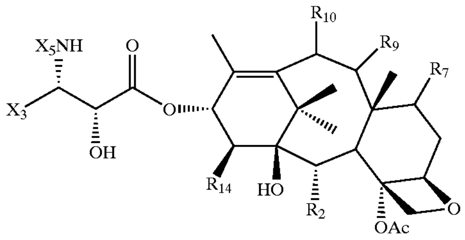

| Series | $X_5$ | $X_3$ | $R_{10}$ | $R_2$ | $R_9$ | $R_{14}$ |
|---|---|---|---|---|---|---|
| G4 | —$COOX_{10}$ | optionally substituted $C_2$ to $C_8$ alkyl | $R_{10a}OCOO$— | $R_{2a}COO$— | OH | H |
| G5 | —$COX_{10}$ | optionally substituted $C_2$ to $C_8$ alkyl | $R_{10a}OCOO$— | $R_{2a}COO$— | OH | H |
| G6 | —$CONHX_{10}$ | optionally substituted $C_2$ to $C_8$ alkyl | $R_{10a}OCOO$— | $R_{2a}COO$— | OH | H |
| G7 | —$COOX_{10}$ | optionally substituted $C_2$ to $C_8$ alkenyl | $R_{10a}OCOO$— | $R_{2a}COO$— | OH | H |
| G8 | —$COX_{10}$ | optionally substituted $C_2$ to $C_8$ alkenyl | $R_{10a}OCOO$— | $R_{2a}COO$— | OH | H |
| G9 | —$CONHX_{10}$ | optionally substituted $C_2$ to $C_8$ alkenyl | $R_{10a}OCOO$— | $R_{2a}COO$— | OH | H |
| G10 | —$COOX_{10}$ | optionally substituted $C_2$ to $C_8$ alkynyl | $R_{10a}OCOO$— | $R_{2a}COO$— | OH | H |
| G11 | —$COX_{10}$ | optionally substituted $C_2$ to $C_8$ alkynyl | $R_{10a}OCOO$— | $R_{2a}COO$— | OH | H |
| G12 | —$CONHX_{10}$ | optionally substituted $C_2$ to $C_8$ alkynyl | $R_{10a}OCOO$— | $R_{2a}COO$— | OH | H |
| H1 | —$COOX_{10}$ | heterocyclo | $R_{10a}OCOO$— | $C_6H_5COO$— | OH | OH |
| H2 | —$COX_{10}$ | heterocyclo | $R_{10a}OCOO$— | $C_6H_5COO$— | OH | OH |
| H3 | —$CONHX_{10}$ | heterocyclo | $R_{10a}OCOO$— | $C_6H_5COO$— | OH | OH |
| H4 | —$COOX_{10}$ | optionally substituted $C_2$ to $C_8$ alkyl | $R_{10a}OCOO$— | $C_6H_5COO$— | OH | OH |
| H5 | —$COX_{10}$ | optionally substituted $C_2$ to $C_8$ alkyl | $R_{10a}OCOO$— | $C_6H_5COO$— | OH | OH |
| H6 | —$CONHX_{10}$ | optionally substituted $C_2$ to $C_8$ alkyl | $R_{10a}OCOO$— | $C_6H_5COO$— | OH | OH |
| H7 | —$COOX_{10}$ | optionally substituted $C_2$ to $C_8$ alkenyl | $R_{10a}OCOO$— | $C_6H_5COO$— | OH | OH |
| H8 | —$COX_{10}$ | optionally substituted $C_2$ to $C_8$ alkenyl | $R_{10a}OCOO$— | $C_6H_5COO$— | OH | OH |
| H9 | —$CONHX_{10}$ | optionally substituted $C_2$ to $C_8$ alkenyl | $R_{10a}OCOO$— | $C_6H_5COO$— | OH | OH |
| H10 | —$COOX_{10}$ | optionally substituted $C_2$ to $C_8$ alkynyl | $R_{10a}OCOO$— | $C_6H_5COO$— | OH | OH |
| H11 | —$COX_{10}$ | optionally substituted $C_2$ to $C_8$ alkynyl | $R_{10a}OCOO$— | $C_6H_5COO$— | OH | OH |
| H12 | —$CONHX_{10}$ | optionally substituted $C_2$ to $C_8$ alkynyl | $R_{10a}OCOO$— | $C_6H_5COO$— | OH | OH |
| I1 | —$COOX_{10}$ | heterocyclo | $R_{10a}OCOO$— | $R_{2a}COO$— | O | OH |
| I2 | —$COX_{10}$ | heterocyclo | $R_{10a}OCOO$— | $R_{2a}COO$— | O | OH |
| I3 | —$CONHX_{10}$ | heterocyclo | $R_{10a}OCOO$— | $R_{2a}COO$— | O | OH |

-continued (20)

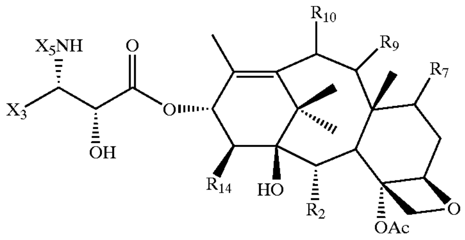

| Series | $X_5$ | $X_3$ | $R_{10}$ | $R_2$ | $R_9$ | $R_{14}$ |
|---|---|---|---|---|---|---|
| I4 | —$COOX_{10}$ | optionally substituted $C_2$ to $C_8$ alkyl | $R_{10a}OCOO$— | $R_{2a}COO$— | O | OH |
| I5 | —$COX_{10}$ | optionally substituted $C_2$ to $C_8$ alkyl | $R_{10a}OCOO$— | $R_{2a}COO$— | O | OH |
| I6 | —$CONHX_{10}$ | optionally substituted $C_2$ to $C_8$ alkyl | $R_{10a}OCOO$— | $R_{2a}COO$— | O | OH |
| I7 | —$COOX_{10}$ | optionally substituted $C_2$ to $C_8$ alkenyl | $R_{10a}OCOO$— | $R_{2a}COO$— | O | OH |
| I8 | —$COX_{10}$ | optionally substituted $C_2$ to $C_8$ alkenyl | $R_{10a}OCOO$— | $R_{2a}COO$— | O | OH |
| I9 | —$CONHX_{10}$ | optionally substituted $C_2$ to $C_8$ alkenyl | $R_{10a}OCOO$— | $R_{2a}COO$— | O | OH |
| I10 | —$COOX_{10}$ | optionally substituted $C_2$ to $C_8$ alkynyl | $R_{10a}OCOO$— | $R_{2a}COO$— | O | OH |
| I11 | —$COX_{10}$ | optionally substituted $C_2$ to $C_8$ alkynyl | $R_{10a}OCOO$— | $R_{2a}COO$— | O | OH |
| I12 | —$CONHX_{10}$ | optionally substituted $C_2$ to $C_8$ alkynyl | $R_{10a}OCOO$— | $R_{2a}COO$— | O | OH |
| J1 | —$COOX_{10}$ | heterocyclo | $R_{10a}OCOO$— | $R_{2a}COO$— | OH | OH |
| J2 | —$COX_{10}$ | heterocyclo | $R_{10a}OCOO$— | $R_{2a}COO$— | OH | OH |
| J3 | —$CONHX_{10}$ | heterocyclo | $R_{10a}OCOO$— | $R_{2a}COO$— | OH | OH |
| J4 | —$COOX_{10}$ | optionally substituted $C_2$ to $C_8$ alkyl | $R_{10a}OCOO$— | $R_{2a}COO$— | OH | OH |
| J5 | —$COX_{10}$ | optionally substituted $C_2$ to $C_8$ alkyl | $R_{10a}OCOO$— | $R_{2a}COO$— | OH | OH |
| J6 | —$CONHX_{10}$ | optionally substituted $C_2$ to $C_8$ alkyl | $R_{10a}OCOO$— | $R_{2a}COO$— | OH | OH |
| J7 | —$COOX_{10}$ | optionally substituted $C_2$ to $C_8$ alkenyl | $R_{10a}OCOO$— | $R_{2a}COO$— | OH | OH |
| J8 | —$COX_{10}$ | optionally substituted $C_2$ to $C_8$ alkenyl | $R_{10a}OCOO$— | $R_{2a}COO$— | OH | OH |
| J9 | —$CONHX_{10}$ | optionally substituted $C_2$ to $C_8$ alkenyl | $R_{10a}OCOO$— | $R_{2a}COO$— | OH | OH |
| J10 | —$COOX_{10}$ | optionally substituted $C_2$ to $C_8$ alkynyl | $R_{10a}OCOO$— | $R_{2a}COO$— | OH | OH |
| J11 | —$COX_{10}$ | optionally substituted $C_2$ to $C_8$ alkynyl | $R_{10a}OCOO$— | $R_{2a}COO$— | OH | OH |
| J12 | —$CONHX_{10}$ | optionally substituted $C_2$ to $C_8$ alkynyl | $R_{10a}OCOO$— | $R_{2a}COO$— | OH | OH |
| K1 | —$COOX_{10}$ | heterocyclo | $R_{10a}OCOO$— | $R_{2a}COO$— | $R_{9a}COO$— | OH |
| K2 | —$COX_{10}$ | heterocyclo | $R_{10a}OCOO$— | $R_{2a}COO$— | $R_{9a}COO$— | OH |
| K3 | —$CONHX_{10}$ | heterocyclo | $R_{10a}OCOO$— | $R_{2a}COO$— | $R_{9a}COO$— | OH |

-continued (20)

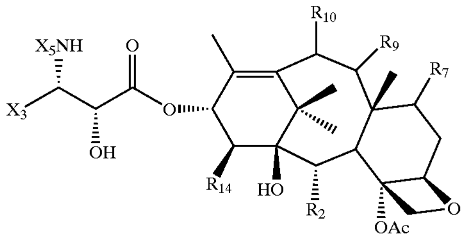

| Series | $X_5$ | $X_3$ | $R_{10}$ | $R_2$ | $R_9$ | $R_{14}$ |
|---|---|---|---|---|---|---|
| K4 | $—COOX_{10}$ | optionally substituted $C_2$ to $C_8$ alkyl | $R_{10a}OCOO—$ | $R_{2a}COO—$ | $R_{9a}COO—$ | OH |
| K5 | $—COX_{10}$ | optionally substituted $C_2$ to $C_8$ alkyl | $R_{10a}OCOO—$ | $R_{2a}COO—$ | $R_{9a}COO—$ | OH |
| K6 | $—CONHX_{10}$ | optionally substituted $C_2$ to $C_8$ alkyl | $R_{10a}OCOO—$ | $R_{2a}COO—$ | $R_{9a}COO—$ | OH |
| K7 | $—COOX_{10}$ | optionally substituted $C_2$ to $C_8$ alkenyl | $R_{10a}OCOO—$ | $R_{2a}COO—$ | $R_{9a}COO—$ | OH |
| K8 | $—COX_{10}$ | optionally substituted $C_2$ to $C_8$ alkenyl | $R_{10a}OCOO—$ | $R_{2a}COO—$ | $R_{9a}COO—$ | OH |
| K9 | $—CONHX_{10}$ | optionally substituted $C_2$ to $C_8$ alkenyl | $R_{10a}OCOO—$ | $R_{2a}COO—$ | $R_{9a}COO—$ | OH |
| K10 | $—COOX_{10}$ | optionally substituted $C_2$ to $C_8$ alkynyl | $R_{10a}OCOO—$ | $R_{2a}COO—$ | $R_{9a}COO—$ | OH |
| K11 | $—COX_{10}$ | optionally substituted $C_2$ to $C_8$ alkynyl | $R_{10a}OCOO—$ | $R_{2a}COO—$ | $R_{9a}COO—$ | OH |
| K12 | $—CONHX_{10}$ | optionally substituted $C_2$ to $C_8$ alkynyl | $R_{10a}OCOO—$ | $R_{2a}COO—$ | $R_{9a}COO—$ | OH |

EXAMPLE 30

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 27 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 1755 | <1 |
| 1767 | <10 |
| 1781 | <1 |
| 1799 | <1 |
| 1808 | <10 |
| 1811 | <1 |
| 1822 | <1 |
| 1838 | <1 |
| 1841 | <1 |
| 1855 | <10 |
| 1867 | <1 |
| 1999 | <1 |
| 2002 | <1 |
| 2011 | <10 |
| 2020 | <1 |
| 2032 | <1 |
| 2044 | <1 |
| 2050 | <1 |
| 2062 | <10 |
| 2077 | <10 |
| 2086 | <1 |
| 2097 | <1 |
| 2666 | <1 |
| 2972 | <10 |

-continued

| Compound | IN VITRO ID 50 (nm) HCT116 |
|---|---|
| 2988 | <1 |
| 2999 | <1 |
| 3003 | <10 |
| 3011 | <1 |
| 3020 | <1 |
| 3033 | <10 |
| 3155 | <1 |
| 3181 | <1 |
| 3243 | <1 |
| 3300 | <10 |
| 3393 | >50 |
| 3433 | 22.3 |
| 3911 | <1 |
| 3929 | <1 |
| 3963 | <1 |
| 4000 | <1 |
| 4020 | <1 |
| 4074 | <1 |
| 4088 | <10 |
| 4090 | <1 |
| 4374 | <1 |
| 4636 | <10 |
| 6466 | <10 |
| 4959 | <1 |
| 4924 | <10 |
| 4844 | <1 |
| 5171 | <1 |
| 5155 | <10 |
| 1788 | <1 |
| 1767 | <10 |
| 1771 | <10 |
| 1866 | <1 |
| 2060 | <10 |
| 2092 | <1 |
| 2088 | <1 |

EXAMPLE 31

Preparation of Taxane Having C-7 Carbamoyloxy and C-10 Hydroxy

N-Debenzoyl-N-isobutenyl-3'-desphenyl-3'-(2-furyl)-7-phenylcarbamoyl taxol (5535)

To a solution of N-debenzoyl-N-isobutenyl-3'-desphenyl-3'-(2-furyl)-2'-(2-methoxy-2-propyl)-10-triethylsilyl taxol (400 mg, 0.413 mmol) in 4 mL anhydrous pyridine was added 4-dimethylaminopyridine (10 mg, 0.08 mmol) under a nitrogen atmosphere. To this mixture was added dropwise phenyl isocyanate (112 L, 1.034 mmol). TLC (silica gel, 2:3 ethyl acetate:hexane) after 3 h showed no starting material. The reaction mixture was cooled to 0° C. (ice-water bath) and quenched by adding 50 L of water.

To the reaction at 0° C. (ice-water bath) was added 4 mL of acetonitrile and 2 mL of 48% aqueous hyderofluoric acid and the cooling bath removed. The reaction was stirred at room temperature for 12.5 h and then diluted with 60 mL of ethyl acetate and washed with 10 mL of saturated aqueous $NaHCO_3$ followed by 15 mL of saturated aqueous NaCl. The organic layer was dried over $Na_2SO_4$ and concentrated under reduce pressure to give 390 mg of an off-white solid which was purified by flash-chromatography (silica gel, 1:1 ethyl acetate:hexane) to give 320 mg (86%) of N-debenzoyl-N-isobutenyl-3'-desphenyl-3'-(2-furyl)-7-phenylcarbamoyl taxol: mp 188–89C; $^1H$ NMR ($CDCl_3$) 8.11 (m, 2H), 7.60 (m, 1H), 7.46–7.51(m, 2H), 7.26–7.40(m, 6H), 6.34(dd, J=3.1, 1.5 Hz, 1H), 6.25 (d, J=3.1 Hz,1H), 6.21 (dd, J=8.8, 8.7 Hz,1H), 5.67(2H), 5.47(2H), 4.98–5.01 (m, 3H), 4.76(m, 1H), 4.32(d, J=8.0 Hz, 1H), 4.21(d, J=8.0 Hz,1H), 4.09(d, J=7.6 Hz,1H), 3.99 (m,1H), 3.30 (d, J=5.5 Hz,1H), 2.60–2.68(m,1H), 2.43 (s, 3H), 2.37 (m, 1H), 2.08(m, 1H), 1.98 (s, 3H), 1.91 (bs, 3H), 1.84 (bs, 3H), 1.80 (s, 3H), 1.23(s, 3H), 1.10(s, 3H); Anal. Calcd. for $C_{48}H_{54}N_2O_{15}$: C, 64.13; H, 6.05. Found: C, 63.78; H, 6.20.

EXAMPLE 32

Taxanes having C7-Carbamoyloxy and C-10 Hydroxy Substituents

The procedures described in Example 31 were repeated, but other suitably protected β-lactams and acylating agents were substituted for the β-lactam and acylating agent of Example 31 to prepare the series of compounds having structural formula (21) and the combination of substituents identified in the following table.

(21)

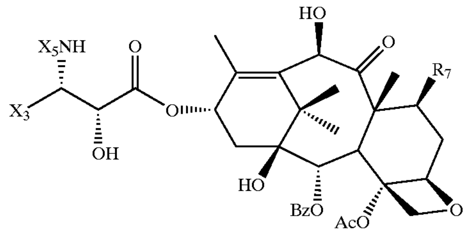

| Compound | $X_5$ | $X_3$ | $R_7$ |
|---|---|---|---|
| 5522 | ibueCO— | 2-furyl | 3,4-diFPhNHCOO— |
| 6404 | tAmOCO— | 2-furyl | 3,4-diFPhNHCOO— |
| 5415 | tBuOCO— | 2-furyl | 3,4-diFPhNHCOO— |
| 5800 | $tC_3H_5CO$— | 2-furyl | 3,4-diFPhNHCOO— |
| 5575 | ibueCO— | 2-furyl | $C_3H_5NHCOO$— |
| 5385 | tbuOCO— | 2-furyl | $C_3H_5NHCOO$— |
| 5844 | $tC_3H_5CO$— | 2-furyl | $C_3H_5NHCOO$— |
| 5373 | tBuOCO— | 2-furyl | chexNHCOO— |
| 5895 | $tC_3H_5CO$— | 2-furyl | chexNHCOO— |
| 5588 | ibueCO— | 2-furyl | EtNHCOO— |
| 5393 | tBuOCO— | 2-furyl | EtNHCOO— |
| 6696 | tBuOCO— | 2-furyl | EtNHCOO— |
| 5822 | $tC_3H_5CO$— | 2-furyl | EtNHCOO— |
| 5565 | ibueCO— | 2-furyl | mnipNHCOO— |
| 6476 | tAmOCO— | 2-furyl | mnipNHCOO— |
| 5400 | tBuOCO— | 2-furyl | mnipNHCOO— |
| 5747 | $tC_3H_5CO$— | 2-furyl | mnipNHCOO— |
| 5535 | ibueCO— | 2-furyl | PhNHCOO— |
| 6399 | tAmOCO— | 2-furyl | PhNHCOO— |
| 5757 | $tC_3H_5CO$— | 2-furyl | PhNHCOO— |
| 5665 | tBuOCO— | 2-furyl | PrNHCOO— |
| 5454 | tBuOCO— | 2-furyl | tBuNHCOO— |

EXAMPLE 33

Taxanes having C7-Carbamoyloxy and C-10 Hydroxy Substituents

Following the processes described in Example 31 and elsewhere herein, the following specific taxanes having structural formula (22) and the combinations of substituents identified in the following table may be prepared, wherein $R_7$ is as previously defined, including wherein $R_7$ is $R_{7a}R_{7b}NCOO$— and (a) $R_{7a}$ and $R_{7b}$ are each hydrogen, (b) one of $R_{7a}$ and $R_{7b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_3$ to $C_8$ alkenyl such as ethenyl or straight, branched or cyclic propenyl, butenyl, pentenyl or hexenyl; (iii) substituted or unsubstituted $C_3$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl, or (c) $R_{7a}$ and $R_{7b}$ are independently (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl. The substituents may be those identified elsewhere herein for substituted hydrocarbyl. For example, $R_7$ may be $R_{7a}R_{7b}NCOO—$ wherein one of $R_{7a}$ and $R_{7b}$ is hydrogen and the other is methyl, ethyl, or straight, branched or cyclic propyl.

(22)

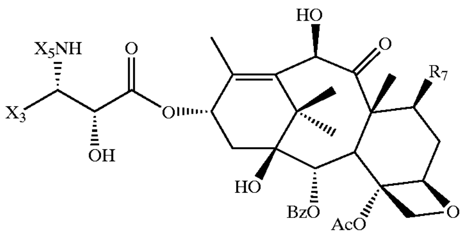

| $X_5$ | $X_3$ | $R_7$ |
|---|---|---|
| tBuOCO— | 2-furyl | $R_{7a}R_{7b}NCOO—$ |
| tBuOCO— | 3-furyl | $R_{7a}R_{7b}NCOO—$ |
| tBuOCO— | 2-thienyl | $R_{7a}R_{7b}NCOO—$ |
| tBuOCO— | 3-thienyl | $R_{7a}R_{7b}NCOO—$ |
| tBuOCO— | 2-pyridyl | $R_{7a}R_{7b}NCOO—$ |
| tBuOCO— | 3-pyridyl | $R_{7a}R_{7b}NCOO—$ |
| tBuOCO— | 4-pyridyl | $R_{7a}R_{7b}NCOO—$ |
| tBuOCO— | isobutenyl | $R_{7a}R_{7b}NCOO—$ |
| tBuOCO— | isopropyl | $R_{7a}R_{7b}NCOO—$ |
| tBuOCO— | cyclopropyl | $R_{7a}R_{7b}NCOO—$ |
| tBuOCO— | cyclobutyl | $R_{7a}R_{7b}NCOO—$ |
| tBuOCO— | cyclopentyl | $R_{7a}R_{7b}NCOO—$ |
| tBuOCO— | phenyl | $R_{7a}R_{7b}NCOO—$ |
| benzoyl | 2-furyl | $R_{7a}R_{7b}NCOO—$ |
| benzoyl | 3-furyl | $R_{7a}R_{7b}NCOO—$ |
| benzoyl | 2-thienyl | $R_{7a}R_{7b}NCOO—$ |
| benzoyl | 3-thienyl | $R_{7a}R_{7b}NCOO—$ |
| benzoyl | 2-pyridyl | $R_{7a}R_{7b}NCOO—$ |
| benzoyl | 3-pyridyl | $R_{7a}R_{7b}NCOO—$ |
| benzoyl | 4-pyridyl | $R_{7a}R_{7b}NCOO—$ |
| benzoyl | isobutenyl | $R_{7a}R_{7b}NCOO—$ |
| benzoyl | isopropyl | $R_{7a}R_{7b}NCOO—$ |
| benzoyl | cyclopropyl | $R_{7a}R_{7b}NCOO—$ |
| benzoyl | cyclobutyl | $R_{7a}R_{7b}NCOO—$ |
| benzoyl | cyclopentyl | $R_{7a}R_{7b}NCOO—$ |
| benzoyl | phenyl | $R_{7a}R_{7b}NCOO—$ |
| 2-FuCO— | 2-furyl | $R_{7a}R_{7b}NCOO—$ |
| 2-FuCO— | 3-furyl | $R_{7a}R_{7b}NCOO—$ |
| 2-FuCO— | 2-thienyl | $R_{7a}R_{7b}NCOO—$ |
| 2-FuCO— | 3-thienyl | $R_{7a}R_{7b}NCOO—$ |
| 2-FuCO— | 2-pyridyl | $R_{7a}R_{7b}NCOO—$ |
| 2-FuCO— | 3-pyridyl | $R_{7a}R_{7b}NCOO—$ |
| 2-FuCO— | 4-pyridyl | $R_{7a}R_{7b}NCOO—$ |
| 2-FuCO— | isobutenyl | $R_{7a}R_{7b}NCOO—$ |
| 2-FuCO— | isopropyl | $R_{7a}R_{7b}NCOO—$ |
| 2-FuCO— | cyclopropyl | $R_{7a}R_{7b}NCOO—$ |
| 2-FuCO— | cyclobutyl | $R_{7a}R_{7b}NCOO—$ |
| 2-FuCO— | cyclopentyl | $R_{7a}R_{7b}NCOO—$ |
| 2-FuCO— | phenyl | $R_{7a}R_{7b}NCOO—$ |
| 2-ThCO— | 2-furyl | $R_{7a}R_{7b}NCOO—$ |

-continued (22)

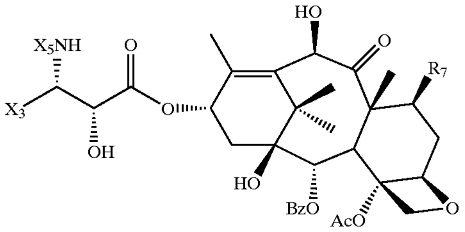

| $X_5$ | $X_3$ | $R_7$ |
|---|---|---|
| 2-ThCO— | 3-furyl | $R_{7a}R_{7b}NCOO—$ |
| 2-ThCO— | 2-thienyl | $R_{7a}R_{7b}NCOO—$ |
| 2-ThCO— | 3-thienyl | $R_{7a}R_{7b}NCOO—$ |
| 2-ThCO— | 2-pyridyl | $R_{7a}R_{7b}NCOO—$ |
| 2-ThCO— | 3-pyridyl | $R_{7a}R_{7b}NCOO—$ |
| 2-ThCO— | 4-pyridyl | $R_{7a}R_{7b}NCOO—$ |
| 2-ThCO— | isobutenyl | $R_{7a}R_{7b}NCOO—$ |
| 2-ThCO— | isopropyl | $R_{7a}R_{7b}NCOO—$ |
| 2-ThCO— | cyclopropyl | $R_{7a}R_{7b}NCOO—$ |
| 2-ThCO— | cyclobutyl | $R_{7a}R_{7b}NCOO—$ |
| 2-ThCO— | cyclopentyl | $R_{7a}R_{7b}NCOO—$ |
| 2-ThCO— | phenyl | $R_{7a}R_{7b}NCOO—$ |
| 2-PyCO— | 2-furyl | $R_{7a}R_{7b}NCOO—$ |
| 2-PyCO— | 3-furyl | $R_{7a}R_{7b}NCOO—$ |
| 2-PyCO— | 2-thienyl | $R_{7a}R_{7b}NCOO—$ |
| 2-PyCO— | 3-thienyl | $R_{7a}R_{7b}NCOO—$ |
| 2-PyCO— | 2-pyridyl | $R_{7a}R_{7b}NCOO—$ |
| 2-PyCO— | 3-pyridyl | $R_{7a}R_{7b}NCOO—$ |
| 2-PyCO— | 4-pyridyl | $R_{7a}R_{7b}NCOO—$ |
| 2-PyCO— | isobutenyl | $R_{7a}R_{7b}NCOO—$ |
| 2-PyCO— | isopropyl | $R_{7a}R_{7b}NCOO—$ |
| 2-PyCO— | cyclopropyl | $R_{7a}R_{7b}NCOO—$ |
| 2-PyCO— | cyclobutyl | $R_{7a}R_{7b}NCOO—$ |
| 2-PyCO— | cyclopentyl | $R_{7a}R_{7b}NCOO—$ |
| 2-PyCO— | phenyl | $R_{7a}R_{7b}NCOO—$ |
| 3-PyCO— | 2-furyl | $R_{7a}R_{7b}NCOO—$ |
| 3-PyCO— | 3-furyl | $R_{7a}R_{7b}NCOO—$ |
| 3-PyCO— | 2-thienyl | $R_{7a}R_{7b}NCOO—$ |
| 3-PyCO— | 3-thienyl | $R_{7a}R_{7b}NCOO—$ |
| 3-PyCO— | 2-pyridyl | $R_{7a}R_{7b}NCOO—$ |
| 3-PyCO— | 3-pyridyl | $R_{7a}R_{7b}NCOO—$ |
| 3-PyCO— | 4-pyridyl | $R_{7a}R_{7b}NCOO—$ |
| 3-PyCO— | isobutenyl | $R_{7a}R_{7b}NCOO—$ |
| 3-PyCO— | isopropyl | $R_{7a}R_{7b}NCOO—$ |
| 3-PyCO— | cyclopropyl | $R_{7a}R_{7b}NCOO—$ |
| 3-PyCO— | cyclobutyl | $R_{7a}R_{7b}NCOO—$ |
| 3-PyCO— | cyclopentyl | $R_{7a}R_{7b}NCOO—$ |
| 3-PyCO— | phenyl | $R_{7a}R_{7b}NCOO—$ |
| 4-PyCO— | 2-furyl | $R_{7a}R_{7b}NCOO—$ |
| 4-PyCO— | 3-furyl | $R_{7a}R_{7b}NCOO—$ |
| 4-PyCO— | 2-thienyl | $R_{7a}R_{7b}NCOO—$ |
| 4-PyCO— | 3-thienyl | $R_{7a}R_{7b}NCOO—$ |
| 4-PyCO— | 2-pyridyl | $R_{7a}R_{7b}NCOO—$ |
| 4-PyCO— | 3-pyridyl | $R_{7a}R_{7b}NCOO—$ |
| 4-PyCO— | 4-pyridyl | $R_{7a}R_{7b}NCOO—$ |
| 4-PyCO— | isobutenyl | $R_{7a}R_{7b}NCOO—$ |
| 4-PyCO— | isopropyl | $R_{7a}R_{7b}NCOO—$ |
| 4-PyCO— | cyclopropyl | $R_{7a}R_{7b}NCOO—$ |
| 4-PyCO— | cyclobutyl | $R_{7a}R_{7b}NCOO—$ |
| 4-PyCO— | cyclopentyl | $R_{7a}R_{7b}NCOO—$ |
| 4-PyCO— | phenyl | $R_{7a}R_{7b}NCOO—$ |
| $C_4H_7CO—$ | 2-furyl | $R_{7a}R_{7b}NCOO—$ |
| $C_4H_7CO—$ | 3-furyl | $R_{7a}R_{7b}NCOO—$ |
| $C_4H_7CO—$ | 2-thienyl | $R_{7a}R_{7b}NCOO—$ |
| $C_4H_7CO—$ | 3-thienyl | $R_{7a}R_{7b}NCOO—$ |
| $C_4H_7CO—$ | 2-pyridyl | $R_{7a}R_{7b}NCOO—$ |
| $C_4H_7CO—$ | 3-pyridyl | $R_{7a}R_{7b}NCOO—$ |
| $C_4H_7CO—$ | 4-pyridyl | $R_{7a}R_{7b}NCOO—$ |
| $C_4H_7CO—$ | isobutenyl | $R_{7a}R_{7b}NCOO—$ |
| $C_4H_7CO—$ | isopropyl | $R_{7a}R_{7b}NCOO—$ |
| $C_4H_7CO—$ | cyclopropyl | $R_{7a}R_{7b}NCOO—$ |
| $C_4H_7CO—$ | cyclobutyl | $R_{7a}R_{7b}NCOO—$ |
| $C_4H_7CO—$ | cyclopentyl | $R_{7a}R_{7b}NCOO—$ |

-continued (22)

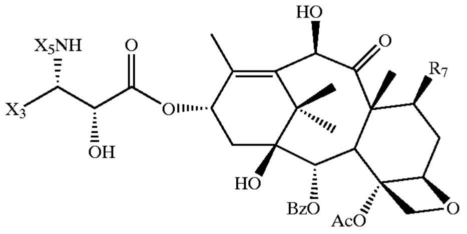

| $X_5$ | $X_3$ | $R_7$ |
|---|---|---|
| $C_4H_7CO$— | phenyl | $R_{7a}R_{7b}$NCOO— |
| EtOCO— | 2-furyl | $R_{7a}R_{7b}$NCOO— |
| EtOCO— | 3-furyl | $R_{7a}R_{7b}$NCOO— |
| EtOCO— | 2-thienyl | $R_{7a}R_{7b}$NCOO— |
| EtOCO— | 3-thienyl | $R_{7a}R_{7b}$NCOO— |
| EtOCO— | 2-pyridyl | $R_{7a}R_{7b}$NCOO— |
| EtOCO— | 3-pyridyl | $R_{7a}R_{7b}$NCOO— |
| EtOCO— | 4-pyridyl | $R_{7a}R_{7b}$NCOO— |
| EtOCO— | isobutenyl | $R_{7a}R_{7b}$NCOO— |
| EtOCO— | isopropyl | $R_{7a}R_{7b}$NCOO— |
| EtOCO— | cyclopropyl | $R_{7a}R_{7b}$NCOO— |
| EtOCO— | cyclobutyl | $R_{7a}R_{7b}$NCOO— |
| EtOCO— | cyclopentyl | $R_{7a}R_{7b}$NCOO— |
| EtOCO— | phenyl | $R_{7a}R_{7b}$NCOO— |
| ibueCO— | 2-furyl | $R_{7a}R_{7b}$NCOO— |
| ibueCO— | 3-furyl | $R_{7a}R_{7b}$NCOO— |
| ibueCO— | 2-thienyl | $R_{7a}R_{7b}$NCOO— |
| ibueCO— | 3-thienyl | $R_{7a}R_{7b}$NCOO— |
| ibueCO— | 2-pyridyl | $R_{7a}R_{7b}$NCOO— |
| ibueCO— | 3-pyridyl | $R_{7a}R_{7b}$NCOO— |
| ibueCO— | 4-pyridyl | $R_{7a}R_{7b}$NCOO— |
| ibueCO— | isobutenyl | $R_{7a}R_{7b}$NCOO— |
| ibueCO— | isopropyl | $R_{7a}R_{7b}$NCOO— |
| ibueCO— | cyclopropyl | $R_{7a}R_{7b}$NCOO— |
| ibueCO— | cyclobutyl | $R_{7a}R_{7b}$NCOO— |
| ibueCO— | cyclopentyl | $R_{7a}R_{7b}$NCOO— |
| ibueCO— | phenyl | $R_{7a}R_{7b}$NCOO— |
| iBuCO— | 2-furyl | $R_{7a}R_{7b}$NCOO— |
| iBuCO— | 3-furyl | $R_{7a}R_{7b}$NCOO— |
| iBuCO— | 2-thienyl | $R_{7a}R_{7b}$NCOO— |
| iBuCO— | 3-thienyl | $R_{7a}R_{7b}$NCOO— |
| iBuCO— | 2-pyridyl | $R_{7a}R_{7b}$NCOO— |
| iBuCO— | 3-pyridyl | $R_{7a}R_{7b}$NCOO— |
| iBuCO— | 4-pyridyl | $R_{7a}R_{7b}$NCOO— |
| iBuCO— | isobutenyl | $R_{7a}R_{7b}$NCOO— |
| iBuCO— | isopropyl | $R_{7a}R_{7b}$NCOO— |
| iBuCO— | cyclopropyl | $R_{7a}R_{7b}$NCOO— |
| iBuCO— | cyclobutyl | $R_{7a}R_{7b}$NCOO— |
| iBuCO— | cyclopentyl | $R_{7a}R_{7b}$NCOO— |
| iBuCO— | phenyl | $R_{7a}R_{7b}$NCOO— |
| iBuOCO— | 2-furyl | $R_{7a}R_{7b}$NCOO— |
| iBuOCO— | 3-furyl | $R_{7a}R_{7b}$NCOO— |
| iBuOCO— | 2-thienyl | $R_{7a}R_{7b}$NCOO— |
| iBuOCO— | 3-thienyl | $R_{7a}R_{7b}$NCOO— |
| iBuOCO— | 2-pyridyl | $R_{7a}R_{7b}$NCOO— |
| iBuOCO— | 3-pyridyl | $R_{7a}R_{7b}$NCOO— |
| iBuOCO— | 4-pyridyl | $R_{7a}R_{7b}$NCOO— |
| iBuOCO— | isobutenyl | $R_{7a}R_{7b}$NCOO— |
| iBuOCO— | isopropyl | $R_{7a}R_{7b}$NCOO— |
| iBuOCO— | cyclopropyl | $R_{7a}R_{7b}$NCOO— |
| iBuOCO— | cyclobutyl | $R_{7a}R_{7b}$NCOO— |
| iBuOCO— | cyclopentyl | $R_{7a}R_{7b}$NCOO— |
| iBuOCO— | phenyl | $R_{7a}R_{7b}$NCOO— |
| iPrOCO— | 2-furyl | $R_{7a}R_{7b}$NCOO— |
| iPrOCO— | 3-furyl | $R_{7a}R_{7b}$NCOO— |
| iPrOCO— | 2-thienyl | $R_{7a}R_{7b}$NCOO— |
| iPrOCO— | 3-thienyl | $R_{7a}R_{7b}$NCOO— |
| iPrOCO— | 2-pyridyl | $R_{7a}R_{7b}$NCOO— |
| iPrOCO— | 3-pyridyl | $R_{7a}R_{7b}$NCOO— |
| iPrOCO— | 4-pyridyl | $R_{7a}R_{7b}$NCOO— |
| iPrOCO— | isobutenyl | $R_{7a}R_{7b}$NCOO— |
| iPrOCO— | isopropyl | $R_{7a}R_{7b}$NCOO— |
| iPrOCO— | cyclopropyl | $R_{7a}R_{7b}$NCOO— |

-continued (22)

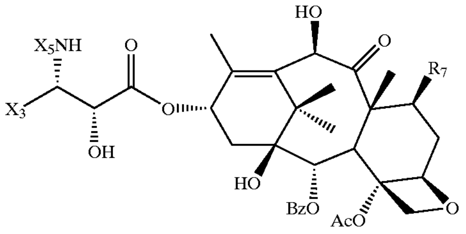

| $X_5$ | $X_3$ | $R_7$ |
|---|---|---|
| iPrOCO— | cyclobutyl | $R_{7a}R_{7b}$NCOO— |
| iPrOCO— | cyclopentyl | $R_{7a}R_{7b}$NCOO— |
| iPrOCO— | phenyl | $R_{7a}R_{7b}$NCOO— |
| nPrOCO— | 2-furyl | $R_{7a}R_{7b}$NCOO— |
| nPrOCO— | 3-furyl | $R_{7a}R_{7b}$NCOO— |
| nPrOCO— | 2-thienyl | $R_{7a}R_{7b}$NCOO— |
| nPrOCO— | 3-thienyl | $R_{7a}R_{7b}$NCOO— |
| nPrOCO— | 2-pyridyl | $R_{7a}R_{7b}$NCOO— |
| nPrOCO— | 3-pyridyl | $R_{7a}R_{7b}$NCOO— |
| nPrOCO— | 4-pyridyl | $R_{7a}R_{7b}$NCOO— |
| nPrOCO— | isobutenyl | $R_{7a}R_{7b}$NCOO— |
| nPrOCO— | isopropyl | $R_{7a}R_{7b}$NCOO— |
| nPrOCO— | cyclopropyl | $R_{7a}R_{7b}$NCOO— |
| nPrOCO— | cyclobutyl | $R_{7a}R_{7b}$NCOO— |
| nPrOCO— | cyclopentyl | $R_{7a}R_{7b}$NCOO— |
| nPrOCO— | phenyl | $R_{7a}R_{7b}$NCOO— |
| nPrCO— | 2-furyl | $R_{7a}R_{7b}$NCOO— |
| nPrCO— | 3-furyl | $R_{7a}R_{7b}$NCOO— |
| nPrCO— | 2-thienyl | $R_{7a}R_{7b}$NCOO— |
| nPrCO— | 3-thienyl | $R_{7a}R_{7b}$NCOO— |
| nPrCO— | 2-pyridyl | $R_{7a}R_{7b}$NCOO— |
| nPrCO— | 3-pyridyl | $R_{7a}R_{7b}$NCOO— |
| nPrCO— | 4-pyridyl | $R_{7a}R_{7b}$NCOO— |
| nPrCO— | isobutenyl | $R_{7a}R_{7b}$NCOO— |
| nPrCO— | isopropyl | $R_{7a}R_{7b}$NCOO— |
| nPrCO— | cyclopropyl | $R_{7a}R_{7b}$NCOO— |
| nPrCO— | cyclobutyl | $R_{7a}R_{7b}$NCOO— |
| nPrCO— | cyclopentyl | $R_{7a}R_{7b}$NCOO— |
| nPrCO— | phenyl | $R_{7a}R_{7b}$NCOO— |

EXAMPLE 34

Taxanes having C7-Carbamoyloxy and C-10 Hydroxy Substituents

Following the processes described in Example 31 and elsewhere herein, the following specific taxanes having structural formula (23) may be prepared, wherein $R_{10}$ is hydroxy and $R_7$ in each of the series (that is, each of series "A" through "K") is as previously defined, including wherein $R_7$ is $R_{7a}R_{7b}$NCOO— and one of $R_{7a}$ and $R_{7b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) phenyl or substituted phenyl such as nitro, alkoxy or halosubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_7$ substituents include $R_{7a}R_{7b}$NCOO— wherein one of $R_{7a}$ and $R_{7b}$ is hydrogen and the other is methyl, ethyl, or straight, branched or cyclic propyl. In another embodiment, preferred $R_7$ substituents include $R_{7a}R_{7b}NCOO$— wherein one of $R_{7a}$ and $R_{7b}$ is hydrogen and the other is substituted methyl, ethyl, or straight, branched or cyclic propyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(23)

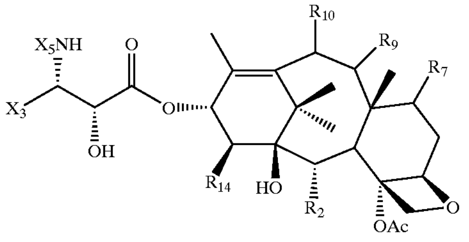

| Series | $X_5$ | $X_3$ | $R_7$ | $R_2$ | $R_9$ | $R_{14}$ |
|---|---|---|---|---|---|---|
| A1 | —$COOX_{10}$ | heterocyclo | $R_{7a}R_{7b}NCOO$— | $C_6H_5COO$— | O | H |
| A2 | —$COX_{10}$ | heterocyclo | $R_{7a}R_{7b}NCOO$— | $C_6H_5COO$— | O | H |
| A3 | —$CONHX_{10}$ | heterocyclo | $R_{7a}R_{7b}NCOO$— | $C_6H_5COO$— | O | H |
| A4 | —$COOX_{10}$ | optionally substituted $C_2$ to $C_8$ alkyl | $R_{7a}R_{7b}NCOO$— | $C_6H_5COO$— | O | H |

-continued (23)

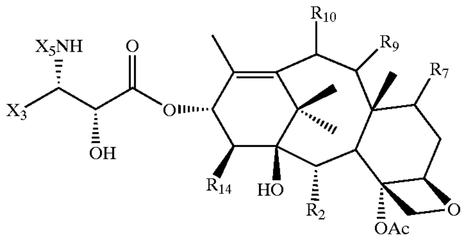

| Series | $X_5$ | $X_3$ | $R_7$ | $R_2$ | $R_9$ | $R_{14}$ |
|---|---|---|---|---|---|---|
| A5 | —$COX_{10}$ | optionally substituted $C_2$ to $C_8$ alkyl | $R_{7a}R_{7b}NCOO$— | $C_6H_5COO$— | O | H |
| A6 | —$CONHX_{10}$ | optionally substituted $C_2$ to $C_8$ alkyl | $R_{7a}R_{7b}NCOO$— | $C_6H_5COO$— | O | H |
| A7 | —$COOX_{10}$ | optionally substituted $C_2$ to $C_8$ alkenyl | $R_{7a}R_{7b}NCOO$— | $C_6H_5COO$— | O | H |
| A8 | —$COX_{10}$ | optionally substituted $C_2$ to $C_8$ alkenyl | $R_{7a}R_{7b}NCOO$— | $C_6H_5COO$— | O | H |
| A9 | —$CONHX_{10}$ | optionally substituted $C_2$ to $C_8$ alkenyl | $R_{7a}R_{7b}NCOO$— | $C_6H_5COO$— | O | H |
| A10 | —$COOX_{10}$ | optionally substituted $C_2$ to $C_8$ alkynyl | $R_{7a}R_{7b}NCOO$— | $C_6H_5COO$— | O | H |
| A11 | —$COX_{10}$ | optionally substituted $C_2$ to $C_8$ alkynyl | $R_{7a}R_{7b}NCOO$— | $C_6H_5COO$— | O | H |
| A12 | —$CONHX_{10}$ | optionally substituted $C_2$ to $C_8$ alkynyl | $R_{7a}R_{7b}NCOO$— | $C_6H_5COO$— | O | H |
| B1 | —$COOX_{10}$ | heterocyclo | $R_{7a}R_{7b}NCOO$— | $R_{2a}COO$— | O | H |
| B2 | —$COX_{10}$ | heterocyclo | $R_{7a}R_{7b}NCOO$— | $R_{2a}COO$— | O | H |
| B3 | —$CONHX_{10}$ | heterocyclo | $R_{7a}R_{7b}NCOO$— | $R_{2a}COO$— | O | H |
| B4 | —$COOX_{10}$ | optionally substituted $C_2$ to $C_8$ alkyl | $R_{7a}R_{7b}NCOO$— | $R_{2a}COO$— | O | H |
| B5 | —$COX_{10}$ | optionally substituted $C_2$ to $C_8$ alkyl | $R_{7a}R_{7b}NCOO$— | $R_{2a}COO$— | O | H |
| B6 | —$CONHX_{10}$ | optionally substituted $C_2$ to $C_8$ alkyl | $R_{7a}R_{7b}NCOO$— | $R_{2a}COO$— | O | H |
| B7 | —$COOX_{10}$ | optionally substituted $C_2$ to $C_8$ alkenyl | $R_{7a}R_{7b}NCOO$— | $R_{2a}COO$— | O | H |
| B8 | —$COX_{10}$ | optionally substituted $C_2$ to $C_8$ alkenyl | $R_{7a}R_{7b}NCOO$— | $R_{2a}COO$— | O | H |
| B9 | —$CONHX_{10}$ | optionally substituted $C_2$ to $C_8$ alkenyl | $R_{7a}R_{7b}NCOO$— | $R_{2a}COO$— | O | H |
| B10 | —$COOX_{10}$ | optionally substituted $C_2$ to $C_8$ alkynyl | $R_{7a}R_{7b}NCOO$— | $R_{2a}COO$— | O | H |
| B11 | —$COX_{10}$ | optionally substituted $C_2$ to $C_8$ alkynyl | $R_{7a}R_{7b}NCOO$— | $R_{2a}COO$— | O | H |
| B12 | —$CONHX_{10}$ | optionally substituted $C_2$ to $C_8$ alkynyl | $R_{7a}R_{7b}NCOO$— | $R_{2a}COO$— | O | H |
| C1 | —$COOX_{10}$ | heterocyclo | $R_{7a}R_{7b}NCOO$— | $C_6H_5COO$— | $R_{9a}COO$— | H |
| C2 | —$COX_{10}$ | heterocyclo | $R_{7a}R_{7b}NCOO$— | $C_6H_5COO$— | $R_{9a}COO$— | H |
| C3 | —$CONHX_{10}$ | heterocyclo | $R_{7a}R_{7b}NCOO$— | $C_6H_5COO$— | $R_{9a}COO$— | H |
| C4 | —$COOX_{10}$ | optionally substituted $C_2$ to $C_8$ alkyl | $R_{7a}R_{7b}NCOO$— | $C_6H_5COO$— | $R_{9a}COO$— | H |
| C5 | —$COX_{10}$ | optionally substituted $C_2$ to $C_8$ alkyl | $R_{7a}R_{7b}NCOO$— | $C_6H_5COO$— | $R_{9a}COO$— | H |

-continued (23)

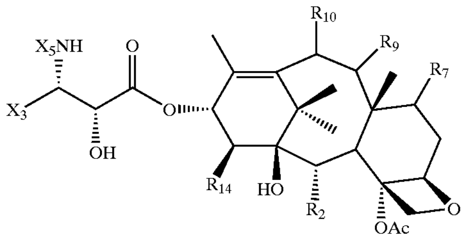

| Series | $X_5$ | $X_3$ | $R_7$ | $R_2$ | $R_9$ | $R_{14}$ |
|---|---|---|---|---|---|---|
| C6 | —$CONHX_{10}$ | optionally substituted $C_2$ to $C_8$ alkyl | $R_{7a}R_{7b}NCOO$— | $C_6H_5COO$— | $R_{9a}COO$— | H |
| C7 | —$COOX_{10}$ | optionally substituted $C_2$ to $C_8$ alkenyl | $R_{7a}R_{7b}NCOO$— | $C_6H_5COO$— | $R_{9a}COO$— | H |
| C8 | —$COX_{10}$ | optionally substituted $C_2$ to $C_8$ alkenyl | $R_{7a}R_{7b}NCOO$— | $C_6H_5COO$— | $R_{9a}COO$— | H |
| C9 | —$CONHX_{10}$ | optionally substituted $C_2$ to $C_8$ alkenyl | $R_{7a}R_{7b}NCOO$— | $C_6H_5COO$— | $R_{9a}COO$— | H |
| C10 | —$COOX_{10}$ | optionally substituted $C_2$ to $C_8$ alkynyl | $R_{7a}R_{7b}NCOO$— | $C_6H_5COO$— | $R_{9a}COO$— | H |
| C11 | —$COX_{10}$ | optionally substituted $C_2$ to $C_8$ alkynyl | $R_{7a}R_{7b}NCOO$— | $C_6H_5COO$— | $R_{9a}COO$— | H |
| C12 | —$CONHX_{10}$ | optionally substituted $C_2$ to $C_8$ alkynyl | $R_{7a}R_{7b}NCOO$— | $C_6H_5COO$— | $R_{9a}COO$— | H |
| D1 | —$COOX_{10}$ | heterocyclo | $R_{7a}R_{7b}NCOO$— | $C_6H_5COO$— | OH | H |
| D2 | —$COX_{10}$ | heterocyclo | $R_{7a}R_{7b}NCOO$— | $C_6H_5COO$— | OH | H |
| D3 | —$CONHX_{10}$ | heterocyclo | $R_{7a}R_{7b}NCOO$— | $C_6H_5COO$— | OH | H |
| D4 | —$COOX_{10}$ | optionally substituted $C_2$ to $C_8$ alkyl | $R_{7a}R_{7b}NCOO$— | $C_6H_5COO$— | OH | H |
| D5 | —$COX_{10}$ | optionally substituted $C_2$ to $C_8$ alkyl | $R_{7a}R_{7b}NCOO$— | $C_6H_5COO$— | OH | H |
| D6 | —$CONHX_{10}$ | optionally substituted $C_2$ to $C_8$ alkyl | $R_{7a}R_{7b}NCOO$— | $C_6H_5COO$— | OH | H |
| D7 | —$COOX_{10}$ | optionally substituted $C_2$ to $C_8$ alkenyl | $R_{7a}R_{7b}NCOO$— | $C_6H_5COO$— | OH | H |
| D8 | —$COX_{10}$ | optionally substituted $C_2$ to $C_8$ alkenyl | $R_{7a}R_{7b}NCOO$— | $C_6H_5COO$— | OH | H |
| D9 | —$CONHX_{10}$ | optionally substituted $C_2$ to $C_8$ alkenyl | $R_{7a}R_{7b}NCOO$— | $C_6H_5COO$— | OH | H |
| D10 | —$COOX_{10}$ | optionally substituted $C_2$ to $C_8$ alkynyl | $R_{7a}R_{7b}NCOO$— | $C_6H_5COO$— | OH | H |
| D11 | —$COX_{10}$ | optionally substituted $C_2$ to $C_8$ alkynyl | $R_{7a}R_{7b}NCOO$— | $C_6H_5COO$— | OH | H |
| D12 | —$CONHX_{10}$ | optionally substituted $C_2$ to $C_8$ alkynyl | $R_{7a}R_{7b}NCOO$— | $C_6H_5COO$— | OH | H |
| E1 | —$COOX_{10}$ | heterocyclo | $R_{7a}R_{7b}NCOO$— | $C_6H_5COO$— | O | OH |
| E2 | —$COX_{10}$ | heterocyclo | $R_{7a}R_{7b}NCOO$— | $C_6H_5COO$— | O | OH |
| E3 | —$CONHX_{10}$ | heterocyclo | $R_{7a}R_{7b}NCOO$— | $C_6H_5COO$— | O | OH |
| E4 | —$COOX_{10}$ | optionally substituted $C_2$ to $C_8$ alkyl | $R_{7a}R_{7b}NCOO$— | $C_6H_5COO$— | O | OH |
| E5 | —$COX_{10}$ | optionally substituted $C_2$ to $C_8$ alkyl | $R_{7a}R_{7b}NCOO$— | $C_6H_5COO$— | O | OH |
| E6 | —$CONHX_{10}$ | optionally substituted $C_2$ to $C_8$ alkyl | $R_{7a}R_{7b}NCOO$— | $C_6H_5COO$— | O | OH |

-continued (23)

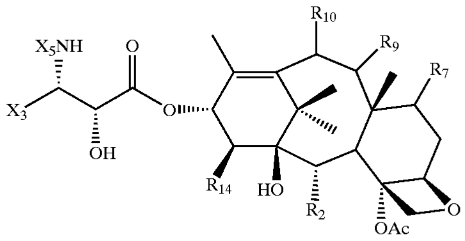

| Series | $X_5$ | $X_3$ | $R_7$ | $R_2$ | $R_9$ | $R_{14}$ |
|---|---|---|---|---|---|---|
| E7 | —$COOX_{10}$ | optionally substituted $C_2$ to $C_8$ alkenyl | $R_{7a}R_{7b}NCOO$— | $C_6H_5COO$— | O | OH |
| E8 | —$COX_{10}$ | optionally substituted $C_2$ to $C_8$ alkenyl | $R_{7a}R_{7b}NCOO$— | $C_6H_5COO$— | O | OH |
| E9 | —$CONHX_{10}$ | optionally substituted $C_2$ to $C_8$ alkenyl | $R_{7a}R_{7b}NCOO$— | $C_6H_5COO$— | O | OH |
| E10 | —$COOX_{10}$ | optionally substituted $C_2$ to $C_8$ alkynyl | $R_{7a}R_{7b}NCOO$— | $C_6H_5COO$— | O | OH |
| E11 | —$COX_{10}$ | optionally substituted $C_2$ to $C_8$ alkynyl | $R_{7a}R_{7b}NCOO$— | $C_6H_5COO$— | O | OH |
| E12 | —$CONHX_{10}$ | optionally substituted $C_2$ to $C_8$ alkynyl | $R_{7a}R_{7b}NCOO$— | $C_6H_5COO$— | O | OH |
| F1 | —$COOX_{10}$ | heterocyclo | $R_{7a}R_{7b}NCOO$— | $R_{2a}COO$— | $R_{9a}COO$— | H |
| F2 | —$COX_{10}$ | heterocyclo | $R_{7a}R_{7b}NCOO$— | $R_{2a}COO$— | $R_{9a}COO$— | H |
| F3 | —$CONHX_{10}$ | heterocyclo | $R_{7a}R_{7b}NCOO$— | $R_{2a}COO$— | $R_{9a}COO$— | H |
| F4 | —$COOX_{10}$ | optionally substituted $C_2$ to $C_8$ alkyl | $R_{7a}R_{7b}NCOO$— | $R_{2a}COO$— | $R_{9a}COO$— | H |
| F5 | —$COX_{10}$ | optionally substituted $C_2$ to $C_8$ alkyl | $R_{7a}R_{7b}NCOO$— | $R_{2a}COO$— | $R_{9a}COO$— | H |
| F6 | —$CONHX_{10}$ | optionally substituted $C_2$ to $C_8$ alkyl | $R_{7a}R_{7b}NCOO$— | $R_{2a}COO$— | $R_{9a}COO$— | H |
| F7 | —$COOX_{10}$ | optionally substituted $C_2$ to $C_8$ alkenyl | $R_{7a}R_{7b}NCOO$— | $R_{2a}COO$— | $R_{9a}COO$— | H |
| F8 | —$COX_{10}$ | optionally substituted $C_2$ to $C_8$ alkenyl | $R_{7a}R_{7b}NCOO$— | $R_{2a}COO$— | $R_{9a}COO$— | H |
| F9 | —$CONHX_{10}$ | optionally substituted $C_2$ to $C_8$ alkenyl | $R_{7a}R_{7b}NCOO$— | $R_{2a}COO$— | $R_{9a}COO$— | H |
| F10 | —$COOX_{10}$ | optionally substituted $C_2$ to $C_8$ alkynyl | $R_{7a}R_{7b}NCOO$— | $R_{2a}COO$— | $R_{9a}COO$— | H |
| F11 | —$COX_{10}$ | optionally substituted $C_2$ to $C_8$ alkynyl | $R_{7a}R_{7b}NCOO$— | $R_{2a}COO$— | $R_{9a}COO$— | H |
| F12 | —$CONHX_{10}$ | optionally substituted $C_2$ to $C_8$ alkynyl | $R_{7a}R_{7b}NCOO$— | $R_{2a}COO$— | $R_{9a}COO$— | H |
| G1 | —$COOX_{10}$ | heterocyclo | $R_{7a}R_{7b}NCOO$— | $R_{2a}COO$— | OH | H |
| G2 | —$COX_{10}$ | heterocyclo | $R_{7a}R_{7b}NCOO$— | $R_{2a}COO$— | OH | H |
| G3 | —$CONHX_{10}$ | heterocyclo | $R_{7a}R_{7b}NCOO$— | $R_{2a}COO$— | OH | H |
| G4 | —$COOX_{10}$ | optionally substituted $C_2$ to $C_8$ alkyl | $R_{7a}R_{7b}NCOO$— | $R_{2a}COO$— | OH | H |
| G5 | —$COX_{10}$ | optionally substituted $C_2$ to $C_8$ alkyl | $R_{7a}R_{7b}NCOO$— | $R_{2a}COO$— | OH | H |
| G6 | —$CONHX_{10}$ | optionally substituted $C_2$ to $C_8$ alkyl | $R_{7a}R_{7b}NCOO$— | $R_{2a}COO$— | OH | H |
| G7 | —$COOX_{10}$ | optionally substituted $C_2$ to $C_8$ alkenyl | $R_{7a}R_{7b}NCOO$— | $R_{2a}COO$— | OH | H |

-continued (23)

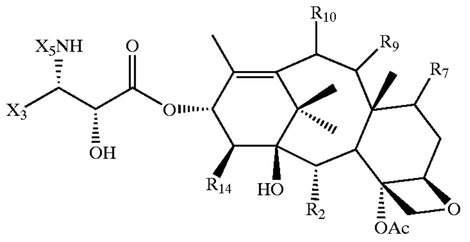

| Series | $X_5$ | $X_3$ | $R_7$ | $R_2$ | $R_9$ | $R_{14}$ |
|---|---|---|---|---|---|---|
| G8 | —$COX_{10}$ | optionally substituted $C_2$ to $C_8$ alkenyl | $R_{7a}R_{7b}NCOO$— | $R_{2a}COO$— | OH | H |
| G9 | —$CONHX_{10}$ | optionally substituted $C_2$ to $C_8$ alkenyl | $R_{7a}R_{7b}NCOO$— | $R_{2a}COO$— | OH | H |
| G10 | —$COOX_{10}$ | optionally substituted $C_2$ to $C_8$ alkynyl | $R_{7a}R_{7b}NCOO$— | $R_{2a}COO$— | OH | H |
| G11 | —$COX_{10}$ | optionally substituted $C_2$ to $C_8$ alkynyl | $R_{7a}R_{7b}NCOO$— | $R_{2a}COO$— | OH | H |
| G12 | —$CONHX_{10}$ | optionally substituted $C_2$ to $C_8$ alkynyl | $R_{7a}R_{7b}NCOO$— | $R_{2a}COO$— | OH | H |
| H1 | —$COOX_{10}$ | heterocyclo | $R_{7a}R_{7b}NCOO$— | $C_6H_5COO$— | OH | OH |
| H2 | —$COX_{10}$ | heterocyclo | $R_{7a}R_{7b}NCOO$— | $C_6H_5COO$— | OH | OH |
| H3 | —$CONHX_{10}$ | heterocyclo | $R_{7a}R_{7b}NCOO$— | $C_6H_5COO$— | OH | OH |
| H4 | —$COOX_{10}$ | optionally substituted $C_2$ to $C_8$ alkyl | $R_{7a}R_{7b}NCOO$— | $C_6H_5COO$— | OH | OH |
| H5 | —$COX_{10}$ | optionally substituted $C_2$ to $C_8$ alkyl | $R_{7a}R_{7b}NCOO$— | $C_6H_5COO$— | OH | OH |
| H6 | —$CONHX_{10}$ | optionally substituted $C_2$ to $C_8$ alkyl | $R_{7a}R_{7b}NCOO$— | $C_6H_5COO$— | OH | OH |
| H7 | —$COOX_{10}$ | optionally substituted $C_2$ to $C_8$ alkenyl | $R_{7a}R_{7b}NCOO$— | $C_6H_5COO$— | OH | OH |
| H8 | —$COX_{10}$ | optionally substituted $C_2$ to $C_8$ alkenyl | $R_{7a}R_{7b}NCOO$— | $C_6H_5COO$— | OH | OH |
| H9 | —$CONHX_{10}$ | optionally substituted $C_2$ to $C_8$ alkenyl | $R_{7a}R_{7b}NCOO$— | $C_6H_5COO$— | OH | OH |
| H10 | —$COOX_{10}$ | optionally substituted $C_2$ to $C_8$ alkynyl | $R_{7a}R_{7b}NCOO$— | $C_6H_5COO$— | OH | OH |
| H11 | —$COX_{10}$ | optionally substituted $C_2$ to $C_8$ alkynyl | $R_{7a}R_{7b}NCOO$— | $C_6H_5COO$— | OH | OH |
| H12 | —$CONHX_{10}$ | optionally substituted $C_2$ to $C_8$ alkynyl | $R_{7a}R_{7b}NCOO$— | $C_6H_5COO$— | OH | OH |
| I1 | —$COOX_{10}$ | heterocyclo | $R_{7a}R_{7b}NCOO$— | $R_{2a}COO$— | O | OH |
| I2 | —$COX_{10}$ | heterocyclo | $R_{7a}R_{7b}NCOO$— | $R_{2a}COO$— | O | OH |
| I3 | —$CONHX_{10}$ | heterocyclo | $R_{7a}R_{7b}NCOO$— | $R_{2a}COO$— | O | OH |
| I4 | —$COOX_{10}$ | optionally substituted $C_2$ to $C_8$ alkyl | $R_{7a}R_{7b}NCOO$— | $R_{2a}COO$— | O | OH |
| I5 | —$COX_{10}$ | optionally substituted $C_2$ to $C_8$ alkyl | $R_{7a}R_{7b}NCOO$— | $R_{2a}COO$— | O | OH |
| I6 | —$CONHX_{10}$ | optionally substituted $C_2$ to $C_8$ alkyl | $R_{7a}R_{7b}NCOO$— | $R_{2a}COO$— | O | OH |
| I7 | —$COOX_{10}$ | optionally substituted $C_2$ to $C_8$ alkenyl | $R_{7a}R_{7b}NCOO$— | $R_{2a}COO$— | O | OH |
| I8 | —$COX_{10}$ | optionally substituted $C_2$ to $C_8$ alkenyl | $R_{7a}R_{7b}NCOO$— | $R_{2a}COO$— | O | OH |

-continued (23)

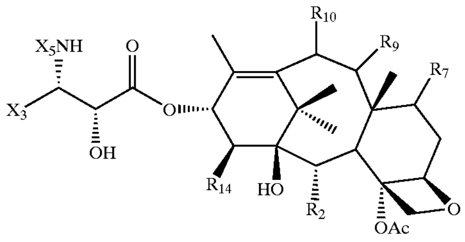

| Series | $X_5$ | $X_3$ | $R_7$ | $R_2$ | $R_9$ | $R_{14}$ |
|---|---|---|---|---|---|---|
| I9 | —$CONHX_{10}$ | optionally substituted $C_2$ to $C_8$ alkenyl | $R_{7a}R_{7b}NCOO$— | $R_{2a}COO$— | O | OH |
| I10 | —$COOX_{10}$ | optionally substituted $C_2$ to $C_8$ alkynyl | $R_{7a}R_{7b}NCOO$— | $R_{2a}COO$— | O | OH |
| I11 | —$COX_{10}$ | optionally substituted $C_2$ to $C_8$ alkynyl | $R_{7a}R_{7b}NCOO$— | $R_{2a}COO$— | O | OH |
| I12 | —$CONHX_{10}$ | optionally substituted $C_2$ to $C_8$ alkynyl | $R_{7a}R_{7b}NCOO$— | $R_{2a}COO$— | O | OH |
| J1 | —$COOX_{10}$ | heterocyclo | $R_{7a}R_{7b}NCOO$— | $R_{2a}COO$— | OH | OH |
| J2 | —$COX_{10}$ | heterocyclo | $R_{7a}R_{7b}NCOO$— | $R_{2a}COO$— | OH | OH |
| J3 | —$CONHX_{10}$ | heterocyclo | $R_{7a}R_{7b}NCOO$— | $R_{2a}COO$— | OH | OH |
| J4 | —$COOX_{10}$ | optionally substituted $C_2$ to $C_8$ alkyl | $R_{7a}R_{7b}NCOO$— | $R_{2a}COO$— | OH | OH |
| J5 | —$COX_{10}$ | optionally substituted $C_2$ to $C_8$ alkyl | $R_{7a}R_{7b}NCOO$— | $R_{2a}COO$— | OH | OH |
| J6 | —$CONHX_{10}$ | optionally substituted $C_2$ to $C_8$ alkyl | $R_{7a}R_{7b}NCOO$— | $R_{2a}COO$— | OH | OH |
| J7 | —$COOX_{10}$ | optionally substituted $C_2$ to $C_8$ alkenyl | $R_{7a}R_{7b}NCOO$— | $R_{2a}COO$— | OH | OH |
| J8 | —$COX_{10}$ | optionally substituted $C_2$ to $C_8$ alkenyl | $R_{7a}R_{7b}NCOO$— | $R_{2a}COO$— | OH | OH |
| J9 | —$CONHX_{10}$ | optionally substituted $C_2$ to $C_8$ alkenyl | $R_{7a}R_{7b}NCOO$— | $R_{2a}COO$— | OH | OH |
| J10 | —$COOX_{10}$ | optionally substituted $C_2$ to $C_8$ alkynyl | $R_{7a}R_{7b}NCOO$— | $R_{2a}COO$— | OH | OH |
| J11 | —$COX_{10}$ | optionally substituted $C_2$ to $C_8$ alkynyl | $R_{7a}R_{7b}NCOO$— | $R_{2a}COO$— | OH | OH |
| J12 | —$CONHX_{10}$ | optionally substituted $C_2$ to $C_8$ alkynyl | $R_{7a}R_{7b}NCOO$— | $R_{2a}COO$— | OH | OH |
| K1 | —$COOX_{10}$ | heterocyclo | $R_{7a}R_{7b}NCOO$— | $R_{2a}COO$— | $R_{9a}COO$— | OH |
| K2 | —$COX_{10}$ | heterocyclo | $R_{7a}R_{7b}NCOO$— | $R_{2a}COO$— | $R_{9a}COO$— | OH |
| K3 | —$CONHX_{10}$ | heterocyclo | $R_{7a}R_{7b}NCOO$— | $R_{2a}COO$— | $R_{9a}COO$— | OH |
| K4 | —$COOX_{10}$ | optionally substituted $C_2$ to $C_8$ alkyl | $R_{7a}R_{7b}NCOO$— | $R_{2a}COO$— | $R_{9a}COO$— | OH |
| K5 | —$COX_{10}$ | optionally substituted $C_2$ to $C_8$ alkyl | $R_{7a}R_{7b}NCOO$— | $R_{2a}COO$— | $R_{9a}COO$— | OH |
| K6 | —$CONHX_{10}$ | optionally substituted $C_2$ to $C_8$ alkyl | $R_{7a}R_{7b}NCOO$— | $R_{2a}COO$— | $R_{9a}COO$— | OH |
| K7 | —$COOX_{10}$ | optionally substituted $C_2$ to $C_8$ alkenyl | $R_{7a}R_{7b}NCOO$— | $R_{2a}COO$— | $R_{9a}COO$— | OH |
| K8 | —$COX_{10}$ | optionally substituted $C_2$ to $C_8$ alkenyl | $R_{7a}R_{7b}NCOO$— | $R_{2a}COO$— | $R_{9a}COO$— | OH |
| K9 | —$CONHX_{10}$ | optionally substituted $C_2$ to $C_8$ alkenyl | $R_{7a}R_{7b}NCOO$— | $R_{2a}COO$— | $R_{9a}COO$— | OH |

-continued (23)

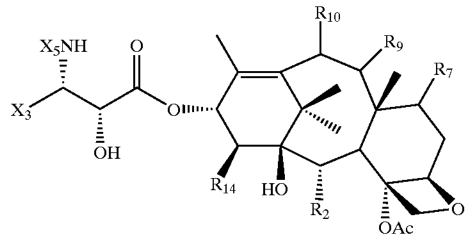

| Series | $X_5$ | $X_3$ | $R_7$ | $R_2$ | $R_9$ | $R_{14}$ |
|---|---|---|---|---|---|---|
| K10 | $—COOX_{10}$ | optionally substituted $C_2$ to $C_8$ alkynyl | $R_{7a}R_{7b}NCOO—$ | $R_{2a}COO—$ | $R_{9a}COO—$ | OH |
| K11 | $—COX_{10}$ | optionally substituted $C_2$ to $C_8$ alkynyl | $R_{7a}R_{7b}NCOO—$ | $R_{2a}COO—$ | $R_{9a}COO—$ | OH |
| K12 | $—CONHX_{10}$ | optionally substituted $C_2$ to $C_8$ alkynyl | $R_{7a}R_{7b}NCOO—$ | $R_{2a}COO—$ | $R_{9a}COO—$ | OH |

EXAMPLE 35

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 32 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 5522 | <1 |
| 6404 | <10 |
| 5415 | <1 |
| 5800 | <10 |
| 5575 | <1 |
| 5385 | <1 |
| 5844 | <10 |
| 5373 | <10 |
| 5895 | <1 |
| 5588 | <1 |
| 5393 | <1 |
| 6696 | <1 |
| 5822 | <10 |
| 5565 | <1 |

-continued

| Compound | IN VITRO ID 50 (nm) HCT116 |
|---|---|
| 6476 | <10 |
| 5400 | <1 |
| 5747 | <10 |
| 5535 | <1 |
| 6399 | <10 |
| 5757 | <10 |
| 5665 | >50 |
| 5454 | <10 |

EXAMPLE 36

Preparation of Taxane having C-10 Carbamoyloxy and C-7 Hydroxy Substituents

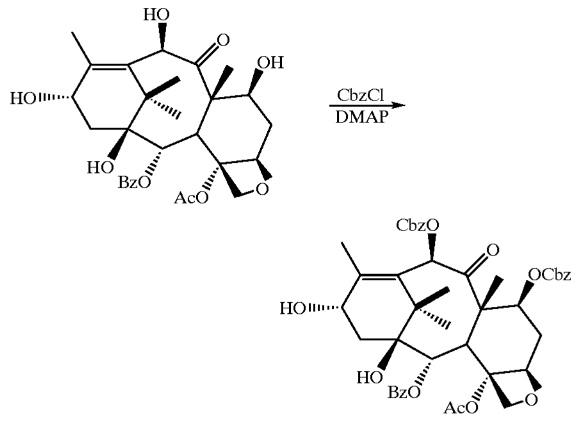

7,10-(bis)-carbobenzyloxy-10-deacetyl baccatin III.

To a solution of 10-DAB (1.14 g, 2.11 mmol) in 20 mL of methylene chloride was added DMAP (6.20 g, 50.6 mmol) and benzyl chloroformate (1.8 mL, 12.7 mmol) slowly under a nitrogen atmosphere. The mixture was heated to 40–45° C., kept at this temperature for 2 h, and an additional 1.8 mL (12.7 mmol) of benzyl chloroformate was added. Heating at 40–45° C. was continued for an additional 6 h, the mixture was diluted with 200 mL of $CH_2Cl_2$ and washed three times first with 1N HCl and then with saturated sodium bicarbonate solution. The combined washings were extracted three times with 30 mL of $CH_2Cl_2$, the organic layers were combined, washed with brine, dried over $Na_2SO_4$, and concentrated under reduced pressure. Chromatography of the residue on silica gel eluting with $CH_2Cl_2$/EtOAc gave 1.48 g (86%) of 7,10-(bis)-carbobenzyloxy-10-deacetyl baccatin III.

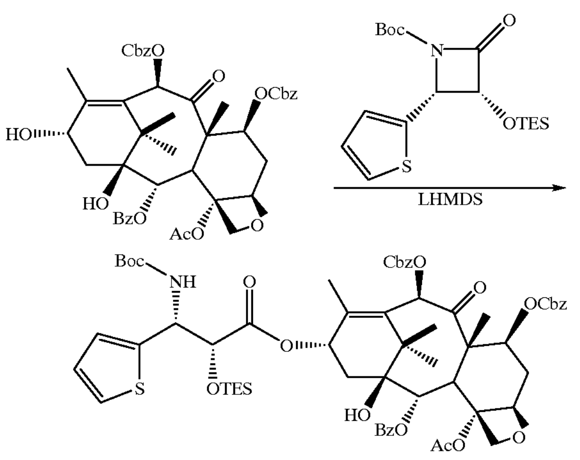

7,10-(bis)-carbobenzyloxy-3'-desphenyl-3'-(2-thienyl)-2'-O-triethylsilyl docetaxel.

To a solution of 425 mg (0.523 mmol) of 7,10-(bis)-carbobenzyloxy-10-deacetyl baccatin III in THF (4.5 mL) at −45° C. under a nitrogen atmosphere was added 0.80 mL of a solution of LHMDS (0.98 M) in THF dropwise. The mixture was kept at −45° C. for 1 h prior to addition of a solution of 341 mg (0.889 mmol) of cis-N-tbutoxycarbonyl-3-triethylsilyloxy-4-(2-thienyl) azetidin-2-one in 2 mL of THF. The mixture was allowed to warm to 0° C., and after 2 h was poured into 20 mL of saturated ammonium chloride solution. The aqueous layer was extracted three times with 50 mL of EtOAc/Hexanes (1:1) and the organic layers were combined, washed with brine, dried over $Na_2SO_4$ and concentrated. Chromatography of the residue on silica gel eluting with EtOAc/Hexanes gave 576 mg (92%) of 7,10-(bis)-carbobenzyloxy-3'-desphenyl-3'-(2-thienyl)-2'-O-triethylsilyl docetaxel.

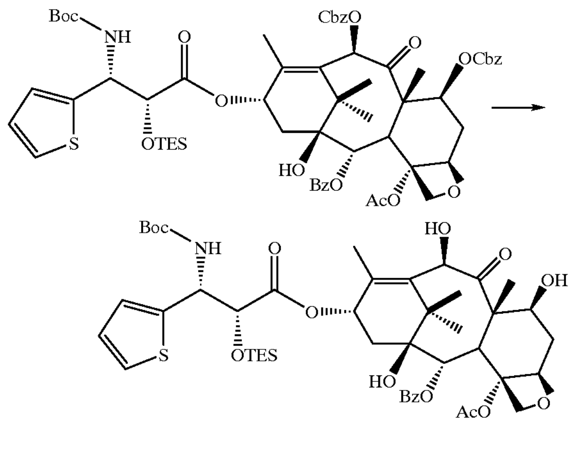

3'-Desphenyl-3'-(2-thienyl)-2'-O-triethylsilyl docetaxel.

A suspension of 550 mg of 7,10-(bis)-carbobenzyloxy-3'-desphenyl-3'-(2-thienyl)-2'-O-triethylsilyl docetaxel and 50 mg of 10% Pd/C in 30 mL of EtOH and 10 mL of EtOAc was stirred under a hydrogen atmosphere for 2 h at room temperature. The slurry was filtered through a pad of celite 545 which was then washed with EtOAc. The washings were concentrated and the residue was purified by column chromatography on silica gel using EtOAc/Hexanes as eluent to give 405 mg (95%) of 3'-desphenyl-3'-(2-thienyl)-2'-O-triethylsilyl docetaxel.

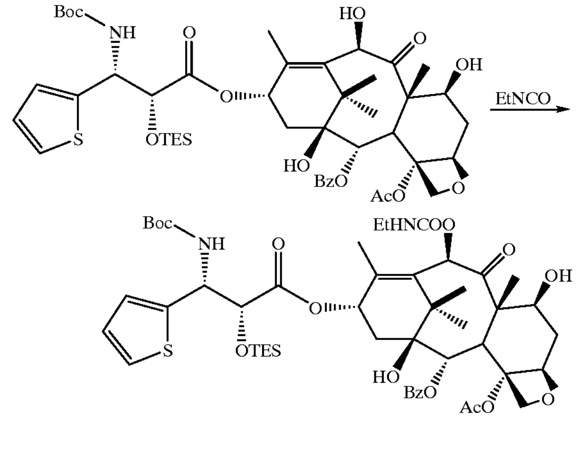

3'-Desphenyl-3'-(2-thienyl)-2'-O-triethylsilyl-10-N-ethylcarbamoyl docetaxel.

To a slurry of 3'-desphenyl-3'-(2-thienyl)-2'-O-triethylsilyl docetaxel (201 mg, 0.217 mmol) and CuCl (43.0 mg, 0.434 mmol) in THF (3.5 mL) at −15° C. under a nitrogen atmosphere was added a solution of 51.5 mL (0.651 mmol) of ethyl isocynate in 1.9 mL of THF. The mixture was warmed to 0° C. and after 1.4 h 5 mL of saturated aqueous sodium bicarbonate solution and 20 mL of ethyl acetate were added. The water layer was extracted three times with 50 mL of EtOAc/Hexanes (1:1). The organic layers were combined, dried over $Na_2SO_4$ and evaporated to give 218 mg of a residue which was used directly without purification.

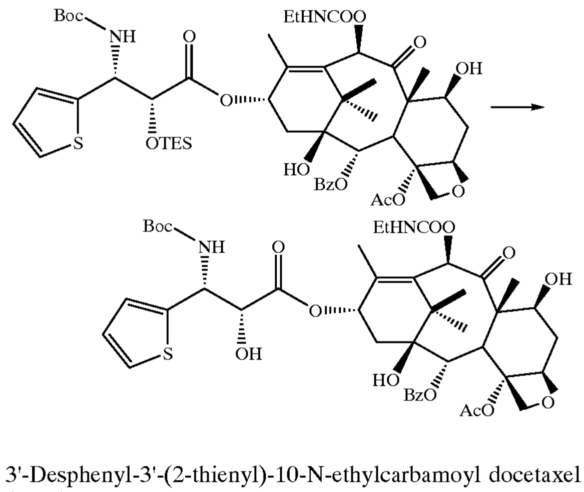

3'-Desphenyl-3'-(2-thienyl)-10-N-ethylcarbamoyl docetaxel (2722).

To a solution of the 218 mg of 3'-desphenyl-3'-(2-thienyl)-2'-O-triethylsilyl-10-N-ethylcarbamoyl docetaxel obtained above in 6 mL of pyridine and 12 mL of $CH_3CN$ at 0° C. was added 1.0 mL of 49% aqueous HF. The mixture was warmed to room temperature and after 2.5 h 50 mL of EtOAc was added. The mixture was washed with saturated aqueous sodium bicarbonate solution and brine, dried over sodium sulfate, and concentrated under reduced pressure. Chromatography of the residue on silica gel using $CH_2Cl_2$/MeOH as eluent gave 169 mg (88% for 2 steps) of 3'-desphenyl-3'-(2-thienyl)-10-N-ethylcarbamoyl docetaxel.

EXAMPLE 37

Taxanes having C-10 Carbamoyloxy and C-7 Hydroxy Substituents

The procedures described in Example 36 were repeated, but other suitably protected β-lactams were substituted for the cis-N-tbutoxycarbonyl-3-triethylsilyloxy-4-(2-thienyl) azetidin-2-one of Example 36 to prepare the series of compounds having structural formula (24) and the combinations of substituents identified in the following table. The following table also includes characterization data for certain of these compounds, along with characterization data for the compound (2722) prepared in Example 36.

(24)

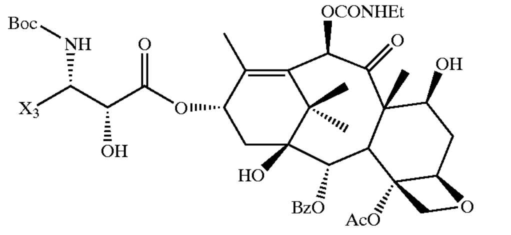

| No. | $X_3$ | m.p.(° C.) | $[\alpha]_D$ ($CHCl_3$) | Elemental Analysis |
|---|---|---|---|---|
| 2600 | 2-pyridyl | 173–175 | −71.4 (c 0.22) | Found: C, 60.70; H, 6.69 (Calcd. for $C_{45}H_{57}N_3O_{15}$.0.5-$H_2O$: C, 60.79; H, 6.58) |
| 2616 | 3-pyridyl | 183–185 | −61.0 (c 0.20) | Found: C, 58.96; H, 6.51 (Calcd. for $C_{45}H_{57}N_3O_{15}$.2-$H_2O$: C, 59.00; H, 6.69) |
| 2622 | 3-thienyl | 173–175 | −68.1 (c 0.19) | Found: C, 58.40; H, 6.42 (Calcd. for $C_{44}H_{56}N_2O_{15}S$.-$H_2O$: C, 58.47; H, 6.47) |
| 2633 | i-propyl | 170–172 | −75.7 (c 0.22) | Found: C, 60.10; H, 7.15 (Calcd. for $C_{43}H_{60}N_2O_{15}$.-$H_2$): C, 59.84; H, 7.24) |
| 2686 | i-butenyl | 167–169 | −106.7 (c 0.17) | Found: C, 61.12; H, 7.10 (Calcd. for $C_{44}H_{60}N_2O_{15}$.0.5-$H_2O$: C, 61.02; H, 7.10) |
| 2692 | 4-pyridyl | 203–205 | −69.7 (c 0.18) | Found: C, 60.19; H, 6.61 (Calcd. for $C_{45}H_{57}N_3O_{15}H_2O$: C, 60.13; H, 6.62) |
| 2700 | 2-furyl | 169–171 | −73.6 (c 0.22) | Found: C, 60.59; H, 6.58 (Calcd. for $C_{44}H_{56}N_2O_{16}$: |

-continued (24)

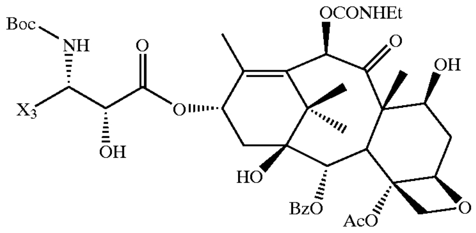

| No. | $X_3$ | m.p.(° C.) | $[\alpha]_D$ ($CHCl_3$) | Elemental Analysis |
|---|---|---|---|---|
| | | | | C, 60.82; H, 6.50) |
| 2717 | 3-furyl | 165–167 | −53.8 (c 0.23) | Found: C, 60.07; H, 6.48 (Calcd. for $C_{44}H_{56}N_2O_{16}$.-0.5$H_2O$: C, 60.14; H, 6.54 |
| 2722 | 2-thienyl | 166–168 | −52.2 (c 0.25) | Found: C, 58.28; H, 6.32 (Calcd. for $C_{44}H_{56}N_2O_{15}S$.-$H_2O$: C, 58.47; H, 6.47) |
| 2733 | cyclobutyl | 168–170 | −73.9 (c 0.23) | Found: C, 60.96; H, 7.02 (Calcd. for $C_{44}H_{60}N_2O_{15}$.0.5-$H_2O$: C, 61.02; H, 7.10) |
| 2757 | cyclopropyl | 168–170 | −91.7 (c 0.23) | Found: C, 66.07; H, 6.86 (Calcd. for $C_{43}H_{58}N_2O_{15}.H_2O$: C, 59.98; H, 7.02) |

EXAMPLE 38

Taxanes Having C-10 Carbomoyloxy and C-7 Hydroxy Substituents

The procedures described in Example 36 were repeated, but other suitably protected β-lactams were substituted for the β-lactam of Example 36 to prepare the series of compounds having structural formula (25) and the combinations of substituents identified in the following table.

(25)

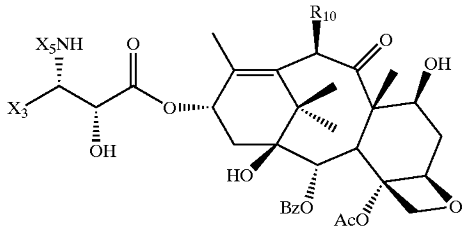

| Compound | $X_5$ | $X_3$ | $R_{10}$ |
|---|---|---|---|
| 2640 | tBuOCO— | phenyl | EtNHCOO— |
| 2743 | tBuOCO— | p-nitrophenyl | EtNHCOO— |
| 6015 | $tC_3H_5CO$— | 2-furyl | 3,4-diFPhNHCOO— |
| 6024 | $tC_3H_5CO$— | 2-furyl | PhNHCOO— |
| 6072 | $tC_3H_5CO$— | 2-furyl | EtNHCOO— |

EXAMPLE 39

Additional Taxanes having C-10 Carbamoyloxy and C-7 Hydroxy Substituents

Following the processes described in Example 36 and elsewhere herein, the following specific taxanes having structural formula (26) may be prepared, wherein $R_7$ is as previously defined including wherein $R_{10}$ is $R_aR_bNCOO$— and (a) $R_a$ and $R_b$ are each hydrogen, (b) one of $R_a$ and $R_b$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_3$ to $C_8$ alkenyl such as ethenyl or straight, branched or cyclic propenyl, butenyl, pentenyl or hexenyl; (iii) substituted or unsubstituted $C_3$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl, or (c) $R_a$ and $R_b$ are independently (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) substituted or unsubstituted phenyl, or (v) substituted or unsubstituted heteroaromatic such as furyl, thienyl, or pyridyl. For example, $R_{10}$ may be $R_aR_bNCOO$— wherein one of $R_a$ and $R_b$ is hydrogen and the other is methyl, ethyl, or straight, branched or cyclic propyl. The substituents may be those identified elsewhere herein for substituted hydrocarbyl.

(26)

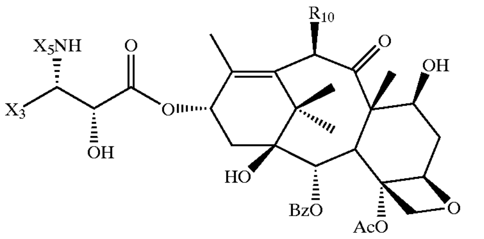

| $X_5$ | $X_3$ | $R_{10}$ |
|---|---|---|
| tBuOCO | 2-furyl | $R_aR_bNCOO$— |
| tBuOCO | 3-furyl | $R_aR_bNCOO$— |
| tBuOCO | 2-thienyl | $R_aR_bNCOO$— |
| tBuOCO | 3-thienyl | $R_aR_bNCOO$— |
| tBuOCO | 2-pyridyl | $R_aR_bNCOO$— |
| tBuOCO | 3-pyridyl | $R_aR_bNCOO$— |
| tBuOCO | 4-pyridyl | $R_aR_bNCOO$— |
| tBuOCO | isobutenyl | $R_aR_bNCOO$— |
| tBuOCO | isopropyl | $R_aR_bNCOO$— |
| tBuOCO | cyclopropyl | $R_aR_bNCOO$— |
| tBuOCO | cyclobutyl | $R_aR_bNCOO$— |
| tBuOCO | cyclopentyl | $R_aR_bNCOO$— |
| tBuOCO | phenyl | $R_aR_bNCOO$— |
| benzoyl | 2-furyl | $R_aR_bNCOO$— |
| benzoyl | 3-furyl | $R_aR_bNCOO$— |
| benzoyl | 2-thienyl | $R_aR_bNCOO$— |
| benzoyl | 3-thienyl | $R_aR_bNCOO$— |
| benzoyl | 2-pyridyl | $R_aR_bNCOO$— |
| benzoyl | 3-pyridyl | $R_aR_bNCOO$— |
| benzoyl | 4-pyridyl | $R_aR_bNCOO$— |
| benzoyl | isobutenyl | $R_aR_bNCOO$— |
| benzoyl | isopropyl | $R_aR_bNCOO$— |
| benzoyl | cyclopropyl | $R_aR_bNCOO$— |
| benzoyl | cyclobutyl | $R_aR_bNCOO$— |
| benzoyl | cyclopentyl | $R_aR_bNCOO$— |
| benzoyl | phenyl | $R_aR_bNCOO$— |
| 2-FuCO— | 2-furyl | $R_aR_bNCOO$— |
| 2-FuCO— | 3-furyl | $R_aR_bNCOO$— |
| 2-FuCO— | 2-thienyl | $R_aR_bNCOO$— |
| 2-FuCO— | 3-thienyl | $R_aR_bNCOO$— |
| 2-FuCO— | 2-pyridyl | $R_aR_bNCOO$— |

-continued (26)

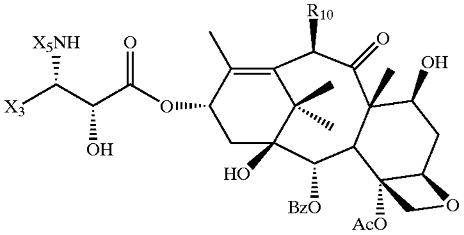

| $X_5$ | $X_3$ | $R_{10}$ |
|---|---|---|
| 2-FuCO— | 3-pyridyl | $R_aR_bNCOO$— |
| 2-FuCO— | 4-pyridyl | $R_aR_bNCOO$— |
| 2-FuCO— | isobutenyl | $R_aR_bNCOO$— |
| 2-FuCO— | isopropyl | $R_aR_bNCOO$— |
| 2-FuCO— | cyclopropyl | $R_aR_bNCOO$— |
| 2-FuCO— | cyclobutyl | $R_aR_bNCOO$— |
| 2-FuCO— | cyclopentyl | $R_aR_bNCOO$— |
| 2-FuCO— | phenyl | $R_aR_bNCOO$— |
| 2-ThCO— | 2-furyl | $R_aR_bNCOO$— |
| 2-ThCO— | 3-furyl | $R_aR_bNCOO$— |
| 2-ThCO— | 2-thienyl | $R_aR_bNCOO$— |
| 2-ThCO— | 3-thienyl | $R_aR_bNCOO$— |
| 2-ThCO— | 2-pyridyl | $R_aR_bNCOO$— |
| 2-ThCO— | 3-pyridyl | $R_aR_bNCOO$— |
| 2-ThCO— | 4-pyridyl | $R_aR_bNCOO$— |
| 2-ThCO— | isobutenyl | $R_aR_bNCOO$— |
| 2-ThCO— | isopropyl | $R_aR_bNCOO$— |
| 2-ThCO— | cyclopropyl | $R_aR_bNCOO$— |
| 2-ThCO— | cyclobutyl | $R_aR_bNCOO$— |
| 2-ThCO— | cyclopentyl | $R_aR_bNCOO$— |
| 2-ThCO— | phenyl | $R_aR_bNCOO$— |
| 2-PyCO— | 2-furyl | $R_aR_bNCOO$— |
| 2-PyCO— | 3-furyl | $R_aR_bNCOO$— |
| 2-PyCO— | 2-thienyl | $R_aR_bNCOO$— |
| 2-PyCO— | 3-thienyl | $R_aR_bNCOO$— |
| 2-PyCO— | 2-pyridyl | $R_aR_bNCOO$— |
| 2-PyCO— | 3-pyridyl | $R_aR_bNCOO$— |
| 2-PyCO— | 4-pyridyl | $R_aR_bNCOO$— |
| 2-PyCO— | isobutenyl | $R_aR_bNCOO$— |
| 2-PyCO— | isopropyl | $R_aR_bNCOO$— |
| 2-PyCO— | cyclopropyl | $R_aR_bNCOO$— |
| 2-PyCO— | cyclobutyl | $R_aR_bNCOO$— |
| 2-PyCO— | cyclopentyl | $R_aR_bNCOO$— |
| 2-PyCO— | phenyl | $R_aR_bNCOO$— |
| 3-PyCO— | 2-furyl | $R_aR_bNCOO$— |
| 3-PyCO— | 3-furyl | $R_aR_bNCOO$— |
| 3-PyCO— | 2-thienyl | $R_aR_bNCOO$— |
| 3-PyCO— | 3-thienyl | $R_aR_bNCOO$— |
| 3-PyCO— | 2-pyridyl | $R_aR_bNCOO$— |
| 3-PyCO— | 3-pyridyl | $R_aR_bNCOO$— |
| 3-PyCO— | 4-pyridyl | $R_aR_bNCOO$— |
| 3-PyCO— | isobutenyl | $R_aR_bNCOO$— |
| 3-PyCO— | isopropyl | $R_aR_bNCOO$— |
| 3-PyCO— | cyclopropyl | $R_aR_bNCOO$— |
| 3-PyCO— | cyclobutyl | $R_aR_bNCOO$— |
| 3-PyCO— | cyclopentyl | $R_aR_bNCOO$— |
| 3-PyCO— | phenyl | $R_aR_bNCOO$— |
| 4-PyCO— | 2-furyl | $R_aR_bNCOO$— |
| 4-PyCO— | 3-furyl | $R_aR_bNCOO$— |
| 4-PyCO— | 2-thienyl | $R_aR_bNCOO$— |
| 4-PyCO— | 3-thienyl | $R_aR_bNCOO$— |
| 4-PyCO— | 2-pyridyl | $R_aR_bNCOO$— |
| 4-PyCO— | 3-pyridyl | $R_aR_bNCOO$— |
| 4-PyCO— | 4-pyridyl | $R_aR_bNCOO$— |
| 4-PyCO— | isobutenyl | $R_aR_bNCOO$— |
| 4-PyCO— | isopropyl | $R_aR_bNCOO$— |
| 4-PyCO— | cyclopropyl | $R_aR_bNCOO$— |
| 4-PyCO— | cyclobutyl | $R_aR_bNCOO$— |
| 4-PyCO— | cyclopentyl | $R_aR_bNCOO$— |
| 4-PyCO— | phenyl | $R_aR_bNCOO$— |
| $C_4H_7CO$— | 2-furyl | $R_aR_bNCOO$— |
| $C_4H_7CO$— | 3-furyl | $R_aR_bNCOO$— |
| $C_4H_7CO$— | 2-thienyl | $R_aR_bNCOO$— |

-continued (26)

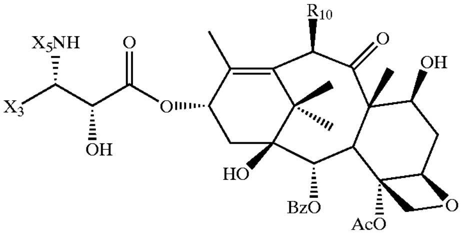

| $X_5$ | $X_3$ | $R_{10}$ |
|---|---|---|
| $C_4H_7CO$— | 3-thienyl | $R_aR_bNCOO$— |
| $C_4H_7CO$— | 2-pyridyl | $R_aR_bNCOO$— |
| $C_4H_7CO$— | 3-pyridyl | $R_aR_bNCOO$— |
| $C_4H_7CO$— | 4-pyridyl | $R_aR_bNCOO$— |
| $C_4H_7CO$— | isobutenyl | $R_aR_bNCOO$— |
| $C_4H_7CO$— | isopropyl | $R_aR_bNCOO$— |
| $C_4H_7CO$— | cyclopropyl | $R_aR_bNCOO$— |
| $C_4H_7CO$— | cyclobutyl | $R_aR_bNCOO$— |
| $C_4H_7CO$— | cyclopentyl | $R_aR_bNCOO$— |
| $C_4H_7CO$— | phenyl | $R_aR_bNCOO$— |
| EtOCO— | 2-furyl | $R_aR_bNCOO$— |
| EtOCO— | 3-furyl | $R_aR_bNCOO$— |
| EtOCO— | 2-thienyl | $R_aR_bNCOO$— |
| EtOCO— | 3-thienyl | $R_aR_bNCOO$— |
| EtOCO— | 2-pyridyl | $R_aR_bNCOO$— |
| EtOCO— | 3-pyridyl | $R_aR_bNCOO$— |
| EtOCO— | 4-pyridyl | $R_aR_bNCOO$— |
| EtOCO— | isobutenyl | $R_aR_bNCOO$— |
| EtOCO— | isopropyl | $R_aR_bNCOO$— |
| EtOCO— | cyclopropyl | $R_aR_bNCOO$— |
| EtOCO— | cyclobutyl | $R_aR_bNCOO$— |
| EtOCO— | cyclopentyl | $R_aR_bNCOO$— |
| EtOCO— | phenyl | $R_aR_bNCOO$— |
| ibueCO— | 2-furyl | $R_aR_bNCOO$— |
| ibueCO— | 3-furyl | $R_aR_bNCOO$— |
| ibueCO— | 2-thienyl | $R_aR_bNCOO$— |
| ibueCO— | 3-thienyl | $R_aR_bNCOO$— |
| ibueCO— | 2-pyridyl | $R_aR_bNCOO$— |
| ibueCO— | 3-pyridyl | $R_aR_bNCOO$— |
| ibueCO— | 4-pyridyl | $R_aR_bNCOO$— |
| ibueCO— | isobutenyl | $R_aR_bNCOO$— |
| ibueCO— | isopropyl | $R_aR_bNCOO$— |
| ibueCO— | cyclopropyl | $R_aR_bNCOO$— |
| ibueCO— | cyclobutyl | $R_aR_bNCOO$— |
| ibueCO— | cyclopentyl | $R_aR_bNCOO$— |
| ibueCO— | phenyl | $R_aR_bNCOO$— |
| iBuCO— | 2-furyl | $R_aR_bNCOO$— |
| iBuCO— | 3-furyl | $R_aR_bNCOO$— |
| iBuCO— | 2-thienyl | $R_aR_bNCOO$— |
| iBuCO— | 3-thienyl | $R_aR_bNCOO$— |
| iBuCO— | 2-pyridyl | $R_aR_bNCOO$— |
| iBuCO— | 3-pyridyl | $R_aR_bNCOO$— |
| iBuCO— | 4-pyridyl | $R_aR_bNCOO$— |
| iBuCO— | isobutenyl | $R_aR_bNCOO$— |
| iBuCO— | isopropyl | $R_aR_bNCOO$— |
| iBuCO— | cyclopropyl | $R_aR_bNCOO$— |
| iBuCO— | cyclobutyl | $R_aR_bNCOO$— |
| iBuCO— | cyclopentyl | $R_aR_bNCOO$— |
| iBuCO— | phenyl | $R_aR_bNCOO$— |
| iBuOCO— | 2-furyl | $R_aR_bNCOO$— |
| iBuOCO— | 3-furyl | $R_aR_bNCOO$— |
| iBuOCO— | 2-thienyl | $R_aR_bNCOO$— |
| iBuOCO— | 3-thienyl | $R_aR_bNCOO$— |
| iBuOCO— | 2-pyridyl | $R_aR_bNCOO$— |
| iBuOCO— | 3-pyridyl | $R_aR_bNCOO$— |
| iBuOCO— | 4-pyridyl | $R_aR_bNCOO$— |
| iBuOCO— | isobutenyl | $R_aR_bNCOO$— |
| iBuOCO— | isopropyl | $R_aR_bNCOO$— |
| iBuOCO— | cyclopropyl | $R_aR_bNCOO$— |
| iBuOCO— | cyclobutyl | $R_aR_bNCOO$— |
| iBuOCO— | cyclopentyl | $R_aR_bNCOO$— |
| iBuOCO— | phenyl | $R_aR_bNCOO$— |
| iPrOCO— | 2-furyl | $R_aR_bNCOO$— |

-continued (26)

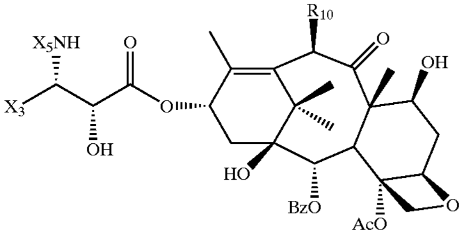

| $X_5$ | $X_3$ | $R_{10}$ |
|---|---|---|
| iPrOCO— | 3-furyl | $R_aR_bNCOO$— |
| iPrOCO— | 2-thienyl | $R_aR_bNCOO$— |
| iPrOCO— | 3-thienyl | $R_aR_bNCOO$— |
| iPrOCO— | 2-oyridyl | $R_aR_bNCOO$— |
| iPrOCO— | 3-pyridyl | $R_aR_bNCOO$— |
| iPrOCO— | 4-pyridyl | $R_aR_bNCOO$— |
| iPrOCO— | isobutenyl | $R_aR_bNCOO$— |
| iPrOCO— | isopropyl | $R_aR_bNCOO$— |
| iPrOCO— | cyclopropyl | $R_aR_bNCOO$— |
| iPrOCO— | cyclobutyl | $R_aR_bNCOO$— |
| iPrOCO— | cyclopentyl | $R_aR_bNCOO$— |
| iPrOCO— | phenyl | $R_aR_bNCOO$— |
| nPrOCO— | 2-furyl | $R_aR_bNCOO$— |
| nPrOCO— | 3-furyl | $R_aR_bNCOO$— |
| nPrOCO— | 2-thienyl | $R_aR_bNCOO$— |
| nPrOCO— | 3-thienyl | $R_aR_bNCOO$— |
| nPrOCO— | 2-pyridyl | $R_aR_bNCOO$— |
| nPrOCO— | 3-pyridyl | $R_aR_bNCOO$— |
| nPrOCO— | 4-pyridyl | $R_aR_bNCOO$— |
| nPrOCO— | isobutenyl | $R_aR_bNCOO$— |
| nPrOCO— | isopropyl | $R_aR_bNCOO$— |
| nPrOCO— | cyclopropyl | $R_aR_bNCOO$— |
| nPrOCO— | cyclobutyl | $R_aR_bNCOO$— |
| nPrOCO— | cyclopentyl | $R_aR_bNCOO$— |
| nPrOCO— | phenyl | $R_aR_bNCOO$— |
| nPrCO— | 2-furyl | $R_aR_bNCOO$— |
| nPrCO— | 3-furyl | $R_aR_bNCOO$— |
| nPrCO— | 2-thienyl | $R_aR_bNCOO$— |
| nPrCO— | 3-thienyl | $R_aR_bNCOO$— |
| nPrCO— | 2-pyridyl | $R_aR_bNCOO$— |
| nPrCO— | 3-pyridyl | $R_aR_bNCOO$— |
| nPrCO— | 4-pyridyl | $R_aR_bNCOO$— |
| nPrCO— | isobutenyl | $R_aR_bNCOO$— |
| nPrCO— | isopropyl | $R_aR_bNCOO$— |
| nPrCO— | cyclopropyl | $R_aR_bNCOO$— |
| nPrCO— | cyclobutyl | $R_aR_bNCOO$— |
| nPrCO— | cyclopentyl | $R_aR_bNCOO$— |
| nPrCO— | phenyl | $R_aR_bNCOO$— |

EXAMPLE 40

Additional Taxanes having C-10 Carbamoyloxy and C-7 Hydroxy Substituents

Following the processes described in Example 36 and elsewhere herein, the following specific taxanes having structural formula (27) may be prepared, wherein $R_7$ is hydroxy and $R_{10}$ in each of the series (that is, each of series "A" through "K") is as previously defined, including wherein $R_{10}$ is $R_{10a}R_{10b}NCOO$— and one of $R_{10a}$ and $R_{10b}$ is hydrogen and the other is (i) substituted or unsubstituted $C_1$ to $C_8$ alkyl such as methyl, ethyl, or straight, branched or cyclic propyl, butyl, pentyl, or hexyl; (ii) substituted or unsubstituted $C_2$ to $C_8$ alkenyl such as ethenyl or straight, branched or cyclic propenyl, butenyl, pentenyl or hexenyl; (iii) substituted or unsubstituted $C_2$ to $C_8$ alkynyl such as ethynyl or straight or branched propynyl, butynyl, pentynyl, or hexynyl; (iv) phenyl or substituted phenyl such as nitro, alkoxy or halosubstituted phenyl, or (v) substituted or unsubstituted heteroaromatic such as furyl, thienyl, or pyridyl. The substituents may be those identified elsewhere herein for substituted hydrocarbyl. In one embodiment, preferred $R_{10}$ substituents include $R_{10a}R_{10b}NCOO$— wherein one of $R_{10a}$ and $R_{10b}$ is hydrogen and the other is methyl, ethyl, or straight, branched or cyclic propyl. In another embodiment, preferred $R_{10}$ substituents include $R_{10a}R_{10b}NCOO$— wherein one of $R_{10a}$ and $R_{10b}$ is hydrogen and the other is substituted methyl, ethyl, or straight, branched or cyclic propyl.

In the "A" series of compounds, $X_{10}$ is as otherwise as defined herein. Preferably, heterocyclo is substituted or unsubstitued furyl, thienyl, or pyridyl, $X_{10}$ is substituted or unsubstitued furyl, thienyl, pyridyl, phenyl, or lower alkyl (e.g., tert-butyl), and $R_7$ and $R_{10}$ each have the beta stereochemical configuration.

In the "B" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "C" series of compounds, $X_{10}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{9a}$ is preferably substituted or unsubstitued furyl, thienyl, pyridyl, phenyl, or lower alkyl, and $R_7$, $R_9$ and $R_{10}$ each have the beta stereochemical configuration.

In the "D" and "E" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), and $R_7$, $R_9$ (series D only) and $R_{10}$ each have the beta stereochemical configuration.

In the "F" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "G" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "H" series of compounds, $X_{10}$ is as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "I" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$ and $R_{10}$ each have the beta stereochemical configuration.

In the "J" series of compounds, $X_{10}$ and $R_{2a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

In the "K" series of compounds, $X_{10}$, $R_{2a}$ and $R_{9a}$ are as otherwise as defined herein. Preferably, heterocyclo is preferably substituted or unsubstitued furyl, thienyl, or pyridyl, $X_{10}$ is preferably substituted or unsubstitued furyl, thienyl, pyridyl, phenyl, or lower alkyl (e.g., tert-butyl), $R_{2a}$ is preferably substituted or unsubstitued furyl, thienyl, pyridyl, phenyl, or lower alkyl, and $R_7$, $R_9$ and $R_{10}$ each have the beta stereochemical configuration.

Any substituents of each of $X_3$, $X_5$, $R_2$, $R_7$, and $R_9$ may be hydrocarbyl or any of the heteroatom containing substituents selected from the group consisting of heterocyclo, alkoxy, alkenoxy, alkynoxy, aryloxy, hydroxy, protected hydroxy, keto, acyloxy, nitro, amino, amido, thiol, ketal, acetal, ester and ether moieties, but not phosphorous containing moieties.

(27)

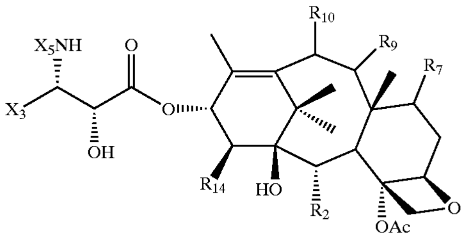

| Series | $X_5$ | $X_3$ | $R_{10}$ | $R_2$ | $R_9$ | $R_{14}$ |
|---|---|---|---|---|---|---|
| A1 | —$COOX_{10}$ | heterocyclo | $R_{10a}R_{10b}NCOO$— | $C_6H_5COO$— | O | H |
| A2 | —$COX_{10}$ | heterocyclo | $R_{10a}R_{10b}NCOO$— | $C_6H_5COO$— | O | H |
| A3 | —$CONHX_{10}$ | heterocyclo | $R_{10a}R_{10b}NCOO$— | $C_6H_5COO$— | O | H |

-continued (27)

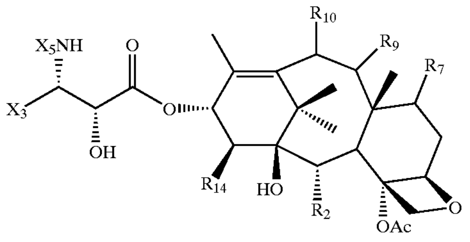

| Series | $X_5$ | $X_3$ | $R_{10}$ | $R_2$ | $R_9$ | $R_{14}$ |
|---|---|---|---|---|---|---|
| A4 | $—COOX_{10}$ | optionally substituted $C_2$ to $C_8$ alkyl | $R_{10a}R_{10b}NCOO—$ | $C_6H_5COO—$ | O | H |
| A5 | $—COX_{10}$ | optionally substituted $C_2$ to $C_8$ alkyl | $R_{10a}R_{10b}NCOO—$ | $C_6H_5COO—$ | O | H |
| A6 | $—CONHX_{10}$ | optionally substituted $C_2$ to $C_8$ alkyl | $R_{10a}R_{10b}NCOO—$ | $C_6H_5COO—$ | O | H |
| A7 | $—COOX_{10}$ | optionally substituted $C_2$ to $C_8$ alkenyl | $R_{10a}R_{10b}NCOO—$ | $C_6H_5COO—$ | O | H |
| A8 | $—COX_{10}$ | optionally substituted $C_2$to $C_8$ alkenyl | $R_{10a}R_{10b}NCOO—$ | $C_6H_5COO—$ | O | H |
| A9 | $—CONHX_{10}$ | optionally substituted $C_2$to $C_8$ alkenyl | $R_{10a}R_{10b}NCOO—$ | $C_6H_5COO—$ | O | H |
| A10 | $—COOX_{10}$ | optionally substituted $C_2$ to $C_8$ alkynyl | $R_{10a}R_{10b}NCOO—$ | $C_6H_5COO—$ | O | H |
| A11 | $—COX_{10}$ | optionally substituted $C_2$to $C_8$ alkynyl | $R_{10a}R_{10b}NCOO—$ | $C_6H_5COO—$ | O | H |
| A12 | $—CONHX_{10}$ | optionally substituted $C_2$ to $C_8$ alkynyl | $R_{10a}R_{10b}NCOO—$ | $C_6H_5COO—$ | O | H |
| B1 | $—COOX_{10}$ | heterocyclo | $R_{10a}R_{10b}NCOO—$ | $R_{2a}COO—$ | O | H |
| B2 | $—COX_{10}$ | heterocyclo | $R_{10a}R_{10b}NCOO—$ | $R_{2a}COO—$ | O | H |
| B3 | $—CONHX_{10}$ | heterocyclo | $R_{10a}R_{10b}NCOO—$ | $R_{2a}COO—$ | O | H |
| B4 | $—COOX_{10}$ | optionally substituted $C_2$ to $C_8$ alkyl | $R_{10a}R_{10b}NCOO—$ | $R_{2a}COO—$ | O | H |
| B5 | $—COX_{10}$ | optionally substituted $C_2$ to $C_8$ alkyl | $R_{10a}R_{10b}NCOO—$ | $R_{2a}COO—$ | O | H |
| B6 | $—CONHX_{10}$ | optionally substituted $C_2$ to $C_8$ alkyl | $R_{10a}R_{10b}NCOO—$ | $R_{2a}COO—$ | O | H |
| B7 | $—COOX_{10}$ | optionally substituted $C_2$ to $C_8$ alkenyl | $R_{10a}R_{10b}NCOO—$ | $R_{2a}COO—$ | O | H |
| B8 | $—COX_{10}$ | optionally substituted $C_2$ to $C_8$ alkenyl | $R_{10a}R_{10b}NCOO—$ | $R_{2a}COO—$ | O | H |
| B9 | $—CONHX_{10}$ | optionally substituted $C_2$ to $C_8$ alkenyl | $R_{10a}R_{10b}NCOO—$ | $R_{2a}COO—$ | O | H |
| B10 | $—COOX_{10}$ | optionally substituted $C_2$ to $C_8$ alkynyl | $R_{10a}R_{10b}NCOO—$ | $R_{2a}COO—$ | O | H |

-continued (27)

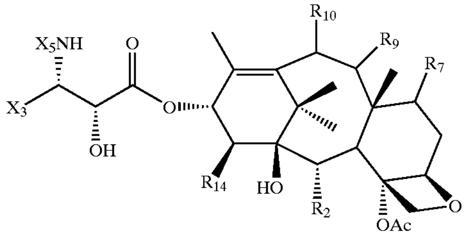

| Series | $X_5$ | $X_3$ | $R_{10}$ | $R_2$ | $R_9$ | $R_{14}$ |
|---|---|---|---|---|---|---|
| B11 | —$COX_{10}$ | optionally substituted $C_2$ to $C_8$ alkynyl | $R_{10a}R_{10b}NCOO$— | $R_{2a}COO$— | O | H |
| B12 | —$CONHX_{10}$ | optionally substituted $C_2$ to $C_8$ alkynyl | $R_{10a}R_{10b}NCOO$— | $C_{2a}COO$— | O | H |
| C1 | —$COOX_{10}$ | heterocyclo | $R_{10a}R_{10b}NCOO$— | $C_6H_5COO$— | $R_{9a}COO$— | H |
| C2 | —$COX_{10}$ | heterocyclo | $R_{10a}R_{10b}NCOO$— | $C_6H_5COO$— | $R_{9a}COO$— | H |
| C3 | —$CONHX_{10}$ | heterocyclo | $R_{10a}R_{10b}NCOO$— | $C_6H_5COO$— | $R_{9a}COO$— | H |
| C4 | —$COOX_{10}$ | optionally substituted $C_2$ to $C_8$ alkyl | $R_{10a}R_{10b}NCOO$— | $C_6H_5COO$— | $R_{9a}COO$— | H |
| C5 | —$COX_{10}$ | optionally substituted $C_2$ to $C_8$ alkyl | $R_{10a}R_{10b}NCOO$— | $C_6H_5COO$— | $R_{9a}COO$— | H |
| C6 | —$CONHX_{10}$ | optionally substituted $C_2$ to $C_8$ alkyl | $R_{10a}R_{10b}NCOO$— | $C_6H_5COO$— | $R_{9a}COO$— | H |
| C7 | —$COOX_{10}$ | optionally substituted $C_2$ to $C_8$ alkenyl | $R_{10a}R_{10b}NCOO$— | $C_6H_5COO$— | $R_{9a}COO$— | H |
| C8 | —$COX_{10}$ | optionally substituted $C_2$ to $C_8$ alkenyl | $R_{10a}R_{10b}NCOO$— | $C_6H_5COO$— | $R_{9a}COO$— | H |
| C9 | —$CONHX_{10}$ | optionally substituted $C_2$ to $C_8$ alkenyl | $R_{10a}R_{10b}NCOO$— | $C_6H_5COO$— | $R_{9a}COO$— | H |
| C10 | —$COOX_{10}$ | optionally substituted $C_2$ to $C_8$ alkynyl | $R_{10a}R_{10b}NCOO$— | $C_6H_5COO$— | $R_{9a}COO$— | H |
| C11 | —$COX_{10}$ | optionally substituted $C_2$ to $C_8$ alkynyl | $R_{10a}R_{10b}NCOO$— | $C_6H_5COO$— | $R_{9a}COO$— | H |
| C12 | —$CONHX_{10}$ | optionally substituted $C_2$ to $C_8$ alkynyl | $R_{10a}R_{10b}NCOO$— | $C_6H_5COO$— | $R_{9a}COO$— | H |
| D1 | —$COOX_{10}$ | heterocyclo | $R_{10a}R_{10b}NCOO$— | $C_6H_5COO$— | OH | H |
| D2 | —$COX_{10}$ | heterocyclo | $R_{10a}R_{10b}NCOO$— | $C_6H_5COO$— | OH | H |
| D3 | —$CONHX_{10}$ | heterocyclo | $R_{10a}R_{10b}NCOO$— | $C_6H_5COO$— | OH | H |
| D4 | —$COOX_{10}$ | optionally substituted $C_2$ to $C_8$ alkyl | $R_{10a}R_{10b}NCOO$— | $C_6H_5COO$— | OH | H |
| D5 | —$COX_{10}$ | optionally substituted $C_2$ to $C_6$ alkyl | $R_{10a}R_{10b}NCOO$— | $C_6H_5COO$— | OH | H |
| D6 | —$CONHX_{10}$ | optionally substituted $C_2$ to $C_8$ alkyl | $R_{10a}R_{10b}NCOO$— | $C_6H_5COO$— | OH | H |
| D7 | —$COOX_{10}$ | optionally substituted $C_2$ to $C_8$ alkenyl | $R_{10a}R_{10b}NCOO$— | $C_6H_5COO$— | OH | H |

-continued (27)

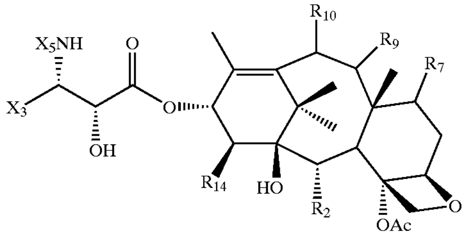

| Series | $X_5$ | $X_3$ | $R_{10}$ | $R_2$ | $R_9$ | $R_{14}$ |
|---|---|---|---|---|---|---|
| D8 | $—COX_{10}$ | optionally substituted $C_2$ to $C_8$ alkenyl | $R_{10a}R_{10b}NCOO—$ | $C_6H_5COO—$ | OH | H |
| D9 | $—CONHX_{10}$ | optionally substituted $C_2$to $C_8$ alkenyl | $R_{10a}R_{10b}NCOO—$ | $C_6H_5COO—$ | OH | H |
| D10 | $—COOX_{10}$ | optionally substituted $C_2$ to $C_8$ alkynyl | $R_{10a}R_{10b}NCOO—$ | $C_6H_5COO—$ | OH | H |
| D11 | $—COX_{10}$ | optionally substituted $C_2$ to $C_8$ alkynyl | $R_{10a}R_{10b}NCOO—$ | $C_6H_5COO—$ | OH | H |
| D12 | $—CONHX_{10}$ | optionally substituted $C_2$ to $C_8$ alkynyl | $R_{10a}R_{10b}NCOO—$ | $C_6H_5COO—$ | OH | H |
| E1 | $—COOX_{10}$ | heterocyclo | $R_{10a}R_{10b}NCOO—$ | $C_6H_5COO—$ | O | OH |
| E2 | $—COX_{10}$ | heterocyclo | $R_{10a}R_{10b}NCOO—$ | $C_6H_5COO—$ | O | OH |
| E3 | $—CONHX_{10}$ | heterocyclo | $R_{10a}R_{10b}NCOO—$ | $C_6H_5COO—$ | O | OH |
| E4 | $—COOX_{10}$ | optionally substituted $C_2$ to $C_8$ alkyl | $R_{10a}R_{10b}NCOO—$ | $C_6H_5COO—$ | O | OH |
| E5 | $—COX_{10}$ | optionally substituted $C_2$ to $C_8$ alkyl | $R_{10a}R_{10b}NCOO—$ | $C_6H_5COO—$ | O | OH |
| E6 | $—CONHX_{10}$ | optionally substituted $C_2$ to $C_8$ alkyl | $R_{10a}R_{10b}NCOO—$ | $C_6H_5COO—$ | O | OH |
| E7 | $—COOX_{10}$ | optionally substituted $C_2$ to $C_8$ alkenyl | $R_{10a}R_{10b}NCOO—$ | $C_6H_5COO—$ | O | OH |
| E8 | $—COX_{10}$ | optionally substituted $C_2$ to $C_8$ alkenyl | $R_{10a}R_{10b}NCOO—$ | $C_6H_5COO—$ | O | OH |
| E9 | $—CONHX_{10}$ | optionally substituted $C_2$ to $C_8$ alkenyl | $R_{10a}R_{10b}NCOO—$ | $C_6H_5COO—$ | O | OH |
| E10 | $—COOX_{10}$ | optionally substituted $C_2$ to $C_8$ alkynyl | $R_{10a}R_{10b}NCOO—$ | $C_6H_5COO—$ | O | OH |
| E11 | $—COX_{10}$ | optionally substituted $C_2$ to $C_8$ alkynyl | $R_{10a}R_{10b}NCOO—$ | $C_6H_5COO—$ | O | OH |
| E12 | $—CONHX_{10}$ | optionally substituted $C_2$ to $C_8$ alkynyl | $R_{10a}R_{10b}NCOO—$ | $C_6H_5COO—$ | O | OH |
| F1 | $—COOX_{10}$ | heterocyclo | $R_{10a}R_{10b}NCOO—$ | $R_{2a}COO—$ | $R_{9a}COO—$ | H |
| F2 | $—COX_{10}$ | heterocyclo | $R_{10a}R_{10b}NCOO—$ | $R_{2a}COO—$ | $R_{9a}COO—$ | H |
| F3 | $—CONHX_{10}$ | heterocyclo | $R_{10a}R_{10b}NCOO—$ | $R_{2a}COO—$ | $R_{9a}COO—$ | H |
| F4 | $—COOX_{10}$ | optionally substituted $C_2$ to $C_8$ alkyl | $R_{10a}R_{10b}NCOO—$ | $R_{2a}COO—$ | $R_{9a}COO—$ | H |
| F5 | $—COX_{10}$ | optionally substituted $C_2$ to $C_8$ alkyl | $R_{10a}R_{10b}NCOO—$ | $R_{2a}COO—$ | $R_{9a}COO—$ | H |

-continued (27)

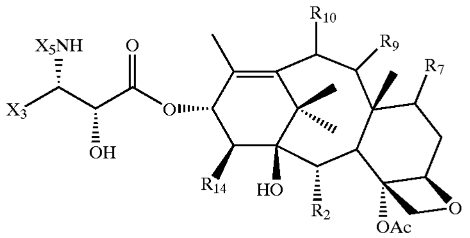

| Series | $X_5$ | $X_3$ | $R_{10}$ | $R_2$ | $R_9$ | $R_{14}$ |
|---|---|---|---|---|---|---|
| F6 | —$CONHX_{10}$ | optionally substituted $C_2$ to $C_8$ alkyl | $R_{10a}R_{10b}NCOO$— | $R_{2a}COO$— | $R_{9a}COO$— | H |
| F7 | —$COOX_{10}$ | optionally substituted $C_2$ to $C_8$ alkenyl | $R_{10a}R_{10b}NCOO$— | $R_{2a}COO$— | $R_{9a}COO$— | H |
| F8 | —$COX_{10}$ | optionally substituted $C_2$ to $C_8$ alkenyl | $R_{10a}R_{10b}NCOO$— | $R_{2a}COO$— | $R_{9a}COO$— | H |
| F9 | —$CONHX_{10}$ | optionally substituted $C_2$ to $C_8$ alkenyl | $R_{10a}R_{10b}NCOO$— | $R_{2a}COO$— | $R_{9a}COO$— | H |
| F10 | —$COOX_{10}$ | optionally substituted $C_2$ to $C_8$ alkynyl | $R_{10a}R_{10b}NCOO$— | $R_{2a}COO$— | $R_{9a}COO$— | H |
| F11 | —$COX_{10}$ | optionally substituted $C_2$ to $C_8$ alkynyl | $R_{10a}R_{10b}NCOO$— | $R_{2a}COO$— | $R_{9a}COO$— | H |
| F12 | —$CONHX_{10}$ | optionally substituted $C_2$ to $C_8$ alkynyl | $R_{10a}R_{10b}NCOO$— | $R_{2a}COO$— | $R_{9a}COO$— | H |
| G1 | —$COOX_{10}$ | heterocyclo | $R_{10a}R_{10b}NCOO$— | $R_{2a}COO$— | OH | H |
| G2 | —$COX_{10}$ | heterocyclo | $R_{10a}R_{10b}NCOO$— | $R_{2a}COO$— | OH | H |
| G3 | —$CONHX_{10}$ | heterocyclo | $R_{10a}R_{10b}NCOO$— | $R_{2a}COO$— | OH | H |
| G4 | —$COOX_{10}$ | optionally substituted $C_2$ to $C_8$ alkyl | $R_{10a}R_{10b}NCOO$— | $R_{2a}COO$— | OH | H |
| G5 | —$COX_{10}$ | optionally substituted $C_2$ to $C_8$ alkyl | $R_{10a}R_{10b}NCOO$— | $R_{2a}COO$— | OH | H |
| G6 | —$CONHX_{10}$ | optionally substituted $C_2$ to $C_8$ alkyl | $R_{10a}R_{10b}NCOO$— | $R_{2a}COO$— | OH | H |
| G7 | —$COOX_{10}$ | optionally substituted $C_2$ to $C_8$ alkenyl | $R_{10a}R_{10b}NCOO$— | $R_{2a}COO$— | OH | H |
| G8 | —$COX_{10}$ | optionally substituted $C_2$ to $C_8$ alkenyl | $R_{10a}R_{10b}NCOO$— | $R_{2a}COO$— | OH | H |
| G9 | —$CONHX_{10}$ | optionally substituted $C_2$ to $C_8$ alkenyl | $R_{10a}R_{10b}NCOO$— | $R_{2a}COO$— | OH | H |
| G10 | —$COOX_{10}$ | optionally substituted $C_2$ to $C_8$ alkynyl | $R_{10a}R_{10b}NCOO$— | $R_{2a}COO$— | OH | H |
| G11 | —$COX_{10}$ | optionally substituted $C_2$ to $C_8$ alkynyl | $R_{10a}R_{10b}NCOO$— | $R_{2a}COO$— | OH | H |
| G12 | —$CONHX_{10}$ | optionally substituted $C_2$ to $C_8$ alkynyl | $R_{10a}R_{10b}NCOO$— | $R_{2a}COO$— | OH | H |

-continued (27)

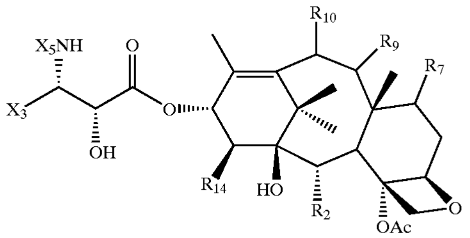

| Series | $X_5$ | $X_3$ | $R_{10}$ | $R_2$ | $R_9$ | $R_{14}$ |
|---|---|---|---|---|---|---|
| H1 | —$COOX_{10}$ | heterocyclo | $R_{10a}R_{10b}NCOO$— | $C_6H_5COO$— | OH | OH |
| H2 | —$COX_{10}$ | heterocyclo | $R_{10a}R_{10b}NCOO$— | $C_6H_5COO$— | OH | OH |
| H3 | —$CONHX_{10}$ | heterocyclo | $R_{10a}R_{10b}NCOO$— | $C_6H_5COO$— | OH | OH |
| H4 | —$COOX_{10}$ | optionally substituted $C_2$ to $C_8$ alkyl | $R_{10a}R_{10b}NCOO$— | $C_6H_5COO$— | OH | OH |
| H5 | —$COX_{10}$ | optionally substituted $C_2$ to $C_8$ alkyl | $R_{10a}R_{10b}NCOO$— | $C_6H_5COO$— | OH | OH |
| H6 | —$CONHX_{10}$ | optionally substituted $C_2$ to $C_8$ alkyl | $R_{10a}R_{10b}NCOO$— | $C_6H_5COO$— | OH | OH |
| H7 | —$COOX_{10}$ | optionally substituted $C_2$ to $C_8$ alkenyl | $R_{10a}R_{10b}NCOO$— | $C_6H_5COO$— | OH | OH |
| H8 | —$COX_{10}$ | optionally substituted $C_2$ to $C_8$ alkenyl | $R_{10a}R_{10b}NCOO$— | $C_6H_5COO$— | OH | OH |
| H9 | —$CONHX_{10}$ | optionally substituted $C_2$ to $C_8$ alkenyl | $R_{10a}R_{10b}NCOO$— | $C_6H_5COO$— | OH | OH |
| H10 | —$COOX_{10}$ | optionally substituted $C_2$ to $C_8$ alkynyl | $R_{10a}R_{10b}NCOO$— | $C_6H_5COO$— | OH | OH |
| H11 | —$COX_{10}$ | optionally substituted $C_2$ to $C_8$ alkynyl | $R_{10a}R_{10b}NCOO$— | $C_6H_5COO$— | OH | OH |
| H12 | —$CONHX_{10}$ | optionally substituted $C_2$ to $C_8$ alkynyl | $R_{10a}R_{10b}NCOO$— | $C_6H_5COO$— | OH | OH |
| I1 | —$COOX_{10}$ | heterocyclo | $R_{10a}R_{10b}NCOO$— | $R_{2a}COO$— | O | OH |
| I2 | —$COX_{10}$ | heterocyclo | $R_{10a}R_{10b}NCOO$— | $R_{2a}COO$— | O | OH |
| I3 | —$CONHX_{10}$ | heterocyclo | $R_{10a}R_{10b}NCOO$— | $R_{2a}COO$— | O | OH |
| I4 | —$COOX_{10}$ | optionally substituted $C_2$ to $C_8$ alkyl | $R_{10a}R_{10b}NCOO$— | $R_{2a}COO$— | O | OH |
| I5 | —$COX_{10}$ | optionally substituted $C_2$ to $C_8$ alkyl | $R_{10a}R_{10b}NCOO$— | $R_{2a}COO$— | O | OH |
| I6 | —$CONHX_{10}$ | optionally substituted $C_2$ to $C_8$ alkyl | $R_{10a}R_{10b}NCOO$— | $R_{2a}COO$— | O | OH |
| I7 | —$COOX_{10}$ | optionally substituted $C_2$ to $C_8$ alkenyl | $R_{10a}R_{10b}NCOO$— | $R_{2a}COO$— | O | OH |
| I8 | —$COX_{10}$ | optionally substituted $C_2$ to $C_8$ alkenyl | $R_{10a}R_{10b}NCOO$— | $R_{2a}COO$— | O | OH |
| I9 | —$CONHX_{10}$ | optionally substituted $C_2$ to $C_8$ alkenyl | $R_{10a}R_{10b}NCOO$— | $R_{2a}COO$— | O | OH |

-continued (27)

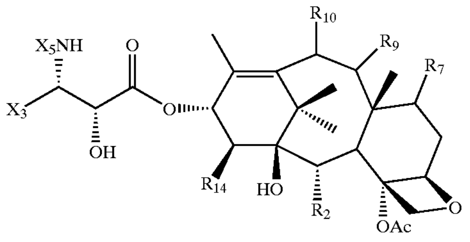

| Series | $X_5$ | $X_3$ | $R_{10}$ | $R_2$ | $R_9$ | $R_{14}$ |
|---|---|---|---|---|---|---|
| I10 | —$COOX_{10}$ | optionally substituted $C_2$ to $C_8$ alkynyl | $R_{10a}R_{10b}NCOO$— | $R_{2a}COO$— | O | OH |
| I11 | —$COX_{10}$ | optionally substituted $C_2$ to $C_8$ alkynyl | $R_{10a}R_{10b}NCOO$— | $R_{2a}COO$— | O | OH |
| I12 | —$CONHX_{10}$ | optionally substituted $C_2$ to $C_8$ alkynyl | $R_{10a}R_{10b}NCOO$— | $R_{2a}COO$— | O | OH |
| J1 | —$COOX_{10}$ | heterocyclo | $R_{10a}R_{10b}NCOO$— | $R_{2a}COO$— | OH | OH |
| J2 | —$COX_{10}$ | heterocyclo | $R_{10a}R_{10b}NCOO$— | $R_{2a}COO$— | OH | OH |
| J3 | —$CONHX_{10}$ | heterocyclo | $R_{10a}R_{10b}NCOO$— | $R_{2a}COO$— | OH | OH |
| J4 | —$COOX_{10}$ | optionally substituted $C_2$ to $C_8$ alkyl | $R_{10a}R_{10b}NCOO$— | $R_{2a}COO$— | OH | OH |
| J5 | —$COX_{10}$ | optionally substituted $C_2$ to $C_8$ alkyl | $R_{10a}R_{10b}NCOO$— | $R_{2a}COO$— | OH | OH |
| J6 | —$CONHX_{10}$ | optionally substituted $C_2$ to $C_8$ alkyl | $R_{10a}R_{10b}NCOO$— | $R_{2a}COO$— | OH | OH |
| J7 | —$COOX_{10}$ | optionally substituted $C_2$ to $C_8$ alkenyl | $R_{10a}R_{10b}NCOO$— | $R_{2a}COO$— | OH | OH |
| J8 | —$COX_{10}$ | optionally substituted $C_2$ to $C_8$ alkenyl | $R_{10a}R_{10b}NCOO$— | $R_{2a}COO$— | OH | OH |
| J9 | —$CONHX_{10}$ | optionally substituted $C_2$ to $C_8$ alkenyl | $R_{10a}R_{10b}NCOO$— | $R_{2a}COO$— | OH | OH |
| J10 | —$COOX_{10}$ | optionally substituted $C_2$ to $C_8$ alkynyl | $R_{10a}R_{10b}NCOO$— | $R_{2a}COO$— | OH | OH |
| J11 | —$COX_{10}$ | optionally substituted $C_2$ to $C_8$ alkynyl | $R_{10a}R_{10b}NCOO$— | $R_{2a}COO$— | OH | OH |
| J12 | —$CONHX_{10}$ | optionally substituted $C_2$ to $C_8$ alkynyl | $R_{10a}R_{10b}NCOO$— | $R_{2a}COO$— | OH | OH |
| K1 | —$COOX_{10}$ | heterocyclo | $R_{10a}R_{10b}NCOO$— | $R_{2a}COO$— | $R_{2a}COO$— | OH |
| K2 | —$COX_{10}$ | heterocyclo | $R_{10a}R_{10b}NCOO$— | $R_{2a}COO$— | $R_{2a}COO$— | OH |
| K3 | —$CONHX_{10}$ | heterocyclo | $R_{10a}R_{10b}NCOO$— | $R_{2a}COO$— | $R_{2a}COO$— | OH |
| K4 | —$COOX_{10}$ | optionally substituted $C_2$ to $C_8$ alkyl | $R_{10a}R_{10b}NCOO$— | $R_{2a}COO$— | $R_{2a}COO$— | OH |
| K5 | —$COX_{10}$ | optionally substituted $C_2$ to $C_8$ alkyl | $R_{10a}R_{10b}NCOO$— | $R_{2a}COO$— | $R_{2a}COO$— | OH |
| K6 | —$CONHX_{10}$ | optionally substituted $C_2$ to $C_8$ alkyl | $R_{10a}R_{10b}NCOO$— | $R_{2a}COO$— | $R_{2a}COO$— | OH |

-continued (27)

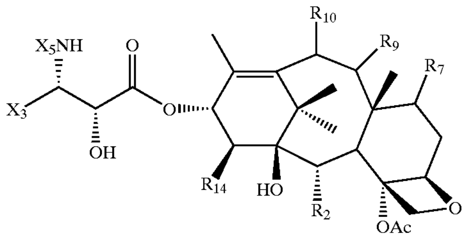

| Series | $X_5$ | $X_3$ | $R_{10}$ | $R_2$ | $R_9$ | $R_{14}$ |
|---|---|---|---|---|---|---|
| K7 | —$COOX_{10}$ | optionally substituted $C_2$ to $C_8$ alkenyl | $R_{10a}R_{10b}NCOO$— | $R_{2a}COO$— | $R_{2a}COO$— | OH |
| K8 | —$COX_{10}$ | optionally substituted $C_2$ to $C_8$ alkenyl | $R_{10a}R_{10b}NCOO$— | $R_{2a}COO$— | $R_{2a}COO$— | OH |
| K9 | —$CONHX_{10}$ | optionally substituted $C_2$ to $C_8$ alkenyl | $R_{10a}R_{10b}NCOO$— | $R_{2a}COO$— | $R_{2a}COO$— | OH |
| K10 | —$COOX_{10}$ | optionally substituted $C_2$ to $C_8$ alkynyl | $R_{10a}R_{10b}NCOO$— | $R_{2a}COO$— | $R_{2a}COO$— | OH |
| K11 | —$COX_{10}$ | optionally substituted $C_2$ to $C_8$ alkynyl | $R_{10a}R_{10b}NCOO$— | $R_{2a}COO$— | $R_{2a}COO$— | OH |
| K12 | —$CONHX_{10}$ | optionally substituted $C_2$ to $C_8$ alkynyl | $R_{10a}R_{10b}NCOO$— | $R_{2a}COO$— | $R_{2a}COO$— | OH |

EXAMPLE 41

In Vitro cytotoxicity measured by the cell colony formation assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a $CO_2$ incubator at 37° C. for 5 h for attachment to the bottom of Petri dishes. The compounds identified in Example 37 were made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of ID50 (the drug concentration producing 50% inhibition of colony formation) were determined for each tested compound.

| Compound | IN VITRO ID 50 (nm) HCT116 |
|---|---|
| taxol | 2.1 |
| docetaxel | 0.6 |
| 2600 | <1 |
| 2616 | 27 |
| 2622 | <1 |
| 2633 | <10 |
| 2686 | <1 |
| 2692 | <1 |
| 2700 | <1 |
| 2717 | <1 |
| 2722 | <1 |
| 2733 | <10 |
| 2757 | <1 |
| 2640 | <1 |
| 2743 | <1 |
| 6015 | <10 |
| 6024 | <1 |
| 6072 | <1 |

EXAMPLE 42

Preparation of Solutions for Oral Administration

Solution 1: Antitumor compound 1393 was dissolved in ethanol to form a solution containing 140 mg of the compound per ml of solution. An equal volume of Cremophor® EL solution was added to the solution while stirring to form a solution containing 70 mg of compound 1393 per ml. This solution was diluted using 9 parts by weight of saline to form a pharmaceutically acceptable solution for administration to a patient.

Solution 2: Antitumor compound 1458 was dissolved in ethanol to form a solution containing 310 mg of the compound per ml of solution. An equal volume of Cremophor® EL solution was added to the solution while stirring to form a solution containing 155 mg of compound 1458 per ml. This solution was diluted using 9 parts by weight of saline to form a pharmaceutically acceptable solution for administration to a patient.

Solution 3: Antitumor compound 1351 was dissolved in ethanol to form a solution containing 145 mg of the compound per ml of solution. An equal volume of Cremophor® EL solution was added to the solution while stirring to form a solution containing 72.5 mg of compound 1351 per ml. This solution was diluted using 9 parts by weight of saline to form a pharmaceutically acceptable solution for administration to a patient.

Solution 4: Antitumor compound 4017 was dissolved in ethanol to form a solution containing 214 mg of the compound per ml of solution. An equal volume of Cremophor® EL solution was added to the solution while stirring to form a solution containing 107 mg of compound 4017 per ml. This solution was diluted using 9 parts by weight of saline to form a pharmaceutically acceptable solution for administration to a patient.

Solution 5: Antitumor compound 1393 was dissolved in 100% ethanol then mixed with an equal volume of Cremophor® EL solution to form a solution containing 70 mg of compound 1393 per ml. This solution was diluted using 9 parts by weight of D % W (an aqueous solution containing 5% weight by volume of dextrose) or 0.9% saline to form a pharmaceutically acceptable solution for administration to a patient.

Solution 6: Antitumor compound 1771 was dissolved in ethanol to form a solution containing 145 mg of the compound per ml of solution. An equal volume of Cremophor® EL solution was added to the solution while stirring to form a solution containing 72.5 mg of compound 1771 per ml of solution. This solution was diluted using 9 parts by weight of saline to form a pharmaceutically acceptable solution for administration to a patient.

Solution 7: Antitumor compound 1781 was dissolved in ethanol to form a solution containing 98 mg of the compound per ml of solution. An equal volume of Cremophor® EL was added to the solution while stirring to form an solution containing 49 mg of compound 1781 per ml of solution. This solution was diluted using 9 parts by weight of saline to form a pharmaceutically acceptable solution for administration to a patient.

Solution 8: Antitumor compound 0499 was dissolved in ethanol to form a solution containing 106 mg of the compound per ml of solution. An equal volume of Cremophor® EL solution was added to the solution while stirring to form a solution containing 53 mg of compound 0499 per ml of solution. This solution was diluted using 9 parts by weight of saline to form a pharmaceutically acceptable solution for administration to a patient.

Solution 9: Antitumor compound 0550 was dissolved in ethanol to form a solution containing 140 mg of the compound per ml of solution. An equal volume of Cremophor® EL solution was added to the solution while stirring to form a solution containing 70 mg of compound 0550 per ml of solution. This solution was diluted using 9 parts by weight of saline to form a pharmaceutically acceptable solution for administration to a patient.

Solution 10: Antitumor compound 0611 was dissolved in ethanol to form a solution containing 150 mg of the compound per ml of solution. An equal volume of Cremophor® EL solution was added to the solution while stirring to form a solution containing 75 mg of compound 0611 per ml of solution. This solution was diluted using 9 parts by weight of saline to form a pharmaceutically acceptable solution for administration to a patient.

Solution 11: Antitumor compound 0748 was dissolved in ethanol to form a solution containing 266 mg of the compound per ml of solution. An equal volume of Cremophor® EL solution was added to the solution while stirring to form a solution containing 133 mg of compound 0748 per ml of solution. This solution was diluted using 9 parts by weight of saline to form a pharmaceutically acceptable solution for administration to a patient.

EXAMPLE 43

Preparation of a Suspension Containing Compound 1393 for Oral Administration An oral composition of antitumor compound 1393 was prepared by suspending 25 mg of compound 1393 as a fine powder in one ml of carrier containing 1% carboxymethylcellulose (CMC) in deionized water.

EXAMPLE 44

Preparation of a Tablet Containing Compound 1393 for Oral Administration

Antitumor compound 1393 (100 mg) was dissolved in methylene chloride (2 ml) and Cremophor® EL solution (100mg) was added. The methylene chloride was evaporated under vacuum to form a glass. Microcrystalline cellulose (600 mg) was added to the glass and mixed to form a powder which can be processed to form a tablet.

EXAMPLE 45

Preparation of Emulsions Containing Compound 1393 for Parenteral Administration Emulsion 1: Antitumor compound 1393 was dissolved in 100% ethanol to form a solution containing 40 mg of compound 1393 per ml of the solution. The solution was then diluted with 19 parts by weight of Liposyn® II (20%) with stirring to form an emulsion containing 2 mg of compound 1393 per ml for parenteral administration.

Emulsion 2: Antitumor compound 1393 was dissolved in 100% ethanol to form a solution containing 40 mg of compound 1393 per ml of the solution. The solution was then diluted with 19 parts by weight of Liposyn® III (2%) with stirring to form an emulsion containing 2 mg of compound 1393 per ml for parenteral administration.

Emulsion 3: Antitumor compound 1393 was dissolved in 100% ethanol to form a solution containing mg of compound 1393 per ml of the solution. The solution was then diluted with 9 parts by weight of Liposyn® III (2%) with stirring to form an emulsion containing 4 mg of compound 1393 per ml for parenteral administration.

Example 46

Preparation of Solutions Containing Compound 1393 for Parenteral Administration Solution 1: Antitumor compound 1393 was dissolved in 100% ethanol to form a solution containing 140 mg of compound 1393 per ml. The solution was then diluted with an equal volume of Cremophor® EL solution with stirring and was then diluted with 9 parts by weight of normal saline to form a solution containing 7 mg of compound 1393 per ml of solution for parenteral administration.

Solution 2: Antitumor compound 1393 was dissolved in 100% ethanol to form a solution containing 140 mg of compound 1393 per ml of the solution. The solution was then diluted with an equal volume of Cremophor® EL solution with stirring and was then diluted with 4 parts by weight of normal saline to form a solution containing 11.7 mg of compound 1393 per ml of solution for parenteral administration.

Solution 3: Antitumor compound 1393 was dissolved in 100% ethanol to form a solution containing 140 mg of compound 1393 per ml of the solution. The solution was then diluted with an equal volume of Cremophor® EL solution with stirring and was then diluted with 2.33 parts by weight of normal saline to form a solution containing 16.2 mg of compound 1393 per ml of solution for parenteral administration.

What is claimed is:

1. A pharmaceutical composition comprising a taxane and at least one nonaqueous, pharmaceutically acceptable solvent, wherein the taxane has a solubility in ethanol at room temperature of at least 200 mg/ml and an $ID_{50}$ value determined relative to the HCT116 cell line that is at least 4 times less than that of paclitaxel.

2. The composition of claim 1 wherein the $ID_{50}$ value of the taxane is at least 5 times less than that of paclitaxel.

3. The composition of claim 2 wherein the $ID_{50}$ value of the taxane is at least 6 times less than that of paclitaxel.

4. The composition of claim 3 wherein the $ID_{50}$ value of the taxane is at least 7 times less than that of paclitaxel.

5. The composition of claim 4 wherein the $ID_{50}$ value of the taxane is at least 8 times less than that of paclitaxel.

6. The composition of claim 5 wherein the $ID_{50}$ value of the taxane is at least 9 times less than that of paclitaxel.

7. The composition of claim 6 wherein the $ID_{50}$ value of the taxane is at least 10 times less than that of paclitaxel.

8. The composition of claim 1 wherein the taxane concentration is between 0.01 mg and 10 mg per ml of the composition.

9. The composition of claim 1 wherein the taxane dosage is at least 20 mg/$m^2$.

10. The composition of claim 9 wherein the taxane dosage is between 20 mg/$m^2$ and about 600 mg/$m^2$.

11. The composition of claim 10 wherein the taxane dosage is between about 25 mg/$m^2$ and about 400 mg/$m^2$.

12. The composition of claim 11 wherein the taxane dosage is between about 40 mg/$m^2$ and about 300 mg/$m^2$.

13. The composition of claim 12 wherein the taxane dosage is between about 50 mg/$m^2$ and about 200 mg/$m^2$.

14. The composition of claim 1 wherein the taxane has the formula:

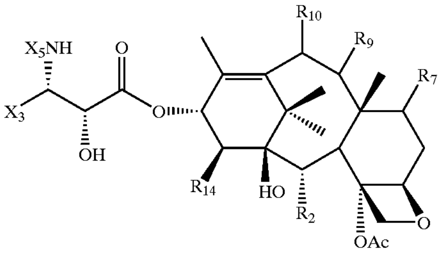

wherein one of $R_7$ and $R_{10}$ is hydroxy and the other is acyloxy;

$X_3$ is substituted or unsubstituted alkyl, alkenyl, alkynyl, phenyl or heterocyclo;

$X_5$ is —$COX_{10}$, —$COOX_{10}$, or —$CONHX_{10}$;

$X_{10}$ is hydrocarbyl, substituted hydrocarbyl, or heterocyclo;

$R_2$ is acyloxy;

$R_9$ is keto, hydroxy, or acyloxy;

$R_{14}$ is hydrido or hydroxy; and

Ac is acetyl.

15. The composition of claim 14 wherein the composition is for parenteral administration.

16. The composition of claim 14 wherein the composition is for oral administration.

17. The composition of claim 14 wherein $X_3$ is phenyl, 2-furyl, 3-furyl, 2-thienyl, 3-thienyl, 2-pyridyl, 3-pyridyl, 4-pyridyl, $C_2$–$C_8$ alkyl, $C_2$–$C_8$ alkenyl, or $C_2$–$C_8$ alkynyl.

18. The composition of claim 14 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

19. The composition of claim 14 wherein $R_{14}$ is hydrido and $R_2$ is benzoyloxy.

20. The composition of claim 14 wherein $R_7$ is hydroxy and $R_{10}$ is $R_{10a}C(O)O$—, $R_{10a}R_{10b}NC(O)O$—, $R_{10a}OC(O)O$— or $R_{10a}SC(O)O$— wherein $R_{10a}$ is hydrocarbyl, substituted hydrocarbyl or heterocyclo and $R_{10b}$ is hydrogen, hydrocarbyl, substituted hydrocarbyl or heterocyclo.

21. The composition of claim 20 wherein $X_3$ is phenyl, 2-furyl, 3-furyl, 2-thienyl, 3-thienyl, 2-pyridyl, 3-pyridyl, 4-pyridyl, $C_2$–$C_8$ alkyl, $C_2$–$C_8$ alkenyl, or $C_2$–$C_8$ alkynyl.

22. The composition of claim 20 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

23. The composition of claim 20 wherein $R_{14}$ is hydrido and $R_2$ is benzoyloxy.

24. The composition of claim 20 wherein $R_{14}$ is hydroxy; $X_3$ is phenyl, 2-furyl, 3-furyl, 2-thienyl, 3-thienyl, 2-pyridyl, 3-pyridyl, 4-pyridyl, $C_2$–$C_8$ alkyl, $C_2$–$C_8$ alkenyl, or $C_2$–$C_8$ alkynyl; $X_5$ is —$COX_{10}$ and $X_{10}$ is phenyl, or $X_5$ is —$COOX_{10}$ and $X_{10}$ is t-butyl.

25. The composition of claim 24 wherein $X_3$ is furyl or thienyl.

26. The composition of claim 25 wherein $X_5$ is —$COOX_{10}$ and $X_{10}$ is t-butyl.

27. The composition of claim 14 wherein $R_{10}$ is hydroxy and $R_7$ is $R_{7a}C(O)O$—, $R_{7a}R_{7b}NC(O)O$—, $R_{7a}OC(O)O$— or $R_{7a}SC(O)O$— wherein $R_{7a}$ is hydrocarbyl, substituted hydrocarbyl or heterocyclo and $R_{7b}$ is hydrogen, hydrocarbyl, substituted hydrocarbyl or heterocyclo.

28. The composition of claim 27 wherein $X_3$ is phenyl, 2-furyl, 3-furyl, 2-thienyl, 3-thienyl, 2-pyridyl, 3-pyridyl, 4-pyridyl, $C_2$–$C_8$ alkyl, $C_2$–$C_8$ alkenyl, or $C_2$–$C_8$ alkynyl.

29. The composition of claim 27 wherein $X_5$ is —$COX_{10}$ and $X_{10}$ is substituted or unsubstituted phenyl, 2-furyl, 3-furyl, 2-thienyl, 3-thienyl, 2-pyridyl, 3-pyridyl, 4-pyridyl, $C_1$–$C_8$ alkyl, $C_2$–$C_8$ alkenyl, or $C_2$–$C_8$ alkynyl or $X_5$ is —$COOX_{10}$ and $X_{10}$ is substituted or unsubstituted $C_1$–$C_8$ alkyl, $C_2$–$C_8$ alkenyl, or $C_2$–$C_8$ alkynyl.

30. The composition of claim 27 wherein $R_{14}$ is hydrido and $R_2$ is benzoyloxy.

31. The composition of claim 27 wherein $R_{14}$ is hydroxy; $X_3$ is phenyl, 2-furyl, 3-furyl, 2-thienyl, 3-thienyl, 2-pyridyl, 3-pyridyl, 4-pyridyl, $C_2$–$C_8$ alkyl, $C_2$–$C_8$ alkenyl, or $C_2$–$C_8$ alkynyl; $X_5$ is —$COX_{10}$ and $X_{10}$ is phenyl, or $X_5$ is —$COOX_{10}$ and $X_{10}$ is t-butyl.

32. The composition of claim 31 wherein $X_3$ is furyl or thienyl.

33. The composition of claim 32 wherein $X_5$ is —$COOX_{10}$ and $X_{10}$ is t-butyl.

* * * * *